United States Patent
Rogers et al.

(10) Patent No.: US 10,292,263 B2
(45) Date of Patent: May 14, 2019

(54) BIODEGRADABLE MATERIALS FOR MULTILAYER TRANSIENT PRINTED CIRCUIT BOARDS

(71) Applicant: The Board of Trustees of the University of Illinois, Urbana, IL (US)

(72) Inventors: John A. Rogers, Champaign, IL (US); Xian Huang, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 568 days.

(21) Appl. No.: 14/818,109

(22) Filed: Aug. 4, 2015

(65) Prior Publication Data
US 2016/0050750 A1 Feb. 18, 2016

Related U.S. Application Data

(63) Continuation-in-part of application No. 14/251,259, filed on Apr. 11, 2014.
(Continued)

(51) Int. Cl.
*H05K 1/02* (2006.01)
*H05K 1/09* (2006.01)
(Continued)

(52) U.S. Cl.
CPC .......... *H05K 1/0286* (2013.01); *A61B 5/686* (2013.01); *H05K 1/0275* (2013.01); *H05K 1/0386* (2013.01); *H05K 1/095* (2013.01); *H05K 3/22* (2013.01); *H05K 3/285* (2013.01); *H05K 1/028* (2013.01); *H05K 1/0212* (2013.01); *H05K 1/0283* (2013.01); *H05K 1/097* (2013.01); *H05K 1/144* (2013.01); *H05K 3/1216* (2013.01); *H05K 3/207* (2013.01); *H05K 3/287* (2013.01); *H05K 3/288* (2013.01); *H05K 3/4626* (2013.01); *H05K 2201/0133* (2013.01); *H05K 2201/0266* (2013.01); *H05K 2201/041* (2013.01); *H05K 2201/10083* (2013.01);
(Continued)

(58) Field of Classification Search
CPC .................................................... H05K 1/0286
USPC ......................................................... 174/260
See application file for complete search history.

(56) References Cited

U.S. PATENT DOCUMENTS 5,376,820 A 12/1994 Crafts et al.
7,195,733 B2 3/2007 Rogers et al.
(Continued)

FOREIGN PATENT DOCUMENTS

WO WO 2004/000915 12/2003
WO WO 2004/062697 7/2004
(Continued)

OTHER PUBLICATIONS

U.S. Appl. No. 11/001,689, filed Dec. 1, 2004, 2006/0286488, Dec. 21, 2006, U.S. Pat. No. 7,704,684, Apr. 27, 2010.
(Continued)

*Primary Examiner* — Stanley Tso
(74) *Attorney, Agent, or Firm* — Leydig, Voit & Mayer, Ltd.

(57) ABSTRACT

The invention provides transient printed circuit board devices, including active and passive devices that electrically and/or physically transform upon application of at least one internal and/or external stimulus.

50 Claims, 75 Drawing Sheets

Related U.S. Application Data

(60) Provisional application No. 62/034,443, filed on Aug. 7, 2014, provisional application No. 61/811,603, filed on Apr. 12, 2013, provisional application No. 61/828,935, filed on May 30, 2013, provisional application No. 61/829,028, filed on May 30, 2013.

(51) Int. Cl.

| | | |
|---|---|---|
| *A61B 5/00* | (2006.01) | |
| *H05K 3/22* | (2006.01) | |
| *H05K 3/28* | (2006.01) | |
| *H05K 1/03* | (2006.01) | |
| H05K 1/14 | (2006.01) | |
| H05K 3/12 | (2006.01) | |
| H05K 3/20 | (2006.01) | |
| H05K 3/46 | (2006.01) | |

(52) U.S. Cl.
CPC .......... *H05K 2201/10098* (2013.01); *H05K 2201/10151* (2013.01); *H05K 2201/10196* (2013.01); *H05K 2201/10212* (2013.01); *H05K 2203/0271* (2013.01); *H05K 2203/0292* (2013.01); *H05K 2203/0514* (2013.01); *H05K 2203/0769* (2013.01); *H05K 2203/0776* (2013.01); *H05K 2203/0786* (2013.01); *H05K 2203/105* (2013.01); *H05K 2203/1105* (2013.01); *H05K 2203/1142* (2013.01); *H05K 2203/175* (2013.01); *H05K 2203/178* (2013.01); *Y02P 70/611* (2015.11); *Y02P 70/613* (2015.11); *Y10T 29/49124* (2015.01); *Y10T 137/0318* (2015.04); *Y10T 428/239* (2015.01)

(56) References Cited

U.S. PATENT DOCUMENTS

| | | | |
|---|---|---|---|
| 7,521,292 | B2 | 4/2009 | Rogers et al. |
| 7,557,367 | B2 | 7/2009 | Rogers et al. |
| 7,622,367 | B1 | 11/2009 | Nuzzo et al. |
| 7,704,684 | B2 | 4/2010 | Rogers et al. |
| 7,705,280 | B2 | 4/2010 | Nuzzo et al. |
| 7,799,699 | B2 | 9/2010 | Nuzzo et al. |
| 7,932,123 | B2 | 4/2011 | Rogers et al. |
| 7,943,491 | B2 | 5/2011 | Nuzzo et al. |
| 7,972,875 | B2 | 7/2011 | Rogers et al. |
| 7,982,296 | B2 | 7/2011 | Nuzzo et al. |
| 8,039,847 | B2 | 10/2011 | Nuzzo et al. |
| 8,198,621 | B2 | 6/2012 | Rogers et al. |
| 8,217,381 | B2 | 7/2012 | Rogers et al. |
| 8,367,035 | B2 | 2/2013 | Rogers et al. |
| 8,394,706 | B2 | 3/2013 | Nuzzo et al. |
| 8,440,546 | B2 | 5/2013 | Nuzzo et al. |
| 8,470,701 | B2 | 6/2013 | Rogers et al. |
| 8,552,299 | B2 | 10/2013 | Rogers et al. |
| 8,562,095 | B2 | 10/2013 | Alleyene et al. |
| 8,664,699 | B2 | 3/2014 | Nuzzo et al. |
| 8,666,471 | B2 | 3/2014 | Rogers et al. |
| 8,679,888 | B2 | 3/2014 | Rogers et al. |
| 8,722,458 | B2 | 5/2014 | Rogers et al. |
| 8,729,524 | B2 | 5/2014 | Rogers et al. |
| 8,754,396 | B2 | 6/2014 | Rogers et al. |
| 8,865,489 | B2 | 10/2014 | Rogers et al. |
| 8,895,406 | B2 | 11/2014 | Rogers et al. |
| 8,934,965 | B2 | 1/2015 | Rogers et al. |
| 8,946,683 | B2 | 2/2015 | Rogers et al. |
| 9,057,994 | B2 | 6/2015 | Rogers et al. |
| 9,061,494 | B2 | 6/2015 | Rogers et al. |
| 9,105,555 | B2 | 8/2015 | Rogers et al. |
| 9,105,782 | B2 | 8/2015 | Rogers et al. |
| 9,117,940 | B2 | 8/2015 | Rogers et al. |
| 2004/0020689 | A1* | 2/2004 | Kagami ............... G03F 7/0047 174/261 |
| 2004/0152332 | A1* | 8/2004 | Schwalbe ......... H01L 21/02063 438/725 |
| 2006/0100478 | A1 | 5/2006 | Connors et al. |
| 2007/0115640 | A1* | 5/2007 | Shibasaki ............... B41J 29/02 361/704 |
| 2008/0055581 | A1 | 3/2008 | Rogers et al. |
| 2008/0171182 | A1* | 7/2008 | Kawate .................. H05K 3/323 428/209 |
| 2008/0306359 | A1 | 12/2008 | Zdeblick et al. |
| 2009/0163895 | A1 | 6/2009 | Ausiello et al. |
| 2011/0316120 | A1 | 12/2011 | Rogers et al. |
| 2012/0035740 | A1 | 2/2012 | Koo et al. |
| 2012/0157804 | A1 | 6/2012 | Rogers et al. |
| 2012/0165759 | A1 | 6/2012 | Rogers et al. |
| 2012/0261551 | A1 | 10/2012 | Rogers et al. |
| 2012/0320581 | A1 | 12/2012 | Rogers et al. |
| 2013/0036928 | A1 | 2/2013 | Rogers et al. |
| 2013/0041235 | A1 | 2/2013 | Rogers et al. |
| 2013/0140649 | A1 | 6/2013 | Rogers et al. |
| 2013/0197158 | A1* | 8/2013 | Kim ...................... C08L 75/04 524/590 |
| 2013/0249104 | A1* | 9/2013 | Chi ...................... H01L 21/561 257/774 |
| 2013/0333094 | A1 | 12/2013 | Rogers et al. |
| 2014/0163390 | A1 | 6/2014 | Rogers et al. |
| 2014/0191236 | A1 | 7/2014 | Nuzzo et al. |
| 2014/0220422 | A1 | 8/2014 | Rogers et al. |
| 2014/0252608 | A1* | 9/2014 | Chen ................... H01L 21/4846 257/738 |
| 2014/0305900 | A1 | 10/2014 | Rogers et al. |
| 2014/0323968 | A1 | 10/2014 | Rogers et al. |
| 2014/0361409 | A1 | 12/2014 | Rogers et al. |
| 2014/0374872 | A1 | 12/2014 | Rogers et al. |
| 2015/0001462 | A1 | 1/2015 | Rogers et al. |
| 2015/0080695 | A1 | 3/2015 | Rogers et al. |
| 2015/0132873 | A1 | 5/2015 | Rogers et al. |
| 2015/0141767 | A1 | 5/2015 | Rogers et al. |
| 2015/0181700 | A1 | 6/2015 | Rogers et al. |
| 2015/0207012 | A1 | 7/2015 | Rogers et al. |
| 2015/0237711 | A1 | 8/2015 | Rogers et al. |
| 2015/0290938 | A1 | 10/2015 | Rogers et al. |
| 2015/0373831 | A1 | 12/2015 | Rogers et al. |
| 2015/0380355 | A1 | 12/2015 | Rogers et al. |
| 2016/0005700 | A1 | 1/2016 | Rogers et al. |
| 2016/0027737 | A1 | 1/2016 | Rogers et al. |

FOREIGN PATENT DOCUMENTS

| | | | |
|---|---|---|---|
| WO | WO 2005/012606 | 2/2005 | |
| WO | WO 2005/122285 | 12/2005 | |
| WO | WO 2005/123114 | 12/2005 | |
| WO | WO 2007/016524 | 2/2007 | |
| WO | WO 2008/085904 | 7/2008 | |
| WO | WO 2008/108838 | 9/2008 | |
| WO | WO 2013/144420 | * 3/2012 ............ C08L 97/00 |
| WO | PCT/US2015/044573 | 8/2015 | |
| WO | PCT/US2015/044588 | 8/2015 | |
| WO | PCT/US2015/044638 | 8/2015 | |
| WO | PCT/US2015/053452 | 10/2015 | |

OTHER PUBLICATIONS

U.S. Appl. No. 11/115,954, filed Apr. 27, 2005, 2005/0238967, Oct. 27, 2005, U.S. Pat. No. 7,195,733, Mar. 27, 2007.
U.S. Appl. No. 11/145,574, filed Jun. 2, 2005, 2009/0294803, Dec. 3, 2009, U.S. Pat. No. 7,622,367, Nov. 24, 2009.
U.S. Appl. No. 11/145,542, filed Jun. 2, 2005, 2006/0038182, Feb. 23, 2006, U.S. Pat. No. 7,557,367, Jul. 7, 2009.
U.S. Appl. No. 11/421,654, filed Jun. 1, 2006, 2007/0032089, Feb. 8, 2007, U.S. Pat. No. 7,799,699, Sep. 21, 2010.
U.S. Appl. No. 11/423,287, filed Jun. 9, 2006, 2006/0286785, Dec. 21, 2006, U.S. Pat. No. 7,521,292, Apr. 21, 2009.
U.S. Appl. No. 11/423,192, filed Jun. 9, 2006, 2009/0199960, Aug. 13, 2009, U.S. Pat. No. 7,943,491, May 17, 2011.
U.S. Appl. No. 11/462,317, filed Aug. 17, 2006.
U.S. Appl. No. 11/675,659, filed Feb. 16, 2007, 2008/0055581, Mar. 6, 2008.

(56) References Cited

OTHER PUBLICATIONS

U.S. Appl. No. 11/782,799, filed Jul. 25, 2007, 2008/0212102, Sep. 4, 2008, U.S. Pat. No. 7,705,280, Apr. 27, 2010.
U.S. Appl. No. 11/851,182, filed Sep. 6, 2007, 2008/0157235, Jul. 3, 2008, U.S. Pat. No. 8,217,381, Jul. 10, 2012.
U.S. Appl. No. 11/858,788, filed Sep. 20, 2007, 2008/0108171, May 8, 2008, U.S. Pat. No. 7,932,123, Apr. 26, 2011.
U.S. Appl. No. 11/981,380, filed Oct. 31, 2007, 2010/0283069, Nov. 11, 2010, U.S. Pat. No. 7,972,875, Jul. 5, 2011.
U.S. Appl. No. 12/375,605, filed Feb. 17, 2009.
U.S. Appl. No. 12/398,811, filed Mar. 5, 2009, 2010/0002402, Jan. 7, 2010, U.S. Pat. No. 8,552,299, Oct. 8, 2013.
U.S. Appl. No. 12/405,475, filed Mar. 17, 2009, 2010/0059863, Mar. 11, 2010, U.S. Pat. No. 8,198,621, Jun. 12, 2012.
U.S. Appl. No. 12/418,071, filed Apr. 3, 2009, 2010/0052112, Mar. 4, 2010, U.S. Pat. No. 8,470,701, Jun. 25, 2013.
U.S. Appl. No. 12/564,566, filed Sep. 22, 2009, 2010/0072577, Mar. 25, 2010, U.S. Pat. No. 7,982,296, Jul. 19, 2011.
U.S. Appl. No. 12/669,287, filed Jan. 15, 2010, 2011/0187798, Aug. 4, 2011, U.S. Pat. No. 9,061,494, Jun. 23, 2015.
U.S. Appl. No. 12/778,588, filed May 12, 2010, 2010/0317132, Dec. 16, 2010, U.S. Pat. No. 8,865,489, Oct. 21, 2014.
U.S. Appl. No. 12/844,492, filed Jul. 27, 2010, 2010/0289124, Nov. 18, 2010, U.S. Pat. No. 8,039,847, Oct. 18, 2011.
U.S. Appl. No. 12/892,001, filed Sep. 28, 2010, 2011/0230747, Sep. 22, 2011, U.S. Pat. No. 8,666,471, Mar. 4, 2014.
U.S. Appl. No. 12/916,934, filed Nov. 1, 2010, 2012/0105528, May 3, 2012, U.S. Pat. No. 8,562,095, Oct. 22, 2013.
U.S. Appl. No. 12/947,120, filed Nov. 16, 2010, 2011/0170225, Jul. 14, 2011, U.S. Pat. No. 9,057,994, Jun. 16, 2015.
U.S. Appl. No. 12/996,924, filed Dec. 8, 2010, 2011/0147715, Jun. 23, 2011, U.S. Pat. No. 8,946,683, Feb. 3, 2015.
U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/120,486, filed Aug. 4, 2011, 2011/0277813, Nov. 17, 2011, U.S. Pat. No. 8,679,888, Mar. 25, 2014.
U.S. Appl. No. 13/228,041, filed Sep. 8, 2011, 2011/0316120, Dec. 29, 2011.
U.S. Appl. No. 13/270,954, filed Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/472,165, filed May 15, 2012, 2012/0320581, Dec. 20, 2012.
U.S. Appl. No. 13/486,726, filed Jun. 1, 2012, 2013/0072775, Mar. 21, 2013, U.S. Pat. No. 8,934,965, Jan. 13, 2015.
U.S. Appl. No. 13/492,636, filed Jun. 8, 2012, 2013/0041235, Feb. 14, 2013.
U.S. Appl. No. 13/549,291, filed Jul. 13, 2012, 2013/0036928, Feb. 14, 2013.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/385,284, filed Mar. 15, 2013, 2014/0220422, Aug. 7, 2014.
U.S. Appl. No. 13/853,770, filed Mar. 29, 2013, 2013/0333094, Dec. 19, 2013.
U.S. Appl. No. 14/140,299, filed Dec. 24, 2013, 2014/0163390, Jun. 12, 2014.
U.S. Appl. No. 14/155,010, filed Jan. 14, 2013, 2014/0191236, Jul. 10, 2014.
U.S. Appl. No. 14/173,525, filed Feb. 5, 2014, 2014/0216524, Aug. 7, 2014, U.S. Pat. No. 9,105,782, Aug. 11, 2015.
U.S. Appl. No. 14/209,481, filed Mar. 13, 2014, 2014/0373898, Dec. 25, 2014, U.S. Pat. No. 9,117,940, Aug. 25, 2015.
U.S. Appl. No. 14/220,910, filed Mar. 20, 2014, 2014/0374872, Dec. 25, 2014.
U.S. Appl. No. 14/220,923, filed Mar. 20, 2014, 2015/0001462, Jan. 1, 2015, U.S. Pat. No. 9,105,555, Aug. 11, 2015.
U.S. Appl. No. 14/246,962, filed Apr. 7, 2014, 2014/0361409, Dec. 11, 2014.
U.S. Appl. No. 14/251,259, filed Apr. 11, 2014, 2014/0323968, Oct. 30, 2014.
U.S. Appl. No. 14/250,671, filed Apr. 11, 2014, 2014/0305900, Oct. 16, 2014.
U.S. Appl. No. 14/479,100, filed Sep. 5, 2014, 2015/0132873, May 14, 2015.
U.S. Appl. No. 14/504,736, filed Oct. 2, 2014, 2015/0141767, May 21, 2015.
U.S. Appl. No. 14/521,319, filed Oct. 22, 2014, 2015/0181700, Jun. 25, 2015.
U.S. Appl. No. 14/532,687, filed Nov. 4, 2014, 2015/0080695, Mar. 19, 2015.
U.S. Appl. No. 14/599,290, filed Jan. 16, 2015, 2015/0207012, Jul. 23, 2015.
U.S. Appl. No. 14/686,304, filed Apr. 14, 2015, 2015/0290938, Oct. 15, 2015.
U.S. Appl. No. 14/706,733, filed May 7, 2015, 2015/0237711, Aug. 20, 2015.
U.S. Appl. No. 14/789,645, filed Jul. 1, 2015, 2016/0027737, Jan. 28, 2016.
U.S. Appl. No. 14/800,363, filed Jul. 15, 2015.
U.S. Appl. No. 14/818,109, filed Aug. 4, 2015.
U.S. Appl. No. 14/766,333, filed Aug. 6, 2015, 2015/0380355, Dec. 31, 2015.
U.S. Appl. No. 14/766,929, filed Aug. 10, 2015.
U.S. Appl. No. 14/772,354, filed Sep. 2, 2015, 2016/0005700, Jan. 7, 2016.
U.S. Appl. No. 14/772,312, filed Sep. 2, 2015.
U.S. Appl. No. 14/944,039, filed Nov. 17, 2015.
U.S. Appl. No. 14/766,301, filed Dec. 24, 2015, 2015/0373831, Dec. 24, 2015.
Adeyeye et al. (2002) "Viscoelastic evaluation of topical creams containing microcrystalline cellulose/sodium carboxymethyl cellulose as stabilizer," AAPS PharmSciTech 3(2):16-25.
Aharoni (1972) "Electrical Resistivity of a Composite of Conducting Particles in an Insulating Matrix," Journal of Applied Physics. 43:2463.
Al-Hardan et al. (2010) "The effect of oxygen ratio on the crystallography and optical emission properties of reactive RF sputtered ZnO films," Physica B. 405:1081-1085.
Ambat et al. (2000) "Studies on the influence of chloride ion and pH on the corrosion and electrochemical behaviour of AZ91D magnesium alloy," J. Appl. Electrochem. 30(7):865-874.
Ambrose et al. (2004) "Bioabsorbable implants: review of clinical experience in orthopedic surgery," Ann. Biomed. Eng. 32:171-177.
Anik et al. (2002) "Effect of pH on the Anodic Behavior of Tungsten," Journal of The Electrochemical Society. 149(6):B224-B233.
Anik et al. (2006) "Dissolution kinetics of $WO_3$ in acidic solutions," J. Appl. Electrochem. 36(5):603-608.
Athanasiou et al. (1998) "Orthopaedic applications for PLA-PGA biodegradable polymers," Arthroscopy 14:726-737.
Badawy et al. (1998) "Corrosion and passivation behaviors of molybdenum in aqueous solutions of different pH," Electrochimica Acta. 44(4):693-702.

(56) References Cited

OTHER PUBLICATIONS

Barceloux et al. (1999) "Molybdenum," Journal of Toxicology: Clinical Toxicology. 37(2):231-237.
Barreca et al. (2001) "A Study of Nanophase Tungsten Oxides Thin Films by XPS," Surface Science Spectra. 8(4):258-267.
Barreca et al. (2001) "Chemical Vapor Deposited $Fe_2O_3$ Thin Films Analyzed by XPS," Surface Science Spectra. 8(3):240-245.
Baskoutas et al. (2011) "Transition in the Optical Emission Polarization of ZnO Nanorods," J. Phys. Chem. C. 115:15862-15867.
Bayarri et al. (2009) "Viscoelastic properties of aqueous and milk systems with carboxymethyl cellulose," Food Hydrocolloids. 23:441-450.
Bayliss et al. (1999) "The culture of neurons on silicon," Sensors and Actuators A: Physical. 74(1-3):139-142.
Bernardini et al. (1997) "Spontaneous polarization and piezoelectric constants of III-V nitrides," Physical Review B. 56:R10024.
Bettinger et al. (2010) "Biomaterial-Based Organic Electronic Devices," Polym. Int. 59:563-567.
Bettinger et al. (2010) "Organic Thin Film Transistors Fabricated on Resorbable Biomaterial Substrates," Adv. Mater. 22:651-655.
Bevers et al. (2009) "The bioinorganic chemistry of tungsten," Coordination Chemistry Reviews. 253(3-4):269-290.
Bhrany et al. (Jan. 1, 2013) "Evaluation of a Sphere-Templated Polymeric Scaffold as a Subcutaneous Implant," JAMA Facial Plast. Surg. 15:29-33.
Blawert et al. (2009) "Different Underlying Corrosion Mechanism for Mg Bulk Alloys and Mg Thin Films," Plasma Processes and Polymers. 6:S690-S694.
Blom et al. (1990) "Thin-film ZnO as micromechanical actuator at low frequencies," Sensors and Actuators. 21:226-228.
Bowen et al. (May 14, 2013) "Zinc exhibits ideal physiological corrosion behavior for bioabsorbable stents," Advanced Materials. 25(18):2577-2582.
Carcia et al. (2006) "High-performance ZnO thin-film transistors on gate dielectrics grown by atomic layer deposition," Appl. Phys. Lett. 88:123509.
Cho et al. (1999) "UV-photoassisted etching of GaN in KOH," J. Electron. Mater. 28:290-294.
Choi-Yim et al. (1998) "The effect of silicon on the glass forming ability of the $Cu_{47}Ti_{34}Zr_{11}Ni_8$ bulk metallic glass forming alloy during processing of composites," J. Appl. Phys. 83:7993.
Czekalla et al. (2008) "Spatial fluctuations of optical emission from single ZnO/MgZnO nanowire quantum wells," Nanotechnology. 19:115202.
Dagdeviren et al. (Apr. 19, 2013) "Transient, Biocompatible Electronics and Energy Harvesters Based on ZnO," Small. 9:3398-3404.
Danckwerts (1950) "Absorption by Simultaneous Diffusion and Chemical Reaction," Tran. Faraday Soc. 46:300-304.
David et al. (Apr. 26, 2012) "Dissolution Kinetics and Solubility of ZnO Nanoparticles Followed by AGNES," J. Phys. Chem. 116:11758-11767.
De Rosa et al. (2004) "The wet corrosion of molybdenum thin film—. Part I: Behavior at 25° C.," Materials and Corrosion. 55(8):602-609.
Deng et al. (2007) "Distribution of PBDEs in air particles from an electronic waste recycling site compared with Guangzhou and Hong Kong, South China," Environment International. 33:1063-1069.
Dharmadasa et al. (Apr. 8, 2014) "Intense Pulsed Light Sintering of Electrodeposited CdS Thin Films," Advanced Engineering Materials. 16(11):1351-1361.
Diftis et al. (2003) "Improvement of emulsifying properties of soybean protein isolate by conjugation with carboxymethyl cellulose," Food Chemistry. 81(1):1-6.
Dong et al. (2011) "Initiation and repassivation of pitting corrosion of carbon steel in carbonated concrete pore solution," Corrosion Science. 53(4):1322-1330.
Edwards et al. (2012) "Optically monitoring and controlling nanoscale topography during semiconductor etching," Light Sci. Appl. 1:e30.
Erogbogbo et al. (2008) "Biocompatible Luminescent Silicon Quantum Dots for Imaging of Cancer Cells," ACS Nano. 2(5):873-878.
Erogbogbo et al. (2010) "Biocompatible Magnetofluorescent Probes: Luminescent Silicon Quantum Dots Coupled with Superparamagnetic Iron(III) Oxide," ACS Nano. 4(9):5131-5138.
Fosmire (1990) Am. J. Clin. Nutr. 51:225.
Gad et al. (2008) "Formulation and Evaluation of PLA and PLGA In Situ Implants Containing Secnidazole and/or Doxycycline for Treatment of Periodontitis," AAPS PharmSciTech. 9:878-884.
Gatti et al. (2004) "Detection of micro- and nano-sized biocompatible particles in the blood," Journal of Materials Science: Materials in Medicine. 15(4):469-472.
Gerischer et al. (1992) "Chemical dissolution of zinc oxide crystals in aqueous electrolytes—An analysis of the kinetics," Electrochimica Acta. 37:827-835.
Grant et al. (Oct. 30, 2013) "Health consequences of exposure to e-waste: a systematic review," The Lancet Global Health. 1:e350-e361.
Grosjean et al. (2006) "Hydrolysis of Mg—salt and MgH2—salt mixtures prepared by ball milling for hydrogen production," Journal of Alloys and Compounds. 416:296-302.
Gullapalli et al. (2010) "Flexible Piezoelectric ZnO—Paper Nanocomposite Strain Sensor," Small. 6:1641-1646.
Gupta et al. (2010) "Development of gas sensors using ZnO nanostructures," J. Chem. Sci. 122:57-62.
Hebeish et al. (Jan. 30, 2013) "Development of CMC hydrogels loaded with silver nano-particles for medical applications," Carbohydrate Polymers. 92:407-413.
Hermawan et al. (2010) "Fe—Mn alloys for metallic biodegradable stents: Degradation and cell viability studies," Acta Biomaterialia. 6(5):1852-1860.
Hixson et al. (1995) "Valence-band and core photoelectron spectroscopic studies of molybdenum aqueous oxidation and the influence of argon-ion etching," Journal of the Chemical Society, Faraday Transactions. 91(20):3593-3601.
Hoffman et al. (2003) "ZnO-based transparent thin-film transistors," Appl. Phys. Lett. 82:733.
Huang et al. (2009) "Recycling of waste printed circuit boards: A review of current technologies and treatment status in China," Journal of Hazardous Materials. 164:399-408.
Huang et al. (Apr. 6, 2014) "Stretchable, Wireless Sensors and Functional Substrates for Epidermal Characterization of Sweat," Small. 10(15):3083-3090.
Huang et al. (Mar. 2, 2014) "Materials and Designs for Wireless Epidermal Sensors of Hydration and Strain," Advanced Functional Materials. 24:3846-3854.
Huang et al. (Sep. 22, 2014) "Biodegradable Materials for Multilayer Transient Printed Circuit Boards," Advanced Materials. 26(43):7371-7377.
Hwang et al. (Apr. 11, 2013) "Materials and Fabrication Processes for Transient and Bioresorbable High-Performance Electronics," Adv. Funct. Mater. 23(33):4087-4093.
Hwang et al. (May 17, 2013) "Materials for Bioresorbable Radio Frequency Electronics," Advanced Materials. 25:3526-3531.
Hwang et al. (Sep. 28, 2012) "A Physically Transient Form of Silicon Electronics, With Integrated Sensors, Actuators and Power Supply," Science 337(6102):1640-1644.
Ilican et al. (2008) "Preparation and characterization of ZnO thin deposited by sol-gel spin coating method," Journal of Optoelectronics and Advance Materials. 10:2578-2583.
International Search Report with Written Opinion corresponding to International Patent Application No. PCT/US2014/033817, dated Dec. 24, 2014.
Irimia-Vladu et al. (2010) "Biocompatible and Biodegradable Materials for Organic-Field Transistors," Adv. Funct. Mater. 20:4069-4076.
Irimia-Vladu et al. (2010) "Environmentally Sustainable Organic Field Effect Transistors," Org. Electron. 11:1974-1990.
Israelachvili (1997) "The different faces of poly(ethylene glycol)," Proceedings of the National Academy of Sciences USA. 94:8378-8379.
Jang et al. (Mar. 25, 2013) "Effect of Biologically Relevant Ions on the Corrosion Products formed on Alloy AZ31B: An Improved Understanding of Magnesium Corrosion," Acta Biomaterialia, (9):8761-8770.

(56) References Cited

OTHER PUBLICATIONS

Jeon et al. (2007) "Low-Voltage Zinc-Oxide Thin-Film Transistors on a Conventional SiO2 Gate Insulator Grown by Radio-Frequency Magnetron Sputtering at Room Temperature," J. Kor. Phys. Soc. 51:1999-2003.
Jimbo et al. (2008) "Gastric-fluid-utilizing micro battery for micro medical devices," Sensors Actuators B: Chem. 134:219-224.
Kang et al. (2005) "Electronic waste recycling: A review of U.S. infrastructure and technology options," Resources, Conservation and Recycling. 45:368-400.
Kang et al. (Apr. 22, 2013) "Potential Environmental and Human Health Impacts of Rechargeable Lithium Batteries in Electronic Waste," Environmental Science & Technology. 47:5495-5503.
Kang et al. (Jul. 23, 2014) "Dissolution Behaviors and Applications of Silicon Oxides and Nitrides in Transient Electronics," Adv. Funct. Mater. 24:4427-4434.
Keim et al. (2011) "Control of magnesium corrosion and biocompatibility with biomimetic coatings," Journal of Biomedical Materials Research Part B: Applied Biomaterials. 96B:84-90.
Kim et al. (2009) "Intense pulsed light sintering of copper nanoink for printed electronics," Appl. Phys. A. 97:791-798.
Kim et al. (2009) "Silicon Electronics on Silk as a Path to Bioresorbable, Implantable Devices," Appl. Phys. Lett. 95:133701.
Kim et al. (2010) "Dissolvable Films of Silk Fibroin for Ultrathin Conformal Bio Integrated Electronics," Nature Materials. 9(6):511-517.
Kim et al. (Dec. 9, 2013) "Biologically derived melanin electrodes in aqueous sodium-ion energy storage devices," Proceedings of the National Academy of Sciences. 110(52):20912-20917.
Kim et al. (Mar. 7, 2013) "Self-deployable current sources fabricated from edible materials," Journal of Materials Chemistry B. 1:3781-3788.
Kirkland et al. (Mar. 2012) "Assessing the corrosion of biodegradable magnesium implants: A critical review of current methodologies and their limitations," Acta Biomaterialia. 8(3): p. 925-936.
Kirkpatrick (1973) "Percolation and Conduction," Reviews of Modern Physics. 45:574.
Kneer et al. (1997) "Electrochemical Measurements During the Chemical-Mechanical Polishing of Tungsten Thin-Films," Journal of The Electrochemical Society.144(9):3041-3049.
Kozicki et al. (Nov. 10, 2005) "Programmable Metallization Cell Memory Based on Ag—Ge—S and Cu—Ge—S Solid Electrolytes," In; Non-Volatile Memory Technology Symposium 2005. Dallas, Texas. pp. 83-89.
Kumar et al. (2002) "Polyanhydrides: an overview," Adv. Drug Del. Rev. 54:889-910.
Kumar et al. (2006) "Ultrasensitive DNA sequence detection using nanoscale ZnO sensor arrays," Nanotechnology. 17:2875.
Kumar et al. (2011) "ZnO nanoparticle as catalyst for efficient green one-pot synthesis of coumarins through Knoevenagel condensation," J. Chem. Sci. 123:615-621.
Lang et al. (1986) "Salting-out of oxygen from aqueous electrolyte solutions: prediction and measurement," Industrial & Engineering Chemistry Fundamentals. 25(4):775-782.
Larson et al. (2008) "Silica Nanoparticle Architecture Determines Radiative Properties of Encapsulated Fluorophores," Chemistry of Materials. 20(8):2677-2684.
Lee et al. (2005) "Effect of nano-sized silver particles on the resistivity of polymeric conductive adhesives," International Journal of Adhesion and Adhesives. 25:437-441.
Lee et al. (2011) "Pulsed light sintering characteristics of inkjet-printed nanosilver films on a polymer substrate," Journal of Micromechanics and Microengineering. 21:125023.
Legnani et al. (2008) "Bacterial Cellulose Membrane as Flexible Substrate for Organic Light Emitting Devices," Thin Solid Films. 517:1016-1020.
Leung et al. (2006) "Environmental contamination from electronic waste recycling at Guiyu, southeast China," Journal of Material Cycles and Waste Management. 8:21-33.
Li et al (2008) "Cellular Level Biocompatibility and Biosafety of ZnO Nanowires," J. Phys. Chem. C. 112:20114-20117.
Li et al. (2005) "Enhanced ionic conductivity of poly(ethylene oxide) (PEO) electrolyte by adding mesoporous molecular sieve LiAISBA," J. Solid State Electrochem. 9:609-615.
Li et al. (2007) "Recycle Technology for Recovering Resources and Products from Waste Printed Circuit Boards," Environmental Science & Technology. 41:1995-2000.
Li et al. (Jan. 21, 2013) "An Analytical Model of Reactive Diffusion for Transient Electronics," Adv. Funct. Mater. 23:3106-3114.
Lillard et al. (1998) "The Nature of Oxide Films on Tungsten in Acidic and Alkaline Solutions," Journal of The Electrochemical Society. 145(8):2718-2725.
Lin et al. (2010) "ZnO and $\epsilon$-$Zn(OH)_2$ Composite Nanoparticles by Pulsed Laser Ablation on Zn in Water," The Journal of Physical Chemistry C. 115(12):5003-5010.
Liu et al. (2009) "A first quantitative XPS study of the surface films formed, by exposure to water, on Mg and on the Mg—Al intermetallics: $Al_3Mg_2$ and $Mg_{17}Al_{12}$," Corrosion Science. 51(5):1115-1127.
Longobardo (2010) "Glass Fibers for Printed Circuit Boards," In; *Fiberglass and Glass Technology*. Eds: Wallenberger et al. Springer. pp. 175-196.
Lou et al. (Aug. 20, 2012) "Imprint Lithography with Degradable Elastomeric Polyanhydrides," ACS Applied Materials & Interfaces. 4:4457-4460.
Low et al. (2009) "The biocompatibility of porous silicon in tissues of the eye," Biomaterials. 30(15):2873-2880.
Luther (2010) *Managing Electronic Waste: Issues with Exporting E-Waste*. CRS Report for Congress. Document No. 7-5700.
Maher et al. (2000) "Smooth wet etching by ultraviolet-assisted photoetching and its application to the fabrication of AlGaN/GaN heterostructure field-effect transistors," Appl. Phys. Lett. 77:3833.
Makadia et al. (Aug. 26, 2011) "Poly Lactic-co-Glycolic Acid (PLGA) as Biodegradable Controlled Drug Delivery Carrier," Polymers. 3:1377-1397.
Mann et al. (1977) "Catalytic oxidation of methanol over molybdenum oxide—tungsten oxide," Journal of Applied Chemistry and Biotechnology. 27:198-204.
MG Chemicals (2015) "Silver Conductive Epoxy: 10 Mins. Working Time / High Conductivity," MG Chemicals. Accessible on the Internet at URL: http://www.mgchemicals.com/products/adhesives/electrically-conductive/silver-conductive-epoxy-8331/. [Last Accessed Nov. 10, 2015].
Middleton et al. (2000) "Synthetic biodegradable polymers as orthopedic devices," Biomaterials. 21:2335-2346.
Minsky et al. (1996) "Room-temperature photoenhanced wet etching of GaN," Appl. Phys. Lett. 68:1531.
Miyake et al. (1994) "Formation of iron film by ion beam deposition," Surface and Coatings Technology. 65(1-3):208-213.
Miyamoto et al. (2004) "High-electron-mobility ZnO epilayers grown by plasma-assisted molecular beam epitaxy," Journal of Crystal Growth. 265:34-40.
Mondal et al. (2008) "Preparation of Al-doped ZnO (AZO) Thin Film by Silar," Journal of Physical Sciences. 12:221-229.
Moore et al. (1959) "II. Diffusion of zinc and oxygen in zinc oxide," Discussions of the Faraday Society. 28:86-93.
Mudunkotuwa et al. (Nov. 28, 2011) "Dissolution of ZnO Nanoparticles at Circumneutral pH: A Study of Size Effects in the Presence and Absence of Citric Acid," Langmuir. 28:396-403.
Mueller et al. (Nov. 2012) "Histological and molecular evaluation of iron as degradable medical implant material in a murine animal model," Journal of Biomedical Materials Research Part A. 100A(11):2881-2889.
Ng et al. (2010) "Effect of pH on the in vitro corrosion rate of magnesium degradable implant material," Materials Science and Engineering: C. 30(6):898-903.
Nicholas et al. (Oct. 7, 2011) "The mechanism for hydrothermal growth of zinc oxide," CrystEngComm. 14(4):1232-1240.
Nie et al. (2010) "In vitro corrosion, cytotoxicity and hemocompatibility of bulk nanocrystalline pure iron," Biomedical Materials. 5(6):065015.

(56) References Cited

OTHER PUBLICATIONS

Oikawa (1975) "Ellipsometric Investigation of Corrosion of Deposited Thin Molybdenum Film," Japanese Journal of Applied Physics. 14(5):629-635.
Okonkwo et al. (Jul. 31, 2012) "Oxidation states of molybdenum in oxide films formed in sulphuric acid and sodium hydroxide," Thin Solid Films. 520(19):6318-6327.
Ondo-Ndong et al. (2003) "Electrical properties of zinc oxide sputtered thin films," Microelectronics Journal. 34:1087-1092.
Pal et al. (2006) "Development of carboxymethyl cellulose acrylate for various biomedical applications," Biomedical Materials. 1:85-91.
Park et al. (2003) "Electrocatalytic Enhancement of Methanol Oxidation at Pt—WOx Nanophase Electrodes and In-Situ Observation of Hydrogen Spillover Using Electrochromism," The Journal of Physical Chemistry B. 107:4352-4355.
Park et al. (2008) "Theoretical and Experimental Studies of Bending of Inorganic Electronic Materials on Plastic Substrates," Adv. Funct. Mater. 18:2673-2684.
Park et al. (2009) "Biodegradable Luminescent Porous Silicon Nanoparticles for in Vivo Applications," Nature Mater. 8:331-336.
Patrick et al. (2011) "Corrosion of tungsten microelectrodes used in neural recording applications," Journal of Neuroscience Methods. 198(2)158-171.
Perry et al. (2008) "Nano- and Micropatterning of Optically Transparent, Mechanically Robust, Biocompatible Silk Fibroin Films," Adv. Mater. 20:3070-3072.
Petrova et al. (2011) "Mechanism of anodic oxidation of molybdenum in nearly-neutral electrolytes studied by electrochemical impedance spectroscopy and X-ray photoelectron spectroscopy," Electrochimica Acta. 56(23):7899-7906.
Peuster et al. (2003) "Biocompatibility of Corroding Tungsten Coils: In Vitro Assessment of Degradation Kinetics and Cytotoxicity on Human Cells," Biomaterials. 24:4057-4061.
Peuster et al. (2006) "Long-term biocompatibility of a corrodible peripheral iron stent in the porcine descending aorta," Biomaterials. 27(28):4955-4962.
Pham et al. (2012) "Fast phase reconstruction in white light diffraction phase microscopy," Appl. Opt. 52:A97-A101.
Popescu et al. (2006) "Diffraction phase microscopy for quantifying cell structure and dynamics," Optics Letters. 31:775-777.
Preechatiwong et al. (1996) "Electrical conductivity of poly(ethylene oxide)—alkali metal salt systems and effects of mixed salts and mixed molecular weights," Polymer 37:5109-5116.
Proteus® Digital Health (2014) "Digital Health Feedback System," Proteus® Digital Health Accessible on the Internet at URL: http://www.proteus.com/. [Last Accessed Nov. 5, 2014].
Reed et al. (Dec. 9, 2011) "Solubility of nano-zinc oxide in environmentally and biologically important matrices," Environ. Toxicol. Chem. 31:93-99.
Robinson (2009) "E-waste: An assessment of global production and environmental impacts," Science of The Total Environment. 408:183-191.
Rodriguez et al. (2007) "Dual-frequency resonance-tracking atomic force microscopy," Nanotechnology. 18:475-504.
Rutherglen (2010) "Polyanhydride Networks from Thiol-Ene Polymerizations," Macromolecules. 43:10297-10303.
Saad et al. (2008) "Characterization of various zinc oxide catalysts and their activity in the dehydration-dehydrogenation of isobutanol," J. Serb. Chem. Soc. 2008, 73, 997.
Samaniego et al. (Mar. 2013) "Combined effect of composition and surface condition on corrosion behaviour of magnesium alloys AZ31 and AZ61," Corrosion Science. 68:66-71.
Sammoura et al. (2004) "Water-activated disposable and long shelf life microbatteries," Sensors and Actuators A: Physical. 111:79-86.
Sancaktar et al. (2011) "Electrically Conductive Epoxy Adhesives," Polymers. 3:427-466.

Santamaria et al. (2007) "Initial surface film on magnesium metal: A characterization by X-ray photoelectron spectroscopy (XPS) and photocurrent spectroscopy (PCS)," Electrochimica Acta. 53(3):1314-1324.
Schluter et al. (2010) "Comparison of the corrosion behaviour of bulk and thin film magnesium alloys," Corrosion Science. 52(12):3973-3977.
Schwertmann (1991) "Solubility and dissolution of iron oxides," Plant and Soil. 130(1-2):1-25.
Seidel et al. (1990) "Anisotropic Etching of Crystalline Silicon in Alkaline Solutions," Electrochem. Soc. 137(11):3612-3626.
Seidel et al. (1990) "Anisotropic Etching of Crystalline Silicon in Alkaline Solutions II . Influence of Dopants," J. Electrochem. Soc. 137:3626-3632.
Shelanski et al. (1948) "Physiological Action OP Sodium Carboxymethyl-Cellulose on Laboratory Animals and Humans," Journal of Food Science. 13:29-35.
Sherif et al. (2010) "In situ Raman spectroscopy and electrochemical techniques for studying corrosion and corrosion inhibition of iron in sodium chloride solutions," Electrochimica Acta. 55(11):3657-3663.
Shimizu et al. (Jun. 2012) "Letter: Zinc Oxide Paste as Sunscreen in the Postoperative Period," Dermatologic Surgery. 38:965-966.
Shipp et al. (2009) "Elastomeric and degradable polyanhydride network polymers by step-growth thiol-ene photopolymerization," Chem. Commun. pp. 6415-6417.
Shpak et al. (2007) "XPS studies of active elements surface of gas sensors based on WO3-x nanoparticles," Journal of Electron Spectroscopy and Related Phenomena. 156:172-175.
Sofia et al. (2001) "Functionalized Silk-Based Biomaterials for Bone Formation," J. Biomed. Mater. Res. 54:139-148.
Song (2007) "Control of Biodegradation of Biocompatible Magnesium Alloys," Corrosion Science. 49:1696-1701.
Song et al. (2003) "Understanding Magnesium Corrosion—A Framework for Improved Alloy Performance," Advanced Engineering Materials. 5(12):837-858.
Song et al. (2009) "Mechanics of noncoplanar mesh design for stretchable electronic circuits," Journal of Applied Physics. 105:123516.
Spi©Supplies (2015) "Conductive (Silver) Expoxies," Structure Probe, Inc. Accessible on the Internet at URL: http://www.2spi.com/category/conductive-epoxies/. [Last Accessed Nov. 10, 2015].
Stefaniak (2010) "Persistence of tungsten oxide particle/fiber mixtures in artificial human lung fluids," Particle and Fibre Toxicology. 7:38.
Strigul (2010) "Does speciation matter for tungsten ecotoxicology?" Ecotoxicology and Environmental Safety. 73(6):1099-1113.
Sun et al. (2007) "Nano- to Microscale Porous Silicon as a Cell Interface for Bone-Tissue Engineering," Advanced Materials. 19(7):921-924.
Suzuki et al. (2000) "XPS study of oxides formed on the surface of high-purity iron exposed to air," Surface and Interface Analysis. 30(1):372-376.
Taheri et al. (Jun. 2012) "Analysis of the surface film formed on Mg by exposure to water using a FIB cross-section and STEM-EDS," Corrosion Science. 59:222-228.
Tamboli et al. (1999) "Studies of Passivation Behavior of Tungsten in Application to Chemical Mechanical Polishing," J. Vac. Sci. Technol. A-Vac. Surf. Films. 17(4):1168-1173.
Terazono et al. (2006) "Current status and research on E-waste issues in Asia," Journal of Material Cycles and Waste Management. 8:1-12.
Tie et al. (2010) "XPS Studies of Magnesium Surfaces after Exposure to Dulbecco's Modified Eagle Medium, Hank's Buffered Salt Solution, and Simulated Body Fluid," Advanced Engineering Materials. 12(12):B699-B704.
Trumbo et al. (2001) "Dietary Reference Intakes," Journal of the American Dietetic Association. 101(3):294-301.
Valtiner et al. (2008) "Stabilization and Acidic Dissolution Mechanism of Single-Crystalline ZnO(0001) Surfaces in Electrolytes Studied by In-Situ AFM Imaging and Ex-Situ LEED," Langmuir. 24:5350-5358.
van de Ven et al. (1991) "Photo-Assisted Etching of p-Type Semiconductors," J. Electrochem. Soc. 138(11):3401-3406.

(56) References Cited

OTHER PUBLICATIONS

Vuorilehto (2003) "An environmentally friendly water-activated manganese dioxide battery," J. Appl. Electrochem. 33:15-21.
Wales et al. (2003) "Stationary points and dynamics in high-dimensional systems," J. Chem. Phys. 119:12409.
Walker et al. (Feb. 14, 2012) "Magnesium alloys: Predicting in vivo corrosion with in vitro immersion testing," Journal of Biomedical Materials Research Part B: Applied Biomaterials. 1006(4)1134-1141.
Wang et al. (2009) "The nucleation and growth of metastable pitting on pure iron," Corrosion Science. 51(1):181-185.
Wang et al. (2011) "In vitro biodegradation behavior of magnesium and magnesium alloy," Journal of Biomedical Materials Research Part B: Applied Biomaterials. 98B(2):203-209.
Weber et al. (May 2012) "Temperature responsive bio-compatible polymers based on poly(ethylene oxide) and poly(2-oxazoline)s," Progress in Polymer Science. 37:686-714.
Wegner et al. (2006) "In situ formation and hydrolysis of Zn nanoparticles for H2 production by the 2-step ZnO/Zn water-splitting thermochemical cycle," International Journal of Hydrogen Energy. 31:55-61.
Widmer et al. (2005) "Global perspectives on e-waste," Environmental Impact Assessment Review. 25:436-458.
Wieczorek et al. (1998) "Effect of Salt Concentration on the Conductivity of PEO-Based Composite Polymeric Electrolytes," The Journal of Physical Chemistry B. 102:8725-8731.
Wilcock et al. (1997) "Development of a seawater battery for deep-water applications," J. Power Sources 66:71-75.
Witte (2010) "The History of Biodegradable Magnesium Implants," Acta. Biomater. 6:1680-1692.
Wu et al. (2010) "Surface microstructurization of a sputtered magnesium thin film via a solution—immersion route," Materials Letters. 64(3):475-478.
Xiang et al. (2007) "Printed circuit board recycling process and its environmental impact assessment," Int. J. Adv. Manuf. Technol. 34:1030-1036.
Xie et al. (2012) "XPS studies on surface reduction of tungsten oxide nanowire film by Ar+ bombardment," Journal of Electron Spectroscopy and Related Phenomena. 185(3-4):112-118.
Xu et al. (2012) "Birth outcomes related to informal e-waste recycling in Guiyu, China," Reproductive Toxicology. 33:94-98.
Yao et al. (2000) "An XPS investigation of the oxidation/corrosion of melt-spun Mg," Applied Surface Science. 158(1-2):112-119.
Yin (Mar. 20, 2014) "Materials, Designs, and Operational Characteristics for Fully Biodegradable Primary Batteries," Advanced Materials. 26(23):3879-3884.
Yin et al. (Sep. 25, 2013) "Dissolvable Metals for Transient Electronic," Adv. Funct. Mater. 24:645-658.
Youssef et al. (2004) "Improved corrosion behavior of nanocrystalline zinc produced by pulse-current electrodeposition," Corrosion Science. 46(1):51-64.
Zainal et al. (2011) "Corrosion of high purity Mg, AZ91, ZE41 and $Mg_2Zn_{0.2}Mn$ in Hank's solution at room temperature," Corrosion Science. 53(3):862-872.
Zeng et al. (2008) "Progress and Challenge for Magnesium Alloys as Biomaterials," Advanced Engineering Materials. 10(8):B3-B14.
Zhang (1996) *Corrosion and Electrochemistry of Zinc*. Plenum Press. New York, New York, pp. 1-474.
Zhang et al. (2010) "Fabrication and Comparative Study of Top-Gate and Bottom-Gate ZnO TFTs with Various Insulator Layers," J. Mater. Sci.: Mater. Electron. 21:671-675.
Zhao et al. (2004) "Piezoelectric Characterization of Individual Zinc Oxide Nanobelt Probed by Piezoresponse Force Microscope," Nano Lett. 4:587-590.
Zhao et al. (2009) "An exploratory study of the corrosion of Mg alloys during interrupted salt spray testing," Corrosion Science. 51(6):1277-1292.
Zheng et al. (2009) "In vitro and in vivo biocompatibility studies of ZnO nanoparticles," International Journal of Modern Physics B. 23:1566.
Zhou et al. (2006) "Dissolving Behavior and Stability of ZnO Wires in Biofluids: A Study on Biodegradability and Biocompatibility of ZnO Nanostructures," Advanced Materials. 18(18):2432-2435.
Zhu et al. (2009) "Biocompatibility of Pure Iron: In Vitro Assessment of Degradation Kinetics and Cytotoxicity on Endothelial Cells," Materials Science and Engineering C. 29:1589-1592.

\* cited by examiner

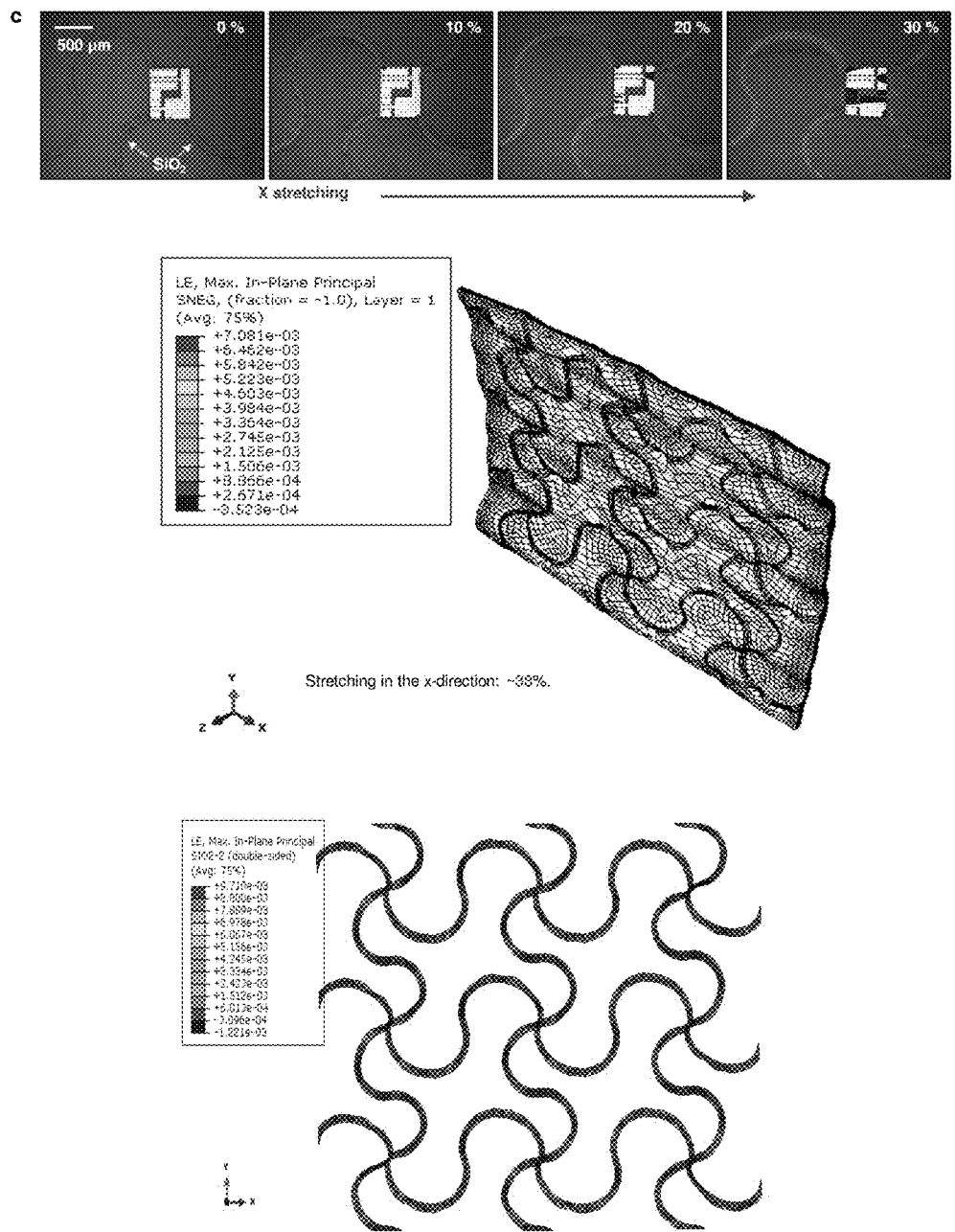
Figure 41 (con't)

Figure 41 (con't)

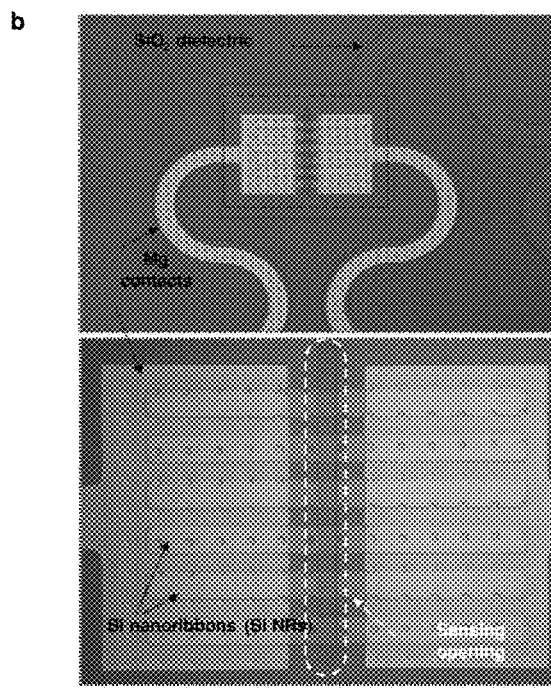
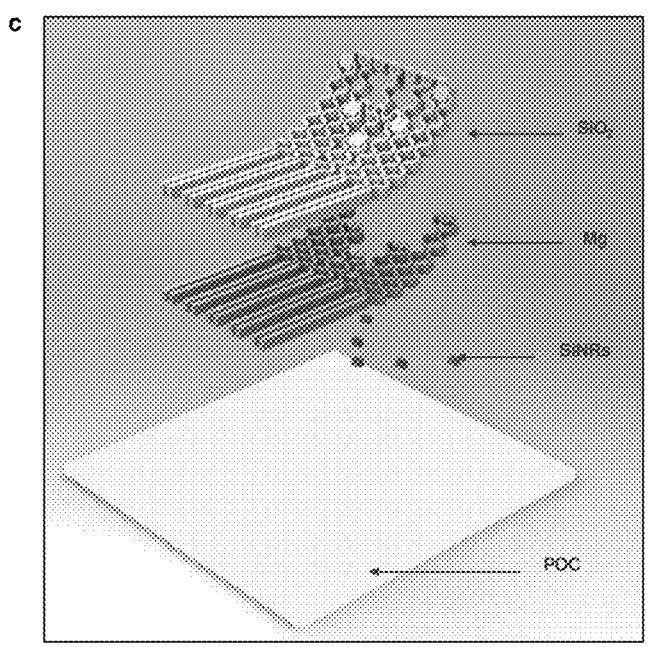
Figure 42 (con't)

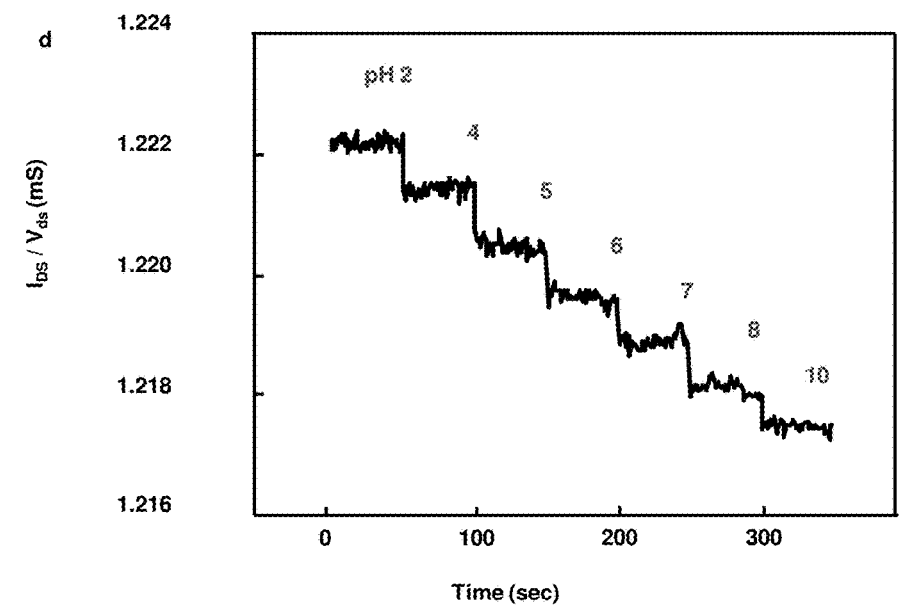
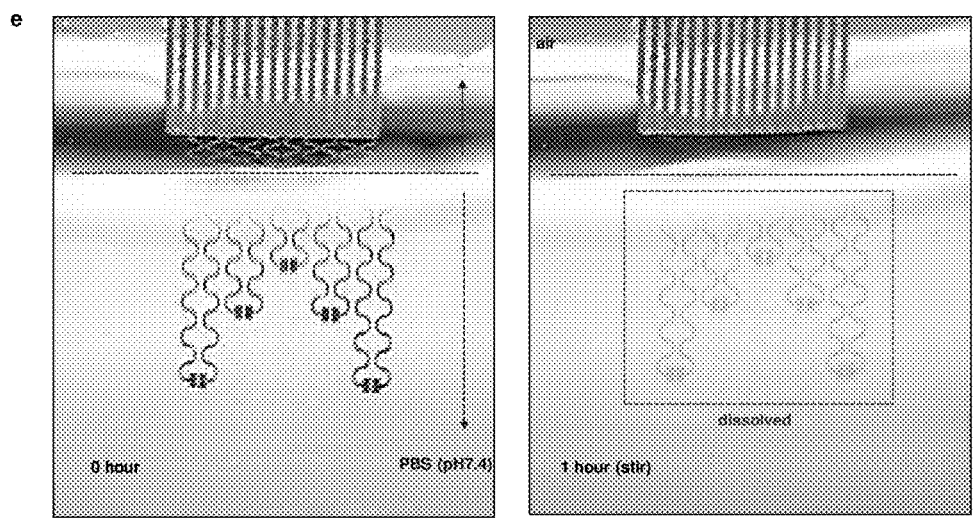
Figure 42 (con't)

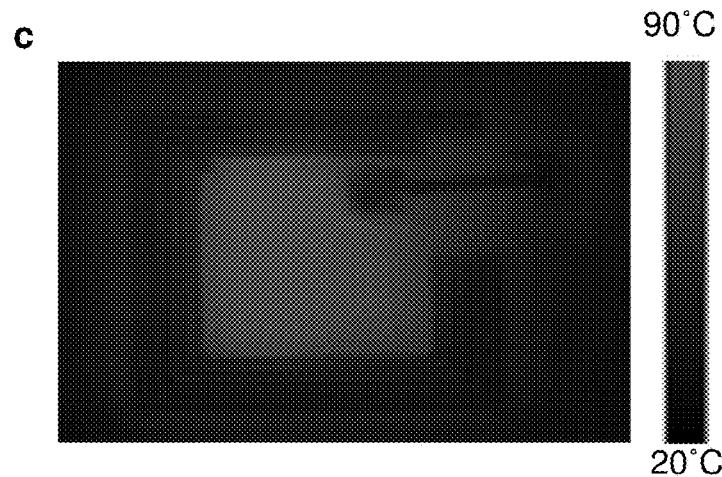
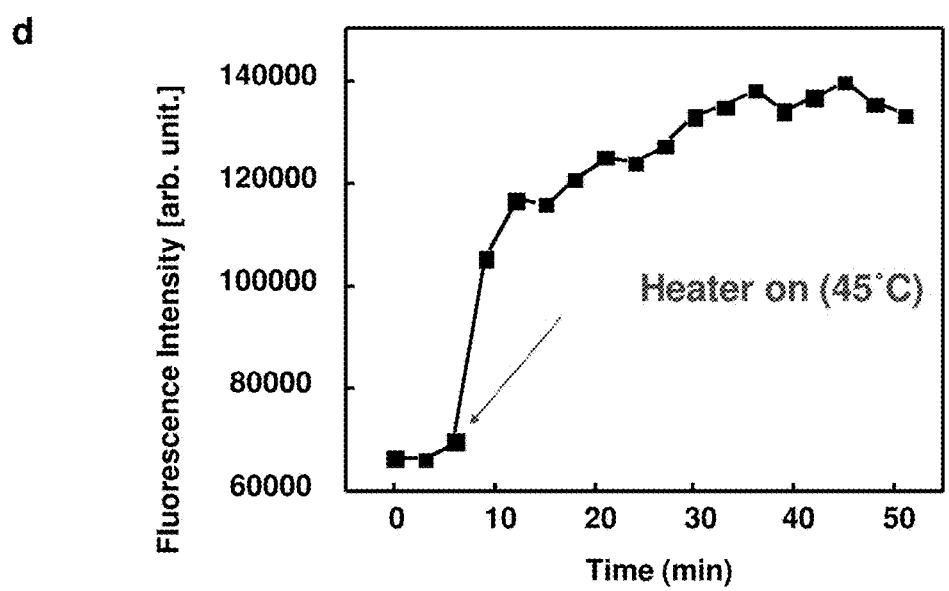
Figure 43 (con't)

*Molecular Weight: 90000*     *Molecular Weight:250000*     *Molecular Weight:700000*

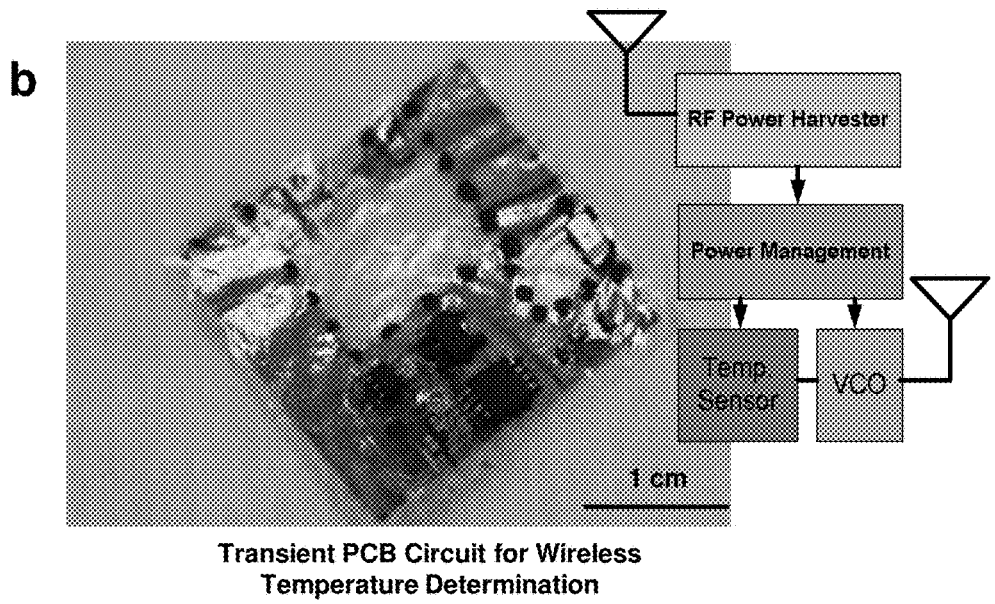
Transient PCB Circuit for Wireless Temperature Determination
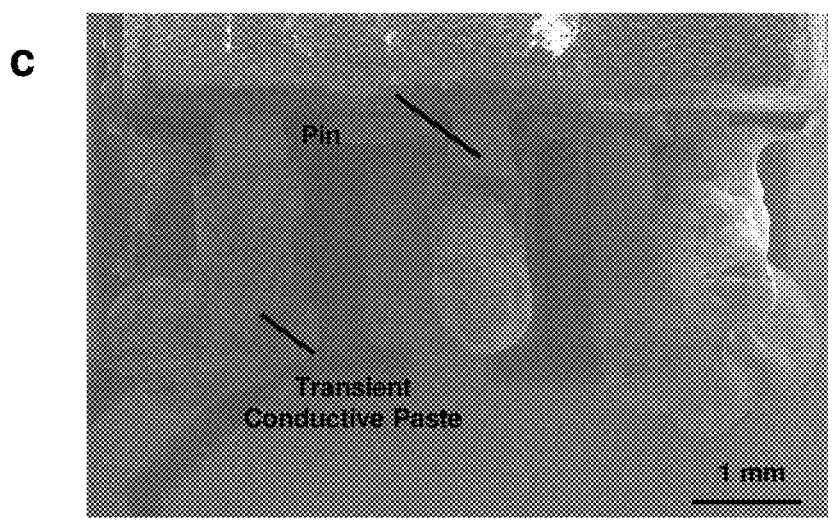
Pins with Conductive Paste on the Circuit
Figure 45 (con't)

Figure 45 (con't)

b
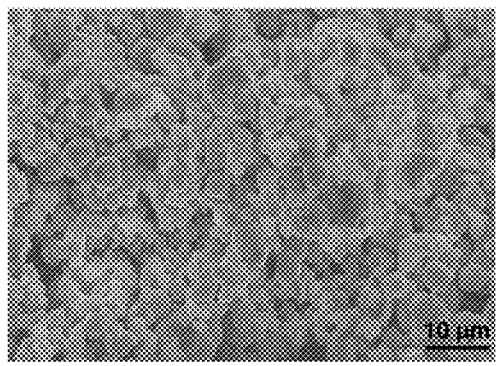
Cross-section view of Tungsten Paste
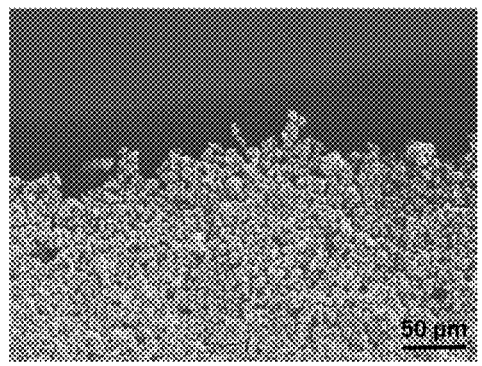
Top view of Tungsten Paste
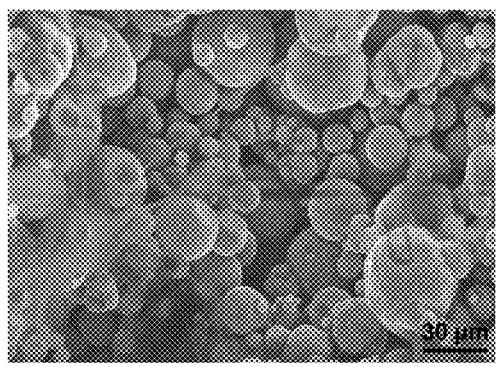
Cross-section view of Zinc Paste
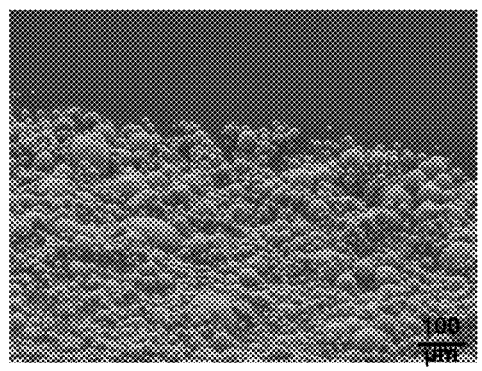
Top view of Zinc Paste
Figure 47 (con't)

d
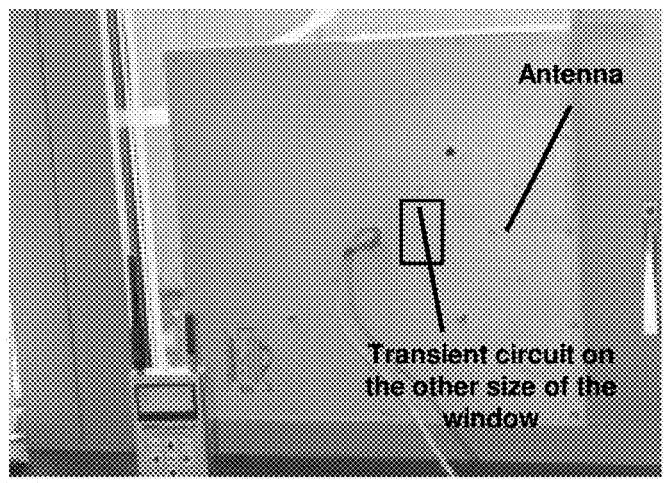
Wireless signal capture through a antenna
e
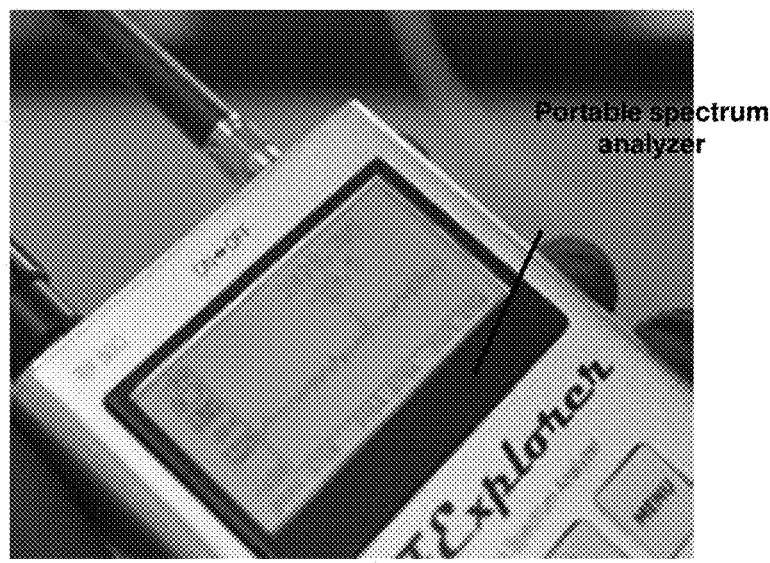
Wireless signal capture through a portable spectrum
analyzer (3 meter away from the transient circuit)
Figure 48 (con't)

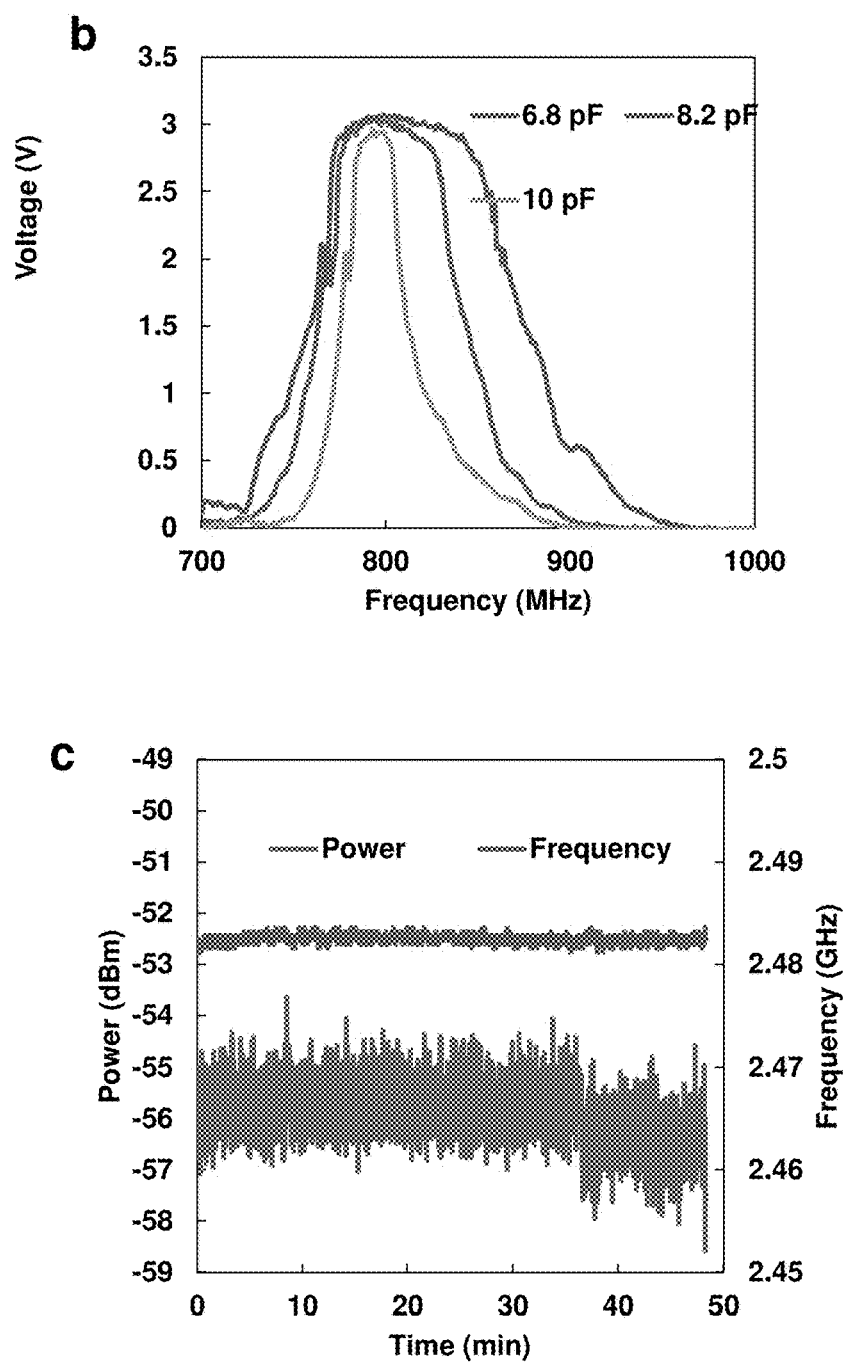
Figure 49 (con't)

BIODEGRADABLE MATERIALS FOR MULTILAYER TRANSIENT PRINTED CIRCUIT BOARDS

CROSS-REFERENCE TO RELATED APPLICATIONS

This application claims the benefit of priority of U.S. Provisional Application No. 62/034,443, filed Aug. 7, 2014, and is a continuation-in-part of U.S. application Ser. No. 14/251,259, filed Apr. 11, 2014, which claimed the benefit of priority of U.S. Provisional Application No. 61/811,603, filed Apr. 12, 2013, U.S. Provisional Application No. 61/828,935, filed on May 30, 2013, and U.S. Provisional Application No. 61/829,028, filed on May 30, 2013. Each of these applications is hereby incorporated by reference to the extent not inconsistent with the disclosure of this application.

STATEMENT REGARDING FEDERALLY SPONSORED RESEARCH OR DEVELOPMENT

This invention was made, at least in part, with United States governmental support awarded by the National Science Foundation award no. DMR-1242240. The United States Government has certain rights in this invention.

BACKGROUND OF INVENTION

This invention is in the field of transient devices, and relates generally to passive and active devices designed to programmably transform.

Transient devices have potential for a range of important applications. For example, eco-degradable environmental sensors avoid the need for device collection and bioresorbable medical devices that degrade and are cleared from the body avoid toxicity and inflammation. Strategically, military devices that degrade after a pre-selected time or upon application of a triggered stimulus avoid transferring knowledge or materials to enemies. As a common feature, these devices, and many others, may include printed circuit boards.

Printed circuit boards (PCBs) are essential components of nearly all forms of commercial electronics, where they provide mechanical supports and electrical interconnections for mounted components. Modern PCBs offer multilayer configurations, capable of high frequency signal conduction with minimal transmission loss, in addition to robust and reliable performance in various environmental conditions over extended periods of time. The constituent materials typically include metals such as gold, silver, palladium, tin, and copper, on substrates and interlayer dielectrics of fiber glass or polyimide, for rigid or flexible PCBs, respectively. These materials are designed explicitly for chemical stability and negligible degradation under long-term use.

Increasing demands for the latest technology generations together with an accelerated rate of obsolescence generates expanding volumes of electronic waste ($25 \times 10^6$ ton/year), the majority (82%) of which appears in landfills, where the circuits are slow to degrade due to designs that are optimized for robustness and survivability. Release of toxic materials such as lead, mercury, cadmium, polyvinyl chloride, and brominated flame retardants can pollute ground water and soil, with lasting and significant environmental effects that can adversely affect both physiological and psychological wellness. Recovering metals and plastics from PCBs involves chemical separation, burning, and mechanical shredding, each of which involves occupational and environmental hazards.

One potential route to reduce electronic waste streams is to build the electronics using materials that can naturally degrade into biologically and environmentally benign end products on timescales that exceed desired device lifetimes. Recently developed classes of 'transient' electronic components, such as transistors, mechanical energy harvesters, electrodes, and primary batteries as well as functional circuits for radio transmission and power harvesting offer these characteristics in systems that involve water soluble active and passive materials. Transient PCBs have not, however, been demonstrated.

Implementation of transient devices is dependent upon design strategies. Design strategies for transient devices may (i) support device fabrication using degradable device component materials and degradable substrates, (ii) provide for accurate control of the useful lifetime of the device, and (iii) utilize materials that are compatible with and perform adequately for a given application within a target environment.

Recently, a number of patents and publications have disclosed devices with transient properties. For example, Kim et al., "Silicon electronics on silk as a path to bioresorbable implantable devices", Appl. Phys. Lett. 95, 133701 (2009); U.S. Patent Application Publication 2011/0230747; and International Patent Application Publication WO 2008/085904 disclose biodegradable electronic devices that may include a biodegradable semiconducting material and a biodegradable substrate. Bettinger et al., "Organic thin film transistors fabricated on resorbable biomaterial substrates", Adv. Mater., 22(5), 651-655 (2010); Bettinger et al., "Biomaterial-based organic electronic devices", Poly. Int. 59(5), 563-576 (2010); and Irimai-Vladu, "Environmentally sustainable organic field effect transistors", Organic Electronics, 11, 1974-1990 (2010) disclose biodegradable electronic devices that may include a biodegradable organic conducting material and a biodegradable substrate. International Patent Application Publication WO 2008/108838 discloses biodegradable devices for delivering fluids and/or biological material to tissue. U.S. Patent Application Publication 2008/0306359 discloses ingestible devices for diagnostic and therapeutic applications. Kozicki et al., "Programmable metallization cell memory based on Ag—Ge—S and Cu—Ge—S solid electrolytes", NonVolatile Memory Technology Symposium, 83-89 (2005) discloses memory devices where metal ions within an electrolyte may be reduced or oxidized to form or remove solid metal interconnects.

SUMMARY OF THE INVENTION

The invention provides transient devices, including active and passive devices that physically, chemically and/or electrically transform upon application of at least one internal and/or external stimulus. Incorporation of degradable device components, degradable substrates and/or degradable encapsulating materials each having a programmable, controllable and/or selectable degradation rate provides a means of transforming the device. In some embodiments, for example, transient devices of the invention combine degradable high performance single crystalline inorganic materials with degradable substrates. Incorporation of degradable single crystalline inorganic materials provides state-of-the-art electronic and mechanical properties (e.g., bending stiffness, Young's modulus, radius of curvature, etc.) and device attributes (e.g., flexibility, stretchability, etc.).

A remarkable feature of modern silicon is its ability to remain functionally and physically invariant, almost indefinitely for many practical purposes. Here, a silicon-based technology that offers the opposite behavior is introduced: it gradually vanishes over time, in a well-controlled, programmed manner. Devices that are 'transient' in this sense create application possibilities that cannot be addressed with conventional electronics. The present devices may be used in applications such as active implants that exist for medically useful timeframes, but then completely dissolve and disappear via resorption by the body. A set of materials, manufacturing schemes, device components and theoretical design tools for complementary metal oxide semiconductor (CMOS) electronics of this type is reported, together with different classes of sensors and actuators in addressable arrays, options for power supply and a wireless control strategy. A transient silicon device capable of delivering thermal therapy in an implantable mode as a programmable, non-antibiotic bacteriocide, and its demonstration in vitro and in vivo illustrate a system-level example of this technology.

An overarching goal in the development of nearly any new class of electronics is to achieve high performance operation in physical forms that undergo negligible change with time. Active and passive materials, device and circuit layouts and packaging strategies are each carefully formulated individually and then configured collectively to accomplish this outcome. The transient electronics technology introduced here involves similar attention to engineering design, but in the context of systems that physically disappear or transform, in whole or in part, at prescribed times and with well-defined rates. Use scenarios range from integration with living hosts (human/animal/insect/plant; on-dwelling or in-dwelling) to indoor/outdoor environments such as buildings, roadways or materiel. Enabled devices include medical monitors that fully resorb when implanted into the human body ("bio-resorbable") to avoid adverse, long-term effects, or environmental monitors that dissolve when exposed to water ("eco-resorbable") to eliminate the need for collection and recovery. Other concepts involve circuits that incorporate strategic regions with timed transience, to affect controlled transformation in function.

This description presents a set of materials, modeling tools, manufacturing approaches, device designs and system level examples of transient electronics. Because this technology is based on silicon, it can exploit many modern, established aspects of device and circuit design, with operational characteristics that can match those of non-transient counterparts formed in the usual way on wafer substrates. This result, taken together with supporting technologies in sensors, actuators, power supply and wireless control, provides access to qualitatively more sophisticated capabilities than those available with recently reported forms of organic electronics in which certain constituent materials are water soluble[1-3] or simple non-transient transistors formed on bioresorbable substrates[4].

Provided herein are transient devices and methods of making and using transient devices. For example, devices of the invention are useful for ex vivo, in vitro or in vivo sensing of a parameter associated with an environment, such as a chemical composition (e.g., pH, ionic strength, presence or concentration of a biomarker, protein, carbohydrate, etc.), an electrochemical parameter (e.g., current or voltage), temperature, and/or an optical parameter (e.g., absorption, scattering, etc.). In other embodiments, devices provided herein include transient printed circuit boards that undergo one or more transformations that disable the device.

In an aspect, a transient printed circuit board (PCB) comprises a substrate and a plurality of electrical interconnects supported by the substrate, wherein at least a portion of the plurality of electrical interconnects comprises at least one pad for receiving a lead from an electronic component, and wherein at least one of the substrate and the plurality of electrical interconnects comprises a selectively transformable material.

In an aspect, a transient electronic device comprises a transient printed circuit board (PCB) comprising a substrate and a plurality of electrical interconnects supported by the substrate, wherein at least a portion of the plurality of electrical interconnects comprises at least one pad, and one or more electronic device components electrically connected to the at least one pad, wherein at least one of the substrate, the plurality of electrical interconnects and the one or more electronic device components comprises a selectively transformable material.

In an embodiment, the selectively transformable material undergoes a transformation upon application of an internal or external stimulus. For example, the transformation may be dissolution or biodegradation to benign end products. In an embodiment, the transformation may be a change from a first functionally operable state to a second functionally inoperable state. In an embodiment, a selectively transformable material undergoes a transformation at a preselected rate. For example, the selectively transformable material may be stable in the absence of an internal or external stimulus for a period of at least 5 days, or at least 3 days, or at least 1 day. In an embodiment, upon exposure to the internal or external stimulus the selectively transformable material may be completely transformed within a period of 5 days or less, or 3 days or less, or 1 day or less.

In an embodiment, a transient PCB may be a double-sided or multilayered PCB. For example, an adhesive layer may join the substrate of a first transient PCB with a substrate of a second transient PCB to form a double-sided transient PCB. In some embodiments, a second transient PCB is laminated to the first transient PCB to form the double-sided transient PCB. The double-sided transient PCB may comprise at least one via structure for electrically connecting the electrical interconnects of the first transient PCB with electrical interconnects of the second transient PCB. In some embodiments, a transient PCB may comprise a plurality of transient PCBs laminated together in a multilayer stacked geometry, optionally with vias connecting different layers of the multilayer stack.

In an embodiment, the transient PCB has an average thickness selected from the range of 1 cm to 5 μm, or 0.5 cm to 10 μm, or 300 μm to 50 μm. In an embodiment, the transient PCB has an average modulus selected from the range of 3 KPa to 10 GPa, or 50 KPa to 5 GPa, or 100 KPa to 1 GPa. In an embodiment, the transient PCB has a net bending stiffness selected from the range of 0.1 nN m to 1 nN m, or 0.2 nN m to 0.8 nN m, or 0.25 nN m to 0.5 nN m.

In some embodiments, one or more electronic components may be mounted on a transient PCB. For example, an electronic component may be selected from the group consisting of a resistor, a capacitor, a diode, an inductor, a sensor, an actuator, an antenna, a coil or an electromagnetic shielding layer. In some embodiments, the electronic component may be an energy harvesting structure, a near-field communication (NFC) device, a radio-frequency identification (RFID) device, an energy storage device, a chemical/biological sensor, a photosensitive element or a combination thereof. Any one of these components may be a commercial off the shelf (COTS) component. In some embodiments, the electronic component is formed by screen printing a conductive paste. In some embodiments, the electronic component comprises a selectively transformable material.

In some embodiments, a transient PCB may comprise an actuator responsive to a user initiated external trigger signal; wherein upon a receiver of the transient PCB receiving the external trigger signal the actuator, which is operationally connected to the receiver, directly or indirectly initiates at least partial transformation of the selectively transformable material, thereby providing a programmable transformation of the transient PCB in response to the external trigger signal, wherein the programmable transformation provides a change in function of the transient PCB from a first condition to a second condition. In some embodiments, the user initiated external trigger signal is a user initiated application of an electric field provided to the transient PCB, a user initiated application of electromagnetic radiation provided to the transient PCB, a user initiated mechanical impact provided to the transient PCB, a user initiated flow of heat provided to the transient PCB, a user initiated flow of heat from the transient PCB or a user initiated application of an RF electric field provided to the transient PCB. In some embodiments, an electronic device is in one-way or two-way communication with a transmitter, wherein the transmitter provides the user initiated external trigger signal to the receiver of the transient PCB operationally connected to the actuator.

In some embodiments, at least a portion of a plurality of electrical interconnects of a transient PCB is formed by a conductive paste. For example, at least a portion of the plurality of electrical interconnects may be formed by screen printing a conductive paste. In an embodiment, a via structure may be filled with a conductive paste.

In some embodiments, a conductive paste is a composite material. For example, the composite material may comprise a water-soluble transient polymer and transient metal particles. In some embodiments, the water-soluble transient polymer and the transient metal particles may be present in a ratio between 1:1000 and 1000:1. In some embodiments, transient metal particles may have an average diameter selected from 10 nm to 100 µm. In some embodiments, the transient metal particles have a bimodal distribution of particle sizes. In some embodiments, transient metal particles are tungsten particles or zinc particles. In some embodiments, the transient metal particles are substantially spherical, substantially polyhedral or a combination thereof. Typically, the conductive paste comprises a conductivity between $5 \times 10^7$ S/m and 0.1 S/m, or $5 \times 10^6$ S/m and 1 S/m, or $5 \times 10^5$ S/m and 10 S/m. In some embodiments, the conductive paste has a net bending stiffness of 0.1 nN m to 1 N m, or 0.2 nN m to 0.8 nN m, or 0.25 nN m to 0.5 nN m.

In some embodiments, a substrate of a transient PCB is a flexible substrate or a stretchable substrate. For example, the substrate may have a net bending stiffness of 0.1 nN m to 1 N m, or 0.2 nN m to 0.8 nN m, or 0.25 nN m to 0.5 nN m. In some embodiments, a substrate is an insulator. For example, the substrate may comprise sodium carboxymethyl cellulose (Na-CMC), poly(ethylene) oxide (PEO), polylactic acid (PLA), polyglycolic acid (PGA), polylactic-co-glycolic acid (PLGA) or combinations thereof. In some embodiments, the substrate has an average thickness selected from a range of 1 cm to 5 µm, or 0.5 cm to 10 µm, or 300 µm to 50 µm. In some embodiments, the substrate is biodegradable, water soluble, ecocompatible or a combination thereof.

In an embodiment, the electrical interconnects of a transient PCB comprise magnesium, tungsten, zinc, iron, molybdenum or an alloy thereof. In some embodiments, electrical interconnects comprise one or more solidified metal thin film structures. In some embodiments, electrical interconnects are formed by screen printing or by metallization and screen printing.

In some embodiments, one or more encapsulating layers at least partially encapsulates one or more electrical interconnects. For example, the encapsulating material may comprise a material selected from the group consisting of MgO, silk, collagen, gelatin, PLGA, polyvinylalcohol (PVA), PLA, Si, $SiO_2$, polyanhydrides (polyesters), polyhydroxyalkanates (PHAs) and polyphosphates.

In some embodiments, each of the pads of the electrical interconnects has an average area of 10 µm² to 5 mm², or 50 µm² to 4 mm², or 100 µm² to 3 mm², or 1 mm² to 2.5 mm².

In an aspect, a method of using a transient PCB comprises: providing the transient PCB comprising: a substrate; and a plurality of electrical interconnects supported by the substrate; wherein at least a portion of the plurality of electrical interconnects comprises at least one pad for receiving a lead from an electronic component; wherein at least one of the substrate and the plurality of electrical interconnects comprises a selectively transformable material; and exposing the transient PCB to an internal or external stimulus, thereby programmably transforming the transient PCB.

In an aspect, a method of making a transient printed circuit board (PCB) comprises: providing a substrate; and generating a plurality of electrical interconnects supported by the substrate; wherein at least a portion of the plurality of electrical interconnects comprises at least one pad for receiving a lead from an electronic component; wherein at least one of the substrate and the plurality of electrical interconnects comprises a selectively transformable material.

In some embodiments, the step of generating a plurality of electrical interconnects comprises chemical vapor deposition, physical vapor deposition, electron beam epitaxy, sputtering, screen printing, lithography, atomic layer deposition, molecular beam epitaxy, pulsed laser deposition, metal-organic vapor phase epitaxy, ink jet printing, electrohydrodynamic printing, soft lithography, transfer printing and any combination of these. In some embodiments, the step of generating a plurality of electrical interconnects comprises screen printing.

In some embodiments, a method of making a transient PCB further comprises a step of electrically connecting an electronic device component to the at least one pad of the electrical interconnect. For example, the step of electrically connecting may comprise bonding the electronic device component to the at least one pad with conductive paste.

In some embodiments, a method of making a transient PCB further comprises providing at least one additional transient PCB and laminating the first transient PCB to the at least one additional transient PCB.

In an aspect, a transient electronic device comprises a substrate; and one or more active or passive electronic device components supported by the substrate, wherein the one or more active or passive electronic device components independently comprise a selectively transformable material; wherein at least partial transformation of the one or more active or passive electronic device components provides a programmable transformation of the transient electronic device in response to an external or internal stimulus and at a pre-selected time or at a pre-selected rate, wherein the programmable transformation provides a change in function of the transient electronic device from a first condition to a second condition; wherein the one or more active or passive electronic device components are independently characterized by an electrical dissolution rate (EDR) higher than a corrosion rate of the selectively transformable material, and wherein the EDR is selected to provide a pre-selected transience profile in response to the external or internal stimulus. In an embodiment, for example, the one or more active or passive electronic device components comprise one or more inorganic semiconductor components, one or more metallic conductor components or one or more inorganic semiconductor components and one or more metallic conductor components.

In an embodiment, the electrical dissolution rate (EDR) of the one or more active or passive electronic device components is selected from the range of 0.1 nm/day to 10 µm/s. In an embodiment, the electrical dissolution rate (EDR) of the one or more active or passive electronic device components is selected from the range of 0.01 nm/day to 100 µm/s, or selected from the range of 0.05 nm/day to 50 µm/s, or selected from the range of 0.07 nm/day to 20 µm/hr, or selected from the range of 0.1 nm/day to 10 µm/hr. In an embodiment, the one or more metallic conductor components is individually selected from Mg, Mg alloy and Zn, and the EDR is selected from the range of 0.5-3 µm/hour. In an embodiment, the one or more metallic conductor components is individually selected from W, Mo and Fe, and the EDR is selected from the range of $10^{-4}$-0.02 µm/hour. In an embodiment, the EDR of the one or more active or passive electronic device components is higher than the corrosion rate of the one or more active or passive electronic device components. In an embodiment, the EDR of the one or more active or passive electronic device components is at least 10 times higher than the corrosion rate of the one or more active or passive electronic device components. In an embodiment, the EDR of the one or more active or passive electronic device components is at least 2 times faster than the rate of change in thickness of the one or more active or passive electronic device components. In an embodiment, the EDR is dependent upon a deposition technique for forming the one or more inorganic semiconductor components or the one or more metallic conductor components. For example, the deposition technique may be selected from the group consisting of physical vapor deposition, chemical vapor deposition, sputtering, epitaxial growth, atomic layer deposition, electrochemical deposition, and molecular beam epitaxy.

In an embodiment, one or more of the one or more active or passive electronic device components, such as the one or more inorganic semiconductor components or one or more of the metallic conductor components, has a pre-transformation density selected from the range of 0.1 g/cm$^3$ to 25 g/cm$^3$, or selected from the range of 0.5 g/cm$^3$ to 15 g/cm$^3$, or selected from the range of 1 g/cm$^3$ to 10 g/cm$^3$. In an embodiment, one or more of the one or more active or passive electronic device components, such as one or more inorganic semiconductor components or one or more of the metallic conductor components, has a pre-transformation porosity selected from the range of 0.01% to 99.9%, or selected from the range of 1% to 90%, or selected from the range of 5% to 80%, or selected from the range of 10% to 60%, or selected from the range of 15% to 40%. In an embodiment, one or more of the one or more active or passive electronic device components, such as one or more inorganic semiconductor components or one or more of the metallic conductor components, has a pre-transformation degree of crystallinity selected from the range of 0.01% to 99.9%, or selected from the range of 1% to 90%, or selected from the range of 5% to 80%, or selected from the range of 10% to 60%, or selected from the range of 15% to 40%. In an embodiment, one or more of the one or more active or passive electronic device components, such as one or more inorganic semiconductor components or one or more of the metallic conductor components, has a pre-transformation dopant concentration selected from the range of $10^{10}$/cm$^3$ to $10^{25}$/cm$^3$, or selected from the range of $10^{12}$/cm$^3$ to $10^{20}$/cm$^3$, or selected from the range of $10^{14}$/cm$^3$ to $10^{18}$/cm$^3$.

In an embodiment, one or more active or passive electronic device components, such as one or more inorganic semiconductor components or one or more of the metallic conductor components, is deposited by a deposition technique at a rate selected from the range of 0.01 nm/s to 100,000 nm/s, or selected from the range of 1 nm/s to 10,000 nm/s, or selected from the range of 10 nm/s to 1,000 nm/s. For example, the deposition technique may be selected from the group consisting of physical vapor deposition, chemical vapor deposition, sputtering, epitaxial growth, atomic layer deposition, electrochemical deposition, molecular beam epitaxy, pulsed laser deposition, and metal-organic vapor phase epitaxy.

In an embodiment, the one or more metallic conductor components independently comprise Mg, Zn, W, Mo or an alloy thereof. In an embodiment, the one or more metallic conductor components independently comprise an alloy of Mg with one or more additional materials selected from the group consisting of Al, Ag, Ca, Li, Mn, Si, Sn, Y, Zn, and Zr, wherein the one or more additional materials of the alloy has a concentration equal to or less than 10% by weight.

In an embodiment, the substrate comprises a selectively transformable material.

In an embodiment, the device further comprises one or more dielectric components supported by the substrate, wherein the one or more dielectric components comprise a selectively transformable material. In an embodiment, each of the one or more dielectric components comprises one or more thin film structures. In an embodiment, each of the one or more dielectric components has a thickness selected over the range of 1 nm to 100 µm, or 10 nm to 50 µm. In an embodiment, the one or more dielectric components comprise one or more materials selected from the group consisting of Si, SiO$_2$, MgO, silk, collagen, gelatin, PVA and PLGA.

In an embodiment, the device further comprises an encapsulating material at least partially encapsulating one or more active or passive electronic device components, such as one or more inorganic semiconductor components or one or more of the metallic conductor components, wherein the encapsulating material comprises a selectively transformable material that is at least partially removed in response to the external or internal stimulus to expose underlying active or passive electronic device components, such as inorganic semiconductor components or metallic conductor components. In an embodiment, the encapsulating material comprises a material selected from the group consisting of MgO, silk, collagen, gelatin, PLGA, polyvinylalcohol (PVA), PLA, Si, SiO$_2$, polyanhydrides (polyesters), polyhdroxyalkanates (PHAs) and polyphosphates.

In an embodiment, the one or more active or passive electronic device components, such as the one or more inorganic semiconductor components or the one or more metallic conductor components, independently comprise one or more thin film structures. In an embodiment, the one or more active or passive electronic device components, such as the one or more inorganic semiconductor components or the one or more metallic conductor components, each independently have a thickness selected over the range of 1 nm to 100 µm, or 10 nm to 100 µm. In an embodiment, each of the one or more inorganic semiconductor components independently comprises Si, Ga, GaAs, ZnO or any combination of these.

In an embodiment, the transient electronic device is a communication system, a photonic device, a sensor, an optoelectronic device, a biomedical device, a temperature sensor, a photodetector, a photovoltaic device, a strain gauge, an imaging system, a wireless transmitter, an antenna, a battery, a nanoelectromechanical system or a microelectromechanical system.

In an embodiment, the device further comprises a reservoir of chemical reagents that react to produce a volume of gas, wherein the volume of gas increases pressure within at least a portion of the reservoir until mechanical failure of the portion of the reservoir is achieved. In an embodiment, the mechanical failure of the portion of the reservoir exposes the one or more active or passive electronic device components, such as the one or more inorganic semiconductor components or the one or more metallic conductor components, to a chemical agent. In an embodiment, the chemical agent is selected from the group consisting of water, a nonaqueous solvent, an aqueous solution, an acid, a base, an etchant, oxygen, and combinations thereof. In an embodiment, the gas is selected from the group consisting of $H_2$, $O_2$, $N_2$, CO, $CO_2$, $XeF_2$, $SF_6$, $CHF_3$, $CF_4$, and combihations thereof. In an embodiment, the chemical reagents react in an electrochemical reaction or an electrolysis reaction.

In an embodiment, the device further comprises an actuator responsive to a user initiated external trigger signal and operably connected to the one or more active or passive electronic device components, such as the one or more inorganic semiconductor components or the one or more metallic conductor components, wherein upon the device receiving the external trigger signal the actuator directly or indirectly initiates at least partial transformation of the one or more active or passive electronic device components, such as the one or more inorganic semiconductor components or the one or more metallic conductor components, in response to the internal or external stimulus, thereby providing a programmable transformation of the transient electronic device in response to the external trigger signal, wherein the programmable transformation provides a change in function of the transient electronic device from a first condition to a second condition.

In an embodiment, upon the device receiving the user initiated external trigger signal, the actuator disperses chemical reagents into a reservoir, wherein the chemical reagents react to produce a volume of gas, wherein the volume of gas increases pressure within at least a portion of the reservoir until mechanical failure of the portion of the reservoir is achieved. For example, the mechanical failure of the portion of the reservoir may expose the one or more active or passive electronic device components, such as the one or more inorganic semiconductor components or the one or more metallic conductor components, to a chemical agent. In an embodiment, the chemical agent is selected from the group consisting of water, a nonaqueous solvent, an aqueous solution, an acid, a base, an etchant, oxygen, and combinations thereof. In an embodiment, the gas is selected from the group consisting of $H_2$, $O_2$, $N_2$, CO, $CO_2$, $XeF_2$, $SF_6$, $CHF_3$, $CF_4$, and combinations thereof. In an embodiment, the chemical reagents react in an electrochemical reaction or an electrolysis reaction.

In an aspect, a method of using a transient electronic device comprises the steps of: providing the transient electronic device comprising: a substrate; one or more active or passive electronic device components supported by the substrate, wherein the one or more active or passive electronic device components independently comprise a selectively transformable material; wherein at least partial transformation of the one or more active or passive electronic device components provides a programmable transformation of the transient electronic device in response to an external or internal stimulus and at a pre-selected time or at a pre-selected rate; wherein the programmable transformation provides a change in function of the transient electronic device from a first condition to a second condition; wherein the one or more active or passive electronic device components are independently characterized by an electrical dissolution rate (EDR) higher than a corrosion rate of the selectively transformable material, and wherein the EDR is selected to provide a pre-selected transience profile in response to the external or internal stimulus; and exposing the transient electronic device to the external or internal stimulus, thereby programmably transforming the transient electronic device. In an embodiment, for example, the one or more active or passive electronic device components comprise one or more inorganic semiconductor components, one or more metallic conductor components or one or more inorganic semiconductor components and one or more metallic conductor components.

In an embodiment, a method of using a transient electronic device further comprises steps of: providing an actuator responsive to a user initiated external trigger signal and operably connected to the one or more active or passive electronic device components, such as the one or more inorganic semiconductor components or the one or more metallic conductor components, wherein upon the device receiving the external trigger signal the actuator directly or indirectly initiates at least partial transformation of the one or more active or passive electronic device components, such as the one or more inorganic semiconductor components or the one or more metallic conductor components, in response to the internal or external stimulus, thereby providing a programmable transformation of the transient electronic device in response to the external trigger signal, wherein the programmable transformation provides a change of the function of the transient electronic device from a first condition to a second condition; and providing the user initiated external trigger signal to the electronic device, wherein the actuator directly or indirectly initiates at least partial transformation of the one or more active or passive electronic device components, such as the one or more inorganic semiconductor components or the one or more metallic conductor components, thereby providing the programmable transformation.

In an aspect, a method of making a transient electronic device comprises the steps of: providing a device substrate; providing on the device substrate one or more active or passive electronic device components, wherein the one or more active or passive electronic device components independently comprise a selectively transformable material; wherein at least partial transformation of the one or more active or passive electronic device components provides a programmable transformation of the transient electronic device in response to an external or internal stimulus and at a pre-selected time or at a pre-selected rate, wherein the programmable transformation provides a change in function of the transient electronic device from a first condition to a second condition; wherein the one or more active or passive electronic device components are independently characterized by an electrical dissolution rate (EDR) higher than a corrosion rate of the selectively transformable material, and wherein the EDR is selected to provide a pre-selected transience profile in response to the external or internal stimulus; thereby generating the transient electronic device.

In an embodiment, a method of making a transient electronic device further comprises the steps of determining the EDR providing the pre-selected transience profile and selecting the composition and physical dimensions of the one or more active or passive electronic device components, such as the one or more inorganic semiconductor components or the one or more metallic conductor components, to provide the EDR.

In an embodiment, a method of making a transient electronic device further comprises the step of selecting a thickness of the one or more active or passive electronic device components, such as the one or more inorganic semiconductor components or the one or more metallic conductor components, to provide the EDR.

In an embodiment, a method of making a transient electronic device further comprises the step of selecting a morphology of the one or more active or passive electronic device components, such as the one or more inorganic semiconductor components or the one or more metallic conductor components, to provide the EDR.

In an embodiment, a method of making a transient electronic device further comprises the step of selecting a physical state of the one or more active or passive electronic device components, such as the one or more inorganic semiconductor components or the one or more metallic conductor components, to provide the EDR.

In an aspect, the invention provides a transient electrochemical device comprising: (i) an anode; (ii) a cathode; (iii) an electrolyte provided between the anode and cathode, the electrolyte capable of conducting charge carriers (e.g., between the anode and the cathode); and a packaging component at least partially enclosing the anode, cathode and the electrolyte; wherein at least one of the anode, the cathode, the electrolyte and the packaging component independently comprises a selectively transformable material; wherein at least partial transformation of at least one of the anode, the cathode, the electrolyte and the packaging component provides a programmable transformation of the transient electrochemical device in response to an external or internal stimulus. In an embodiment, for example, the programmable transformation is characterized by a pre-selected time or at a pre-selected rate and/or the selectively transformable material is characterized by a selected transience profile.

In an embodiment, each of the anode, the cathode, the electrolyte and the packaging component independently comprise a selectively transformable material, for example, a transient metal or semiconducting film, a metal foil, a polymer layer, etc. In an embodiment, for example, each of the anode, the cathode, the electrolyte and the packaging component independently comprise a biocompatible, bioresorbable, bioinert or ecocompatible material. In an embodiment, the electrochemical device comprises an entirely transient device wherein the programable transformation comprises degradation of each of the anode, the cathode, the electrolyte and the packaging component.

In an embodiment, for example, the electrolyte is provided in physical contact with the cathode, the anode or both, thereby providing the external or internal stimulus providing for at least partial transformation of the cathode, the anode or both. In an embodiment, for example, the electrochemical device further comprises at least one shutter separating the electrolyte from the cathode, anode or both, the at least one shutter allowing for selective modulation of physical contact of the electrolyte with the cathode, the anode or both, thereby providing the external or internal stimulus providing for at least partial transformation of the cathode, the anode or both. In an embodiment, for example, at least partial transformation of the cathode, the anode or both occurs via hydrolysis, disintegration, dissolution or corrosion. In an embodiment, for example, exposure to an external solvent is the external or internal stimulus providing for at least partial transformation of the cathode, the anode or both.

In an embodiment, the anode comprises a first selectively transformable material and the cathode comprises a second selectively transformable material different from the first selectively transformable material. In an embodiment, for example, the first selectively transformable material of the anode comprises Mg or Zn and the second selectively transformable material of the cathode is selected from the group consisting of Fe, W, Zn, Mo and any alloys or combinations thereof. In an embodiment, for example, the anode, the cathode or both are independently a selectively transformable material comprising a metal foil or a metal or semiconducting thin film having a thickness selected from the range of 0.5 µm to 1 cm. In an embodiment, for example, the anode, the cathode or both are independently a selectively transformable material comprising particles having cross sectional dimensions selected over the range of 0.1 µm to 100 µm. In an embodiment, for example, the anode, cathode or both is independently a microstructured or nanostructured material.

In an embodiment, the electrolyte comprises an aqueous electrolyte or nonaqueous electrolyte. In an embodiment, for example, the electrolyte comprises a phosphate buffered saline solution. In an embodiment, for example, the electrochemical device further comprises a fluid containment chamber at least partially enclosing the anode, the cathode, and the electrolyte, optionally wherein the fluid containment chamber independently comprises a selectively transformable material. In an embodiment, for example, the fluid containment chamber comprises an elastomer, such as PDMS. In an embodiment, for example, the packaging component comprises a biodegradable polymer. In an embodiment, for example, the packaging component comprises polyanhydride.

In an embodiment, for example, the electrochemical device provides a discharge current density greater than or equal to 100 $\mu A/cm^2$. In an embodiment, for example, the electrochemical device provides a voltage between 0.1 V and 50 V. In an embodiment, for example, the device provides power selected from the range of 1 $mW/cm^2$ to 100 $mW/cm^2$.

In an embodiment, for example, the electrochemical device comprises an electrochemical storage device or electrochemical conversion device. In an embodiment, for example, the electrochemical device comprises a primary battery, a secondary battery, an electrochemical capacitor, an electrochemical supercapacitor or a fuel cell. In an embodiment, for example, the electrochemical device further comprises one or more additional transient electrochemical devices electronically connected to the transient electrochemical device; wherein each of the additional transient electrochemical devices independently comprises: (i) an anode (ii) a cathode; (iii) an electrolyte provided between the anode and cathode, the electrolyte capable of conducting charge carriers (e.g., between the anode and the cathode); and (iv) a packaging component at least partially enclosing the anode, cathode and the electrolyte; wherein at least one of the anode, the cathode, the electrolyte and the packaging component independently comprises a selectively transformable material; wherein at least partial transformation of at least one of the anode, the cathode, the electrolyte and the packaging component provides a programmable transformation of the additional electrochemical device in response to an external or internal stimulus. In an embodiment, for example, the additional electrochemical devices electronically connected in series or parallel to the electrochemical device. In an embodiment, the electrochemical device of the invention comprises a battery pack. In an aspect, a battery system comprises a plurality of transient primary batteries electrically connected in series or parallel.

In another aspect, the invention provides a transient stretchable electronic device comprising: (i) a substrate; (ii) one or more active or passive electronic device components supported by the substrate; (iii) one or more stretchable interconnects electrically connected to the one or more active or passive electronic device components; wherein at least one of the substrate, the one or more active or passive electronic device components and one or more stretchable interconnects independently comprise a selectively transformable material; wherein at least partial transformation of at least one of the substrate, the one or more active or passive electronic device components and one or more stretchable interconnects provides a programmable transformation of the transient stretchable electronic device in response to an external or internal stimulus.

In another aspect, the invention provides a transient printed circuit board comprising: (i) a substrate; (ii) one or more active or passive electronic device components supported by the substrate; (iii) one or more via or trench structures electrically connected to the one or more active or passive electronic device components; wherein at least one of the substrate, the one or more active or passive electronic device components and the one or more via or trench structures independently comprise a selectively transformable material; wherein at least partial transformation of at least one of the substrate, the one or more active or passive electronic device components and one or more via or trench structures provides a programmable transformation of the transient printed circuit board in response to an external or internal stimulus.

In another aspect, the invention provides a transient biomedical delivery device comprising: (i) a substrate; (ii) a heater supported by the substrate; and (iii) a delivery system containing one or more therapeutic or diagnostic agents, the delivery system in thermal contact with the heater so as to provide release of the one or more therapeutic or diagnostic agents in response to an change in temperature; wherein at least one of the substrate, the heater and the delivery system independently comprise a selectively transformable material; and wherein at least partial transformation of at least one of the substrate, the heater and the delivery system provides a programmable transformation of the transient biomedical delivery device in response to an external or internal stimulus.

In another aspect, the invention provides a transient radio frequency identification (RFID) device comprising: (i) a substrate; (ii) a RFID integrated circuit supported by the substrate; (iii) a RFID antenna supported by the substrate; and (iv) one or more electrical interconnects electrically connecting the an RFID integrated circuit and the RFID antenna; wherein at least one of the substrate, the RFID integrated circuit, the RFID antenna and the one or more electrical interconnects independently comprise a selectively transformable material; wherein at least partial transformation of at least one of the substrate, the RFID integrated circuit, the RFID antenna and the one or more electrical interconnects provides a programmable transformation of the transient radio frequency identification (RFID) device in response to an external or internal stimulus.

In another aspect, the invention provides a transient electronic device comprising: (i) a substrate; (ii) one or more active or passive electronic device components supported by the substrate, wherein the one or more active or passive electronic device components independently comprise a selectively transformable material; (iii) one or more reservoirs independently containing one or more chemical agents; and (iv) a heater in thermal contact with the one or more chambers; wherein at least partial transformation of the one or more active or passive electronic device components provides a programmable transformation of the transient electronic device in response to an change in temperature of the one or more reservoirs generated by the heater, wherein the programmable transformation provides a change in function of the transient electronic device from a first condition to a second condition. In an embodiment, for example, the heater is configured to provide an increase in the temperature of the one or more reservoirs, for example, an increase in temperature selected from the range of 0.1° C. to 50° C., and optionally for some applications selected from the range of 0.1° C. to 20° C. and optionally for some applications selected from the range of 0.1° C. to 10° C.

In an embodiment, for example, the change in temperature results in release of the one or more chemical agents in the one or more reservoirs. In an embodiment, for example, the change in temperature causes an increase of pressure in the one or more reservoirs. In an embodiment, for example, the increase of pressure in the one or more reservoirs is cause by an expansion, chemical reaction, electrolysis, or a phase change of the one or more chemical agents in the one or more reservoirs. In an embodiment, for example, the increase in pressure ruptures the one or more reservoirs, thereby exposing the one or more active or passive electronic device components to the one or more chemical agents or a reaction product thereof. In an embodiment, for example, the change in temperature causes a chemical or physical transformation of the one or more chemical agents, thereby causing rupture of the one or more reservoirs.

In an embodiment, for example, the one or more reservoirs comprise a first reservoir containing a first chemical agent and a second reservoir containing a second chemical agent, wherein the change in temperature results in rupture of at least one of the first and second reservoirs and mixing of the first and second chemical agents, thereby exposing the one or more active or passive electronic device components to a reaction product of the first and second chemical agents. In an embodiment, for example, the one or more chemical agents independently comprise a liquid, a powder, a gel or any combination of these. In an embodiment, for example, the chemical agents or a reaction product thereof comprise water, a nonaqueous solvent, an aqueous solution, an biopolymer-containing solution, an acid, a base, an enzymatic solution, a PBS solution, a catalyst-containing solution, an etchant, a hydrogel or any combination of these.

In an embodiment, for example, the one or more reservoirs comprises a first reservoir containing a first chemical agent and a microfluidic channel in fluid communication with the one or more active or passive electronic device components. In an embodiment, for example, the first chemical agent releases a solvent, which is conducted through the microfluidic channel and into contact with the one or more active or passive electronic device components. In an embodiment, for example, the microfluidic channel contains a second chemical agent, wherein the first chemical agent releases a solvent, which is conducted through the microfluidic channel and reacts with the second chemical agent, thereby generating a reaction product that contacts the one or more active or passive electronic device components. In an embodiment, for example, the second chemical agent comprises a solid that is dissolved by the solvent. In an embodiment, for example, the device further comprises an additional heater in thermal contact with the microfluidic channel so as to increase the temperature in the microfluidic channel.

In an aspect, the invention provides a method of using a transient electronic device, the method comprising the steps of: (i) providing the transient electronic device comprising: (1) a substrate; (2) one or more active or passive electronic device components supported by the substrate, wherein the one or more active or passive electronic device components independently comprise a selectively transformable material; (3) one or more reservoirs independently containing one or more chemical agents; and (4) a heater in thermal contact with the one or more chambers; wherein at least partial transformation of the one or more active or passive electronic device components provides a programmable transformation of the transient electronic device in response to an external or internal stimulus; and (ii) using the heater to increase the temperature of the one or more reservoirs, thereby providing the external or internal stimulus to cause the programmable transformation of the transient electronic device.

In an embodiment, one or more of the active or passive electronic device components, such as one or more inorganic semiconductor components or one or more metallic conductor components, undergo a complete transformation or a substantially complete transformation, thereby providing the programmable transformation of the passive or active transient electronic device. The complete transformation may be characterized by a complete removal, a complete phase change or a complete chemical change of the one or more active or passive electronic device components, such as the one or more inorganic semiconductor components or the one or more metallic conductor components. A "complete transformation" occurs when 100% of a material undergoes a transformation. A "substantially complete transformation" occurs when 95% or greater than 95% (e.g., 97%, 98%, 99%, 99.5% or 99.9%) of a material undergoes a transformation, such as removal, chemical conversion, phase transition or the like. In an embodiment, for example, a material that undergoes a substantially complete transformation also undergoes a change in a physical property, such as conductivity or resistance that is greater than or equal to 95%, for example, by undergoing a decrease in conductivity or an increase in resistance greater than or equal to 95%.

In an embodiment, one or more of the active or passive electronic device components, such as one or more inorganic semiconductor components or one or more metallic conductor components, undergo an incomplete transformation. The incomplete transformation may be characterized by a partial removal, phase change or chemical change of at least 20%, 30%, 50% or 70% of the quantity of the inorganic semiconductor components or at least 20%, 30%, 50% or 70% of the quantity of the metallic conductor components, thereby providing the programmable transformation of the passive or active transient electronic device. The incomplete transformation may be characterized by a partial removal, phase change or chemical change of at least 20%, 30%, 50% or 70% by weight, volume or area of each of the one or more inorganic semiconductor components or at least 20%, 30%, 50% or 70% by weight, volume or area of each of the one or more metallic conductor components, thereby providing the programmable transformation of the passive transient electronic device. In an embodiment, for example, a material that undergoes a incomplete transformation also undergoes a change in a physical property, such as conductivity or resistance that is greater than or equal to 20% (or 30% for some applications or 50% for some applications or 70% for some applications), for example, by undergoing a decrease in conductivity or an increase in resistance greater than or equal to 20% (or 30% for some applications or 50% for some applications or 70% for some applications).

In an embodiment, transformation of the one or more active or passive electronic device components, such as the one or more inorganic semiconductor components or the one or more metallic conductor components, occurs by a process other than bioresorption. For example, the transformation of the one or more active or passive electronic device components, such as the one or more inorganic semiconductor components or the one or more metallic conductor components, may occur by a phase change, wherein at least a portion of the one or more active or passive electronic device components, such as the one or more inorganic semiconductor components or the one or more metallic conductor components, undergoes at least partial sublimation or melting, thereby providing the programmable transformation of the passive transient electronic device.

In another embodiment, transformation of the one or more active or passive electronic device components, such as the one or more inorganic semiconductor components or the one or more metallic conductor components, occurs via at least partial dissolution of the one or more active or passive electronic device components, such as the one or more inorganic semiconductor components or the one or more metallic conductor components, in a solvent. The solvent may be an aqueous solvent or a nonaqueous solvent. An "aqueous solvent" is a liquid at 298 K that predominantly comprises water, i.e., greater than 50% v/v water, whereas a "nonaqueous solvent" is a liquid at 298 K that predominantly comprises liquid(s) other than water, i.e., less than 50% v/v water. Exemplary aqueous solvents include water, water-based solutions, bodily fluids, and the like. Exemplary nonaqueous solvents include organic solvents (e.g., alcohols, esters, ethers, alkanes, ketones) and ionic liquids.

In another embodiment, transformation of the one or more active or passive electronic device components, such as the one or more inorganic semiconductor components or the one or more metallic conductor components, occurs via at least partial hydrolysis of the one or more active or passive electronic device components, such as the one or more inorganic semiconductor components or the one or more metallic conductor components.

In another embodiment, transformation of the one or more active or passive electronic device components, such as the one or more inorganic semiconductor components or the one or more metallic conductor components, occurs via at least partial etching or corrosion of the one or more active or passive electronic device components, such as the one or more inorganic semiconductor components or the one or more metallic conductor components.

In another embodiment, transformation of the one or more active or passive electronic device components, such as the one or more inorganic semiconductor components or the one or more metallic conductor components, occurs by a photochemical reaction wherein at least a portion of the one or more active or passive electronic device components, such as the one or more inorganic semiconductor components or the one or more metallic conductor components, absorb electromagnetic radiation and undergo an at least partial chemical or physical change. In an embodiment, the photochemical reaction is a photodecomposition process.

In another embodiment, transformation of the one or more active or passive electronic device components, such as the one or more inorganic semiconductor components or the one or more metallic conductor components, occurs by an electrochemical reaction. For example, the electrochemical reaction may be at least partial anodic dissolution of the one or more active or passive electronic device components, such as the one or more inorganic semiconductor components or the one or more metallic conductor components.

In another embodiment, transformation of the one or more active or passive electronic device components, such as the one or more inorganic semiconductor components or the one or more metallic conductor components, occurs by a chemical or physical change wherein at least a portion of the one or more active or passive electronic device components, such as the one or more inorganic semiconductor components or the one or more metallic conductor components, undergoes a decrease in conductivity greater than or equal to 50%, optionally for some embodiments greater than or equal to 75%, and optionally for some embodiments greater than or equal to 95%. In another embodiment, transformation of the one or more active or passive electronic device components, such as the one or more inorganic semiconductor components or the one or more metallic conductor components, occurs by a chemical or physical change wherein at least a portion of the one or more active or passive electronic device components, such as the one or more inorganic semiconductor components or the one or more metallic conductor components, is at least partially, and optionally, entirely converted into an insulator, thereby providing the programmable transformation of the passive transient electronic device.

In an aspect, the one or more active or passive electronic device components, such as the one or more inorganic semiconductor components or the one or more metallic conductor components, are selectively removable and undergo a process characterized by removal, loss or other material transfer process (e.g., flaking, delamination, relocation, repositioning, etc.). In some embodiments, for example, the one or more active or passive electronic device components, such as the one or more inorganic semiconductor components or the one or more metallic conductor components, undergo a process characterized by removal that is substantially uniform with respect to one or more regions of the one or more active or passive electronic device components, such as the inorganic semiconductor components or metallic conductor components, for example regions exposed to an internal or external stimulus, such as a process wherein the thickness of the one or more active or passive electronic device components, such as the inorganic semiconductor components or metallic conductor components, decreases substantially uniformly (e.g., within 10%) as a function of time. In some embodiments, for example, the one or more active or passive electronic device components, such as the one or more inorganic semiconductor components or the one or more metallic conductor components, undergo a process characterized by removal that is substantially nonuniform with respect to one or more regions of the one or more active or passive electronic device components, such as the inorganic semiconductor components or metallic conductor components, such as regions exposed to an internal or external stimulus, such as a process wherein the one or more active or passive electronic device components, such as the inorganic semiconductor components or metallic conductor components, are preferentially (e.g., more rapidly) removed at nano-sized or micro-sized features, such as grain boundaries, defect sites, step edges, phase boundaries, etc. as a function of time In an embodiment, for example, the one or more active or passive electronic device components, such as the one or more inorganic semiconductor components or the one or more metallic conductor components, undergo a process characterized by removal that is substantially nonuniform so as to generate a porous material, thereby impacting the electronic properties (e.g., conductivity, resistance, etc.) of the one or more active or passive electronic device components, such as the inorganic semiconductor components or metallic conductor components. In an embodiment, for example, the one or more active or passive electronic device components, such as the one or more inorganic semiconductor components or the one or more metallic conductor components, undergo a process characterized by removal that is substantially nonuniform so as to cause flaking, for example, wherein the formation of cracks, defects and/or pores in the material result in loss of portions (e.g., flakes) of the material, thereby impacting the electronic properties (e.g., conductivity, resistance, etc.) of the one or more active or passive electronic device components, such as the inorganic semiconductor components or metallic conductor components. In an embodiment, the one or more active or passive electronic device components, such as the one or more inorganic semiconductor components or the one or more metallic conductor components, undergo a process characterized by at least partial, and optionally complete, delamination and/or detachment from an underlying substrate or device component, thereby impacting the electronic properties (e.g., conductivity, resistance, etc.) of the one or more active or passive electronic device components, such as the inorganic semiconductor components or metallic conductor components.

In an embodiment, a transient electronic device has a pre-selected transience profile characterized by the transformation of the one or more active or passive electronic device components, such as the one or more inorganic semiconductor components or the one or more metallic conductor components, occurring over a time interval selected from the range of 1 ms to 5 years, or 1 ms to 2 years, or 1 ms to 1 year, or 1 ms to 6 months, or 1 ms to 1 month, or 1 ms to 1 day, or 1 ms to 1 hour, or 1 second to 10 minutes, thereby providing the programmable transformation of the passive transient electronic device. In an embodiment, the pre-selected transience profile is characterized by a transformation of 0.01% to 100%, or 0.1% to 70%, or 0.5% to 50%, or 1% to 20% or 1% to 10% of the one or more active or passive electronic device components, such as the one or more inorganic semiconductor components or the one or more metallic conductor components, over a time interval selected from the range of 1 ms to 5 years, or 1 ms to 2 years, or 1 ms to 1 year, or 1 ms to 6 months, or 1 ms to 1 month, or 1 ms to 1 day, or 1 ms to 1 hour, or 1 second to 10 minutes, thereby providing the programmable transformation of the passive transient electronic device. In an embodiment, the pre-selected transience profile is characterized by a decrease in the average thickness of the one or more active or passive electronic device components, such as the one or more inorganic semiconductor components or the one or more metallic conductor components, at a rate selected over the range of 0.01 nm/day to 100 microns $s^{-1}$, or 0.01 nm/day to 10 microns $s^{-1}$, or 0.1 nm/day to 1 micron $s^{-1}$, or 1 nm/day to 0.5 micron $s^{-1}$. In an embodiment, the pre-selected transience profile is characterized by a decrease in the mass of the one or more active or passive electronic device components, such as the one or more inorganic semiconductor components or the one or more metallic conductor components, at a rate selected over the range of 0.01 nm/day to 10 microns s$^{-1}$, or 0.1 nm/day to 1 micron s$^{-1}$, or 1 nm/day to 0.5 micron s$^{-1}$. In an embodiment, the pre-selected transience profile is characterized by a decrease in the electrical conductivity of the one or more active or passive electronic device components, such as the one or more inorganic semiconductor components or the one or more metallic conductor components, at a rate selected over the range of $10^{10}$ S·m$^{-1}$ s$^{-1}$ to 1 S·m$^{-1}$ s$^{-1}$, or $10^8$ S·m$^{-1}$ s$^{-1}$ to 10 S·m$^{-1}$ S$^{-1}$, or $10^5$ S·m$^{-1}$ s$^{-1}$ to 100 S·m$^{-1}$ s$^{-1}$. In an embodiment, the pre-selected transience profile is characterized by a change in morphology of the one or more active or passive electronic device components, such as the one or more inorganic semiconductor components or the one or more metallic conductor components, where the change in morphology is selected from the group consisting of pitting, flaking, cracking and uniform degradation. In an embodiment, the pre-selected transience profile is characterized by a decrease in density of the one or more active or passive electronic device components, such as the one or more inorganic semiconductor components or the one or more metallic conductor components, at a rate selected over the range of 0.001%/day to 100%/ms, or selected over the range of 0.01%/day to 10%/ms, or selected over the range of 0.1%/day to 1%/ms, selected over the range of 1%/hr to 1%/s. In an embodiment, the pre-selected transience profile is characterized by an increase in porosity of the one or more active or passive electronic device components, such as the one or more inorganic semiconductor components or the one or more metallic conductor components, at a rate selected over the range of 0.001%/day to 100%/ms, or selected over the range of 0.01%/day to 10%/ms, or selected over the range of 0.1%/day to 1%/ms, selected over the range of 1%/hr to 1%/s.

In an embodiment, the device monitors the at least partial transformation of the one or more active or passive electronic device components, such as the one or more inorganic semiconductor components or the one or more metallic conductor components. For example, the device may monitor the rate of the at least partial transformation of the one or more active or passive electronic device components, such as the one or more inorganic semiconductor components or the one or more metallic conductor components, providing the programmable transformation of the passive transient electronic device. Self-monitoring in devices of the invention may provide enhanced functionality, such as providing the basis for signaling to control overall device functionality or to provide signaling to a user providing measurements of the extent of the transformation, timeframe for programmable transformation or a characterization of device performance or functionality as a function of time.

A user initiated external trigger signal may directly or indirectly trigger the programmable transformation of the electronic device. For example, the user initiated external trigger signal may be an electronic signal, an optical signal, a thermal signal, a magnetic signal, acoustic signal, a mechanical signal, a chemical signal, or an electrochemical signal. In some embodiments, the user initiated external trigger signal is a user initiated application of an electric field provided to the device, a user initiated application of electromagnetic radiation provided to the device, a user initiated mechanical impact provided to the device, a user initiated flow of heat provided to the device, a user initiated flow of heat from the device or a user initiated application of an RF electric field provided to the device. The invention includes devices configured to receive a user initiated trigger signal, for example, devices having a receiver and/or microprocessor component in communication with a transmitter providing a user initiated trigger signal to the device.

The user initiated external trigger signal may be provided to the device directly by a user or indirectly via software stored on a computer-readable medium and executed by a microprocessor. The software may, for example, respond to user input data, data acquired from a component of the device, and/or a feedback loop in continuous communication with the device. The transient device may, for example, be in one-way or two-way communication with a transmitter, wherein the transmitter provides the user initiated external trigger signal to a receiver of the device operationally connected to the actuator.

In some embodiments, a transient device includes a receiver for receiving the user initiated external trigger signal, the receiver operationally connected to the actuator so as to initiate the at least partial transformation of the one or more active or passive electronic device components, such as the one or more inorganic semiconductor components or the one or more metallic conductor components, upon receiving the user initiated external trigger signal. For example, the receiver may include an antenna, an electrode, a piezoelectric element, a photoactive material, or a thermally active material for receiving the user initiated external trigger signal.

In some embodiments, the actuator comprises a processor for receiving a signal from the receiver for initiating the at least partial transformation of the one or more active or passive electronic device components, such as the one or more inorganic semiconductor components or the one or more metallic conductor components.

In some embodiments, the actuator acts directly on the one or more inorganic semiconductor components, the one or more metallic conductor components, or the substrate so as to cause the at least partial transformation. Alternatively, in some embodiments, the actuator acts indirectly on the one or more active or passive electronic device components, such as the one or more inorganic semiconductor components or the one or more metallic conductor components, so as to cause the at least partial transformation.

In an embodiment, an actuator comprises a microprocessor. For example, a microprocessor may receive a user initiated external trigger signal, and software stored on a computer-readable medium within the microprocessor may analyze the user initiated external trigger signal to determine that a source of energy should be provided to a component of the device, such as electromagnetic radiation, acoustic energy, thermal energy, etc. In some embodiment, the software then provides instructions to the microprocessor to perform functions necessary to provide the energy to a device component so as to initiate an at least partial transformation of the one or more active or passive electronic device components, such as the one or more inorganic semiconductor components and/or the one or more metallic conductor components.

In some embodiments, the actuator at least partially removes one or more intermediate structures provided on the one or more active or passive electronic device components, such as the one or more inorganic semiconductor components or the one or more metallic conductor components, so as to expose at least a portion of the one or more active or passive electronic device components, such as the one or more inorganic semiconductor components or at least a portion of the one or more metallic conductor components, to the external or internal stimulus, thereby resulting in the at least partial transformation. The one or more intermediate structures may, for example, comprise an encapsulating material provided on the one or more active or passive electronic device components, such as the one or more inorganic semiconductor components or on the one or more metallic conductor components, wherein the actuator causes removal of at least a portion of the encapsulating material so as to expose the one or more active or passive electronic device components, such as the one or more inorganic semiconductor components or the one or more metallic conductor components, to the external or internal stimulus. An encapsulating material may, for example, be an encapsulating layer restricted to the surface(s) of the one or more inorganic semiconductor components or the surface(s) of the one or more metallic conductor components, an encapsulating overlayer on the top surface of the device, or an encapsulating package surrounding the entire device.

In some embodiments, a transient device includes an overlayer at least partially encapsulating the one or more active or passive electronic device components, such as the one or more inorganic semiconductor components or the one or more metallic conductor components, where the overlayer may comprise one or more reservoirs containing a chemical agent or a biological agent. In an embodiment, an actuator comprises the overlayer having the one or more reservoirs. In an embodiment, the overlayer is a polymer layer or SiN layer. In an embodiment, the one or more reservoirs are embedded in the overlayer. For example, the one or more reservoirs of the overlayer may be ruptured in response to the external or internal stimulus, thereby resulting in release of the chemical or biological agent. In some embodiments, the one or more reservoirs of the overlayer independently have physical dimensions selected over the range of 100 nm to 10,000 µm, or 500 nm to 5,000 µm, or 1 µm to 1,000 µm. Reservoirs having these dimensions may, for example, be fabricated via photolithography or soft lithography (e.g., microtransfer printing).

In some embodiments, one or more reservoirs of the overlayer are ruptured in response to a mechanical impact, change in pressure, exposure to electromagnetic radiation, exposure to heat, or exposure to acoustic energy, thereby resulting in the release of the chemical or biological agent. For example, release may result in dispersal of the chemical agent or biological agent leading to physical contact with one or more device components, such as inorganic semiconductor components, metallic conductor components, dielectric components, encapsulating layers, substrate, etc., thereby causing selective transformation and/or selective removal of the device components in contact with the chemical agent or biological agent. Exemplary chemical or biological agents include water, a nonaqueous solvent, an aqueous solution, a biopolymer-containing solution, an acid, a base, an enzymatic solution, a PBS solution or a catalyst-containing solution.

In some embodiments, the overlayer comprises a silk material, and the chemical agent or biological agent comprises a protease containing material, such as a protease containing solution. In some embodiments, protease enzymes may be complexed with small molecule inhibitors, such as EDTA, or antibodies to shut off activity until the agent is dispersed.

In some embodiments, the actuator generates electromagnetic radiation, acoustic energy, an electric field, a magnetic field, heat, a RF signal, a voltage, a chemical change, or a biological change in response to the user initiated external trigger signal, thereby initiating the at least partial transformation. The actuator may, for example, comprise a heater, a reservoir containing a chemical agent capable of causing a chemical change or a biological change, a source of electromagnetic radiation, a source of an electric field, a source of RF energy or a source of acoustic energy. Exemplary heaters include passive heaters, resistive heaters, and active heaters.

In some embodiments, an actuator comprises an encapsulating material at least partially encapsulating one or more of the active or passive electronic device components, such as the inorganic semiconductor components or the metallic conductor components, wherein the encapsulating material comprises a selectively removable material that is at least partially removed upon the device receiving the external trigger signal to expose underlying inorganic semiconductor components or metallic conductor components to the internal or external stimulus, thereby initiating the at least partial transformation. For example, the encapsulating material may be at least partially dissolved, hydrolyzed, or depolymerized by a chemical agent provided by the actuator in response to the user initiated external trigger signal to expose the underlying inorganic semiconductor components or metallic conductor components. In some embodiments, for example, a selectively removable encapsulating material is provided as an overlayer positioned on one or more inorganic semiconductor components and/or one or more metallic conductor components comprising a selectively transformable material, such that at least partial removal of the overlayer of encapsulating material exposes the underlying one or more inorganic semiconductor components and/or one or more metallic conductor components to an internal or external stimulus, such as an environmental stimulus (e.g., solvent, chemical environment, biological environment, ambient pressure, ambient temperature, ambient electromagnetic radiation, etc.), causing an at least partial transformation of the one or more active or passive electronic device components, such as the one or more inorganic semiconductor components and/or one or more metallic conductor components. In some embodiments, removal of the overlayer of encapsulating material occurs as a result of exposure to an environmental stimulus (e.g., solvent, chemical environment, biological environment, ambient pressure, ambient temperature, ambient electromagnetic radiation, etc.). In some embodiments, removal of the overlayer of encapsulating material occurs as a result of an actuator of a device acting on the overlayer of encapsulating material, for example, by releasing a chemical or biological agent capable of causing at least partial removal of the encapsulating material. In some embodiments, removal of the overlayer of encapsulating material occurs as a result of an actuator of a device acting on the overlayer of encapsulating material, for example, by providing energy (e.g., electromagnetic radiation, acoustic energy, thermal energy, mechanical energy, etc.) causing at least partial removal of the encapsulating material.

In another example, the encapsulating material may be a photosensitive material that undergoes a photochemical reaction in response to electromagnetic radiation generated by the actuator to expose the underlying inorganic semiconductor components or metallic conductor components. The actuator may, for example, be a source of the electromagnetic radiation, wherein the actuator is provided in optical communication with the encapsulating material.

In yet another example, the encapsulating material is a thermally sensitive material that undergoes a phase change or chemical change in response to heat generated by the actuator to expose the underlying inorganic semiconductor components or metallic conductor components. For example, the actuator may be a heater provided in thermal contact with the encapsulating material for providing the heat, such as a resistive heater or a passive heater responsive to absorption of electromagnetic radiation. The invention includes devices comprising a heater embedded in an overlayer comprising an encapsulating material, wherein the heater is configured to provide thermal energy, for example, in response to a user initiated trigger signal, that causes at least partial removal of the encapsulating material thereby exposing underlying inorganic semiconductor components and/or metallic conductor components comprising a selectively transformable material.

In some embodiments, the actuator comprises a counter electrode and electrolyte, wherein the electrolyte is provided in contact with the electrode and the one or more active or passive electronic device components, such as the one or more inorganic semiconductor components or the one or more metallic conductor components, wherein the user initiated external trigger signal is a voltage or RF energy provided to the counter electrode, thereby resulting in dissolution of the one or more active or passive electronic device components, such as the one or more inorganic semiconductor components or the one or more metallic conductor components. In an embodiment, for example, and the one or more active or passive electronic device components, such as the one or more inorganic semiconductor components or the one or more metallic conductor components, comprise the electrodes of an electrochemical cell and are in contact with an electrolyte.

In some embodiments, upon the device receiving the user initiated external trigger signal, the actuator performs an operation selected from the group consisting of opening or closing an electronic circuit, generating heat, resisting the flow of electricity, producing electromagnetic radiation, producing acoustic energy, and dispersing a chemical agent or biological agent.

When the actuator resists the flow of electricity, the temperature of at least a portion of the device may be raised by at least 10° C., thereby initiating thermal degradation of an encapsulating material provided on the one or more active or passive electronic device components, such as the one or more inorganic semiconductor components or one or more metallic conductor components, thereby exposing at least a portion of the one or more active or passive electronic device components, such as the one or more inorganic semiconductor components or one or more metallic conductor components, to the internal or external stimulus.

When the actuator produces electromagnetic radiation, it initiates photochemical degradation of an encapsulating material provided on the one or more active or passive electronic device components, such as the one or more inorganic semiconductor components or one or more metallic conductor components, thereby exposing at least a portion of the one or more active or passive electronic device components, such as the one or more inorganic semiconductor components or one or more metallic conductor components, to the internal or external stimulus.

When the actuator disperses a chemical agent, the chemical agent may, for example, be selected from the group consisting of water, saline, an acid, a base, and an enzyme; wherein the actuator delivers the chemical agent to an encapsulating material provided on the one or more active or passive electronic device components, such as the one or more inorganic semiconductor components or one or more metallic conductor components, thereby initiating chemical or enzymatic degradation of the encapsulating material provided on the one or more active or passive electronic device components, such as the one or more inorganic semiconductor components or one or more metallic conductor components, thereby exposing at least a portion of the one or more active or passive electronic device components, such as the one or more inorganic semiconductor components or one or more metallic conductor components, to the internal or external stimulus. As used herein, chemical agent broadly refers generally to a chemical compound or mixture of compounds (e.g. solution) capable of initiating a chemical or physical change of a material, for example, capable of causing an a least partial transformation of a semiconductor component, metallic conductor component, dielectric component, substrate and/or encapsulating material of the device.

When the actuator disperses a biological agent, the biological agent may, for example, be selected from the group consisting of a protein, a modified protein, a peptide, a modified peptide, an oligonucleotide, and a nucleotide; wherein the actuator delivers the biological agent to an encapsulating material provided on the one or more active or passive electronic device components, such as the one or more inorganic semiconductor components or one or more metallic conductor components, thereby initiating chemical or enzymatic degradation of the encapsulating material provided on the one or more active or passive electronic device components, such as the one or more inorganic semiconductor components or one or more metallic conductor components, thereby exposing at least a portion of the one or more active or passive electronic device components, such as the one or more inorganic semiconductor components or one or more metallic conductor components, to the internal or external stimulus. As used herein, biological agent broadly refers generally to a biomolecule or mixture of biomolecules capable of initiating a chemical or physical change of a material, for example, capable of causing an a least partial transformation of a semiconductor component, metallic conductor component, dielectric component, substrate and/or encapsulating material of the device.

In an embodiment, the programmable transformation provides a change of the function of the transient electronic device from a first condition of operability to a second condition of inoperability. In an alternate embodiment, the programmable transformation provides a change of the function of the transient electronic device from a first condition corresponding to a first functionality to a second condition corresponding to a second functionality different from the first functionality. The functionality may, for example, be an electronic functionality. In either embodiment, the programmable transformation may provide a change from a first condition characterized by two or more inorganic semiconductor device components or metallic conductor components in electrical contact with each other to a second condition characterized by the two or more inorganic semiconductor device components or metallic conductor components not in electrical contact with each other. In some embodiments, a programmable transformation physically and/or electronically separates or isolates components of the transient device, thereby resulting in the change of the function of the transient device from the first condition to the second condition.

Incorporation of degradable or transformable materials in the present invention may also be implemented in a manner to facilitate removal, degradation and/or clearance of the transient devices and components thereof. In an embodiment, a device of the invention has a composition, geometry and/or physical dimensions such that upon at least partial degradation or transformation of the substrate the device is broken up into fragments that are efficiently processed and cleared by a subject or environment. In an embodiment, for example, the device is configured such that upon at least partial degradation or transformation of the substrate the device is broken up into fragments having lateral and thickness dimensions less than 100 microns, optionally less than 10 microns and optionally less than 1 micron, so as to facilitate processing and clearance of the device by a subject or environment.

A programmable transformation may be a pre-set programmable transformation or a real-time trigger programmable transformation. For example, a pre-set transformation may occur at an elapsed or current time programmed into a timer of a device. At the specified time, a user initiated external trigger signal that begins the transformation process may be generated. A real-time transformation may be triggered, for example, by energy applied by an external source or by a signal transmitted by an external source and received by the device. Upon receiving the signal from the external source, an actuator may initiate a transformation process.

In an embodiment, a programmable transformation may comprise complete dissolution, degradation, removal or transformation of at least one inorganic device component, at least one metallic conductor component or both. For example, a programmable transformation of one or more inorganic semiconductor components or one or more metallic conductor components occurs by a process selected from the group consisting of resorption, bioresorption, (chemical or enzymatic) hydrolysis, disintegration, de-polymerization, dissolution, sublimation, melting, etching, photodecomposition, corrosion and anodic dissolution. In an embodiment, a programmable transformation electronically isolates one or more inorganic semiconductor device components or metallic conductor components of a transient electronic device, thereby resulting in a change of the function of the transient electronic device from a first condition to a second condition. For example, the function of the transient electronic device may be transformed from: (i) a NOR gate to a NAND gate; (ii) an inverter to an isolated transistor; (iii) a resistor to a diode; (iv) a NAND gate to an inverter; (v) a NOR gate to an isolated transistor; or (vi) a NAND gate to an isolated transistor.

A transient electronic device may be a passive electronic device or an active electronic device. For example, the passive transient electronic device may be a communication system, a photonic device, a sensor, an optoelectronic device, a biomedical device, a temperature sensor, a photodetector, a photovoltaic device, a strain gauge, an imaging system, a wireless transmitter, an antenna, a nanoelectromechanical system, or a microelectromechanical system. In a particular embodiment, the passive transient electronic device is a sensor for detecting temperature, strain, pressure, electric potential, hydration state, incident electromagnetic radiation or chemical composition. In a particular embodiment, the passive transient electronic device is a communication system that is fully dissolvable when in contact with water. In a particular embodiment, the passive transient electronic device is a radio or antennae. In a particular embodiment, the passive transient electronic device is a tissue mounted biomedical device. Exemplary transient electronic devices include but are not limited to transistors, diodes, CMOS devices, MOSFET devices, photodiodes, light emitting diodes, complementary logic circuits, light sensors, temperature sensors, chemical sensors, mechanical sensors, electrical sensors, magnetic sensors, batteries, fuel cells, radios, and thermoelectric or piezoelectric energy harvesters.

In an embodiment, the passive or active transient electronic device has an average thickness less than or equal to 1000 microns, or optionally 100 microns, or optionally 10 microns.

Useful inorganic semiconductor components include, but are not limited to, flexible semiconductor structures, stretchable semiconductor structures and/or semiconductor structures capable of undergoing a change in shape so as to conform to the surface of an environment. In some embodiments, a transient electronic device may comprise a plurality of inorganic semiconductor components. In an embodiment, the inorganic semiconductor components comprise a semiconductor device such as a transistor, a transistor channel, a diode, a p-n junction, a photodiode, a light emitting diode, a laser, an electrode, an integrated electronic device, an integrated circuit, an antenna, an inductor, a resistor, a semiconductor based sensor, MESFETs, MOSFETs or combinations and/or arrays of these.

In some embodiments, the one or more active or passive electronic device components, such as the one or more inorganic semiconductor components or the one or more metallic conductor components, independently comprise a nanostructured material or a microstructured material. In an embodiment, for example, the one or more active or passive electronic device components, such as the inorganic semiconductor components, comprise a microstructured material or a nanostructured material such as a micro- or nano-ribbon, a micro- or nano-membrane, a micro- or nano-wire or a micro- or nano-porous material. As used herein, the term "microstructured" refers to a structure having at least one physical dimension selected over the range of 1 micron to 1000 microns and the term "nanostructured" refers to a structure having at least one physical dimension selected over the range of 10 nanometers to 1000 nanometers. In an embodiment, the invention comprises a nanostructured inorganic semiconductor component, metallic component or dielectric component comprising a microporous material having a plurality of pores with cross section dimensions selected from the range of 1 μm to 1000 μm, optionally provided in an ordered network. In an embodiment, the invention comprises a nanostructured inorganic semiconductor component, metallic component or dielectric component comprising a nanoporous material having a plurality of pores with cross section dimensions selected from the range of 1 nm to 1000 nm, optionally provided in an ordered network.

The physical dimensions and shape of the device, and components thereof, are important parameters, particularly with respect to preselection of a desired transience profile. Use of thin inorganic semiconductor components, metallic conductor components and/or dielectric components (e.g., thickness less than or equal to 100 microns, optionally thickness less than or equal to 10 microns, optionally thickness less than or equal to 1 micron, optionally thickness less than or equal to 500 nanometers, and optionally thickness less than or equal to 100 nanometers) is beneficial for providing a pre-selected transience for a given device application and/or providing useful mechanical properties such as a flexible or otherwise deformable device. In some embodiments, inorganic semiconductor components, metallic conductor components and/or dielectric components independently comprise one or more thin film structures, which may for example be deposited or grown by molecular epitaxy, atomic layer deposition, physical or chemical vapor deposition, or other methods known in the art. In some embodiments, one or more inorganic semiconductor components, metallic conductor components and/or dielectric components independently comprise a biocompatible, bioresorbable, bioinert or ecocompatible material. In some embodiments, at least some of, and optionally all of, the inorganic semiconductor components, metallic conductor components and/or dielectric components of the electronic device have a thickness less than or equal to 100 microns, and for some applications have a thickness less than or equal to 10 microns, and for some applications have a thickness less than or equal to 1 micron, and for some applications have a thickness less than or equal to 500 nanometers, and for some applications have a thickness less than or equal to 100 nanometers, and for some applications have a thickness less than or equal to 20 nanometers. In some embodiments, at least some of, and optionally all of, the inorganic semiconductor components, metallic conductor components and/or dielectric components of the device independently have a thickness selected from a range of 10 nm to 100 μm, optionally for some applications selected from a range of 50 nm to 10 μm, and optionally for some applications selected from a range of 100 nm to 1000 nm. In an embodiment, for example, a device of the invention comprises one or more inorganic semiconductor components each independently having a thickness selected over the range of 10 nm to 1000 nm, optionally for some applications 10 nm to 100 nm and optionally for some applications 10 nm to 30 nm. In some embodiments, at least some of, and optionally all of, the inorganic semiconductor components, metallic conductor components and/or dielectric components of the device independently have lateral physical dimensions (e.g., length, width, diameter, etc.) less than or equal to 10000 μm, and for some applications have lateral physical dimensions less than or equal to 1000 μm, and for some applications have lateral physical dimensions less than or equal to 100 μm, and for some applications have lateral physical dimensions less than or equal to 1 μm. In some embodiments, at least some of, and optionally all of, the inorganic semiconductor components, metallic conductor components and/or dielectric components of the device independently have lateral physical dimensions selected from the range of 10 nm to 10 cm, optionally for some applications selected from a range of 100 nm to 10000 μm, optionally for some applications selected from a range of 500 nm to 1000 μm, optionally for some applications selected from a range of 500 nm to 100 μm, and optionally for some applications selected from a range of 500 nm to 10 μm.

As with other components of the transient device, the physical properties of the inorganic semiconductor components, metallic conductor components and/or dielectric components (e.g., Young's modulus, net bending stiffness, toughness, conductivity, resistance, etc.) impact the performance and transience of the device. In some embodiments, for example, at least a portion, and optionally all, of the inorganic semiconductor components, metallic conductor components and/or dielectric components of the device independently have a Young's modulus less than or equal to 10 GPa, optionally for some applications less than or equal to 100 MPa, optionally for some applications less than or equal to 10 MPa. In some embodiments, for example, at least a portion, and optionally all, of the inorganic semiconductor components, metallic conductor components and/or dielectric components of the device have a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, at least a portion, and optionally all, of the inorganic semiconductor components, metallic conductor components and/or dielectric components of the device have a net bending stiffness less than or equal to $1\times10^8$ GPa μm$^4$, optionally for some applications less than or equal to $5\times10^5$ GPa μm$^4$ and optionally for some applications less than or equal to $1\times10^5$ GPa μm$^4$. In some embodiments, at least a portion, and optionally all, of the inorganic semiconductor, metallic conductor components and/or dielectric components of the device have a net bending stiffness selected over the range of $0.1\times10^4$ GPa μm$^4$ and $1\times10^8$ GPa μm$^4$, and optionally for some applications between $0.1\times10$ GPa μm$^4$ and $5\times10^5$ GPa μm$^4$.

Useful materials for the inorganic semiconductor components include high quality semiconductor materials such as single crystalline semiconductor materials including pure and doped single crystalline semiconductor materials. In an embodiment, all of the inorganic semiconductor components comprise a single crystalline semiconductor material and/or a single crystalline doped semiconductor material, for example, single crystalline silicon and/or doped single crystalline silicon derived from high temperature foundry processing. Integration of single crystalline semiconductor materials into a transient device is particularly beneficial for providing devices exhibiting very good electronic properties. In an embodiment, the semiconductor components comprise a material selected from the group consisting of Si, Ge, Se, diamond, fullerenes, SiC, SiGe, SiO, $SiO_2$, SiN, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. In some embodiments, the inorganic semiconductor components include a material selected from the group consisting of Si, SiC, SiGe, SiO, $SiO_2$, SiN, and any combination of these. In some embodiments, the inorganic semiconductor components independently comprise single crystalline silicon, porous silicon and/or polycrystalline silicon. In some embodiments, the inorganic semiconductor components independently comprise a polycrystalline semiconductor material, single crystalline semiconductor material or doped polycrystalline or single crystalline semiconductor material. In some embodiments, the inorganic semiconductor component is a transformable material. Useful materials for a transformable, inorganic semiconductor component include, but are not limited to, porous silicon, polycrystalline silicon, and any combination of these.

In some embodiments, the transient device may include one or more additional device components selected from the group consisting of an electrode, a dielectric layer, a chemical or biological sensor element, a pH sensor, an optical sensor, an optical source, a temperature sensor, and a capacitive sensor. The additional device component may comprise a bioinert material, a degradable material or a transformable material. Useful bioinert materials include, but are not limited to, titanium, gold, silver, platinum, and any combination of these. Useful degradable or transformable materials include, but are not limited to, iron, magnesium, tungsten and any combination of these.

In some embodiments, electronic devices comprise one or more interconnected island and bridge structures. For example, an island structure may comprise one or more semiconductor circuit components of the transient device. A bridge structure may comprise one or more flexible and/or stretchable electrical interconnections providing electrical communication between elements, for example between different island structures. In this manner, electronic devices of the present invention may comprise stretchable electronic devices having a plurality of electrically interconnected inorganic semiconductor components comprising one or more island structures and one or more flexible and/or stretchable bridge structures providing electrical interconnection; e.g., stretchable electronic interconnects.

In some embodiments, at least a portion of the plurality of inorganic semiconductor components comprise one or more of an amplifier circuit, a multiplexing circuit, a current limiting circuit, an integrated circuit, a transistor or a transistor array. Useful multiplexing circuits include those configured to individually address each of a plurality of electrodes spatially arranged over the degradable substrate. In addition, the transient device may further comprise one or more additional device components selected from the group consisting of an electrode, a dielectric layer, a chemical or biological sensor element, a pH sensor, an optical sensor, an optical source, a temperature sensor, and a capacitive sensor. At least one of the additional device components may comprise a bioinert material or a bioresorbable material.

In some embodiments, the transient device, or components thereof, are assembled on the substrate via a printing-based or molding-based process, for example, by transfer printing, dry contact transfer printing, solution-based printing, soft lithography printing, replica molding, imprint lithography, etc. In some of these embodiments, therefore, the device, or components thereof, comprise printable semiconductor materials and/or devices. Integration of the device and substrate components via a printing-based technique is beneficial in some embodiments, as it allows for independent processing of semiconductor devices/materials and processing for the substrate. For example, the printing-based assembly approach allows semiconductor devices/materials to be processed via techniques that would not be compatible with some substrates. In some embodiments, for example, the semiconductor device/materials are first processed via high temperature processing, physical and chemical deposition processing, etching and/or aqueous processing (e.g. developing, etc.), and, then subsequently assembled on the substrate via a printing-based technique. An advantage of this approach is that it avoids processing of the semiconductor device/materials on the substrate in a manner that could negatively impact the chemical and/or physical properties of the substrate, for example, by negatively impacting biocompatibility, toxicity and/or the degradation properties (e.g., degradation rate, etc.) of the transformable substrate. In some embodiments, for example, this approach allows for effective fabrication of the device without exposing the substrate to aqueous processing, for example, processing involving exposure of the transformable substrate to an etchant, a stripper or a developer.

In some embodiments, at least a portion, and optionally all, of the plurality of inorganic semiconductor components of the device is bonded to the substrate. Bonding between the device and the substrate may be achieved directly involving covalent and noncovalent bonding (e.g., Van der Waals forces, hydrogen bonding, London dispersion forces, etc.) between layers and materials. Alternatively, bonding may be achieved by incorporation of an adhesive layer provided between the device and the substrate. Useful adhesive layers for bonding comprise a polymer, an elastomer (e.g. PDMS), a prepolymer, a thin metal layer, a silk layer, etc.

In some embodiments, for example, an encapsulating material functions to encapsulate portions of, or all of, the device, thereby preventing current leakage to the local environment and/or electrical shorting of the device. In an embodiment, the encapsulating material encapsulates at least 50% of the inorganic semiconductor components and/or metallic conductor components of the device, optionally at least 90% of the inorganic semiconductor components and/or metallic conductor components of the device, and optionally all of the inorganic semiconductor components and/or metallic conductor components of the device. In an embodiment, the encapsulating material completely encapsulates the transient device.

A variety of materials are useful for the degradable substrate of the present devices. In an embodiment, the substrate comprises a selectively removable material. In an embodiment, the selectively removable material of the substrate undergoes removal by a process selected from the group consisting of resorption, bioresorption, (chemical or enzymatic) hydrolysis, disintegration, de-polymerization, dissolution, sublimation, melting, etching and corrosion. In an embodiment, the substrate comprises a biocompatible, bioresorbable or ecocompatible material. Useful materials for the substrate include, for example, a biopolymer (e.g., protein, peptide, carbohydrate, polynucleotide, etc.), a synthetic polymer, a protein, a polysaccharide, silk, poly(glycerol-sebacate) (PGS), polydioxanone, poly(lactic-co-glycolic acid) (PLGA), polylactic acid (PLA), polyvinyl alcohol (PVA), gelatin, collagen, chitosan, fibroin, hyaluronic acid, protease particles, fluorescin, rose Bangal, rhodamine, reflectin, bacteriorhodopsin, hemoglobin, porphyrin and combinations of these. Useful silk materials for bioresorbable substrates include, for example, silkworm fibroin, modified silkworm fibroin, spider silk, insect silk, recombinant silk, and any combination of these. As used herein, modified silkworm fibroin refers to a polymer composition that is derived via chemical modification of silkworm fibroin.

In some embodiments, the substrate and/or encapsulating material comprises silk, which may be in an at least partially crystalline state. For example, the silk may have a degree of crystallinity less than 55%, or selected over the range of 0 to 55%. In one embodiment, the substrate comprises a silk composite material. For example, the silk composite material may comprise silk having a plurality of nanoparticles dispersed throughout the silk material, wherein the nanoparticles comprise a conductor (e.g., metal), semiconductor material, nanotube, nanowire, nanoshell (metallic shell with a dielectric core), pigments, dyes and combinations thereof. In some embodiments, the nanoparticles comprise a material selected from the group consisting of Au, Ag, CsSe and CdTe. Typically, the nanoparticles have physical dimensions equal to or less than 1000 nm, and the nanoparticles are present in the silk material at a concentration selected from the range of 0.1 nM to 100 nM, or from the range of 0.5 nM to 50 nM, or from the range of 1 nM to 25 nM. In some embodiments, the nanoparticles absorb electromagnetic radiation, thereby generating heat that is capable of triggering selective removal of the substrate. Absorption of electromagnetic energy for triggering a thermal degradation process depends upon both nanoparticle concentration and the power of the applied electromagnetic energy. In an embodiment, absorption of electromagnetic radiation is plasmonic-resonance enhanced absorption.

In some embodiments, a transient substrate or encapsulating material may be transformed by exposure to high temperature. For example, the glass transition temperature of silk is ~178° C. and degradation commences at ~220° C.

In some embodiments, transformation of a substrate or encapsulating material may be facilitated or expedited by a high concentration of certain salts (e.g., lithium salts, calcium salts) that permeabilize the substrate or encapsulating material.

In some embodiments, the substrate is a material that undergoes hydrolysis in an aqueous environment at a rate equal to or greater than the hydrolysis rate of the inorganic semiconductor component or metallic conductor component at 298K. In some embodiments, the substrate is a material that undergoes hydrolysis in an aqueous environment at a rate equal to or less than the hydrolysis rate of the inorganic semiconductor component or metallic conductor component at 298K. In other embodiments, the substrate is a material that undergoes sublimation at a temperature equal to or greater than 273 K.

The physical dimensions and physical properties of the transformable substrate are important parameters for supporting a range of device functionalities and compatibility with different environments. In some embodiments, the transformable substrate has a thickness less than or equal to 10,000 μm, and optionally in some embodiments less than or equal to 1000 μm, and optionally in some embodiments less than or equal to 100 μm, and optionally in some embodiments less than or equal to 10 μm; and optionally in some embodiments less than or equal to 1 μm. Use of a thin transformable substrate (e.g., thickness less than or equal to 100 microns, optionally less than or equal to 10 microns and optionally less than or equal to 1 micron) is useful for providing a flexible, or otherwise deformable, device capable of establishing conformal contact with a wide range of environments, including environments having complex, highly contoured surfaces. In some embodiments, the transformable substrate has a thickness selected over the range of 5 nanometers and 200 μm, optionally for some embodiments selected over the range of 10 nanometers and 100 μm, optionally for some embodiments selected over the range of 100 nanometers and 10000 μm, optionally for some applications selected over the range of 1 μm and 1000 μm, and optionally for some embodiments selected over the range of 1 μm and 10 μm. In embodiments where the transformable substrate is only a few nanometers thick, a supporting substrate may be necessary or supportability may be improved by a layer-by-layer deposition technique. In some embodiments, the composition and physical properties (e.g., Young's modulus, net bending stiffness, toughness, etc.) of the transformable substrate are selected to provide sufficient structural support for the device component, while also providing an ability to achieve a high degree of conformal contact upon deployment. In some embodiments, the transformable substrate is a low modulus layer. Alternatively, the invention includes devices having a transformable substrate that is a high modulus layer. In some embodiments, for example, the transformable substrate has a Young's modulus less than or equal to 10 GPa, preferably for some applications a Young's modulus less than or equal to 100 MPa, optionally for some applications less than or equal to 10 MPa. In some embodiments, for example, the transformable substrate has a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, for example, the transformable substrate has a net bending stiffness less than or equal to $1\times10^9$ GPa μm$^4$, optionally for some applications less than or equal to $1\times10^7$ GPa μm$^4$ and optionally for some applications less than or equal to $1\times10^6$ GPa μm$^4$. In some embodiments, for example, the transformable substrate has a net bending stiffness selected over the range of $0.1\times10^4$ GPa μm$^4$ and $1\times10^9$ GPa μm$^4$, and optionally for some applications between $0.1\times10^4$ GPa μm$^4$ and $5\times10^5$ GPa μm$^4$.

The invention includes transformable substrates comprising amorphous materials, crystalline materials, partially amorphous materials, partially crystalline materials or combinations thereof. In an embodiment, the transient device of the invention includes an at least partially crystalline material, wherein the extent of crystallinity of the transformable substrate is selected to provide a useful and/or pre-selected transformable rate for a selected environment and device application. In some embodiments, the larger the degree of crystallinity of the transformable substrate the slower the transformable rate when provided in contact with the environment. For example, the invention includes transient devices having a transformable substrate with a degree of crystallinity less than or equal to 55%, and optionally a degree of crystallinity less than or equal to 30% and optionally a degree of crystallinity less than or equal to 20%, and optionally a degree of crystallinity less than or equal to 5%. For example, the invention includes transient devices having a transformable substrate with a degree of crystallinity selected over the range of 0 to 55%, and optionally for some embodiments a degree of crystallinity selected over the range of 1 to 30%, and optionally for some embodiments a degree of crystallinity selected over the range of 5 to 20%. As used herein, 0% crystallinity refers to an entirely amorphous material and the given degree of crystallinity corresponds to the amount of a material provided in a crystalline state relative to the total amount of material. In some embodiments, for example those having a silk substrate, the degree of crystallinity refers to the beta sheet content of the silk substrate.

In some embodiments, the device includes a transformable substrate having a programmable, controllable and/or selectable transformation rate when provided in contact with an environment. The invention includes devices having transformable substrates exhibiting a range of transformation rates that are selected on the basis of an intended application, device functionality, longevity, etc. In some embodiments, for example, the transformable substrate exhibits a high transformation rate so as to provide rapid and complete transformation upon administration, for example, to facilitate conformational and/or morphological changes useful for deploying the device in a particular environment. In other embodiments, for example, the transformable substrate exhibits a low resorption rate so as to provide slow and/or incomplete degradation upon administration, for example, to provide encapsulation of electronic components of the device and/or to provide structural properties useful for deploying or removing the device.

In an embodiment, a transient electronic device comprises an inorganic semiconductor component and/or metallic conductor component comprising a material engineered to accelerate resorption, bioresorption, hydrolysis, disintegration, de-polymerization, dissolution, etching or corrosion. The engineered material may, for example, be a perforated structure. A "perforated structure" may comprise recessed features, holes, channels, cracks, or other physical defects that prevent a structure from being monolithic and contiguous within at least one major plane of the structure. In an embodiment, one or more inorganic semiconductor components or one or more metallic conductor components independently comprise one or more perforated structures. For example, the one or more perforated structures may have a porosity (or void fraction) selected from the range of 10%-80%, 20%-50% or 30%-40%. In an embodiment, the perforated structures may have a porosity greater than 20%, greater than 30%, greater than 50%, or greater than 70%. "Porosity" generally describes a ratio of the volume of all the pores in a material to the volume of the whole. As is known in the art, the porosity ratio may be expressed as a percentage.

In an embodiment, one or more perforated structures may have a plurality of recessed features or channels. In an embodiment, the recessed features or channels extend entirely through a thickness of the one or more active or passive electronic device components, such as the one or more inorganic semiconductor components or the one or more metallic conductor components. In an embodiment, the recessed features or channels extend 0.1% to 100%, or 1% to 95%, or 5% to 85%, or 10% to 75%, or 25% to 50% through a thickness of the one or more active or passive electronic device components, such as the one or more inorganic semiconductor components or the one or more metallic conductor components. In an embodiment, the recessed features or channels extend a length selected over the range 10 nm to 10 mm through a thickness of the one or more active or passive electronic device components, such as the one or more inorganic semiconductor components or the one or more metallic conductor components. In an embodiment, the recessed features or channels have lateral cross sectional dimensions selected from the range of 0.1 µm² to 10 cm², or 0.5 µm² to 5 cm², or 1 µm² to 1 cm², or 10 µm² to 0.1 cm² and vertical dimensions selected from the range of 0.01 µm to 10 mm, or 0.05 µm to 5 mm, or 0.1 µm to 1 mm, or 10 µm to 0.1 mm.

In some embodiments, a transient electronic device comprises a reservoir fabricated from a material that is susceptible to degradation when exposed to radiation of a particular wavelength. An aqueous solution or other chemical(s) in the reservoir may escape from the reservoir upon degradation of the radiation-susceptible material and interact with device components to accelerate their degradation or transformation.

The internal or external stimulus may, for example, be a change in biological environment, a change in temperature, a change in pressure, exposure to electromagnetic radiation, contact with a chemical agent, application of an electric field, application of a magnetic field, exposure to a solvent, change in pH of an external environment, change in salt concentration of an external environment, or application of an anodic voltage.

In an embodiment, the transient electronic device includes a wireless power component comprising a selectively transformable material. In an embodiment, the wireless power component is a coil, a battery, a fuel cell, an energy harvester, a solar cell, or an inductor. The energy harvester may be selected from a thermoelectric component and a piezoelectric component.

In an embodiment, the transient electronic device is a sensor, a power supply, an optoelectronic device, a nanoelectromechanical (NEM) device, or a microelectromechanical (MEM) device. When the transient electronic device is a sensor, the sensor may detect light intensity changes, light wavelength changes, temperature changes, chemical changes, mechanical changes, electrical changes, magnetic changes, and combinations thereof. When the transient device is a power supply, the power supply may be a coil, a battery, a fuel cell, or an energy harvester. The energy harvester may be selected from a thermoelectric component or a piezoelectric component.

In an embodiment, the wireless power component converts the electromagnetic energy via the photovoltaic effect, non-resonant inductive coupling, near-field mutual inductance coupling, or a combination thereof. When the wireless power component operates via the photovoltaic effect, the wireless power component may be a solar cell or solar array. When the wireless power component operates via non-resonant inductive coupling, the wireless power component may be an inductor that conducts a current in response to an alternating magnetic field. The device component being powered may be a resistor in electrical communication with the inductor. The resistor generates heat when the current is conducted through the inductor. When the wireless power component operates via near-field mutual inductance coupling, the wireless power component includes a scavenging rectifier. The scavenging rectifier absorbs radio energy through a scavenging antenna that collects ambient alternating current (AC) signals, wherein the ambient AC signals are converted into direct current (DC) by a rectifier. An input frequency of the scavenging rectifier is about 2.4 GHz. A rectified output of the scavenging rectifier is selected from the range of 1 V to 3 V.

In an embodiment, the device operates as a radio and further comprises an oscillator coupled to a transmitting antenna for transmitting a signal indicative of a state of the transient electronic device or a parameter of an environment of the transient electronic device. An output frequency of the oscillator may be about 1 GHz.

In an embodiment, a transient electronic device comprises one or more inorganic semiconductor components. In some embodiments, each of the one or more inorganic semiconductor components independently comprise a nanomembrane structure, which may for example have a thickness less than 1000 nm. In an embodiment, each of the inorganic semiconductor components independently comprise Si, Ga, GaAs, ZnO or any combination of these. In an embodiment, the one or more inorganic semiconductor components comprise ZnO.

In an embodiment, one or more inorganic semiconductor components independently comprise a semiconductor material that undergoes hydrolysis in an aqueous environment at a rate equal to or greater than $10^{-10}$ $s^{-1}$ at 298 K, or equal to or greater than $10^{-8}$ $s^{-1}$ at 298 K, or equal to or greater than $10^{-5}$ $s^{-1}$ at 298 K, or equal to or greater than $10^{-2}$ $s^{-1}$ at 298 K.

In an embodiment, the transient electronic device comprises one or more metallic conductor components, and the one or more metallic conductor components of a transient electronic device may comprise Mg, W, Fe or an alloy thereof. In a particular embodiment, the one or more metallic conductor components independently comprise an alloy of Mg with one or more additional materials selected from the group consisting of Al, Ag, Ca, Li, Mn, Si, Sn, Y, Zn, and Zr, wherein the one or more additional materials of the alloy has a concentration equal to or less than 10% by weight. In another embodiment, the one or more metallic conductor components independently comprise an alloy of Mg with one or more rare earth elements, wherein the one or more rare earth elements of the alloy has a concentration equal to or less than 10% by weight. In another embodiment, the transient electronic device includes one or more inorganic semiconductor components comprising ZnO and one or more metallic conductor components comprising Mg, Fe, W or an alloy thereof.

In an embodiment, one or more metallic conductor components independently comprise a semiconductor material that undergoes hydrolysis in an aqueous environment at a rate equal to or greater than $10^{-10}$ s$^{-1}$ at 298 K, or equal to or greater than $10^{-8}$ s$^{-1}$ at 298 K, or equal to or greater than $10^{-5}$ s$^{-1}$ at 298 K, or equal to or greater than $10^{-2}$ s$^{-1}$ at 298 K.

In an embodiment, a transient electronic device may comprise one or more dielectric components supported by the substrate, wherein the one or more dielectric components comprise a selectively removable material. In an embodiment, the selectively removable material of the one or more dielectric components may undergo removal by a process selected from the group consisting of resorption, bioresorption, hydrolysis, disintegration, de-polymerization, dissolution, sublimation, melting, etching and corrosion. In some embodiments, one or more dielectric components comprise biocompatible, bioresorbable or ecocompatible material. In some embodiments, each of the dielectric components comprises one or more thin film structures, which may for example be deposited or grown by molecular epitaxy, atomic layer deposition, physical or chemical vapor deposition, or other methods known in the art. Typically, each of the one or more dielectric components has a thickness selected over the range of 10 nm to 50 μm, or a thickness less than or equal to 100 nm or a thickness less than or equal to 10 nm.

In an embodiment, the one or more dielectric components may comprise one or more materials selected from the group consisting of $SiO_2$, MgO, silk, collagen, gelatin, PVA and PLGA. In a particular embodiment, the transient electronic device includes one or more inorganic semiconductor components selected from the group consisting of ZnO and Si, one or more metallic conductor components selected from the group consisting of Mg, Fe, W and alloys thereof and one or more dielectric components selected from the group consisting of $SiO_2$ and MgO. In another embodiment, the transient electronic device includes one or more inorganic semiconductor components comprising ZnO, one or more metallic conductor components selected from the group consisting of Mg, Fe, W and alloys thereof and one or more dielectric components comprising MgO. In an embodiment, one or more dielectric components comprise a material that undergoes hydrolysis in an aqueous environment at a rate equal to or greater than $10^{-10}$ s$^{-1}$ at 298 K, or equal to or greater than $10^{-8}$ s$^{-1}$ at 298 K, or equal to or greater than $10^{-5}$ s$^{-1}$ at 298 K, or equal to or greater than $10^{-2}$ s$^{-1}$ at 298 K.

The one or more inorganic semiconductor components, the one or more metallic conductor components or the one or more dielectric components may be assembled on the substrate by microtransfer printing.

In an embodiment, the substrate, the one or more inorganic semiconductor components, and the one or more metallic conductor components independently comprise a selectively removable material.

In an embodiment, the transient electronic device may further comprise an adhesion promoting layer disposed between the substrate and at least a portion of the metal conductor components. For example, the adhesion promoting layer may comprise a material selected from the group consisting of magnesium oxide, titanium, and combinations thereof.

The transient electronic device has a neutral mechanical plane and, in some embodiments, at least a portion, and optionally all, of the one or more inorganic semiconductor components are positioned proximate (e.g., within 10 microns, and optionally within 1 micron) to the neutral mechanical plane. A thickness of the transformable substrate may be selected so as to position at least a portion of the one or more inorganic semiconductor components proximate to the neutral mechanical plane. Embodiments having inorganic semiconductor components positioned proximate to the neutral mechanical plane are useful for applications where the device undergoes a significant change in conformation upon deployment, for example, by enhancing the structural integrity of the device when provided in a non-planar (e.g., bent, curved, convex, concave, etc.) conformation and/or in a stretched conformation.

In some embodiments, a transient device may be partially or completely encapsulated in a package material. In an embodiment, the package material comprises a pair of cross-linked silk sheets that completely encapsulate the device when edges of the sheets are laminated together. For example, the sheets may be two freestanding silk films formed by casting and peeling, which are then sealed along the edges by lamination. Generally, the sheets will have a thickness selected from the range of 1 micron to 200 microns, or from 2 microns to 100 microns, or from 5 microns to 50 microns. From a practical point of view, a film thinner than 1 micron (while freestanding) may be difficult to make and handle using some techniques, while a film thicker than 200 microns may be rigid and susceptible to cracking during handling using some techniques. Alternatively, in some embodiments, the package material may be a pre-formed hollow silk tube having a thickness selected over the range of 1 micron to 1 centimeter, optionally for some applications 5 microns to 2 millimeters, and optionally for some applications 10 microns to 50 microns. Typically, the package material has a thickness of about 20 μm per sheet.

In an embodiment, an encapsulating material at least partially encapsulates one or more inorganic semiconductor components or one or more metallic conductor components, wherein the encapsulating material comprises a selectively removable material that is at least partially removed to expose underlying inorganic semiconductor components or metallic conductor components. In an embodiment, the encapsulating material is removed in response to the external or internal stimulus.

In an embodiment, the encapsulating material is an overlayer provided on the one or more inorganic semiconductor components or provided on the one or more metallic conductor components; wherein the overlayer has a thickness selected over the range of 10 nm to 10 mm, or 20 nm to 1 mm, or 50 nm to 0.1 mm. The encapsulating material may be provided directly on the one or more inorganic semiconductor components or the one or more metallic conductor components or indirectly with one or more intermediate structures/layers between the encapsulating material and the one or more inorganic semiconductor components or the one or more metallic conductor components.

In an embodiment, the encapsulating material has a pre-selected transience profile different than the pre-selected transience profile of the one or more active or passive electronic device components, such as the one or more inorganic semiconductor components or the one or more metallic conductor components. For example, in an embodiment, the transience profile may be at least one order of magnitude larger than that of the one or more active or passive electronic device components, such as the one or more inorganic semiconductor components or the one or more metallic conductor components.

In an embodiment, the transience profile may be characterized by the removal of the encapsulating material occurring over a time interval selected from the range of 1 ms to 2 years, or 1 ms to 1 year, or 1 ms to 6 months, or 1 ms to 1 month, or 1 ms to 1 day, or 1 ms to 1 hour, or 1 second to 10 minutes, thereby exposing the underlying inorganic semiconductor components or metallic conductor components. For example, the transience profile may be characterized by the removal of 0.01% to 100%, or 0.1% to 70%, or 0.5% to 50%, or 1% to 20% or 1% to 10% of the encapsulating material over a time interval selected from the range of 1 ms to 2 years, or 1 ms to 1 year, or 1 ms to 6 months, or 1 ms to 1 month, or 1 ms to 1 day, or 1 ms to 1 hour, or 1 second to 10 minutes, thereby exposing the underlying inorganic semiconductor components or metallic conductor components. In an embodiment, the transience profile may be characterized by a decrease in the average thickness of the encapsulating material at a rate selected over the range of 0.01 nm/day to 10 microns $s^{-1}$, or 0.1 nm/day to 1 micron $s^{-1}$, or 1 nm/day to 0.5 micron $s^{-1}$.

In an embodiment, the encapsulating material comprises a material selected from the group consisting of MgO, silk, collagen, gelatin, PLGA, polyvinylalcohol (PVA), PLA, $SiO_2$, polyanhydrides (polyesters), polyhdroxyalkanates (PHAs) and polyphosphates. In an embodiment, the encapsulating material comprises silk, where the silk may be in an at least partially crystalline state. For example, the silk may have a degree of crystallinity less than 55%, or selected over the range of 1 to 55%. In an embodiment, an encapsulating material comprises a pair of cross-linked silk sheets that completely encapsulate the transient electronic device when edges of the sheets are laminated together.

In some embodiments, the encapsulating material comprises a silk composite material. The silk composite material may comprise silk having a plurality of nanoparticles dispersed throughout the silk, wherein each of the nanoparticles independently comprise a conductor or semiconductor material. For example, each of the nanoparticles may independently comprise a material selected from the group consisting of Au, Ag, CsSe and CdTe. Typically, the nanoparticles have physical dimensions equal to or less than 1000 nm, and the nanoparticles are present in the silk at a concentration selected from the range of 0.1 nM to 100 nM. In some embodiments, the nanoparticles absorb electromagnetic radiation, thereby generating heat that is capable of causing selective removal of the encapsulating material. For example, the absorbtion of electromagnetic radiation may be plasmonic-resonance enhanced absorption.

In some embodiments, the encapsulating material is a material that undergoes hydrolysis in an aqueous environment at a rate equal to or greater than $10^{-10}$ $s^{-1}$ at 298 K, or equal to or greater than $10^{-8}$ $s^{-1}$ at 298 K, or equal to or greater than $10^{-5}$ $s^{-1}$ at 298 K, or equal to or greater than $10^{-2}$ $s^{-1}$ at 298 K. In other embodiments, the encapsulating material is a material that undergoes sublimation at a temperature equal to or greater than 273 K. For example, the sublimable encapsulating material may be a material selected from the group consisting of $CO_2$, $I_3$, naphthalene, ammonium chloride, iron chloride, aluminum chloride, melamine, nickelocene, camphor, and caffeine.

In some embodiments, the encapsulating material is a composite material comprising a plurality of sublimable fibers provided in a nonsublimable material, wherein sublimation of the sublimable fibers results in selective removal of the encapsulating material. The composite material may, for example, be solution casted, electrospun or spin casted material.

The time for the thickness of selectively removable materials to reach zero is given by:

$$t_c = \frac{4\rho_m M(H_2O)}{kw_0 M(m)} \frac{\sqrt{\frac{kh_0^2}{D}}}{\tanh\sqrt{\frac{kh_0^2}{D}}}$$

where $t_c$ is the critical time, $\rho_m$ is the mass density of the material, $M(H_2O)$ is the molar mass of water, $M(m)$ is the molar mass of the material, $h_0$ is the initial thickness of the material, D is the diffusivity of water, k is the reaction constant for the dissolution reaction, and $w_0$ is the initial concentration of water, wherein k has a value selected from the range of $10^5$ to $10^{-10}$ $s^{-1}$, or from the range of $10^3$ to $10^{-7}$ $s^{-1}$, or from the range of $10^2$ to $10^{-4}$ $s^{-1}$, or from the range of 10 to $10^{-2}$ $s^{-1}$.

In an embodiment, the physical properties of the transient device (e.g., Young's modulus, net bending stiffness, toughness, etc.) provide rigidity for the device to be self-supporting, while also being capable of achieving a high degree of conformal contact with an environment. In an embodiment, the substrate, the device having one or more inorganic semiconductor components, and the one or more metallic conductor components provide a net bending stiffness of the transient device of less than $1 \times 10^9$ GPa $\mu m^4$, or a net bending stiffness selected from a range of $0.1 \times 10^4$ GPa $\mu m^4$ to $1 \times 10^8$ GPa $\mu m^4$, optionally $1 \times 10^5$ GPa $\mu m^4$ to $1 \times 10^8$ GPa $\mu m^4$. In some embodiments, the substrate, the inorganic semiconductor components and the one or more metallic conductor components each independently comprise a transformable material.

In an embodiment, the transient device, and/or components thereof, are at least partially optically transparent with respect to visible and/or infrared electromagnetic radiation. In an embodiment, for example, the transient device, substrate, inorganic semiconductor components and/or metallic conductor components exhibit a percentage transmission for light in the visible region of the electromagnetic spectrum equal to or greater than 70% and equal to or greater than 90% for some applications. At least partially optically transparent devices are useful for visualizing and/or imaging the device during administration and/or use. In addition, devices of the invention that are at least partially optically transparent are useful for coupling electromagnetic radiation into and/or out of the device. The invention includes, for example, devices having an LED or laser array component for illuminating an environment or optical sensing, wherein the device is capable of transmitting light from the device component through other components of the device, such as the substrate.

In some biological environments, such as an in vivo biological environment, the degradation of the substrate occurs via enzymatic degradation, for example, via protease mediated degradation. In addition, degradation occurs in some embodiments from the surfaces of the bioresorbable substrate that are exposed to the biological environment having degradation enzymes present, such as at the interface with a tissue and/or biological fluid. Accordingly, certain parameters of the degradable substrate may be selected to effectively control the degradation rate. In an embodiment, the chemical composition, physical state and/or thickness of the degradable substrate is selected so as to control the degradation rate. In an embodiment, for example, the degradable substrate comprises a biopolymer exhibiting a useful degradation rate for a selected biological environment.

In some specific embodiments, transient devices of the invention do not include a substrate component. In an embodiment, for example, the transient devices of the invention initially includes a substrate component, which is selectively removed during deployment and/or operation such that the device makes a transition to a transient device not having a substrate. An embodiment of this aspect includes a transient device for biomedical applications, wherein contact with a biological environment, such as contact with a tissue or cell in vivo, results in loss of the substrate via bioresoprtion.

Devices of some aspects are useful generally for in vivo biomedical applications including sensing, actuating, imaging and/or delivery of therapeutic agents to a local biological environment. In an embodiment, for example, devices of the invention are useful for making electrophysiology measurements of a target tissue in a biological environment or for electrophysically actuating a target tissue in a biological environment, where the biological environment may be an in vivo biological environment, and where the target tissue may be selected from, but not limited to, heart tissue, brain tissue, muscle tissue, nerve tissue, epithelial tissue and vascular tissue.

The geometry and/or morphology of the substrate are other characteristics important to establishing the functional capabilities of the present devices. In an embodiment, the substrate is a continuous layer having approximately uniform thickness (e.g., thicknesses within 10% of average thickness of the layer). Alternatively, the invention includes devices having a substrate comprising a discontinuous layer and/or a layer having a nonuniform thickness profile. The invention includes transient devices having additional substrates and/or layers, for example, for partial or full encapsulation and/or electronic isolation of device components (e.g., semiconductors, metallic conductor components, dielectrics, etc.).

The physical dimensions, composition and geometry of metallic conductor components are important parameters of electronic devices of the invention. In an embodiment, metallic conductor components are metal films, for example thin (e.g., thickness <100 microns) metal films. Use of thin metallic conductor components (e.g., thickness less than or equal to 100 microns, optionally less than or equal to 10 microns and optionally less than or equal to 1 micron) is useful for providing a flexible, or otherwise deformable, device. In some embodiments, one or more metallic conductor components comprise one or more thin film structures, which may for example be deposited or grown by molecular epitaxy, atomic layer deposition, physical or chemical vapor deposition, or other methods known in the art. In some embodiments, metallic conductor components comprise a biocompatible, bioresorbable or ecocompatible material. In an embodiment, at least a portion, and optionally all of, the metallic conductor components comprise a biocompatible metal, such as titanium, gold, silver, platinum, and any combination of these. In an embodiment, at least a portion, and optionally all of, the metallic conductor components comprise a transformable metal, such as of iron, magnesium, tungsten and any combination of these. In an embodiment, each of the metallic conductor components has a thickness less than or equal to 10 microns, and optionally each of the metallic conductor components has a thickness less than or equal to 1 micron, and optionally each of the metallic conductor components has a thickness less than or equal to 500 nanometers, and optionally each of the metallic conductor components has a thickness less than or equal to 100 nm, and optionally each of the metallic conductor components has a thickness less than or equal to 20 nm. In an embodiment, each of the metallic conductor components has a thickness selected over the range of 10 nanometers to 100 microns, and optionally a thickness selected over the range of 100 nanometers to 1 micron, and optionally a thickness selected over the range of 100 nanometers to 500 nanometers. In an embodiment, each of the metallic conductor components has lateral dimensions less than or equal to 10000 microns, and optionally lateral dimensions less than or equal to 1000 microns, and optionally lateral dimensions less than or equal to 100 microns, and optionally lateral dimensions less than or equal to 10 microns. In an embodiment, metallic conductor components in an array are separated from adjacent metallic conductor components by a distance greater than or equal to 10 microns, and optionally a distance greater than 100 microns. In an embodiment, adjacent metallic conductor components are separated from each other by a distance selected from the range of 10 microns to 10 millimeters, and optionally the range of 10 microns to 1000 microns, and optionally the range of 10 to 100 microns.

Degradation of the substrate is useful for deploying, or otherwise positioning, manipulating and/or interfacing the transient device (e.g., a surface, a portion and/or component thereof) in a given environment. In some embodiments, for example, the transient device is brought into conformal contact with an environment by a process involving degradation or transformation of the substrate, for example, wherein a degradation process brings the transient device in contact (e.g., physical, electrical, thermal, etc.) with the environment, and optionally wherein the degradation process causes conformal and/or morphological changes to the transient device that assist in interfacing the device with the environment. In some embodiments, the device is deployed in, or otherwise positioned, manipulated and/or interfaced with, an environment via a process involving complete degradation or transformation of the substrate, for example, so as to provide the transient device in physical contact, electrical contact or optical communication with an environment. In some embodiments of this aspect, therefore, the degradable or transformable layer functions as a sacrificial layer during deployment so as to facilitate interfacing the transient device with the environment. Alternatively, in other embodiments, the device is deployed in, or otherwise positioned, manipulated and/or interfaced with, an environment via a process involving partial, but not complete, degradation or transformation of the substrate, for example, so as to provide the transient device in physical contact, electrical contact or optical communication with an environment. In some embodiments of this aspect, therefore, the degradable or transformable layer functions as a partial sacrificial layer during deployment but remains as a structural and/or functional component of the device during use. In some embodiments, for example, partial or complete degradation or transformation of the substrate provides a means of selectively adjusting and/or manipulating the physical dimensions, conformation, morphology and/or shape of the transient device so as to facilitate establishing conformal contact with an environment. In some embodiments, partial or complete degradation or transformation of the substrate provides a means of selectively adjusting the chemical composition of the transient device so as to establish conformal contact with an environment in a compatible manner, such as in a manner suppressing undesirable immune response and/or inflammation.

Methods, disclosed herein, of making and using transient electronic devices may be implemented to produce or utilize all embodiments of the transient electronic devices disclosed herein.

In an aspect, a method of using a passive transient electronic device comprises: providing the passive transient electronic device comprising: a substrate; one or more inorganic semiconductor components, one or more metallic conductor components or one or more inorganic semiconductor components and one or more metallic conductor components supported by the substrate; wherein the one or more inorganic semiconductor components or one or more metallic conductor components independently comprise a selectively transformable material, wherein the one or more inorganic semiconductor components or the one or more metallic conductor components have a pre-selected transience profile in response to an external or internal stimulus; wherein at least partial transformation of the one or more inorganic semiconductor components or the one or more metallic conductor components provides a programmable transformation of the passive transient electronic device in response to the external or internal stimulus and at a pre-selected time or at a pre-selected rate, wherein the programmable transformation provides a change of the function of the passive transient electronic device from a first condition to a second condition; and exposing the passive transient device to the external or internal stimulus, thereby programmably transforming the passive transient electronic device.

In an aspect, a method of using an actively triggered transient electronic device, comprises: providing the actively triggered transient electronic device comprising: a substrate; one or more inorganic semiconductor components, one or more metallic conductor components or one or more inorganic semiconductor components and one or more metallic conductor components supported by the substrate; wherein the one or more inorganic semiconductor components or the one or more metallic conductor components independently comprise a selectively transformable material, wherein the one or more inorganic semiconductor components or the one or more metallic conductor components have a pre-selected transience profile in response to an external or internal stimulus; and an actuator responsive to a user initiated external trigger signal and operably connected to the one or more inorganic semiconductor components or the one or more metallic conductor components, wherein upon the device receiving the external trigger signal the actuator directly or indirectly initiates at least partial transformation of the one or more inorganic semiconductor components or the one or more metallic conductor components in response to the internal or external stimulus, thereby providing a programmable transformation of the actively triggered transient electronic device in response to the external trigger signal, wherein the programmable transformation provides a change of the function of the actively triggered transient electronic device from a first condition to a second condition; and exposing the actively triggered transient electronic device to the external or internal stimulus, thereby programmably transforming the actively triggered transient electronic device.

In an aspect, a method of making a transient electronic device comprises the steps of: providing a device substrate; providing on the device substrate one or more inorganic semiconductor components, one or more metallic conductor components or one or more inorganic semiconductor components and one or more metallic conductor components; wherein the one or more inorganic semiconductor components or one or more metallic conductor components independently comprise a selectively transformable material, wherein the one or more inorganic semiconductor components or the one or more metallic conductor components have a pre-selected transience profile in response to an external or internal stimulus; thereby generating the transient electronic device; wherein at least partial transformation of the one or more inorganic semiconductor components or the one or more metallic conductor components provides a programmable transformation of the passive transient electronic device in response to the external or internal stimulus and at a pre-selected time or at a pre-selected rate, wherein the programmable transformation provides a change in function of the passive transient electronic device from a first condition to a second condition.

In an embodiment, the selectively transformable material is selected from the group consisting of Mg, W, Fe, an alloy of Mg with one or more additional materials selected from the group consisting of Al, Ag, Ca, Li, Mn, Si, Sn, Y, Zn, and Zr, wherein the one or more additional materials of the alloy has a concentration equal to or less than 10% by weight, and an alloy of Mg with one or more rare earth elements, wherein the one or more rare earth elements of the alloy has a concentration equal to or less than 10% by weight.

In an embodiment, the selectively transformable material is selected from the group consisting of Si, Ga, GaAs, and ZnO.

In some fabrication processes, the step of providing on the device substrate the one or more inorganic semiconductor components, one or more metallic conductor components or one or more inorganic semiconductor components and one or more metallic conductor components comprises: fabricating an assembly of device components on a fabrication substrate, wherein the assembly of device components comprises one or more single crystalline inorganic semiconductor structures, one or more dielectric structures or one or more metallic conductor structures; and transferring at least a portion of the assembly of device components from the fabrication substrate to the device substrate. In an embodiment, the device components on the fabrication substrate comprise single crystalline Si, Ga or GaAs. In another embodiment, the device components on the fabrication substrate comprise $SiO_2$.

In an embodiment, a method of making a transient electronic device further comprises a step of providing the one or more inorganic semiconductor components or one or more metallic conductor components comprising the selectively transformable material on the device substrate having the assembly of device components. For example, in an embodiment, the step of providing the one or more inorganic semiconductor components or one or more metallic conductor components comprising the selectively transformable material on the device substrate having the assembly of device components is carried out using a solution processing technique. In another embodiment, the step of providing the one or more inorganic semiconductor components or one or more metallic conductor components comprising the selectively transformable material on the device substrate having the assembly of device components is carried out using electrohydrodynamic printing.

In some embodiments, the step of fabricating the assembly of device components on a fabrication substrate is carried out at a semiconductor foundry. The fabrication substrate may, for example, be a semiconductor wafer substrate, a glass plate-type substrate, or a silicon-on-insulator substrate. In some embodiments, the step of fabricating the assembly of device components on a fabrication substrate is carried out using one or more high temperature deposition techniques selected from the group consisting of chemical vapor deposition, physical vapor deposition, epitaxial growth, atomic layer deposition, electrochemical deposition, and molecular beam epitaxy. The step of fabricating the assembly of device components on a fabrication substrate may be carried out under clean room conditions according to recognized standards, such as US FED STD 209E, ISO 14644-1, or BS 5295 cleanroom standards. Embodiments of the invention using foundry processing are beneficial for accessing high quality semiconductor and dielectric materials, such as single crystalline silicon and $SiO_2$, in useful device formats and layouts. In some embodiments, for example, methods of the invention includes a hybrid processes involving some processing steps carried out in a foundry (e.g., fabrication of high quality single crystalline silicon and $SiO_2$ device elements in a specific devise design) and other processing steps carried out using non-foundry techniques, such as solution phase processing. This hybrid approach leverages access to the high quality materials produced via foundry based techniques with flexibility for integration of a range of selectively transformable materials allowed by non-foundry techniques.

In some embodiments, the step of fabricating the assembly of device components on a fabrication substrate is carried out using one or more high temperature doping techniques and/or one or more high temperature annealing techniques. In some embodiments, the step of fabricating the assembly of device components on the fabrication substrate comprises generating a fully processed primitive or circuit element supported by the fabrication substrate.

In some embodiments, the step of fabricating the assembly of device components on a fabrication substrate is carried out using a photolithography or etching technique.

In some embodiments, the step of fabricating the assembly of device components on a fabrication substrate comprises generating one or more structures selected form the group consisting of: one or more single crystalline silicon semiconductor structures on the fabrication substrate each independently having a thickness less than or equal to 1 micron; one or more $SiO_2$ structures on the fabrication substrate each independently having a thickness less than or equal to 1 micron; and one or more metallic structures on the fabrication substrate each independently having a thickness less than or equal to 5 microns. In an embodiment, the step of fabricating the assembly of device components on a fabrication substrate comprises (1) laterally defining one or more single crystalline silicon semiconductor structures supported by the fabrication substrate, for example via photolithography and etching processing; (2) depositing one or more metallic structures on the fabrication substrate, for example via chemical or physical deposition; and (3) growing one or more $SiO_2$ structures.

In an embodiment, a method of making a transient electronic device further comprises a step of replacing at least a portion of the one or more single crystalline inorganic semiconductor structures, the one or more metallic conductor structures or the one or more dielectric structures with the selectively transformable material. For example, in an embodiment, the step of replacing at least a portion of the one or more single crystalline inorganic semiconductor structures, the one or more metallic conductor structures or the one or more dielectric structures with the selectively transformable material is not carried out at a semiconductor foundry.

In some embodiments, the step of replacing at least a portion of the one or more single crystalline inorganic semiconductor structures, the one or more metallic conductor structures or the one or more dielectric structures with the selectively transformable material is carried out using solution processing. In other embodiments, the step of replacing at least a portion of the one or more single crystalline inorganic semiconductor structures, the one or more metallic conductor structures or the one or more dielectric structures with the selectively transformable material is carried out using electrohydrodynamic printing.

In an embodiment, the method of making a transient electronic device comprises the step of replacing at least a portion of the one or more metallic conductor structures with the one or more selectively transformable metallic conductor materials.

In some embodiments, the one or more metallic conductor structures are replaced with a selectively transformable metal selected from the group consisting of Mg, W, Fe, an alloy of Mg with one or more additional materials selected from the group consisting of Al; Ag, Ca, Li, Mn, Si, Sn, Y, Zn, and Zr, wherein the one or more additional materials of the alloy has a concentration equal to or less than 10% by weight, and an alloy of Mg with one or more rare earth elements, wherein the one or more rare earth elements of the alloy has a concentration equal to or less than 10% by weight.

In an embodiment, the method of making a transient electronic device comprises the step of replacing at least a portion of the one or more metallic conductor structures comprising Au or Al with the selectively transformable material.

In some embodiments, a method of making a transient electronic device further comprises a step of releasing at least a portion of the assembly of device components from the fabrication substrate. For example, the step of releasing at least a portion of the assembly of device components from the fabrication substrate may be carried out by at least partially undercutting the one or more single crystalline inorganic semiconductor structures, the one or more dielectric structures and the one or more metallic conductor structures. Undercutting may be achieved via etching underneath the one or more single crystalline inorganic semiconductor structures, the one or more dielectric structures and the one or more metallic conductor structures.

In an embodiment, the fabrication substrate is a silicon-on-insulator substrate, and the method comprises at least partially etching a buried oxide layer of the silicon-on-insulator substrate, thereby at least partially undercutting the one or more single crystalline inorganic semiconductor structures, the one or more dielectric structures and the one or more metallic conductor structures.

In an embodiment, the step of releasing at least a portion of the assembly of device components from the fabrication substrate is carried out by microtransfer printing, which lifts off at least a portion of the one or more single crystalline inorganic semiconductor structures, the one or more dielectric structures and the one or more metallic conductor structures from the fabrication substrate. In some embodiments, the microtransfer printing fractures one or more anchors connecting the one or more single crystalline inorganic semiconductor structures, the one or more dielectric structures and the one or more metallic conductor structures to the fabrication substrate, thereby providing the liftoff.

In an embodiment, the microtransfer printing is dry transfer contact printing. The microtransfer printing technique may comprise: contacting at least a portion of the one or more single crystalline inorganic semiconductor structures, the one or more dielectric structures and the one or more metallic conductor structures with a contact surface of a conformal transfer device, wherein at least a portion of the one or more single crystalline inorganic semiconductor structures, the one or more dielectric structures and the one or more metallic conductor structures are adhered to the contact surface; and moving the conformal transfer device having the portion of the one or more single crystalline inorganic semiconductor structures, the one or more dielectric structures and the one or more metallic conductor structures adhered to the contact surface, thereby providing the liftoff.

In some embodiments, the microtransfer printing technique further comprises: contacting a receiving surface of the device substrate with the at least a portion of the one or more single crystalline inorganic semiconductor structures, the one or more dielectric structures and the one or more metallic conductor structures adhered to the contact surface; and separating the contact surface of conformal transfer device and the one or more single crystalline inorganic semiconductor structures, the one or more dielectric structures and the one or more metallic conductor structures, thereby transferring the one or more single crystalline inorganic semiconductor structures, the one or more dielectric structures and the one or more metallic conductor structures to the receiving surface of the device substrate. In some embodiments, the conformal transfer device is an elastomeric stamp.

In some embodiments, a method of making a transient electronic device further comprises the step of providing an actuator responsive to a user initiated external trigger signal and operably connected to the one or more inorganic semiconductor components or the one or more metallic conductor components, wherein upon the device receiving the external trigger signal the actuator directly or indirectly initiates the at least partial transformation of the one or more inorganic semiconductor components or the one or more metallic conductor components in response to the internal or external stimulus, thereby providing the programmable transformation of the transient electronic device in response to the external trigger signal.

In some embodiments, a method of making a transient electronic device further comprises the step of providing a receiver for receiving the user initiated external trigger signal, the receiver operationally connected to the actuator so as to initiate the at least partial transformation of the one or more inorganic semiconductor components or the one or more metallic conductor components in response to the user initiated external trigger signal. For example, the actuator may be in one-way or two-way communication with a transmitter, wherein the transmitter provides the user initiated external trigger signal to a receiver of the device operationally connected to the actuator.

In some embodiments, a method of making a transient electronic device further comprises providing an encapsulating material at least partially encapsulating the one or more of the inorganic semiconductor components or the one or more of the metallic conductor components. For example, the step of providing the encapsulating material at least partially encapsulating the one or more of the inorganic semiconductor components or the one or more of the metallic conductor components is carried out using solution processing or is carried out using spin casting or spin coating.

In some embodiments, the encapsulating material comprises a selectively removable material. Exemplary encapsulating materials include a material selected from the group consisting of MgO, silk, collagen, gelatin, PLGA, polyvinylalcohol (PVA), PLA, $SiO_2$, polyanhydrides (polyesters), polyhydroxyalkanates (PHAs) and polyphosphates. In an embodiment, the encapsulating material comprises silk.

In some embodiments, the device substrate comprises a selectively removable material. For example, the device substrate may comprise a biocompatible, bioresorbable or ecocompatible material. In an embodiment, the device substrate comprises a polymer, or a material selected from the group consisting of silk, collagen, gelatin, PLGA, polyvinylalcohol (PVA), PLA, MgO, $SiO_2$, polyanhydrides (polyesters), polyhdroxyalkanates (PHAs) and polyphosphates. In an embodiment, the device substrate comprises silk.

In some embodiments, a method of making a transient electronic device further comprises the step of determining the pre-selected transience profile and selecting the composition and physical dimensions of the one or more active or passive electronic device components, such as the one or more inorganic semiconductor components or the one or more metallic conductor components, to provide the pre-selected transience profile.

In some embodiments, a method of making a transient electronic device further comprises a step of selecting a thickness or morphology of the one or more active or passive electronic device components, such as the one or more inorganic semiconductor components or the one or more metallic conductor components, to provide the pre-selected transience profile.

In some embodiments, each of the one or more active or passive electronic device components, such as the one or more inorganic semiconductor components or the one or more metallic conductor components, independently comprise a selectively transformable material.

"Spatially arranged over the degradable substrate" as used herein, refers to a distribution of elements (e.g. device components) over the surface area of a substrate such that each element is located at a different position. Inter-element spacing can be uniform or variable. In some embodiments, the elements are spatially arranged in a regular array pattern with equal inter-element spacing, for example in a 2D array. In some embodiments, the elements are spatially arranged in a line (e.g., a 1D array). Useful spatial arrangements include regular and irregular distributions of elements.

In some embodiments, the geometry of transient devices may be used to provide stretchability, flexibility, conformability and/or compressibility. In an embodiment, the devices may exploit inorganic semiconductor materials configured into structural shapes that can geometrically accommodate large mechanical deformations without imparting significant strain in the materials themselves. For example, bridges connecting rigid device islands may be wavy, buckled, serpentine or meandering as further described in U.S. patent application Ser. No. 11/851,182 (U.S. Pub. No. 2008/0157235); U.S. patent application Ser. No. 12/405,475 (U.S. Pub. No. 2010/059863); and U.S. patent application Ser. No. 12/398,811 (U.S. Pub. No. 2010/0002402), each of which is hereby incorporated by reference.

In an embodiment, devices disclosed herein comprise one or more stretchable components, such as disclosed in U.S.

patent application Ser. Nos. 11/851,182 and/or 12/405,475 and/or 12/398,811, and are made by one or more of the processes disclosed therein. U.S. patent application Ser. Nos. 11/851,182; 12/405,475; and 12/398,811, which are hereby incorporated by reference.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 22(2). Schematic of a transient electrochemical device comprising a packaging component at least partially enclosing an anode, a cathode, and an electrolyte. A storage component in fluidic communication with the electrolyte compartment holds the electrolyte prior to discharge of the electrochemical device to prevent transience due to dissolution reactions.

(FIG. 53C) Flowchart of a method of using a transient electronic device comprising actively triggered reservoirs.

(FIG. 55A) Top plan view and (FIG. 55B) top perspective views of passive RFID integrated circuit chiplets that are batch fabricated at a foundry using silicon-on-insulator wafers in a fabrication sequence that uses only transient materials.

(FIG. 56A) Top plan view, exploded top plan view, and cross-sectional view along the dashed line shown in the exploded view, (FIG. 56B) top perspective view.

(FIG. 57A) Top plan view, exploded top plan view, and cross-sectional view along the dashed line shown in the exploded view, (FIG. 57B) top. perspective view.

(FIG. 58A) Top plan view, exploded top plan view, and cross-sectional view along the dashed line shown in the exploded view, (FIG. 58B) top perspective view.

(FIG. 59A) Top plan view, exploded top plan view, and cross-sectional view along the dashed line shown in the exploded view, (FIG. 59B) top perspective view.

(FIG. 60A) Top plan view, exploded top plan view, and cross-sectional view along the dashed line shown in the exploded view, (FIG. 60B) top perspective view.

DETAILED DESCRIPTION OF THE INVENTION

Figure 1:
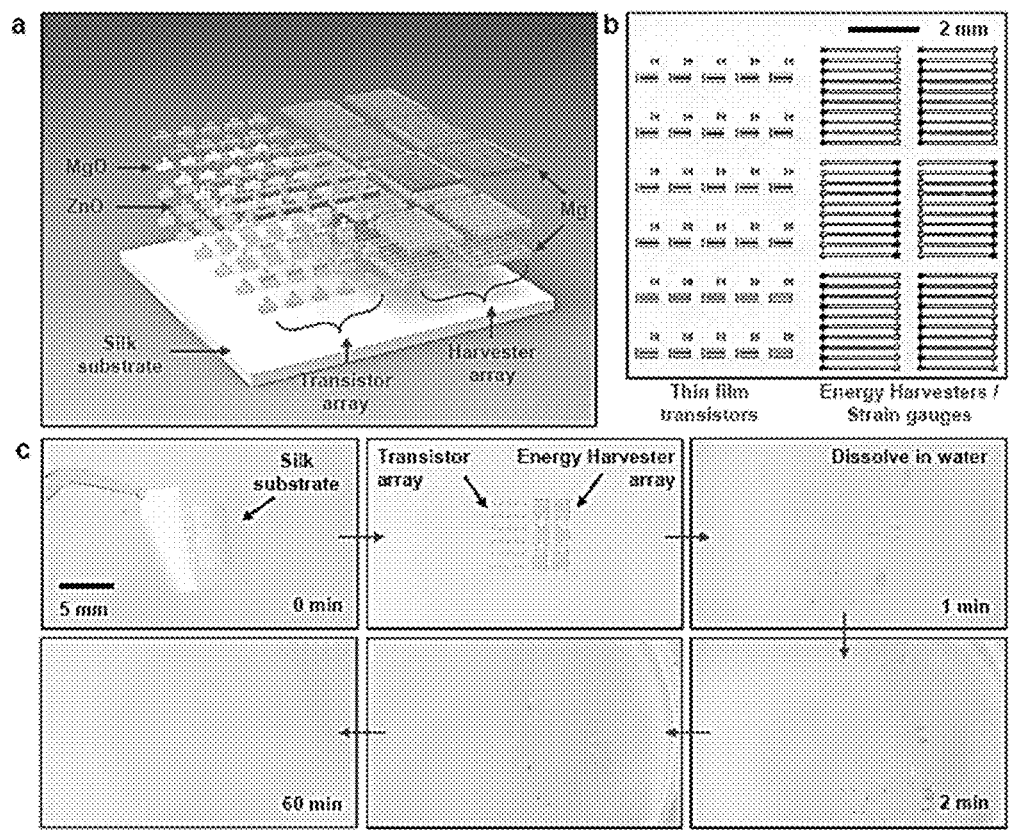
FIG. 1. Materials and designs for transient thin film transistors (TFTs) and mechanical energy harvesters (MEHs)/strain gauges based on ZnO, Mg, MgO and silk. a) Schematic illustration of transient ZnO TFTs and MEHs/strain gauges that consist entirely of water soluble materials: ZnO (semiconductor/piezoelectric), Mg (conductor), MgO (insulator), silk (substrate). b) Photograph of a collection of ZnO TFTs and MEHs on a silk substrate. All electronic materials were deposited through high resolution shadow masks made of polyimide (PI) film (Kapton, 12.5 µm, Dupont, USA). c) A set of images of an array of ZnO TFTs and MEHs on silk, at various times after immersion in deionized water at room temperature.

In general, the terms and phrases used herein have their art-recognized meaning, which can be found by reference to standard texts, journal references and contexts known to those skilled in the art. The following definitions are provided to clarify their specific use in the context of the invention.

"Electrical dissolution rate" (EDR) refers to the rate of change in the effective thickness of a layer of bulk material converted from the electrical resistance changes upon dissolution. The EDR is an effective corrosion rate that illustrates degradation of electrical properties and takes into account structural irregularities in real materials, which usually deviate from traditional corrosion rates due to the sensitivity of the electrical properties on corrosion non-uniformity. "Corrosion rate" refers to a rate at which a portion of material is removed from a bulk material. For example, a corrosion rate may be expressed as an amount of material (e.g., expressed as weight, volume, atoms, molecules, etc.) that is lost per unit time. Corrosion rate may be affected by ambient conditions, such as pH, temperature, UV exposure, chemical exposure, electrical exposure, physical abrasion and the like. The expression "characterized by an electrical dissolution rate (EDR) higher than a corrosion rate of said selectively transformable material" refers a comparison of an EDR to a corrosion rate under similar conditions, such as upon exposure to the same external or internal stimulus.

"Functional layer" refers to a layer that imparts some functionality to the device. For example, the functional layer may contain semiconductor components, metallic components, dielectric components, optical components, piezoelectric components, etc. Alternatively, the functional layer may comprise multiple layers, such as multiple semiconductor layers, metallic layers or dielectric layers separated by support or structural layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of the neutral mechanical plane within a multilayer device.

"Structural layer" refers to a layer that imparts structural functionality, for example by supporting, securing and/or encapsulating device components. The invention includes transient devices having one or more structural layers, such as encapsulating layers, embedding layers, adhesive layers and/or substrate layers.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group 111-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (GIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements, photovoltaic elements (e.g. solar cell), sensors, light emitting elements, actuators, piezoelectric elements, receivers, transmitters, microprocessors, transducers, islands, bridges and combinations thereof. Components may be connected to one or more contact pads as known in the art, such as by metal evaporation, wire bonding, and application of solids or conductive pastes, for example. Electronic devices of the invention may comprise one or more components, optionally provided in an interconnected configuration.

"Neutral mechanical plane" (NMP) refers to an imaginary plane existing in the lateral, b, and longitudinal, I, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element. In some embodiments, proximate to refers to a position of a first element within 100 microns of a second element, or optionally within 10 microns for some embodiments, or optionally within 1 microns for some embodiments.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices.

"Sensing" refers to detecting the presence, absence, amount, magnitude or intensity of a physical and/or chemical property. Useful electronic device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component, such as one or more inorganic semiconductor components, one or more metallic conductor components or an encapsulating material or layer. In an embodiment, actuating refers to a process in which a structure or materials is selectively transformed, for example, so as to undergo a chemical or physical change such as removal, loss or displacement of a material or structure. Useful electronic device components for actuating include, but are not limited to, electrode elements, electromagnetic radiation emitting elements, light emitting diodes, lasers, magnetic elements, acoustic elements, piezoelectric elements, chemical elements, biological elements, and heating elements.

An "actuator" is a device component that directly or indirectly initiates at least partial transformation of a transient electronic device in response to a user initiated external trigger signal, for example by initiating an at least partial transformation of a selectively transformable material of a transient electronic device. For example, an actuator may initiate at least partial transformation of a transient device by absorbing energy supplied to the device and utilizing or converting that energy to affect the at least partial transformation. For example, an actuator may initiate at least partial transformation of a transient device by exposing a device component comprising selectively transformable material to an internal or external stimulus resulting an at least partial transformation. For example, an actuator may initiate at least partial transformation of a transient device by supplying energy (e.g., thermal, electromagnetic radiation, acoustic, RF energy, etc.) to an intermediate material or device component which affects the transformation, such as supplying energy to an encapsulating material, inorganic semiconductor components, or metallic conductor components. Thus, the actuator may comprise a single component or multiple components that alone or in combination facilitate transformation of the transient electronic device. In some embodiments, an actuator of the invention is directly or indirectly provided in one way to two communication with a transmitter, for example, via one or more receiver device components.

A "user initiated trigger signal" includes any action, other than the mere placement of a transient device in a particular environment, by which a person may start or initiate a programmable transformation of a transient device. Exemplary "user initiated trigger signals" include providing real-time user input data to the device or a transmitter in communication with the device (e.g., pressing a button, flipping a switch, setting a timer, etc.), providing at least one non-ambient external source of energy directly or indirectly to the device (e.g., an electric field, a magnetic field, acoustic energy, pressure, strain, heat, light, mechanical energy, etc.), and/or programming software to execute computer-readable instructions, which may be based on data received from the device, for example data from a feedback loop. In an embodiment, the user initiated external trigger signal is an electronic signal, an optical signal, a thermal signal, a magnetic signal, a mechanical signal, a chemical signal, acoustic signal or an electrochemical signal. In an embodiment, the invention provides a transient electronic device configured to receive a user initiated trigger signal, for example, a user initiated trigger signal provided by a transmitter and received by a receiver component of the device.

A "non-ambient external source of energy" includes energy having a magnitude at least 10% greater, or at least 25% greater, or at least 50% greater than the magnitude of ubiquitous energy of the same form found in the environment in which a transient device is located.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Island" refers to a relatively rigid component of an electronic device comprising a plurality of semiconductor components. "Bridge" refers to structures interconnecting two or more islands or one island to another component. Specific bridge structures include semiconductor and metallic interconnects. In an embodiment, a transient device of the invention comprises one or more semiconductor-containing island structures, such as transistors, electrical circuits or integrated circuits, electrically connected via one or more bridge structures comprising electrical interconnects.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90%, of the external surface of the structure is surrounded by one or more structures. "Completely encapsulated" refers to the orientation of one structure such that it is completely surrounded by one or more other structures. The invention includes transient devices having partially or completely encapsulated inorganic semiconductor components, metallic conductor components and/or dielectric components, for example, via incorporation a polymer encapsulant, such as biopolymer, silk, a silk composite, or an elastomer encapsulant.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes device having one or more barrier layers, for example, one or more barrier layers positioned at the interface of the device with an external environment.

A barrier layer(s), and optionally a sacrificial layer on a substrate, may be etched to produce a "mesh structure", where at least a portion of the barrier layer(s), and optionally the sacrificial layer on a substrate, is removed. For example a portion of the barrier layer(s) disposed approximately 10 nanometers or more from an inorganic semiconductor component or additional component is removed. Removal of at least a portion of the barrier layer(s), and optionally the sacrificial layer on the substrate, may produce (i) one or more holes within the barrier layer(s) and/or (ii) electrical components, which are physically joined by a barrier layer(s) at a proximal end and physically separated at a distal end. In one embodiment, a mesh structure may be disposed upon a contiguous substrate, which provides structural support for the device during deployment into an environment.

"Contiguous" refers to materials or layers that are touching or connected throughout in an unbroken sequence. In one embodiment, a contiguous layer of an implantable biomedical device has not been etched to remove a substantial portion (e.g., 10% or more) of the originally provided material or layer.

"Active circuit" and "active circuitry" refer to one or more components configured for performing a specific function. Useful active circuits include, but are not limited to, amplifier circuits, multiplexing circuits, current limiting circuits, integrated circuits, transistors and transistor arrays. The present invention includes devices wherein the one or more active or passive electronic device components, such as the one or more inorganic semiconductor components, one or more metallic conductor components, and/or one or more dielectric components comprise an active circuit or plurality of active circuits.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbounded components or portions of a component, in contrast, are capable of substantial movement relative to the substrate. In an embodiment, the invention provides devices wherein one or more inorganic semiconductor components, one or more metallic conductor components and/or one or more dielectric components are directly or indirectly bonded to the substrate, for example, via an adhesive layer or via an adhesion layer.

A "selectively transformable material" is a material that undergoes a physical change and/or a chemical change under pre-selected and/or predetermined conditions, such as conditions of time, pressure, temperature, chemical or biological composition, and/or electromagnetic radiation. Selectively transformable materials useful for some device applications undergo a physical transformation, such as a phase change including melting, sublimation, etc., optionally at a pre-selected time or at a pre-selected rate or in response to a pre-selected set of conditions or change in conditions. Selectively transformable materials useful for some device applications undergo a chemical transformation, such as decomposition, disintegration, dissolution, hydrolysis, resorption, bioresorption, photodecomposition, depolymerization, etching, or corrosion, optionally at a pre-selected time or at a pre-selected rate or in response to a pre-selected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, magnetic conditions, mechanical strain, or electronic conditions. When the selectively transformable material of a transient electronic device is exposed to the condition(s) that initiate transformation of the material, the selectively transformable material may be substantially completely or completely transformed at a "pre-selected time" or a "pre-selected rate". Devices of the invention include selectively transformable materials that undergo a complete transformation, substantially complete transformation or an incomplete transformation. A selectively transformable material that is "substantially completely" transformed is 95% transformed, or 98% transformed, or 99% transformed, or 99.9% transformed, or 99.99% transformed, but not completely (i.e., 100%) transformed. In some embodiments, a selectively transformable material undergoes a chemical change resulting in a change in a physical, chemical, electronic or optoelectronic property, optionally at a pre-selected time or at a pre-selected rate. In an embodiment, for example, a selectively transformable material undergoes a chemical or physical change resulting in a change of a first composition characterized by a conducting or semiconducting material to a second composition characterized as an insulator. In some embodiments, a selectively transformable material is a selectively removable material.

A "selectively removable material" is a material that is physically and/or chemically removed under pre-selected or predetermined conditions such as conditions of time, pressure, temperature, chemical or biological composition, and/or electromagnetic radiation. In an embodiment, for example, a selectively removable material is removed via a processes selected from the group consisting of decomposition, disintegration, dissolution, hydrolysis, resorption, bioresorption, photodecomposition, and depolymerization, optionally at a pre-selected time or at a pre-selected rate or in response to a pre-selected set of conditions or change in conditions. In an embodiment, for example, a selectively removable material is removed by undergoing a phase change, such as melting or sublimation, resulting in loss or relocation of the material, optionally at a pre-selected time or at a pre-selected rate or in response to a pre-selected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, electronic conditions. When the selectively removable material of a transient electronic device is exposed to the condition(s) that initiate removal of the material, the selectively removable material may be substantially completely, completely removed or incompletely removed at a "pre-selected time" or a "pre-selected rate". A selectively removable material that is "substantially completely" removed is 95% removed, or 98% removed, or 99% removed, or 99.9% removed, or 99.99% removed, but not completely (i.e., 100%) removed.

A "pre-selected time" refers to an elapsed time from an initial time, $t_0$. For example, a pre-selected time may refer to an elapsed time from a component/device fabrication or deployment, to a critical time, $t_c$, for example, when the thickness of a selectively removable material exposed to a pre-selected condition(s) reaches zero, or substantially zero (10% or less of initial thickness, 5% or less of initial thickness, 1% or less of initial thickness) or when a property (e.g. conductance or resistivity) of a selectively removable material reaches a threshold value; e.g., a decrease in conductivity equal to 50%, optionally for some applications 80%, and optionally for some applications 95% or alternatively when conductivity equals 0. In an embodiment, the pre-selected time may be calculated according to:

$$t_c = \frac{4\rho_m M(H_2O)}{kw_0 M(m)} \frac{\sqrt{\frac{kh_0^2}{D}}}{\tanh\sqrt{\frac{kh_0^2}{D}}};$$

where $t_c$ is the critical time, $\rho_m$ is the mass density of the material, $M(H_2O)$ is the molar mass of water, $M(m)$ is the molar mass of the material, $h_0$ is the initial thickness of the material, $D$ is the diffusivity of water, $k$ is the reaction constant for the dissolution reaction, and $w_0$ is the initial concentration of water.

A "pre-selected rate" refers to an amount of selectively removable material removed from a device or component per unit time. The pre-selected rate may be reported as an average rate (over the lifetime of the device or component) or an instantaneous rate. When a rate type is not specified, an average rate is assumed.

A "programmable transformation" refers to a pre-selected or predetermined physical, chemical and/or electrical change within a transient electronic device that provides a change of the function of the device from a first condition to a second condition. A programmable transformation may be pre-set at the time of component/device fabrication or deployment or a real-time triggered programmable transformation controlled by a transmitter that provides a signal received by the device.

A "transience profile" describes a change in physical parameters or properties (e.g., thickness, conductivity, resistance, mass, porosity, etc.) of a material as a function of time, e.g., thickness gained/lost over time. A transience profile may be characterized by a rate, for example, the rate of change of the physical dimensions (e.g., thickness) or physical properties (e.g., mass, conductivity, porosity, resistance, etc.) of a selectively transformable material. The invention includes selectively transformable materials having a transience profile characterized by a rate of change of the physical dimensions (e.g., thickness) or physical properties (e.g., mass, conductivity, etc.) that is constant or varies as a function of time.

"Degradable" refers to material that is susceptible to being chemically and/or physically broken down into smaller segments. Degradable materials may, for example, be decomposed, resorbed, dissolved, absorbed, corroded, de-polymerized and/or disintegrated. In some embodiments, the invention provides degradable devices.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue. A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed. In some embodiments, the invention provides bioresorbable devices.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal. In some embodiments, the invention provides biocompatible devices.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert devices.

"Ecocompatible" refers to a material that is environmentally benign in that it may be degraded or decomposed into one or more compounds that occur naturally in the environment. In some embodiments, the invention provides ecocompatible devices.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides device comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has ratio of thickness to a lateral dimension (e.g., length or width) selected from the range of 0.1 to 0.0001.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide, silk, silk composite, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers; thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied.

Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment.

Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Transient devices and methods of making and using the devices will now be described with reference to the figures. For clarity, multiple items within a figure may not be labeled and the figures may not be drawn to scale.

In some embodiments, implantable biomedical devices advantageously utilize silk as a bioresorbable substrate. Silk is biocompatible, FDA-approved, optically transparent, mechanically robust (high mechanical modulus and toughness), and flexible in thin film form. It is also compatible with aqueous processing, which preserves sensitive electronic functions, and amenable to chemical and biological functionalization. The presence of diverse amino acid side chains facilitates coupling chemistry for functionalizing silks. Silk is also water soluble with programmable rates of proteolytic biodegradation (yielding non-inflammatory amino acids) over a range from minutes to hours to years.

Some other natural polymers that exhibit properties similar to or analogous to silk include, but are not limited to, chitosan, collagen, gelatin, agarose, chitin, polyhydroxyalkanoates, pullan, starch (amylose amylopectin), cellulose, hyaluronic acid, or any combination of these.

Silk may be obtained from various natural sources, for example, from the silkworm *Bombyx mori* or from the spider *Nephila clavipes*. Silk solutions used in accordance with embodiments of the present invention may be obtained, for example, from a solution containing a dissolved silkworm silk (e.g. from *Bombyx mori*), a dissolved spider silk (e.g. from *Nephila clavipes*), or from a solution containing a recombinant silk, such as from bacteria, yeast, mammalian cells, transgenic animals, or transgenic plants.

In an embodiment, the silk of the bioresorbable substrate may be silk fibroin protein, which consists of layers of antiparallel beta sheets and has a primary structure consisting mainly of the recurrent amino acid sequence (Gly-Ser-Gly-Ala-Gly-Ala)$_n$. Fibroin is known to arrange itself in three structures, called silk I, II, and III. Silk I is the natural, amorphous form of fibroin, as emitted from the *Bombyx mori* silk glands. Silk II refers to the crystalline arrangement of fibroin molecules in spun silk, which has greater strength. Silk III is formed principally in solutions of fibroin at an interface (i.e. air-water interface, water-oil interface, etc.). In the disclosed transient devices, silk I, II and/or III may be used.

Silk substrates may be prepared from material derived from *Bombyx mori* cocoons, according to published procedures. See, Sofia, S., McCarthy, M. B., Gronowicz, G. & Kaplan, D. L. Functionalized silk-based biomaterials for bone formation. *J. Biomed. Mater. Res.* 54, 139-148 (2001); Perry, H., Gopinath, A., Kaplan, D. L., Negro, L. D. & Omenetto, F. G. Nano- and micropatterning of optically transparent, mechanically robust, biocompatible silk fibroin films. *Adv. Mater.* 20, 3070-3072 (2008); and WO 2008/108838. Briefly, boiling the cocoons in a 0.02 M aqueous solution of sodium carbonate for 60 minutes removed sericin, a water-soluble glycoprotein that binds fibroin filaments in the cocoon but which can induce undesirable immunological responses. An aqueous solution of lithium bromide at 60° C. solubilized the silk fibroin fibers and subsequent dialysis removed the lithium bromide. Centrifugation followed by microfiltration eliminated particulates to yield solutions of 8-10% silk fibroin with minimal contaminants.

Using an alternate method, silk solutions may be prepared using organic solvents, as described in WO 2008/108838 which is hereby incorporated by reference in its entirety. Use of organic solvents in the preparation of silk materials can alter the biocompatibility and physical properties of silk materials. For example, immersion of silk films in organic solvents, such as methanol, may cause dehydration of the hydrated or swollen structure, leading to crystallization and, thus, loss of solubility in water. Further, the use of organic solvents can render the silk material less degradable.

As noted above, the presence of organic solvents, as compared to aqueous solvents, in the silk solution, may generate silk substrates with more crystalline structures, as compared to amorphous structures. This phenomenon may be used to control, for example, the rate of bioresorption or degradation of the silk. Accordingly, depending on the desired resorption or degradation rate, the silk solution may be prepared using any suitable ratio of aqueous:organic solution, for example, 100% aqueous, about 80% aqueous, about 60% aqueous, about 50% aqueous, about 40% aqueous, about 20% aqueous, or about 10% aqueous.

Additional techniques may be used to control the degradation rate of the silk substrate. For example, the rate at which degradation occurs may be tailored by altering: substrate material, substrate thickness, crosslinking, the extent of inter-chain hydrogen bonding or Van der Waals forces, and/or molecular alignment (e.g., via mono-axial or bi-axial stretching, spinning into fiber, and/or weaving).

Additional bioresorbable polymers including, but not limited to, a biopolymer, a synthetic polymer, a protein, a polysaccharide, poly(glycerol-sebacate) (PGS), polydioxanone, poly(lactic-co-glycolic acid) (PLGA), polylactic acid (PLA), collagen, chitosan, or any combination of these, may be used alone as the degradable substrate or may be added to the silk solution to generate composite silk substrates. In one embodiment, a substrate comprises from about 50 to about 99.99 parts by volume (vol %) silk protein solution and from about 0.01 to about 50 vol % additional polymer.

In some aspects, transient devices described herein may be used for drug delivery. In one embodiment, one or more therapeutic agents may be encapsulated within the substrate material as a liquid, a gel, a dispersed solid, or any other appropriate physical form, to be administered to a patient upon degradation of the substrate. To form these therapeutically enhanced substrate materials, the degradable polymer solution may be mixed with one or more therapeutic agents, and optionally a pharmaceutically acceptable carrier, prior to forming the substrate. Any pharmaceutical carrier that does not dissolve the degradable material may be used.

In some embodiments, transient devices of the invention are used to administer, deliver and/or activate a therapeutic agent provided to a subject. In an embodiment of this aspect, the degradable substrate is a multifunctional component that releases a therapeutic agent upon administration to a biological environment and/or contact with a target tissue. The invention includes, for example, degradable substrates having embedded therapeutic agents, such as drugs (e.g., small molecule therapeutics), nanoparticles and/or biomolecules, such as proteins, peptides, oligonucleotides (e.g., DNA or RNA), etc. This aspect of the present invention may be useful for a range of therapeutic applications including controlled release of therapeutic agents and/or targeted administration of therapeutic agents to a selected tissue type. Release of the therapeutic agent in these embodiments may occur by processes mediated by resorption of the degradable substrate in contact with a target tissue. The invention includes implantable devices and systems wherein the electronic device component mediates release of therapeutic agent from the degradable substrate via thermal means, for example by local heating of components of the implantable device, such as the degradable substrate. The invention includes implantable devices and systems wherein the electronic device component mediates release of therapeutic agent from the degradable substrate via processes driven by generation and control of local electric fields, such as electrophoresis processes for the release of proteins or peptides. The invention includes implantable devices and systems wherein the electronic device component mediates release and/or activation of a therapeutic agent from the degradable substrate via processes driven by absorption of electromagnetic radiation. In an embodiment, the implantable device includes an electronic device component, such as a laser or LED array, capable of optically activating a therapeutic agent during and/or upon release from the degradable substrate. This aspect of the invention is useful for therapeutic applications including phototherapy.

Therapeutic agents that may be used in conjunction with the devices described herein include, but are not limited to: small molecules; proteins; peptides; nucleotides; nucleic acids; carbohydrates; simple sugars; cells; genes; anti-thrombotics; anti-metabolics; anticoagulants; antimitotics; fibrinolytics; anti-inflammatory steroids; monoclonal antibodies; vitamins; sedatives; steroids; hypnotics; antiinfectives, such as antibiotics and antiviral agents; chemotherapeutic agents (i.e., anticancer agents); prostaglandins, radiopharmaceuticals, anti-rejection agents; analgesics; anti-inflammatory agents; hormones, such as steroids; growth factors (inhibitors and promoters), such as epidermal growth factor, fibroblast growth factor, platelet-derived growth factor, insulin-like growth factor, transforming growth factors, and vascular endothelial growth factor; anti-angiogenic proteins such as endostatin; polysaccharides; glycoproteins; lipoproteins; and any combination of these.

For example, a therapeutic agent circulating through an in-vivo biological environment may be activated when it receives electromagnetic radiation from a biomedical device implanted at a therapeutic site. In particular, energy within the ultraviolet and visible regions of the electromagnetic spectrum may be useful.

The invention may be further understood by the following non-limiting examples.

EXAMPLE 1

Transient, Biocompatible Electronics and Energy Harvesters Based on ZnO

Semiconducting oxides are of growing interest as replacements for silicon in thin film transistors for active matrix display backplanes; they are also of potential use in transparent, flexible electronics and energy harvesters. Zinc oxide (ZnO), in particular, has a favorable combination properties, including excellent transparency in the visible wavelength range, [1] high electron mobility, [2] and strong piezoelectric responses. [3] As a result, ZnO, in forms ranging from films to wires and rods, has been explored in sensing, [4-6] catalysis, [7,8] optical emission, [9,10] piezoelectric transduction, [11] and actuation. [12] Previous work also suggests that ZnO is biocompatible, [13-15] and therefore suitable for devices that integrate on or in the human body. Here we introduce classes of ZnO based electronic devices that have, as their key attribute, the ability to dissolve completely in water or biofluids. In this way, ZnO provides an alternative to silicon[11] or organic semiconductors[17, 20] for physically transient forms of electronics and sensors, with expanded capabilities in energy harvesting, light emission and others. In addition to ZnO, the other constituent materials of the devices presented here include magnesium (Mg) for electrodes and interconnects, silicon dioxide (SiO2) or magnesium oxide (MgO) for the dielectrics, and films of silk fibroin film for the substrate and package. We report specific designs and fabrication schemes for ZnO thin film transistors and mechanical energy harvesters (also for use as strain gauges). Detailed studies reveal the kinetics of dissolution and the ability to use materials and design choices to control this kinetics. Combined experimental/theoretical work illustrates the key operational features of the devices.

FIG. 1a and b provide a schematic diagram and an image of water-soluble ZnO thin film transistors (TFTs) and mechanical energy harvesters (MEHs)/strain gauges. Sheets of silk fibroin provide substrates and, in certain cases, encapsulating layers. Magnesium, patterned by electron beam evaporation through fine-line stencil masks made of polyimide (PI) films (Kapton, 12.5 µm, Dupont, USA), serves as the electrodes and interconnects (thicknesses between 200 and 500 nm). A first layer of Mg defines the source/drain electrodes for the TFTs (and, therefore the channel length, Lch) and the bottom electrodes of the MEHs. Sputter deposition of thin films of ZnO (thicknesses between 350 and 500 nm) through PI masks forms semiconducting and piezoelectric components of the devices. The widths of the ZnO films define the channel widths (W) of the transistors. Layers of MgO (thicknesses between 100 and 150 nm) deposited by electron beam evaporation through PI masks form the gate dielectric layers for the TFTs. An additional patterned deposition of Mg (~400 nm) yields top electrodes for MEHs, and source, drain and gate contacts for the TFTs. A top encapsulating layer of silk can be applied by spin casting. All constituent materials, i.e. Mg (electrodes, contacts and interconnects), MgO (gate and interlayer dielectrics), ZnO (active material for the TFTs and energy harvesters/strain gauges) and silk (substrate and encapsulant), dissolve in water. The products of this dissolution include $Mg(OH)_2$, $Si(OH)_4$ and $Zn(OH)_2$. Previous studies suggest that these products, and the device materials themselves, are biocompatible and environmentally benign. [21-23] FIG. 1c includes a set of images collected in a time sequence during dissolution in deionized water (DI) at room temperature. The silk substrate (~25 µm), in the formulation used for this example, quickly disappears by simple dissolution. This process causes the device structures to physically disintegrate. Afterward, each remaining material disappears due to hydrolysis at different rates, as described in the following sections and previous reports. [24-28] The time frames for dissolution can be programmed not only by encapsulation and packaging methods, but also by choices of dimensions, thicknesses and configurations in the materials for the device structures.

Figure 2:
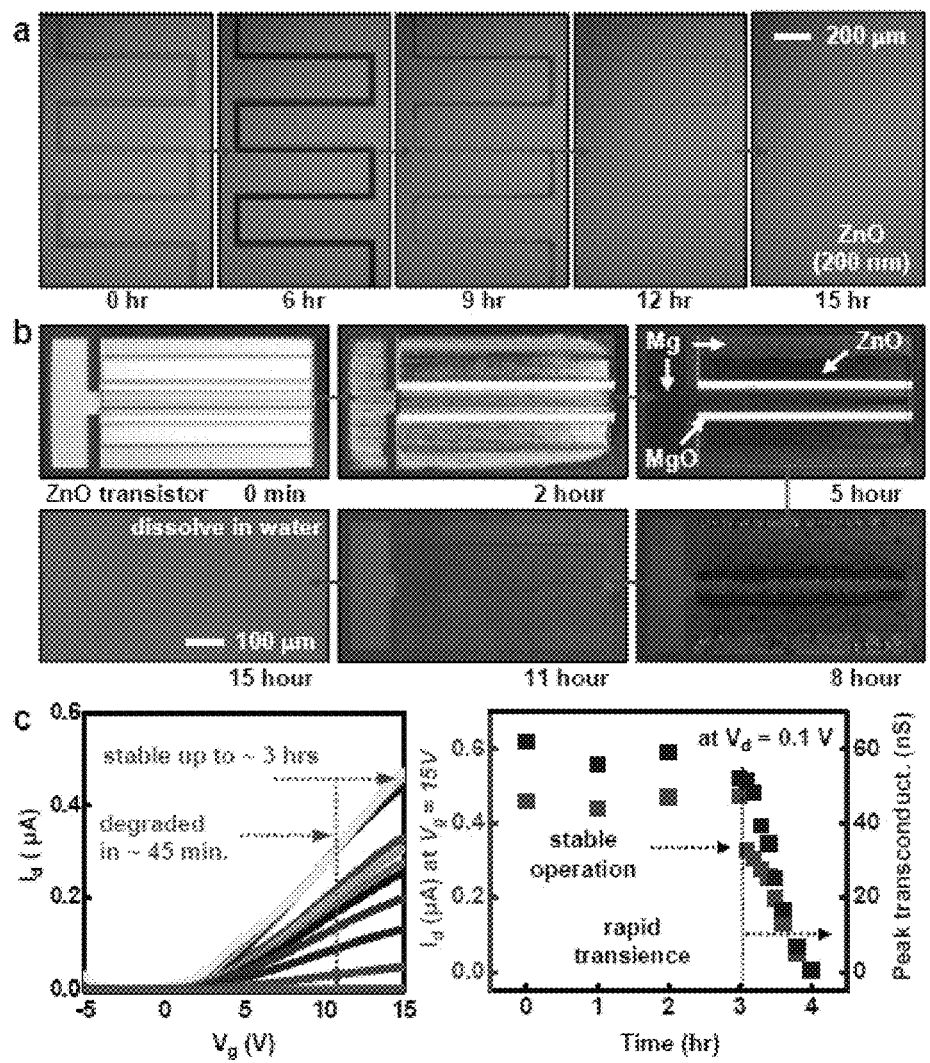
FIG. 2. Dissolution kinetics of water soluble electronic materials, and devices. a) A series of optical microscope images collected at various times during dissolution of a meander trace of ZnO (200 nm) immersed in deionized water at room temperature. b) Images of a representative ZnO TFT at various times during dissolution. All components fully dissolve. c) Experimental results of degradation in electrical properties of a ZnO TFT encapsulated with MgO (500 nm) at various times after immersion in water. The linear scale transfer curves (left) and the drain current ($I_d$) at drain and gate voltages of $V_d$=0.1 V and $V_g$=5 V, respectively, and the peak transconductance (left) show that the operation of the device is stable for ~3 hours, after which the properties quickly degrade in ~45 min.
Figure 4:
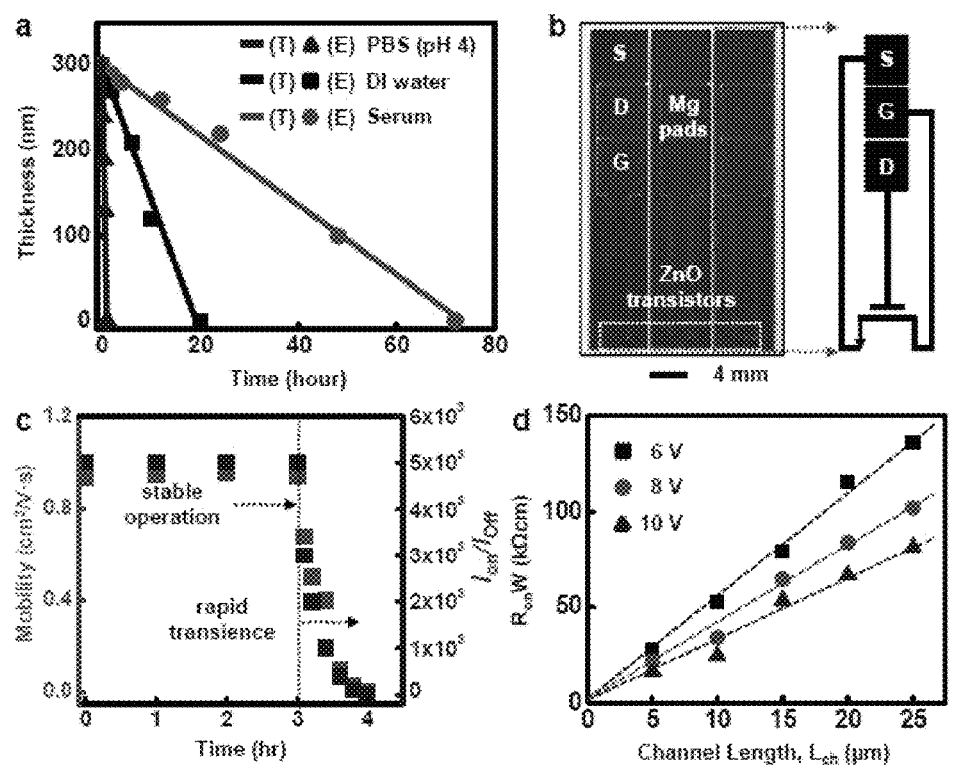
FIG. 4. a) Experimental (E) and theoretical (T) changes in the thickness of a thin film of ZnO as a function of time, during dissolution in different solutions: phosphate buffer solution (PBS, pH 4, blue), DI water (black), bovine serum (red). b) Image of the ZnO TFT used to study dissolution kinetics at the device level, with a circuit diagram. c) Calculated mobility (red) and on/off ratio (blue), corresponding to transfer curves in the right frame of FIG. 2c. d) Width-normalized on-state resistance at various channel lengths and gate biases.

Dissolution of the constituent materials, other than the silk, involves hydrolysis to produce metal hydroxides. In the case of ZnO, the product is zinc hydroxide ($Zn(OH)_2$), as a result of the reaction $ZnO+H_2O \leftrightarrow Zn(OH)_2$. FIG. 2a shows a collection of images of a meander trace of ZnO (200 nm) at various times during hydrolysis. The trace completely disappears after 15 hours, in DI water at room temperature. The mechanisms of dissolution of ZnO can be analytically described by reactive diffusion models, in which water diffusion into the materials is the rate limiting process. Previous reports describe in detail the dissolution behaviors of ZnO and the dependence on pH, temperature, dimensions and surface structures. [21, 29-32] Additional experiments on dissolution, monitored by measurements of thickness as a function of time of immersion in several different types of solutions, such as PBS, serum, and comparison of the results with theoretical models (see SI for details) appear in FIG. 4a. A set of optical micrographs shows a fully formed ZnO TFT undergoing dissolution under similar conditions, as presented in FIG. 2b. All electronic materials, i.e. Mg, MgO and ZnO, completely dissolve in 15 hours after immersion in DI water at room temperature, in a controlled manner, without cracking, flaking or delamination. For the device dimensions studied here, the thicknesses of the layers determine, in large part, the timescales for dissolution.

FIG. 2c summarizes the temporal variation in the electrical properties of a ZnO TFT, as it dissolves. (See FIG. 4a for an image and diagram of the device.) In this case, a plate of glass serves as the substrate, and a layer of MgO (500 nm), deposited by electron beam evaporation, encapsulates the entire system everywhere except at the contacts for source, drain, and gate electrodes which themselves are not immersed. Measured transfer curves, drain currents (Id) and peak transconductances show stable operation for ~3 hours, followed by rapid degradation over the next ~45 min. The encapsulant and the device materials (mainly the Mg in this case) define the first and second timescales, respectively. The results of FIG. 2c are only representative. The encapsulant material and thickness can be selected to achieve stable periods of device operation that match requirements for specific applications.

Figure 3:
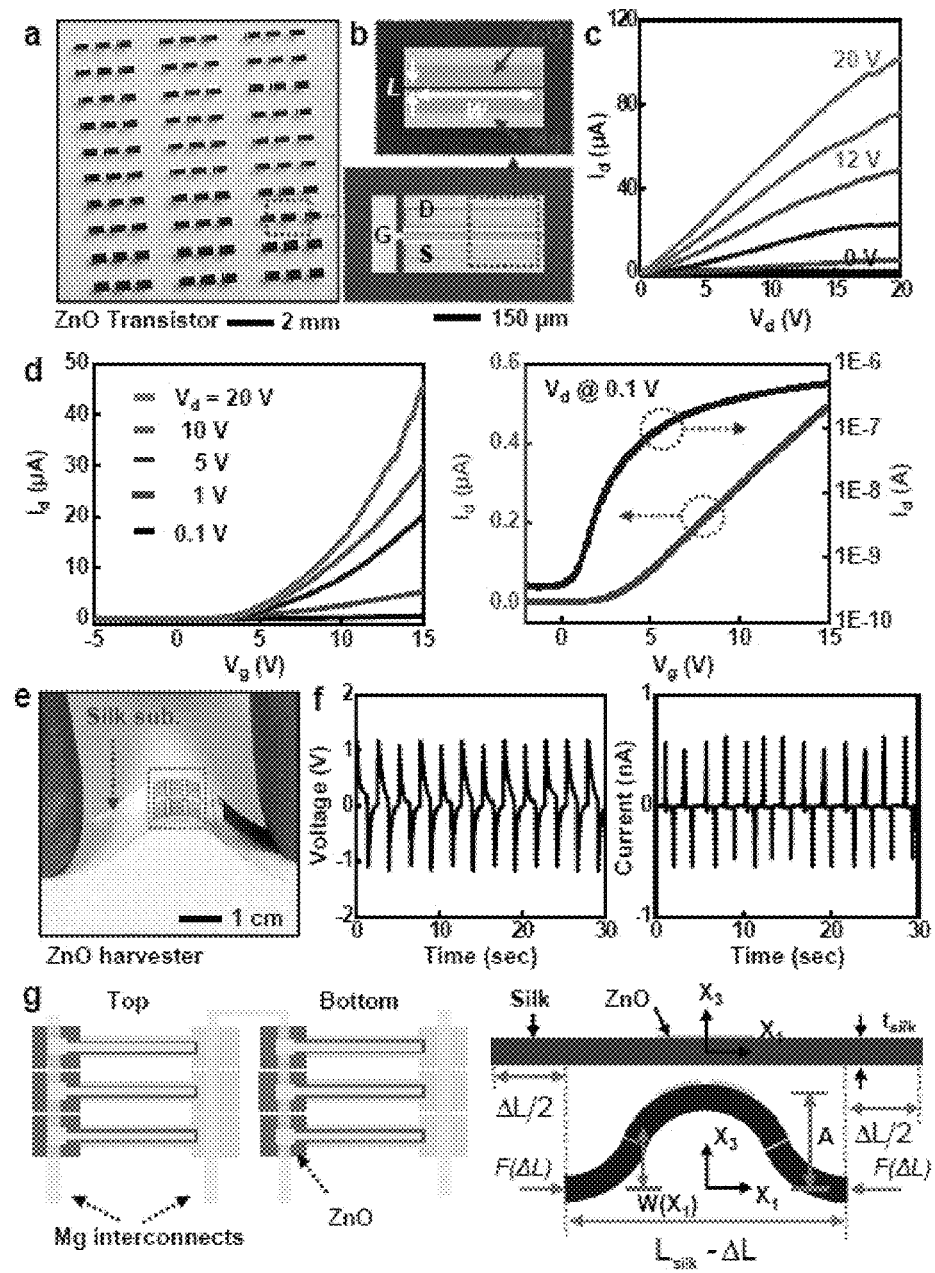
FIG. 3. Electrical characterization of ZnO TFTs and MEHs. a) Image of an array of ZnO TFTs on a silk substrate. The devices use Mg (source, drain, and gate electrodes), ZnO (active layer) and MgO (gate dielectric). b) Optical micrographs of a TFT, after defining the channel configuration (top), and after completing the fabrication (bottom). c) Current-voltage characteristics of a typical device, at different gate biases. d) Linear scale transfer curves at various drain voltages (left), and linear (red) and log scale (blue) transfer curves at a drain voltage of 0.1 V (right). e) Optical image of an array of ZnO MEHs on a silk substrate. f) Output voltage vs time and output current vs time during cycles of bending. g) Schematic illustration of ZnO strips connected in series, and the theoretical shape for buckling of a device under compression.

Complete electrical and mechanical measurements on transient ZnO TFTs and MEHs appear in FIG. 3. Here, the TFTs use Mg (150 nm, source, drain and gate electrodes), ZnO (200 nm, active layer), MgO (100 nm, gate dielectric). FIG. 3b illustrates additional details in optical micrographs of a typical TFT, collected after defining the channel configuration (top) and completing the fabrication (bottom). Analysis of current-voltage (I-V) characteristics, and linear and log scale transfer curves (FIG. 3c-d) of a typical device (channel length (Lch) and width (W) are 20 µm and 500 µm, respectively) yield a mobility of ~0.95 cm2/V·s, an on/off ratio of >103, a sub-threshold swing of ~1 V/dec (at Vd=0.1 V) and a threshold voltage of ~1 V. (See details on contact resistance of Mg in FIG. 4b). These properties are similar to those of non-transient counterparts reported previously.[33-36]

FIG. 3e presents an image of an array of MEHs, each with a capacitor type geometry. A layer of ZnO (500 nm) lies between bottom (300 nm) and top electrodes (500 nm) of Mg, which define an active area of 50 µm×2 mm. An MEH consists of six groups of devices; each group includes ten separate capacitor structures electrically connected in parallel. The six groups are connected in series. A IPC Flexural Endurance Tester (Model: CK-700FET) enables accurate evaluation of properties under bending. The test configuration involves the two edges of the sample fixed within the two sliding fixtures of the instrument. During compression, the sample mechanically buckles upward to generate a well-defined, although non-uniform bending moment. Periodic variations in positive and negative voltage output peaks accompany the application and release of the buckling stresses (tensile at the location of the devices), respectively. The voltage and current outputs from an MEH are ~1.14 V and ~0.55 nA, as shown in FIG. 3f. The peak power density is ~1 nW/cm2. FIG. 3g gives a schematic illustration of narrow strips of ZnO films connected in series, and the theoretically predicted shape of the buckled device.

Analytical models that couple the mechanical deformation and the piezoelectric effect provide additional insights into the behaviours. Compression of the silk substrate of length Lsilk leads to its buckling with a representative out-of-plane displacement $w=A[1+\cos(2\pi x_1/L_{silk})]/2$, where the origin of coordinate x1 is at the center of silk substrate, and the amplitude A is related to the compression ΔL between two ends of the silk substrate by $A \approx (2/\pi)\sqrt{L_{silk} \cdot \Delta L}$ (see SI for details). The ZnO strips, together with the top and bottom electrodes, bend with the buckled silk substrate. The strain in the ZnO consists of membrane and bending strains.

Figure 5:
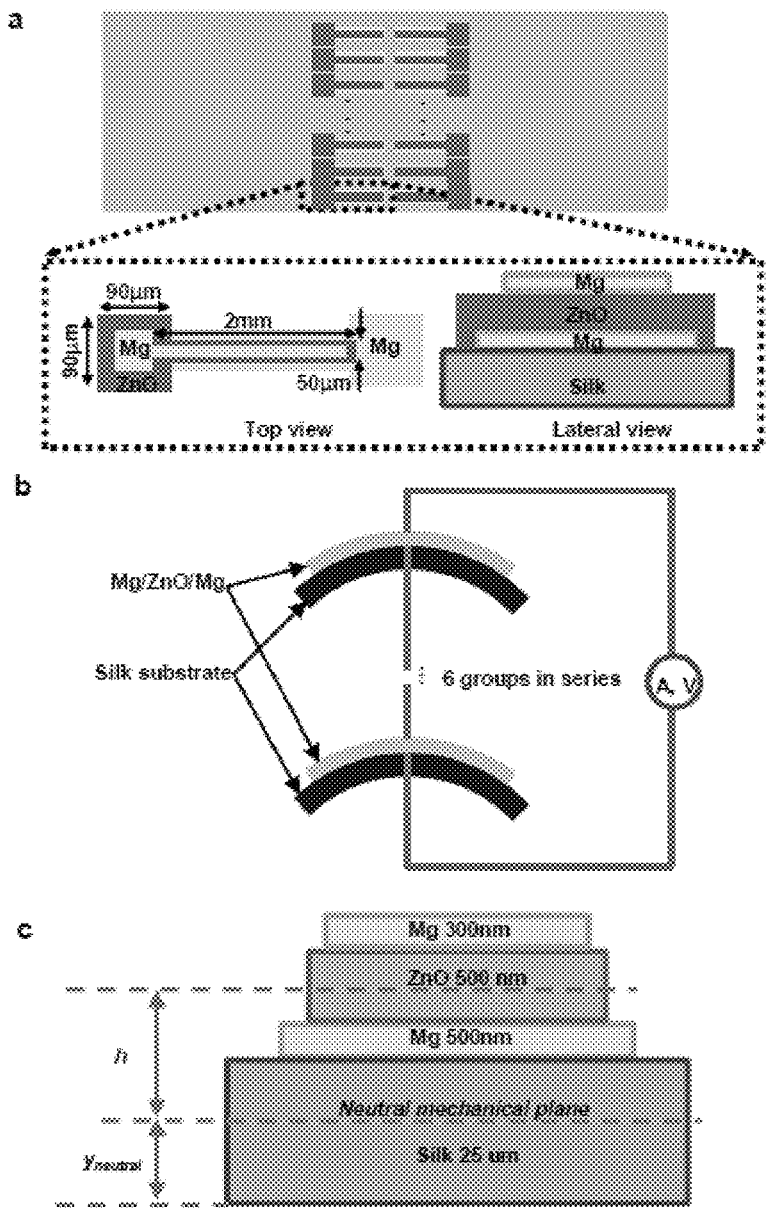
FIG. 5. a) Schematic illustration of an array of ZnO strips, and top and lateral views of a single strip. b) Schematic illustration of a buckled array of ZnO strips on a silk substrate. c) Schematic description of the membrane strain in the various layers of a ZnO MEH and the position of the neutral mechanical plane of the device.

The membrane strain is given analytically by $\varepsilon_m = 4\pi \sqrt{\Delta L/L_{silk}} (\overline{EI}_{silk}/\overline{EI}_{comp})(h/L_{silk})$; [37] (see SI for details), where $\overline{EI}_{silk}$ and $\overline{EI}_{comp}$ are the bending stiffnesses of silk substrate and the composite structure of ZnO strips with electrodes and silk substrate, respectively; and h is the distance between the center of ZnO strips and the neutral mechanical plane of the composite structure (FIG. 5). The bending strain is much smaller than the membrane strain since the ZnO strips on the surface of silk substrate are very thin. As a result, the total strain is essentially the same as the membrane strain. In addition, the bending strain has opposite signs above and below the center of ZnO strips and does not contribute to the voltage and current output of the MEH (see SI for details).

The ZnO strips are transversely isotropic with elastic, piezoelectric, and dielectric constants cij, eij, and kij, respectively. The polarization direction x3 is normal to the surface of the strip and the surface of the silk substrate. For plane-strain deformation ($\varepsilon_{22}=0$) the strain $\varepsilon_{33}$ and the electric field E3 along the polarization direction x3 satisfy the constitutive relations $0 = c_{11}\varepsilon_{11} + c_{13}\varepsilon_{33} - e_{31}E_3$ and $D_3 = e_{31}\varepsilon_{11} + e_{33}\varepsilon_{33} + k_{33}E_3$, where the electric displacement D3 along the polarization direction is a constant to be determined. For measurements of current, the top and bottom electrodes are connected to an ammeter as shown in FIG. 5b. The ammeter has negligible electrical resistance, and therefore negligible voltage drop. The current (through the electrodes and ammeter) results from the moving charge induced by the strain in the ZnO (i.e., piezoelectric effect) even without voltage between the top and bottom electrodes. The zero voltage between the top and bottom electrodes of each ZnO strip, together with the above equations, gives $D_3 = \overline{e}\varepsilon_m$, where $\overline{e} = e_{31} - (c_{13}/c_{33})e_{33}$ is the effective piezoelectric constant which, together with the above equations, gives $D_3 = \overline{e}\varepsilon_m$, where $\overline{e} = e_{31} - (c_{13}/c_{33})e_{33}$ is the effective piezoelectric constant. For each group of device in series, the current I is given by $I = -A_{ZnO}\dot{D}_3$, where $A_{ZnO}$ is total area of ZnO strips in each group. For a representative compression $\Delta L = \Delta L_{max}[1 - \cos(2\pi t/T)]/4$ with the maximum compression $\Delta L_{max}$ and period T, the maximum current is obtained as $$I_{max} = 4\pi^2 \frac{(-\overline{e})A_{ZnO}}{T} \frac{\overline{EI}_{silk} h}{\overline{EI}_{comp} L_{silk}} \sqrt{\frac{\Delta L_{max}}{L_{silk}}}. \tag{1}$$

For $\Delta L_{max} = 1.5$ cm, T=2.3 second and Lsilk=3 cm as in experiments, $\overline{EI}_{silk}/\overline{EI}_{comp} = 0.34$, h=5.5 μm and AZnO=1.08 mm2 from the specimen geometry (see SI for details), and $\overline{e} = -0.67$ C/m², which is on the same order of magnitude as the literature values [38,39] Eq. (1) gives the maximum current $I_{max} = 0.55$ nA, which agrees well with the experimental result as shown in FIG. 3f.

For measurements of voltage, if V denotes the total voltage for n groups of devices in series, then the voltage across each group is V/n. The electric displacement becomes $D_3 = \overline{e}\varepsilon_m + \overline{k}V/(nt_{ZnO})$, where $\overline{k} = k_{33} + (e_{33}^2/c_{33})$ is the effective dielectric constant and $t_{ZnO}$ is the thickness of ZnO strips. The current $I = -A_{ZnO}\dot{D}_3$ is also related to the voltage V and resistance R of the voltmeter by I=V/R, which gives $V/R = -A_{ZnO}\dot{D}_3$, or equivalently $$\frac{dV}{dt} + \frac{nt_{ZnO}}{A_{ZnO} R\overline{k}} V = -\frac{n\overline{e}t_{ZnO}}{\overline{k}} \frac{d\varepsilon_m}{dt}. \tag{2}$$

For $\Delta L = \Delta L_{max}[1 - \cos(2\pi t/T)]^2/4$ and the initial condition V(t=0)=0, the maximum voltage is given by $$V_{max} \approx 4\pi^2 R \frac{(-\overline{e})A_{ZnO}}{T} \frac{\overline{EI}_{silk} h}{\overline{EI}_{comp} L_{silk}} \sqrt{\frac{\Delta L_{max}}{L_{silk}}}. \tag{3}$$

Figure 6:
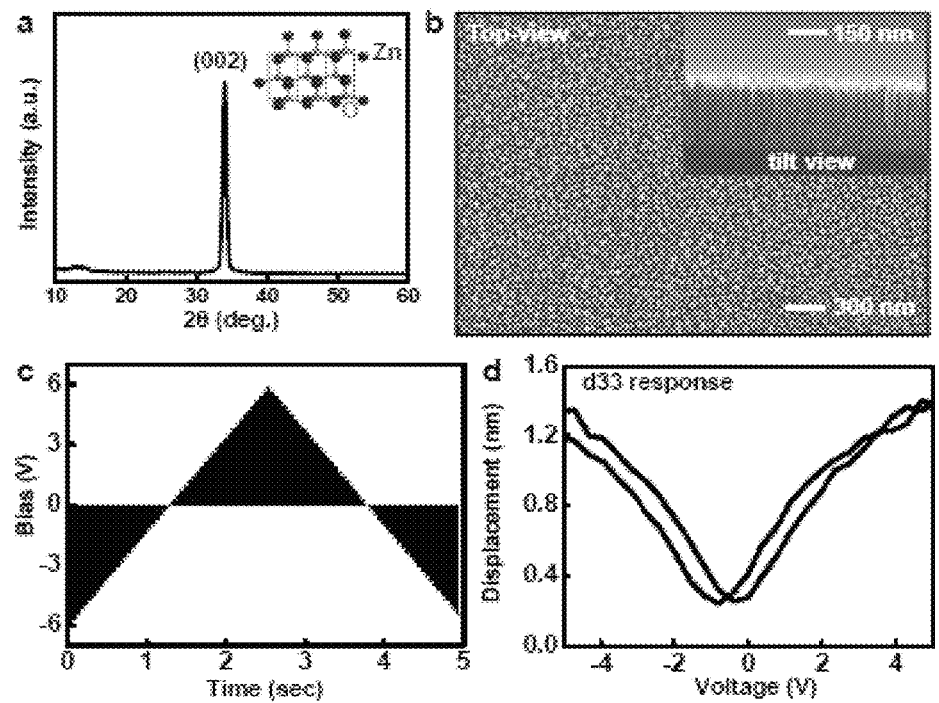
FIG. 6. a) X-ray diffraction pattern of a thin film of ZnO, with preferred orientation labeled (002). b) Top view scanning electron microscope (SEM) image of a sputtered ZnO thin film, with cross sectional image in the inset. c) Typical bias profile for d33 measurement. (Details in SI). d) Measured displacements as a function of voltage applied to the ZnO thin film.

For $R=2.3 \times 10^9 \Omega$ in the experiment, the theory gives the maximum voltage 1.1V, which agrees well with experiment result of 1.14V. In addition to electrical characterization of devices, the intrinsic piezoelectric and morphological properties of active layer ZnO thin film by sputtering system was studied by AFM, SEM, and XRD techniques in detail (FIG. 6).

The results presented here indicate that ZnO can be used effectively as an active material for transient electronics, as well as for energy harvesting and strain sensing devices, for which all of the constituent elements dissolve completely in water. Compared to silicon, ZnO has features, such as wide, direct bandgap and piezoelectric responses, that could enable expanded capabilities in transient devices. The use of this material alone, or in heterogeneous configurations with silicon, open up additional application possibilities for transient technologies, in areas ranging from biomedicine, to environmental monitor and certain areas of consumer electronics.

Experimental Section

Fabrication of ZnO TFTs and MEHs: All electronic materials were directly deposited onto silk through high resolution stencil masks made of polyimide (PI) films (Kapton, 12.5 μm, Dupont, USA). These materials consist of ZnO (semiconductor), Mg (conductors), MgO (insulators), silk (substrate). A layer of Mg (150 nm) deposited by electron beam evaporation (Temescal) defined the source and drain electrodes for the TFTs. ZnO (200 nm) deposited by RF magnetron sputtering (AJA) through a PI mask served as the semiconductor. A high-purity of ZnO target was used (99.99%), with base pressures of 2×10-6 torr, and working pressures of 15 mTorr, maintained with a Ar (99.99%): O2=2:1 (sccm) gas mixture. The sputtering was performed at room temperature (RT) with an RF power of 250 W, immediately after cleaning the target with Ar plasma for 5 min. The deposition rate was ~150 nm/hour. Electron beam evaporation of MgO (100 nm), also through PI masks, defined the gate dielectrics. The gate consisted of Mg (300 nm), deposited and patterned using schemes similar to those for the source and drain.

ZnO MEHs were designed in six groups, each of which contains ten separate devices (ZnO strips with Mg electrodes on top and bottom, in a capacitor type geometry). Devices within each group were connected in parallel; the six groups themselves were connected in series. The fabrication began with deposition of Mg (300 nm) by electron beam evaporation through a PI shadow mask, to form bottom electrodes. Layers of ZnO (400~500 nm) were then formed on top by RF sputtering, under conditions described above. ZnO was deposited through a shadow mask aligned to Mg bottom electrodes. Top electrodes of Mg (~500 nm) were formed in a manner similar to that for the bottom electrodes. Individual ZnO strips defined active areas of 50 μm×2 mm. Square pads at their ends facilitated electrical top and bottom electrode contacts. The ZnO layer was formed in a geometry slightly bigger than that of the bottom electrode to avoid shorting of top to bottom, as seen in FIG. 5.

Investigation of ZnO thin film properties and device analysis: X-ray diffraction (XRD, Philips X'pert) revealed that the films consist of hexagonal ZnO, with preferred orientation of (002). Scanning electron microscope (SEM, Hitachi S4800) imaging determined the surface topography and provided cross sectional views of the films. Measurements of voltage induced displacements in thin films of ZnO were conducted by atomic force microscopy (AFM, Asylum Cypher, USA). A semiconductor parameter analyzer (4155C, Agilent) was used to measure the electrical characteristics of TFTs and MEHs.

Bending tests for energy harvesters/strain gauges: A commercial instrument (IPC Flexural Endurance Tester Model: CK-700FET) was used to perform bending experiments. The test involved compressing a sheet of devices between two clamped edges; the result is a buckling structure whose curvature is defined by the extent of compression. Electrical measurements revealed positive and negative swings in voltage and current output, corresponding to the application and release of such buckling stresses. An analytical model of the mechanical deformations and the associated piezoelectric effects captured the experimental observations.

Dissolution experiments: Dissolution tests were performed to study degradation behaviors of devices and kinetics of materials removal. To observe dissolution of ZnO, a meander trace of ZnO (200 nm) on a glass substrate was submerged in DI water at room temperature. Optically significant changes were observed after 9 hours, and complete disappearance occurred within 15 hours. In a similar way, a ZnO transistor, consisting of Mg, MgO and ZnO, on glass was used to illustrate the various stages of dissolution at the device level. Most components disappeared within 8 hours; complete dissolution occurred within 15 hours. In addition, measurements of changes in electrical properties defined timescales of device function. A transistor with a design similar to that described above was prepared and then encapsulated with a layer of MgO (500 nm). Measured and calculated characteristics revealed two-stage kinetics. The first was determined by the encapsulation layer; the second, primarily by the Mg electrodes.

References

[1] S. Mondal, K. P. Kanta, P. Mitra, *Journal of Physical Sciences* 2008, 12, 221.
[2] K. Miyamoto, M. Sano, H. Kato, T. Yao, *Journal of Crystal Growth* 2004, 265, 34.
[3] M. H. Zhao, Z. L. Wang, S. X. Mao, *Nano Lett.* 2004, 4, 587.
[4] S. K. Gupta, A. Joshi, M. Kaur, *J. Chem. Sci.* 2010, 122, 57.
[5] N. Kumar, A. Dorfman and J. I. Hahm, *Nanotechnology* 2006, 17, 2875.
[6] H. Gullapalli, V. S. M. Vemuru, A. Kumar, A. Botello-Mendez, R. Vajtai, M. Terrones, S. Nagarajaiah, P. M. Ajayan, *Small* 2010, 6, 1641.
[7] L. Saad, M. Riad, *J. Serb. Chem. Soc.* 2008, 73, 997.
[8] B. V. Kumar, H. S. B. Naik, D. Girija, B. V. Kumar, *J. Chem. Sci.* 2011, 123, 615.
[9] S. Baskoutas, G. Bester, *J. Phys. Chem. C* 2011, 115, 15862.
[10] C. Czekalla, J. Guinard, C. Hanisch, B. Q. Cao, E. M. Kaidashev, N. Boukos, A. Travlos, J. Renard, B. Gayral, D. L. S. Dang, M. Lorenz, M. Grundmann, *Nanotechnology* 2008, 19, 115202.
[11] H. Choi-Yim, R. Busch, W. L. Johnson, *J. Appl. Phys.* 1998, 83, 7993.
[12] F. R. Blom, D. J. Yntema, F. C. M. Van De Pol, M. Elwenspoek, J. H. J. Fluitman, T. J. A. Popma, *Sensors and Actuators* 1990, 21, 226.
[13] Z. Li, R. Yang, M. Yu, F. Bai, C. Li, and Z. L. Wang, *J. Phys. Chem. C* 2008, 112, 20114.
[14] Y. F. Zheng, R. Z. Li, Y. D. Wang, *International Journal of Modern Physics B* 2009, 23, 1566.
[15] S. Dutta, S. Basak, P. K. Samanta, International Journal of NanoScience and Nanotechnology 2012, 3, 27.
[16] S. W. Hwang, H. Tao, D. H. Kim, H. Cheng, J. K. Song, E. Rill, M. A. Brenckle, B. Panilaitis, S. M. Won, Y. S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, Science 2012, 337, 1640.
[17] C. Legnani, C. Vilani, V. L. Calil, H. S. Barud, W. G. Quirino, C. A. Achete, S. J. L. Ribeiro, M. Cremona, *Thin Solid Films* 2008, 517, 1016.
[18] M. Irimia-Vladu, P. A. Troshi, M. Reisinger, L. Shmygleva, Y. Kanbur, G. Schwabegger, M. Bodea, R. Schwödiauer, A. Mumyatov, J. W. Fergus, V. F. Razumov, H. Sitter, N. S. Sariciftci, S. Bauer, *Adv. Funct. Mater.* 2010, 20, 4069.
[19] C. J. Bettinger, Z. Bao, *Polym Int* 2010, 59, 563.
[20] C. J. Bettinger, Z. Bao, *Adv. Mater.* 2010, 22, 651.
[21] J. Zhou, N. Xu, Z. L. Wang, *Adv. Mater.* 2006, 18, 2432.
[22] Y. F. Zheng, R. Z. Li, Y. D. Wang, *International Journal of Modern Physics B* 2009, 23, 1566.
[23] I. Shimizu, D. MacFarlane, *Dermatologic Surgery* 2012, 38, 965.
[24] M. H. Grosjean, L. Roué, *Journal of Alloys and Compounds* 2006, 416, 296.
[25] D. J. Wales, J. P. K. Doye, *J. Chem. Phys.* 2003, 119, 12409.
[26] K. Wegnera, H. C. Lya, R. J. Weissa, S. E. Pratsinisa, A. Steinfelda, *International Journal of Hydrogen Energy* 2006, 31, 55.
[27] R. B. Reed, D. A. Ladner, C. P. Higgings, P. Westerhoff, J. F. Ranville, *Environ. Toxicol. Chem.* 2012, 31, 93.
[28] G. Song, A. Atrens, *Advanced Engineering Materials* 2003, 5, 837.
[29] M. Valtiner, S. Borodin, G. Grundmeier, *Langmuir* 2008, 24, 5350.
[30] C. David, J. Galceran, C. Rey-Castro, J. Puy, E. Companys, J. Salvador, J. Monne, R. Wallace, A. Vakourov, *J. Phys. Chem.* 2012, 116, 11758.
[31] H. Gerischer, N. Sorg, *Electrochimica Acta.* 1992, 37, 827.
[32] A. Mudunkotuwa, T. Rupasinghe, C. Wu, V. Grassian, *Langmuir* 2012, 28, 396.
[33] H. Jeon, K. Noh, D. Kim, M. Jeon, *Journal of the Korean Physical Society* 2007, 51, 1999.
[34] X. Zhang, J. Zhang, W. Zhang, X. Hou, *J Mater Sci: Mater Electron* 2010, 21, 671.
[35] R. Hoffman, B. Norris, J. Wagera, *Appl. Phys. Lett.* 2003, 82, 733.
[36] P. F. Carcia, R. S. McLean, M. H. Reilly, *Appl. Phys. Lett.* 2006, 88, 123509.
[37] S.-I. Park, J.-H. Ahn, X. Feng, S. Wang, Y. Huang, J. A. Rogers, *Adv. Funct. Mater.* 2008, 18, 2673.
[38] M. H. Zhao, Z. L. Wang, S. X. Mao, *Nano Lett.* 2004, 4, 587.
[39] F. Bernardini, V. Fiorentini, D. Vanderbilt, *Physical Review B* 1997, 56, 10024.

Dissolution of Zinc Oxide

To understand the dissolution mechanium of a ZnO film, the film thickness as a function of time in various solutions (e.g. PBS, DI water and bovine serum) was studied. Upon disslution, ZnO forms zinc hydroxide, following the equilibrium: $ZnO+H_2O \leftrightarrows Zn(OH)_2$.[1] The initial thickness of ZnO film, $t_{ZnO}$, is much smaller than its width/length and one-dimentional reactive diffusion equation[2] in the thickness direction $x_3$ accounts for the behavior of ZnO hydrolysis. Setting $x_3=0$ at the bottom surface of ZnO film, the water concentration in the ZnO film, w, at time t satisfies the reactive diffusion equation $D\partial^2 w/\partial x_3^2 - kw = \partial w/\partial t$. [2] where D and k are the diffusivity and reaction constant, respectively. The water concentration is constant at the top surface of the ZnO film $w|_{x_3=t_{ZnO}}=w_0$, and the boundary condition at the bottom of the film is zero water flux $\partial w/\partial x_3|_{x_3=0}=0$. The above equation can be solved by the method of separation of variables. At the location $x_3$ and time t, kw water molecules react with ZnO and one water molecule reacts with one ZnO atom. Its integration over the thickness and time gives the mass (per unit area of the cross section) of dissolved ZnO, which in turn gives the remaining thickness of ZnO, $\tilde{t}_{ZnO}$, normalized by its initial thickness $t_{ZnO}$ as $$\frac{\tilde{t}_{ZnO}}{t_{ZnO}} \approx 1 - \frac{t}{t_c}, \quad (S1)$$

where $$t_c = \frac{t_{ZnO}}{\sqrt{kD}} \frac{\rho M_{H_2O}}{w_0 M} \frac{1}{\tanh\sqrt{\frac{k t_{ZnO}^2}{D}}} \quad (S2)$$

is the critical time when the thickness reaches zero, M and $M_{H_2O}$ are the molar masses of ZnO and water, respectively, and $\rho$ is the mass density of ZnO. The diffusivity of water in ZnO sputtered film is independent of pH values and is larger than that in crystalline ZnO.[3] For diffusivity $D > 2.0 \times 10^{-13}$ cm$^2$/s (and $t_{ZnO}=300$ nm as in experiments and a large range of reaction constant k), the critical time in Eq. (S2) is essentially independent of D. This is because dissolution is dominated by reaction (across the entire thickness) for relatively fast diffusion. The remaining thicknesses given by Eq. (S1) agree well with the experimental measurements for the reaction constants of $3.6 \times 10^{-4}$/s, $1.8 \times 10^{-6}$/s, $4.7 \times 10^{-6}$/s in phosphate buffer solution (PBS, pH 4), DI water and bovine serum, respectively. Eq. (S2) gives critical time of 1 h, 19 h and 73 h for PBS, DI water and bovine serum solutions, respectively, which agrees reasonably well with experiments in FIG. 4a. The dissolution rate is then obtained as $$v_{dissolution} = -\frac{d\tilde{t}_{ZnO}}{dt} \approx \sqrt{kD} \frac{w_0 M}{\rho M_{H_2O}} \tanh\sqrt{\frac{k t_{ZnO}^2}{D}}. \quad (S3)$$

It gives 313 nm/h, 15.7 nm/h and 4.09 nm/h in PBS, DI water and bovine serum, respectively, consistent with the values reported in the previous experiments.[4]

Piezoelectric Analysis of ZnO Strips Under Bending

Mechanics Analysis

For the out-of-plane displacement $w=A[1+\cos(2\pi x_1/L_{silk})]/2$ showing FIG. 3g for plane-strain analysis ($\varepsilon_{22}=0$), the bending energy in the silk substrate is related to the curvature w" by where $(\overline{EI}_{silk}/2)\int (w")^2 ds$, where $\overline{EI}_{silk}$ is the plane-strain bending stiffness of the silk substrate, and the integration is over the length of the silk substrate. The membrane energy can be obtained following the same approach of Song et al. [5] Minimization of total energy (sum of bending and membrane energies) gives the amplitude A as $$A = \frac{2}{\pi}\sqrt{L_{silk} \cdot \Delta L - \frac{\pi^2 t_{silk}^2}{3}} \approx \frac{2}{\pi}\sqrt{L_{silk} \cdot \Delta L}, \quad (S4)$$

where $t_{silk}$ is the thickness of the silk substrate, and the last approximation holds when the compression of silk substrate $\Delta L$ is much larger than its critical value $\pi^2 t_{silk}^2/(3 L_{silk})$ to initiate buckling. For a 25 µm-thick and 3 cm-long silk substrate, $\pi^2 t_{silk}^2/(3_{silk})\sim 0.07$ µm is negligible as compared to compression $\Delta L=1.5$ cm in the experiments.

The bending moment M of the silk substrate is related to the curvature w" by $M=\overline{EI}_{silk}w"$, where $\overline{EI}_{silk}=(\overline{E}_{silk}t_{silk}^3)/12$ is the bending stiffness of silk substrate and $\overline{E}_{silk}$ is the plane-strain modulus. For the part of silk substrate covered by the ZnO strips (FIG. 5c), the local curvature is reduced to $M/\overline{EI}_{comp}$ due to the additional bending stiffness of ZnO strips, where $$\overline{EI}_{comp} = \sum_{i=1}^{n} \overline{E}_i t_i \left[ t_i^2/3 + \left(\sum_{j=1}^{i} t_j - y_{neutral}\right)\left(\sum_{j=1}^{i} t_j - y_{neutral} - t_i\right) \right]$$

is the effective bending stiffness of multi-layer structure (FIG. 5c) with the silk substrate as the 1$^{st}$ layer (i=1) and the summation over all n layers, $\overline{E}_i$ and $t_i$ are the plane-strain modulus and thickness of the i$^{th}$ layer, respectively, and $$y_{neutral} = \left[\sum_{i=1}^{n} \overline{E}_i t_i \left(2\sum_{j=1}^{i} t_j - t_i\right)\right] / \left(2\sum_{i=1}^{n} \overline{E}_i t_i\right)$$

is the distance from the neutral mechanical plane to the bottom of 1$^{st}$ (silk) layer. The membrane strain in ZnO is the axial strain at the mid-plane of ZnO strips, and is given by $$\varepsilon_m = (\overline{EI}_{silk}/\overline{EI}_{comp}) w" h, \quad (S5)$$

where h is the distance between the mid-plane of ZnO strips and the neutral mechanical plane. For the length of ZnO strips much smaller than that of the silk substrate, w" is evaluated at the center $x_1=0$ of ZnO strips as $w"=-4\pi\sqrt{\Delta L/L_{silk}}/L_{silk}$. For the structure shown in FIG. 5c, $\overline{E}_1=3.33$ MPa and $t_1=25$ um for silk, $\overline{E}_2=49.1$ MPa and $t_2=0.5$ um for the Mg layer between silk and ZnO strips, $\overline{E}_3=157$ MPa and $t_3=0.5$ um for ZnO, and $t_4=0.3$ um for the top Mg layer; these give $\overline{EI}_{silk}/\overline{EI}_{comp}=0.34$, $y_{neutral}=20.2$ µm and $h=(t_1+t_2+t_3/2)-y_{neutral}=5.52$ µm.

Piezoelectric Analysis

The constitutive model of piezoelectric materials gives the relations among the stress $\sigma_{ij}$, strain $\varepsilon_{ij}$, electric field Ei and electric displacement Di as $$\begin{Bmatrix} \sigma_{11} \\ \sigma_{22} \\ \sigma_{33} \\ \sigma_{23} \\ \sigma_{31} \\ \sigma_{12} \end{Bmatrix} = \begin{pmatrix} c_{11} & c_{12} & c_{13} & 0 & 0 & 0 \\ c_{12} & c_{11} & c_{13} & 0 & 0 & 0 \\ c_{13} & c_{13} & c_{33} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & (c_{11}-c_{12})/2 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} - \begin{pmatrix} 0 & 0 & e_{31} \\ 0 & 0 & e_{31} \\ 0 & 0 & e_{33} \\ 0 & e_{15} & 0 \\ e_{15} & 0 & 0 \\ 0 & 0 & 0 \end{pmatrix} \begin{Bmatrix} E_1 \\ E_2 \\ E_3 \end{Bmatrix},$$ (S6)

$$\begin{Bmatrix} D_1 \\ D_2 \\ D_3 \end{Bmatrix} = \begin{pmatrix} 0 & 0 & 0 & 0 & e_{15} & 0 \\ 0 & 0 & 0 & e_{15} & 0 & 0 \\ e_{31} & e_{31} & e_{33} & 0 & 0 & 0 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} + \begin{pmatrix} k_{11} & 0 & 0 \\ 0 & k_{22} & 0 \\ 0 & 0 & k_{33} \end{pmatrix} \begin{Bmatrix} E_1 \\ E_2 \\ E_3 \end{Bmatrix}.$$ (S7)

The plane-strain condition $\varepsilon_{22}=0$ of ZnO strips, together with $\sigma_{33}=0$ from the traction free on the top surface of the structure, gives $D_3=\bar{e}\varepsilon_{11}+\bar{k}E_3$, where $\bar{e}=e_{31}-(c_{13}/c_{33})e_{33}$ and $\bar{k}=k_{33}+(e_{33}^2/c_{33})$ are the effective piezoelectric constants. The electric displacement can be further obtained as $$D_3 = \bar{e}\varepsilon_m + \frac{\bar{k}V}{nt_3}$$ (S8)

from the charge equation $dD_3/dx_3=0$ and the relation $E_3=\partial\phi/\partial x_3$ between the electric field and the electric potential, together with the boundary condition $\phi(x_3=t_{ZnO}/2)-\phi(x_3=-t_{ZnO}/2)=-V/n$, where V is total voltage between the two ends of the n groups of ZnO strips in series, and $t_3$ is the thickness of ZnO strips. Eq. (S8) shows that the electric displacement is linear with the membrane strain of ZnO strips, and is independent of the bending strain. Therefore the bending strain does not contribute to the voltage and current output of the MEH given in the following.

Current

The voltage V across the two ends of the n groups of ZnO strips in series is zero after the ZnO strips are connected to an ampere meter (FIG. 5b). The electric displacement in Eq. (S8) then becomes $D_3=\bar{e}\varepsilon_m$, where $\varepsilon_m$ is given in Eq. (S5). Its rate gives the current $I=-A_{ZnO}\dot{D}_3$, where $A_{ZnO}=m(w_{ZnO,1}l_{ZnO,1}+w_{ZnO,2}l_{ZnO,2})$ is total area of ZnO strips in each group; m=10 is the number of ZnO strips in each group, $w_{ZnO,1}=50$ um, $w_{ZnO,2}=90$ um, $l_{ZnO,1}=2$ mm and $l_{ZnO,2}=90$ um are the widths and lengths of the two rectangular parts of each ZnO strip, respectively (FIG. 5a). Substitution of the representative $\Delta L$ in the main text into the above formula gives the current, particularly the maximum current in Eq. (1).

Voltage

For voltage measurement, the voltage V in Eq. (S8) across the two ends of the n groups of ZnO strips in series is no longer zero after the ZnO strips are connected to a voltmeter (FIG. 5b). The rate of the displacement in Eq. (S8) gives the current $I=-A_{ZnO}[\bar{e}\dot{\varepsilon}_m+(\bar{k}/nt_3)\dot{V}]$, which, together with the Ohm's law gives Eq. (2) in the main text. Substitution of the representative $\Delta L$ in the main text into solution of Eq. (2) gives the voltage, particularly the maximum voltage in Eq. (3).

FIG. 6 indicates the intrinsic properties of ZnO thin film by sputtering system. X-ray diffraction (XRD, Philips X'pert) patterns shown in FIG. 6a were used to assess the orientation and the crystal structure of sputtered ZnO film. Analysis was carried out by performing 2θ/ω scans, where is the angle of incidence relative to the surface and 2θ is the diffraction angle. The diffraction patterns revealed a (001) orientation with an hexagonal structure where the main peak belonging to (002) ZnO is clearly visible. This crystal structure is consistent with that reported.[6,7] The estimated grain size is ~25 nm, estimated from the width of the XRD peak using the Scherrer formula.[8] FIG. 6b shows scanning electron microscope (SEM) images of a typical ZnO thin film in top and cross-sectional views.

Piezoresponse force microscopy (PFM) studies of ZnO thin films with a Pt bottom electrode were performed using a commercial AFM (Cypher, Asylum Research, USA). Conductive Pt-coated tips (Olympus AC240™ cantilever with a 320 kHz contact resonant frequency, 2N/m spring constant) with a tip radius of 28+/−10 nm were used. A square wave potential was applied to the sample, as shown in FIG. 6c. The piezoresponse was measured using a superimposed AC bias using the Dual AC Resonance Tracking (DART) PFM technique (see FIG. 6d).[9] The effective piezoelectric coefficient $d_{33}$ of ZnO thin film was found to be 14 pm/V.

[1] C. David, J. Galceran, C. Rey-Castro, J. Puy, E. Companys, J. Salvador, J. Monne, R. Wallace, A. Vakourov, *J. Phys. Chem.* 2012, 116, 11758.

[2] P. V. Danckwerts, *Transactions of the Faraday Society* 1950, 46, 300.

[3] W. J. Moore, E. L. William, *Discussions of the Faraday Society* 1959, 28, 86.

[4] H. Gerischer, N. Sorg, *Electrochimica Acta.* 1992, 37, 827.

[5] J. Song, Y. Huang, J. Xiao, S. Wang, K. C. Hwang, H. C. Ko, D. H. Kim, M. P. Stoykovich, J. A. Rogers, *Journal of Applied Physics* 2009, 105, 123516.

[6] N. H. Al-Hardan, M. J. Abdullah, A. A. Aziz, H. Ahmad, M. Rashid, *Physica B* 2010, 405, 1081.

[7] R. Ondo-Ndong, G. Ferblantier, F. Pascal-Delannoy, A. Boyer, A. Foucaran, *Microelectronics Journal* 2003, 34, 1087.

[8] S. Ilican, Y. Caglar, M. Caglar, *Journal of Optoelectronics and Advance Materials* 2008, 10, 2578.

[9] B. J. Rodriguez, C. Callahan, S. Kalinin, R. Proksch, *Nanotechnology* 2007, 18, 475-504.

EXAMPLE 2

Dissolvable Metals for Transient Electronics

Dissolution behavior in terms of electrical property for Mg, AZ31B Mg alloy, Zn, Fe, W and Mo thin films in de-ionized (DI) water and simulated body fluids (Hanks' solution pH 5-8) was systematically studied. Surface chemistries and microstructure of various metals were also investigated during the course of dissolution in DI water. It was found that although with similar surface chemistries, the electrical dissolution rates of thin films were different from reported corrosion rates for bulk materials, mainly due to the non-uniformity (pin-holes, porosity and pitting) of films have pronounced effects on electrical conductivity. Silicon metal oxide field effect transistors (MOSFETs) built on transient metals was demonstrated to be feasible for transient electronics.

1. Introduction

Transient electronics represents an emerging class of technology whose key characteristic is that it physically disappears, in whole or in part, in a controlled fashion after it has served its function.[1] Devices with this property provide capabilities that complement those of traditional integrated circuits. Enabled applications range from biodegradable electronic medical implants, to vanishing environmental sensors and zero-waste consumer electronics.[1] The constituent materials must be carefully formulated to accommodate a desired transient process, such as dissolution in biofluids or ground water. Here, silicon, which undergoes hydrolysis in basic aqueous conditions, is an attractive choice for the semiconductor.[1] Zinc oxide and certain organic semiconductors represent alternatives.[2] In all cases, compatible conductive materials are also essential. By comparison to conductive polymers, conventional metals are appealing due to their low resistivities, stable properties and established roles in commercial devices. Initial reports of silicon transient electronics used magnesium (Mg),[1] due to its combination of ease in processing, rapid rates of hydrolysis and biocompatibility. Alternative metals that share some of these characteristics include zinc (Zn), iron (Fe), tungsten (W) and molybdenum (Mo). Each of these materials, with the exception of W (a facultative bioelement for some species),[3] is essential for biological function, with recommended daily intake values in the range of ~0.05-400 mg/day.[4,5] In addition, Mg, Mg alloys and Fe have been explored for use in bioresorbable implants (e.g., vascular stents) due to their biocompatibility and favorable mechanical properties.[6-9] In simulated body fluids (SBFs) and physiological conditions, Mg dissolves to form $Mg(OH)_2$, which is water soluble, at a rate ~0.05-0.5 μm/hour.[10-13] Addition of small amounts of aluminum (3 wt %-9 wt %) can slow these rates to ~0.02-0.10 μm/hour.[11, 12, 14] In related conditions, Fe dissolves to form hydroxides ($Fe(OH)_2$) and oxides ($Fe_2O_3$ or $Fe_3O_4$) at ~0.02 μm/hour,[15-17] with rates that can be significantly slower in Fe stents evaluated in vivo.[18] In contrast to Mg, Fe degrades in a spatially non-uniform manner, with certain reaction products ($Fe_2O_3$ and $Fe_3O_4$) that have very low solubility.[6, 19] Bowen et al. recently suggested the use of Zn as an alternative metal for the resorbable stents,[20] due to its acceptable in vivo degradation rates (~5×10$^{-3}$ μm/hour) and the soluble dissolution products $ZnO$.[21]

Metals with less comprehensive data on biocompatibility are also worthy of consideration. For example, published results on W and Mo suggest that they can dissolve in physiological solutions forming complex $WO_x$ and $MoO_x$.[22-24] Neural sensor wires made of W dissolve at rates of ~0.02-0.06 μm/hour in SBF at room temperature (RT).[22] Furthermore, in vivo tests of W embolisation coils indicate no obvious adverse biological effects, with minimal toxicity for concentrations <50 μg/ml.[25,26]. Although in vivo dissolution rates of pure Mo has not been reported, the dissolution rate for Mo in pH 7 buffer solutions or NaCl solutions is found to be ~$10^{-4}$-$10^{-3}$ μm/hour at RT.[23] Such low rates can be important for classes of devices that demand continuous contact between electrodes and internal tissues.

These considerations make Mg, Mo, W, Fe and Zn promising candidates for additional study as thin film, patterned traces for transient electronic implants, environmental monitors and others. Although there is an extensive, existing body of knowledge related to corrosion of these metals in bulk form, far less information is available for thin films, where behaviors can be quite different. For example, the grain sizes in films and bulk samples typically lie in qualitatively distinct regimes, with significant consequences.[27] Furthermore, pinholes, pitting, porosity and other aspects of films have dominating effects on specific properties relevant to use in transient electronics, particularly in time dependent variations of the resistances of patterned, thin film traces. The following outlines systematic studies of dissolution behaviors, in terms of electrical conductivity, thickness, morphology and surface chemistry, of Mg, AZ31B (3 wt % Al and 1 wt % Zn) Mg alloy, Zn, Fe, W and Mo thin films and serpentine wires in de-ionized (DI) water and simulated body fluids (Hanks' solution). Silicon metal oxide field effect transistors (MOSFETs) built using electrodes formed with these various metals demonstrates their utility in transient electronics.

2. Results and Discussion 2.1 Dissolution Kinetics

Figure 7:
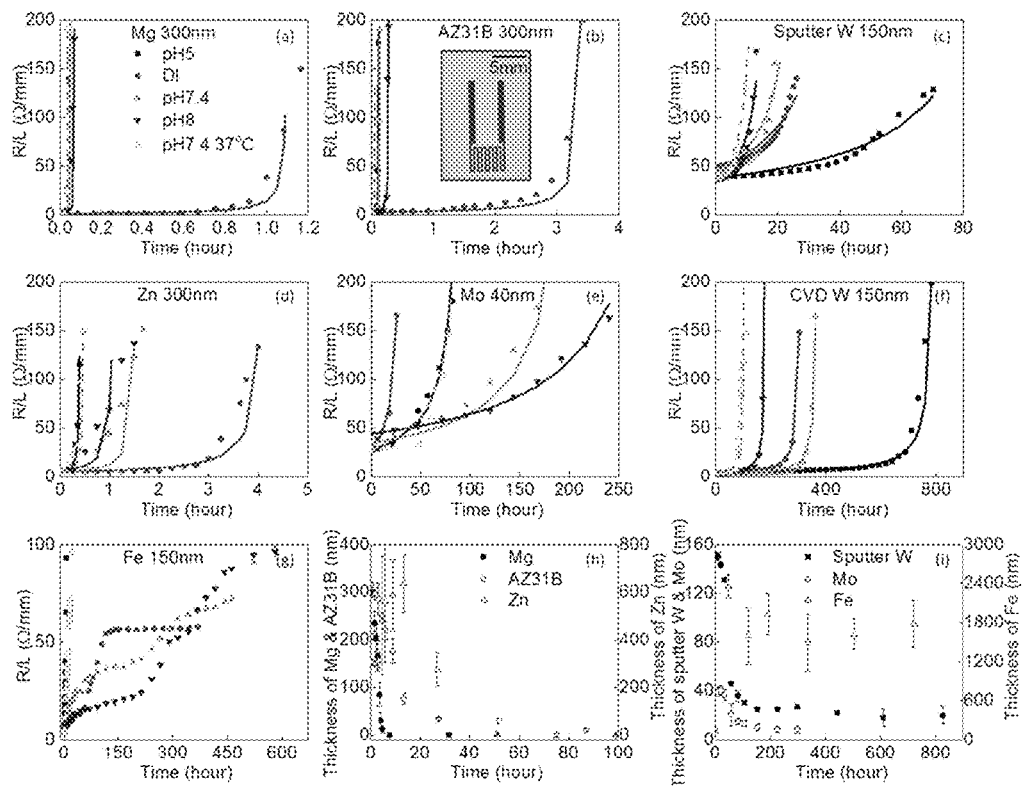
FIG. 7. Change in resistance of serpentine thin film traces as a function of time during dissolution, in Hanks' solution (pH 5, 7.4 and 8 at RT and pH 7.4 at 37 C) and in DI water, for cases of (a) Mg (300 nm); (b) AZ31B Mg alloy (300 nm); (c) sputter deposited W (150 nm); (d) Zn (300 nm); (e) Mo (40 nm); (f) CVD W (150 nm); (g) Fe (150 nm); (a)-(g) share the same legend. Change in thickness of similar traces as a function of time during dissolution in DI water at RT for cases of (h) Mg, AZ31B Mg alloy and Zn; (i) sputter deposited W, Mo and Fe.

FIG. 7 (a)-(g) summarizes representative dissolution behavior in terms of the change in resistance as a function of time for various metal thin films in DI water and Hanks' solutions (for pH values between 5 and 8) at both room temperature (RT) and body temperature (37° C.). The geometry of dissolution serpentine pattern is illustrated in FIG. 7 (b), with width of 300 μm, total length of 45 mm and the top probing pads. The resistance change is normalized over the total length of the serpentine pattern of 45 mm. Changes in thickness over time for dissolution in DI water at RT appear in FIG. 7 (h)-(i). In all cases, an ultrathin layer of Cr (~10 nm) serves as an adhesion promoter to a glass substrate. This layer improves the yields and ensures that the dissolution kinetics are not interrupted by film delamination. (Control experiments without the Cr establish that, in the absence of delamination, this layer has no measurable effect on the dissolution processes.)

The electrical dissolution rates (EDR), as defined by the rate of change in the effective thickness converted from the electrical resistance changes upon dissolution through a reactive diffusion model (will be discussed later), appear in Table 1. Each EDR reported here corresponds to the average of at least three data sets. Overall, (i) Mg, AZ31B Mg alloy and Zn have EDR values that are much higher than those of W, Mo and Fe; (ii) with the exception of Mo, the EDRs increase in salt solutions; (iii) the EDRs increase at elevated temperature (37° C.) for W, Mo and Fe, but not significantly for Mg, AZ31B Mg alloy and Zn. The detailed dissolution chemistries will be discussed in the session 2.2.

As shown in FIG. 7 (a)-(b) and Table 1, the EDR of AZ31B Mg alloy is ~3 times lower than that of Mg in DI water, with $Mg(OH)_2$ as the dissolution products. On the other hand, the EDRs of both Mg and Mg alloy are significantly higher (>ten times) in Hanks' solution regardless of the pH and temperature, likely due to the presence of chlorides ($Cl^-$) that promotes rapid attack, as reported in corrosion studies of mass loss in bulk Mg materials.[28] The weak dependence on pH for values between 5 and 8 is consistent with findings for bulk Mg alloy in NaCl solutions [29]. By contrast, a much stronger pH influence for bulk Mg materials was reported in Hanks' solutions, with dissolution rates ~300 times faster in pH 5.5 compared to the pH 8 solutions.[13]

In a trend qualitatively similar to that for Mg, Zn shows an EDR that is about 3 times lower in DI water than in salt solution, possibly due to the presence of chlorides ($Cl^-$).[30] The dissolution products are mainly $ZnO$ and $Zn(OH)_2$. The EDRs among salt solutions with different pH values and temperatures are similar, which is consistent with reports of mass loss associated with corrosion of bulk Zn in NaCl solutions.[30]

Unlike Mg and Zn, Mo (FIG. 7 (e) and Table 1) exhibits EDRs in DI water that are higher (~2-5 times) than those in salt solutions at room temperature, forming complex Mo oxides on the surface. Such trends are observed in bulk Mo materials.[31] The differences likely arise from the strong dependence of Mo degradation on oxygen solubility in aqueous solution, with rates that increase with oxygen solubility.[32] The presence of ions (e.g., $Na^+$, $Cl^-$),[31, 33] is known to reduce oxygen solubility. This effect, in Mo, dominates the effects of increased corrosion potential associated with chlorides. As illustrated in FIG. 7 (e) and Table 1, Mo has an EDR that is 3 times lower in solutions with pH of 7.4 and 8 compared to pH 5. Although dissolution rates of thin film Mo are reported to be around ten times higher in strong alkaline solution (pH 12) compared to neutral (pH 7) or acidic solution (pH 2),[34] the expected reductions in oxygen solubility with increasing basicity can again surpass the effects of pH in this range.[31,33] In addition, the EDR for Mo is about five times higher at 37° C. than that at room temperature, for Hanks' solution at pH 7.4.

Figure 17:
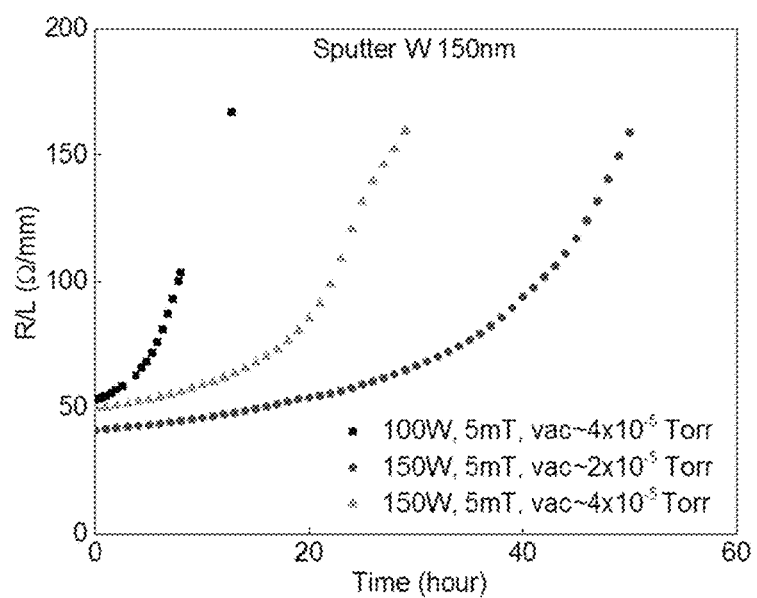
FIG. 17. Influence of sputter conditions on dissolution rates of W 150 nm.

W exhibits an EDR that is 4 times lower in acidic salt solution (pH 5) compared to the more basic solutions (pH 7.4-8), as shown in FIG. 7 (c) and Table 1, with formation of W oxides. The trend is consistent with the corrosion behavior of bulk W materials.[24] The EDR of W in DI water is similar to that in solutions with pH 7.4-8. Elevated temperatures (37° C.) increase the EDR. An additional important observation associated with W dissolution is that the rate is more sensitive to deposition conditions than the other metals. An example appears in FIG. 7 (c)-(f) and Table 1, where W formed by chemical vapor deposition (CVD) has an EDR about 10 times lower compared to the value for sputtered W. The dependence on pH is qualitatively similar. The quality of sputter W thin films can also be adjusted through sputtering power, argon pressure and vacuum level (FIG. 17).

As given in FIG. 7 (g) and Table 1, the EDR for Fe is highest in pH 5 solution (acidic solution) and pH 7.4 at 37° C. (elevated temperature), while lower in the other solutions, with thick iron oxides on the surface in all cases. Furthermore, the resistance as a function of time shows plateaus in certain cases, especially for Fe in DI water, where the dissolution apparently ceases after 120 hours. Such phenomenon could result from the non-uniformity in dissolution, the overall slow kinetics, and the protective nature of iron oxides, as discussed subsequently.

Corresponding changes in thickness during dissolution in DI water appear in FIG. 7 (h)-(i). The apparent morphological dissolution rates, as extracted by linear fitting of the initial stages of dissolution, enable quantitative comparisons to the EDRs. (The later stages of dissolution likely involve significant contributions due to porosity, non-uniformities and residual oxides.) For Zn and Fe, the oxides can result in increases in thickness. Here, the averaged morphological dissolution rate of Zn is defined simply as the initial thickness 300 nm divided by the time for complete dissolution. As for Fe (150 nm), the averaged rate is estimated to be less than $2 \times 10^{-4}$ μm/hour since the measured thickness of Fe almost remains unchanged after 750 hours. These results, which appear in Table 1, show that the decrease in thickness lags the increase in resistance, mainly due to (i) contribution of residual insulating oxides to the measured thickness, especially for the cases of Zn and Fe; (ii) enhanced sensitivity of resistance to local non-uniformities, pinholes and porosity. The most relevant parameter for transient electronics is, of course, the resistance; results indicate that thickness is not an adequate substitute. For example, as shown in FIG. 7 (h)-(i), the thicknesses of films of Mg, Mg alloy and Zn reach zero a few days after the complete loss in electrical continuity. For W and Mo, the thickness decreases quickly in the first 4 days, after which the oxide products slowly dissolve. In the case of Fe, the oxides do not dissolve even over the course of a month. Such retention of corrosion products also occurs in in vivo tests of Fe stents.[6]

The corrosion rates, defined by mass lost for bulk materials in near neutral solutions and as reported in literature, are also summarized in Table 1. The EDRs of Mg, Mg alloys, Zn and Mo thin films are higher (≥10 times) that the corrosion rates under similar conditions; for W and especially Fe, the EDRs are much lower (~10-100 times depending on the conditions). At least three considerations are important in understanding these differences. First, thin films deposited through PVD techniques generally possess higher purity compared to bulk materials obtained through conventional metallurgical process. As a result, the materials themselves in the case of thin films are expected to exhibit improved corrosion resistance due to absence of impurities such as Fe and copper (Cu) for Mg and Zn, and carbon (C) for Fe[14,30,35]. Second, the thin films consist of nanocrystallines (~20-200 nm), with the potential to improve corrosion resistance compared to bulk materials with much larger grain size,[27] possibly due to the formation of surface oxide layers with enhanced barrier qualities. Previous results of corrosion studies of Mg, Fe, Zn, W and Mo nanocrystalline films indicate that the dissolution rates can decrease by ~2-10 times with decreasing grain size.[15, 34-38] In contrast, Mg alloy shows little effect of grain size.[39] Third, and perhaps most important, resistance measurements of thin films are sensitive to non-uniformities, as mentioned previously. The EDR values are therefore expected to be larger than the corrosion rates reported in literature. One consequence is that when non-uniformities (either at large scale or micro scale) are important, EDR is larger than the corrosion rate, as for Mg, Mg alloys, Zn and Mo, which will be further discussed later. On the other hand, if effects of grain size or purity effects are pronounced, then EDR can be strongly reduced, as for W and Fe. The conclusion, then, is that thickness changes and corrosion rates can be important, but they are both distinct and they are different than EDR as it relates to uses in thin films for transient electronics. The following sections summarize systematic studies of detailed microstructure/surface chemistry involved in dissolution.

A concise analytical reactive diffusion model is also embedded to simulate the dissolution behavior, as the solid lines given in FIG. 7.[40] The model considers both surface reaction and water diffusion within metal films, incorporating two free parameters, surface reaction constant k and diffusivity D. As shown in FIG. 7, the model goes well with the dissolution behavior of all the metal thin films except Fe, due to the significant non-uniform behavior. Such model can be possibly used to extrapolate dissolution rates of metal films at different thickness and pH values based on current available data, and provide reasonable theoretical prediction for more complicated transient electronics system.

TABLE 1

Summary of dissolution rates of various metals and comparison with literature data.

| | Electrical dissolution rates [μm/hour] | | Apparent morphological dissolution rates in DI [μm/hour] | Mass lost corrosion rates from literature [μm/hour] | Ref No. |
|---|---|---|---|---|---|
| | DI | Hanks' solutions | | | |
| Mg | ~0.3 | ~3 | ~0.07 | pH 7.4 SBF 37° C.: 0.05-0.5  0.05M NaCl: 0.05-0.3 | [10-13] [41] |
| AZ31B | ~0.1 | ~3 | ~0.02 | pH 7.4 SBF 37° C.: 0.02-0.1  0.05M NaCl: ~0.3  0.6M NaCl: ~0.1 | [11, 12, 14] [41] [42] |
| W (S)[a] | $(4 \pm 1) \times 10^{-3}$ | pH 5: $(1.4 \pm 0.4) \times 10^{-3}$  pH 7.4-8: $(8 \pm 2) \times 10^{-3}$  pH 7.4 37° C.: ~0.02 | $~1.7 \times 10^{-3}$ | pH 7.4 SBF: 0.02-0.06 | [22] |
| W (C)[a] | $(7 \pm 2) \times 10^{-4}$ | pH 5: $~2 \times 10^{-4}$  pH 7.4-8: $(7 \pm 2) \times 10^{-4}$  pH 7.4 37° C.: $~2 \times 10^{-3}$ | $~3 \times 10^{-4}$ | | |
| Mo | $(5 \pm 2) \times 10^{-3}$ | pH 5: $(2 \pm 1) \times 10^{-3}$  pH 7.4-8: $(7 \pm 1) \times 10^{-4}$  pH 7.4 37° C.: $(3 \pm 3) \times 10^{3}$ | $~3 \times 10^{-4}$ | pH 7 buffer: $1 \times 10^{-3}$  pH 7 buffer thin film: $2 \times 10^{-4}$ | [23] [34] |
| Zn | ~0.05 | ~0.15 | $~7 \times 10^{-3}$ | In vivo: $~5 \times 10^{-3}$  DI water: $~3 \times 10^{-3}$  Sea water: $~(2-8) \times 10^{-3}$ | [20] [30] [30] |
| Fe | $<2 \times 10^{-4}$ | pH 5: $~9 \times 10^{-3}$  pH 7.4-8: $<2 \times 10^{-4}$  pH 7.4 37° C.: $<7 \times 10^{-3}$ | $<2 \times 10^{-4}$ | pH 7.4 SBF 37° C.: ~0.02 | [15, 16] |

[a]W(S) and W(C) stand for sputter W and CVD W respectively.
[b] All the data are at room temperature for bulk materials unless specified.

2.2 Microstructure and Surface Chemistry Associated with Dissolution of Thin Metal Films Detailed investigations involve metal films in DI water, to establish the basic mechanisms and effects. In all cases, (i) mass loss occurs at rates lower than EDR, due primarily to the formation of micro-pores and/or pits; (ii) oxides as dissolution products appear on the surfaces, where they can act as partially protective layers to slow the dissolution of underlying metal; (iii) the residual oxide layers dissolve much more slowly than the metal.

2.2.1 Mg and AZ31B Mg Alloy

Figure 8:
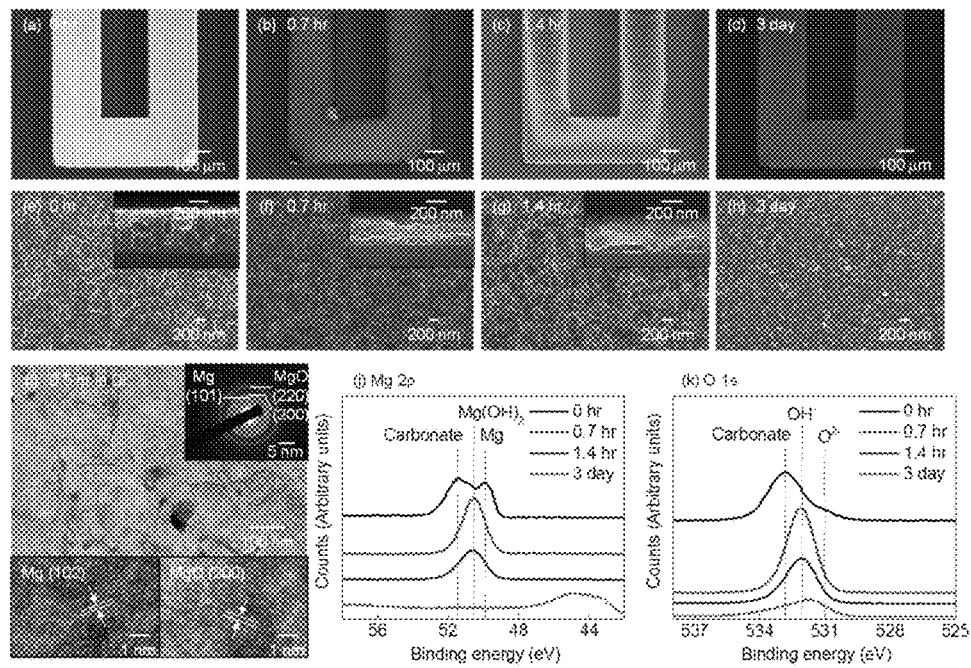
FIG. 8. Evolution of microstructure and surface chemistry of Mg dissolution in DI water. (a)-(d) optical images; (e)-(h) SEM images with cross-sectional view in the sub-graph; (i) TEM bright field image with diffraction patterns and lattice fringes; (j)-(k) XPS data.
Figure 9:
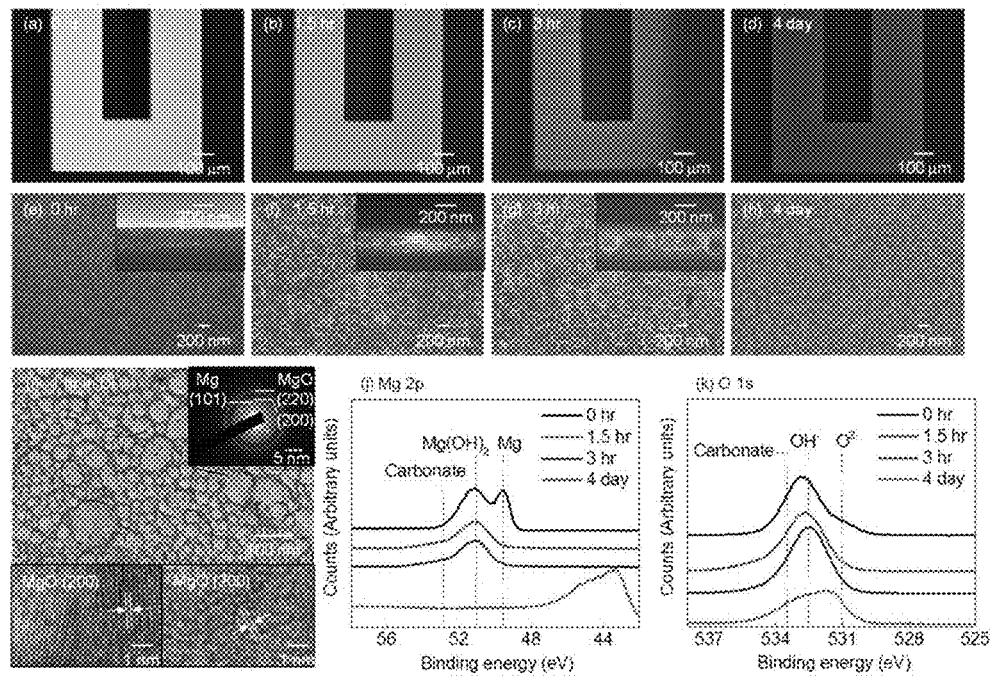
FIG. 9. Evolution of microstructure and surface chemistry of AZ31B Mg alloy during dissolution in DI water. (a)-(d) optical images; (e)-(h) SEM images with cross-sectional view in the sub-graph; (i) TEM bright field image with diffraction patterns and lattice fringes; (j)-(k) XPS data.

The evolution of the microstructure and surface chemistry during the course of dissolution in DI water for Mg and Mg alloy appear in FIG. 8 and FIG. 9 respectively. At a macroscopic scale dissolution is uniform for both Mg and AZ31B Mg alloy (FIG. 8 and FIG. 9 (a)-(d)). Micro-pores develop and the surface roughens and becomes uneven as dissolution proceeds (FIG. 8 and FIG. 9 (f)-(g)). Needle-like dissolution products appear on the surface (FIG. 8 and FIG. 9 (f)-(g)), consistent with previous reports of bulk Mg and AZ31B alloy samples in simulated bio-fluids.[43,44] FIG. 8 and FIG. 9 (j)-(k) present XPS data with peak identifications referenced to data by Liu et al.[45] The assigned binding energies are Mg (49.9 eV), Mg—(OH) (50.5 eV) and carbonate (51.5 eV) for Mg 2p; and Mg—O (531.0 eV), Mg—OH (532.1 eV) and carbonate (532.8 eV) for O 1s. The assigned binding energies for AZ31B Mg alloy are Mg (49.5 eV), Mg—(OH) (51.0 eV) and carbonate (52.8 eV) for Mg 2p; and Mg—O (531.0 eV), Mg—OH (532.5 eV) and carbonate (533.5 eV) for O 1s. The shift of binding energies for hydroxyls and carbonates to increased values for AZ31B Mg alloy likely arises from the presence of Al.[45] Surface oxides/hydroxide/carbonates can be found on the film, even before immersion, due to the presence of water vapor and carbon dioxide in the atmosphere. During dissolution, the outer surface consists mainly of $Mg(OH)_2$, possibly with a small amount of MgO and carbonates (FIG. 8 and FIG. 9 (j)-(k)), as reported previously with bulk samples.[45,46] The layer of $Mg(OH)_2$ is estimated to have a thickness greater than 10 nm, based on the probing depth of the XPS technique and the absence of metallic Mg peaks. As reported by other researchers,[47-49] $Mg(OH)_2$ is a major surface product of Mg corrosion in common biological solutions, the presence of $Na^+$, $Cl^-$, $PO_4^{3-}$ and $CO_3^{2-}$ in these solutions can introduce phosphates and carbonates into the surface layer. The TEM bright field images (FIG. 8 and FIG. 9 (i)) illustrate metallic Mg and needle-like oxide products, consistent with the SEM images. The TEM diffraction patterns and lattice fringes indicate the presence of crystalline MgO, suggesting a possible amorphous nature of the outer $Mg(OH)_2$ layer.[50] These results are consistent with the proposed bi-layer surface oxide structure of bulk Mg dissolved in water or NaCl solution, with a thick outer layer rich in $Mg(OH)_2$ on top of a thin crystalline MgO film.[45,50] It is likely that the MgO forms immediately after the exposure of fresh metallic surface to oxygen in the atmosphere. The $Mg(OH)_2$ layer increases in thickness as the dissolution proceeds, due to hydration of the native MgO layer followed by a dissolution-precipitation mechanism at the expense of based metal.[50] As shown previously in Table 1, the EDR is ~5 times faster than the rate of change in thickness for both Mg and Mg alloy. In particular, 300 nm thick films of Mg and AZ31B Mg alloy become electrically discontinuous in ~1.5 and ~3 hours, respectively, as shown in FIG. 7 (a)-(b). FIG. 8 and FIGS. 9 (c) and (g) show, however, that some base metal still exists at this point. As time process, the remaining metal reacts to leave only residual $Mg(OH)_2$ and MgO behind. Because of the relatively high solubility of $Mg(OH)_2$ and MgO in water,[51] the oxides eventually disappear completely after 2-3 days, leaving only the Cr adhesion layer, as confirmed by the XPS data (FIG. 8 and FIGS. 9 (d), (h), (j) and (k)). The dissolution rates of Mg oxides/hydroxides are estimated to be roughly ~5-7 nm/day, from fits of the later stages of dissolution in FIG. 7 (h).

2.2.2 W and Mo

Figure 10:
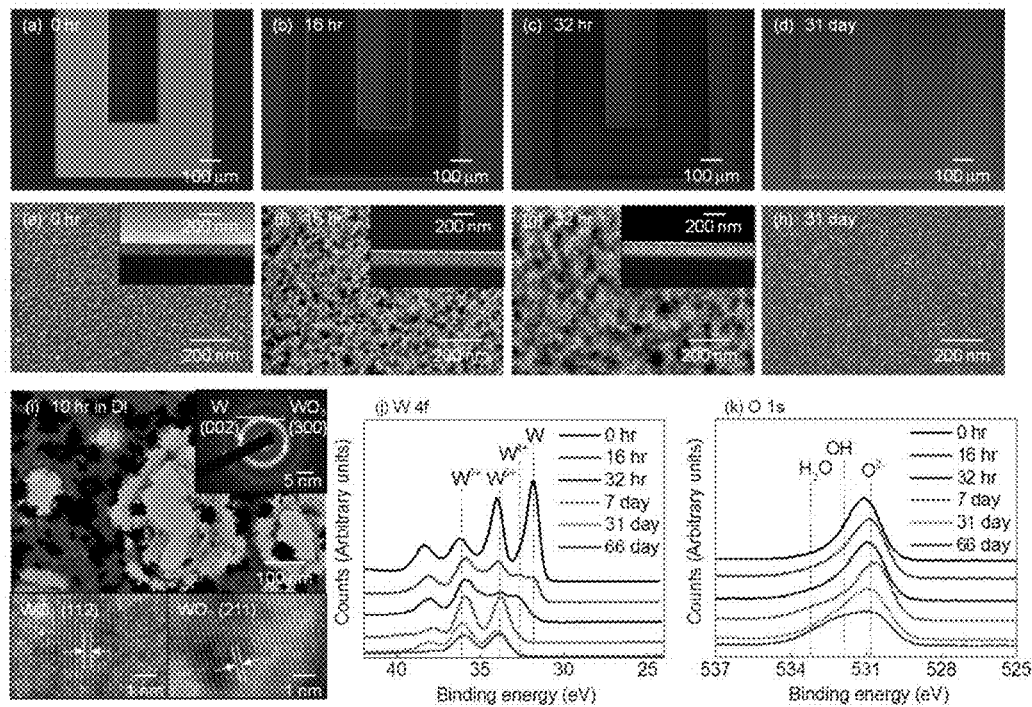
FIG. 10. Evolution of microstructure and surface chemistry for sputtered W dissolution in DI water. (a)-(d) optical images; (e)-(h) SEM images with cross-sectional view in the sub-graph; (i) TEM bright field image with diffraction patterns and lattice fringes; (j)-(k) XPS data.
Figure 11:
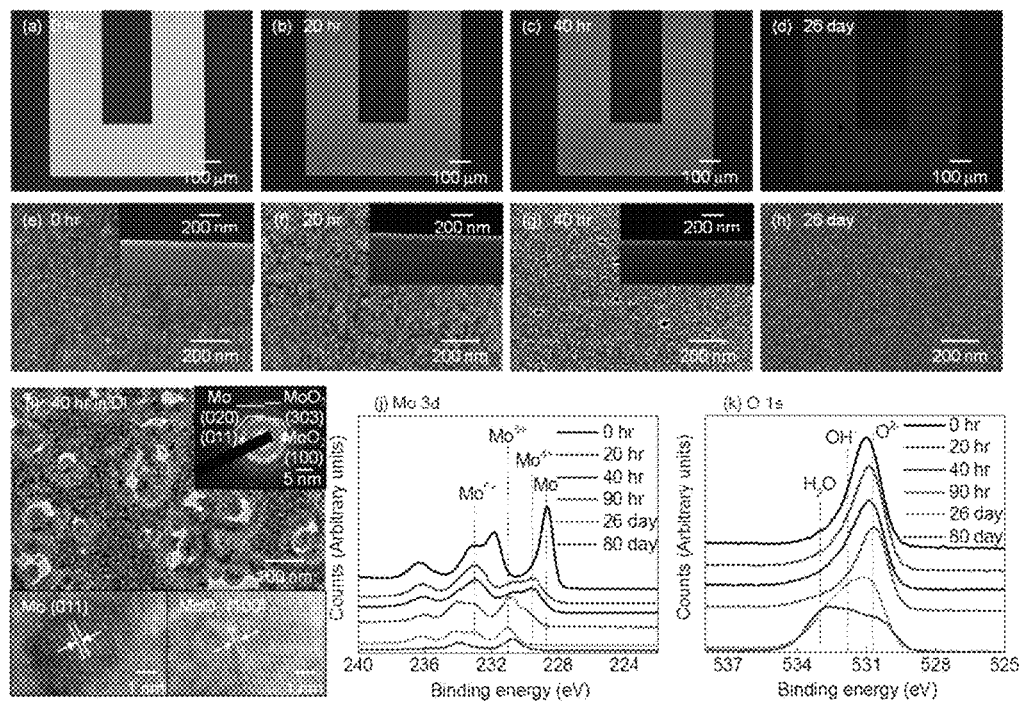
FIG. 11. Evolution of microstructure and surface chemistry for Mo dissolution in DI water. (a)-(d) optical images; (e)-(h) SEM images with cross-sectional view in the sub-graph; (i) TEM bright field image with diffraction patterns and lattice fringes; (j)-(k) XPS data.

Results for dissolution of sputter deposited W and Mo in DI water appear in FIG. 10 and FIG. 11. As transition metals in the same column of the periodic table, W and Mo are expected to have similar and complex surface chemistry. As can be seen, the surface morphology of W and Mo during dissolution is mostly uniform based on the optical observations (FIG. 10 and FIG. 11 (a)-(d)). Micro-pores are evident, however, in SEM results (FIG. 10 and FIG. 11 (f)-(g)) and more clearly in the TEM bright field images (FIG. 10 and FIG. 11 (i)).

XPS analysis reveals that the W film has an initial native oxide, mostly $WO_3$ (FIG. 10 (j-k)). As dissolution proceeds, a mix of W oxides ($W^{4+}$, $W^{5+}$ and $W^{6+}$) develops at the surface. The thickness of the oxide increases to values larger than 10 nm after ~32 hours, as inferred by disappearance of the metallic W signal in the XPS spectra. Further reaction eliminates the $W^{4+}$ and $W^{6+}$ oxides, leaving only the $W^{5+}$ oxide (FIG. 10 (j-k)). The oxygen peaks of W in FIG. 10 (k) suggest the presence of hydroxide ($OH^-$) and absorbed water at surface.[52] The assigned binding energies are W (31.8 eV), $W^{4+}$ (32.7 eV), $W^{5+}$ (33.8 eV) and $W^{6+}$ (36.2 eV) for W $4f_{7/2}$; $O^{2-}$ (530.8 eV), $OH^-$ (531.9 eV) and $H_2O$ (533.2 eV) for O 1s.[52-54] TEM diffraction patterns and lattice fringes also suggest the presence of $WO_3$ as a dissolution product (FIG. 10 (i)). Such surface structure is similar to that of bulk W materials exposed to acidic solution, as reported by Lillard et al., where an inner $WO_3$ layer and an outer loosely bounded W hydroxide layer occur.[55]

As shown in FIG. 11 (j)-(k), the evolution of surface chemistry for Mo is similar to that for W, with an initial $MoO_3$ native oxide, then a mixed valence oxides ($Mo^{4+}$, $Mo^{6+}$ and $Mo^{6+}$) as dissolution products, with terminal formation of $Mo^{5+}$ oxide after 80 days. The presence of hydroxide and sometimes absorbed water are also observed on the Mo surface based on the XPS O 1s data (FIG. 11 (k)). The assigned binding energies are Mo (228.7 eV), $Mo^{4+}$ (229.5 eV), $Mo^{5+}$ (230.9 eV) and $Mo^{6+}$ (233.0 eV) for Mo $4d_{5/2}$; $O^{2-}$ (530.7 eV), $OH^-$ (531.8 eV) and $H_2O$ (533.0 eV) for O 1s.[31, 56] The TEM results of Mo in FIG. 11 (i) support the presence of $MO_3$ and $MoO_2$. These results are consistent with reported dissolution surface chemistry of bulk Mo materials in aqueous solution.[31,57] Degradation of W and Mo in salt solutions with different pH values follows similar dissolution patterns as those in DI water. The pH values can affect the relative concentrations of the various mixed valence surface oxides, in ways that can alter the dissolution rate.[24,57, 58]

Due to the soluble nature of $WO_x$ and $MoO_x$,[23,69] both W and Mo can slowly degrade in water. The EDR is ~2-10 times faster than the rate of change in thickness (Table 1), due to the formation of micro-pores (FIG. 10 and FIGS. 11 (c), (g) and (i)). The corrosion products $WO_x$ and $MoO_x$ require time to fully dissolve after the disappearance of metals; increasing the basicity accelerates the rates.[23, 59, 60] As shown in FIG. 10 and FIG. 11 (j), the slowly decreasing peak to background XPS signals of W and Mo suggest the gradual dissolution of $WO_x$ and $MoO_x$ in DI water, with an estimated residual thickness of 10-20 nm after ~70 days, as indicated by the continued presence of XPS signal up to this point. These oxides are expected to completely disappear given a sufficiently long time. The dissolution rates of W and Mo oxides are estimated to be ~0.2-0.5 nm/day.

2.2.3 Zn and Fe

Figure 12:
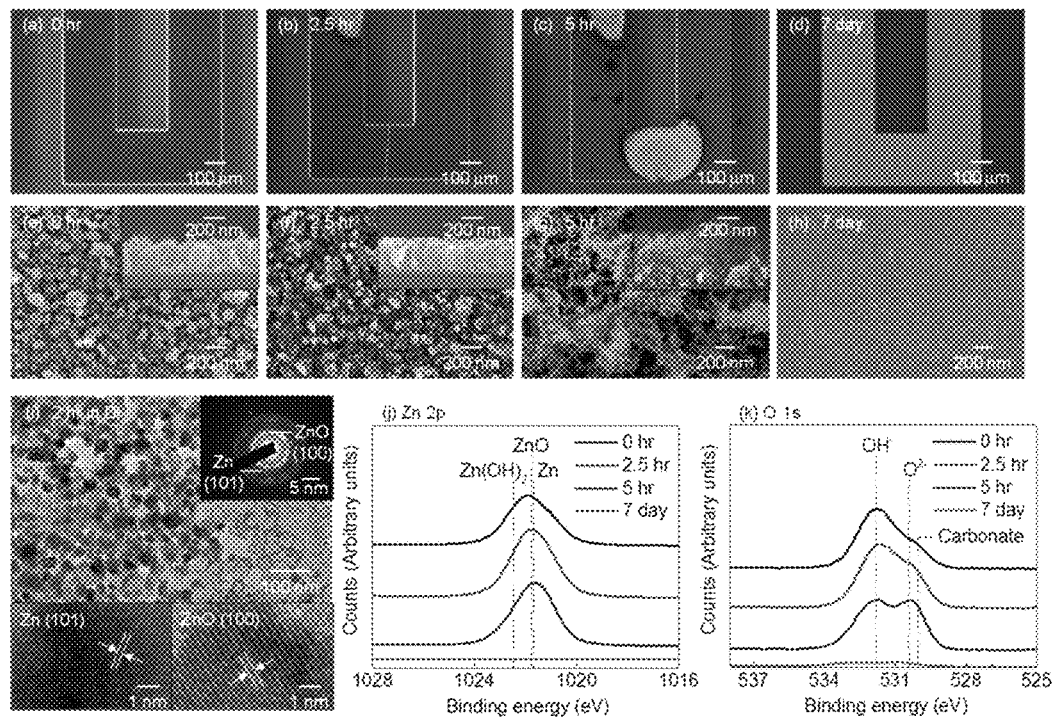
FIG. 12. Evolution of microstructure and surface chemistry for Zn dissolution in DI water. (a)-(d) optical images; (e)-(h) SEM images with cross-sectional view in the sub-graph; (i) TEM bright field image with diffraction patterns and lattice fringes; (j)-(k) XPS data.
Figure 13:
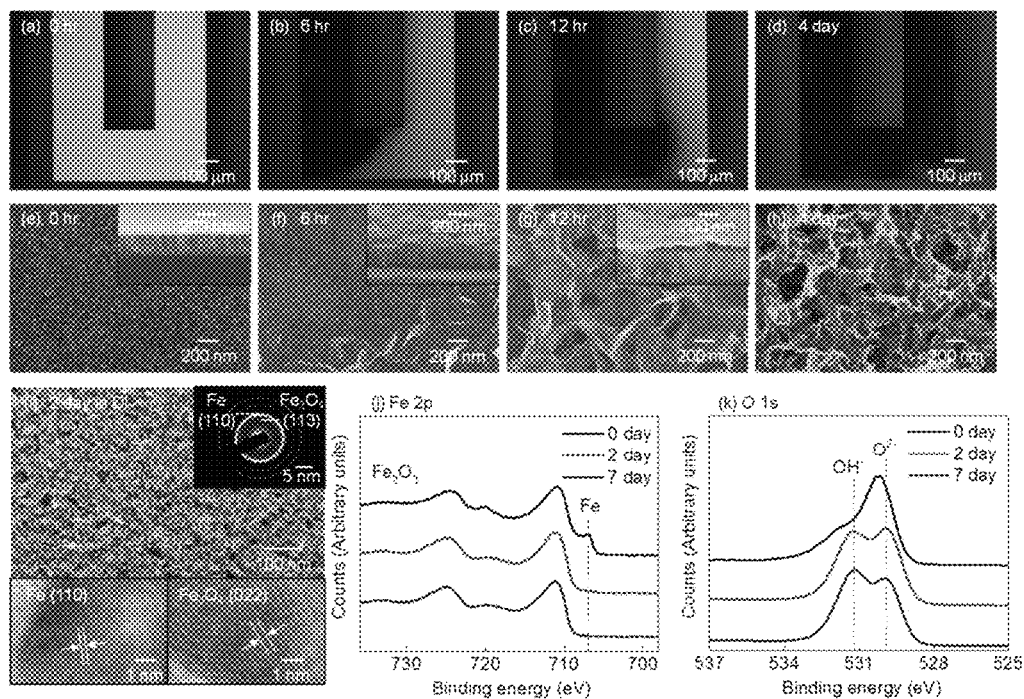
FIG. 13. Evolution of microstructure and surface chemistry for Fe dissolution in DI water. (a)-(d) optical images; (e)-(h) SEM images with cross-sectional view in the sub-graph; (i) TEM bright field image with diffraction patterns and lattice fringes; (j)-(k) XPS data.

Non-uniform dissolution dominates for Zn and Fe thin films in DI water as shown in FIG. 12 and FIG. 13 (a)-(d). Pitting nucleates in random locations and the spreads across the films. Such type of corrosion has been reported to be common for both bulk Zn and Fe materials in aqueous solutions.[30, 61, 62]

The surface morphology evolution of Zn is illustrated in FIG. 12 (e)-(h), where both petal-like and fiber-like dissolution products are observed. Independent of the morphology, the surface products are identified to be mainly ZnO and $Zn(OH)_2$ with occasional presence of a certain amount of carbonates, as the XPS data shown in FIG. 12 (j)-(k). The assigned binding energies of O 1s are Zn—O (530.4 eV), Zn—(OH) (531.8 eV) and carbonates (530.0 eV).[63] The Zn $2p_{3/2}$ peak (remaining at 1021.8 eV) does not shift in accordance with O 1s as shown in FIG. 12 (j), and therefore cannot be unambiguously deconvoluted. The labeled binding energies of Zn 2p in FIG. 12 (j) are Zn (1021.6 eV), Zn—O (1021.7 eV) and Zn—OH (1022.4 eV).[63, 64] The TEM diffraction patterns and lattice fringes confirm the presence of ZnO the surface (FIG. 12 (i)). The TEM bright field image also illustrates a porous morphology and a non-uniform distribution of surface oxide, with more ZnO present on the left part of the image (FIG. 12 (i)). Dissolution of Zn thin films in Hanks' solutions show similar non-uniform behavior, where the dissolution products are also expected to be mainly ZnO and $Zn(OH)_2$ as for bulk Zn materials.[30] Such Zn oxide layers are only partially protective and have relatively high solubility in aqueous solution.[30]

The surface morphology of dissolution products for the case of Fe is shown in FIG. 13 (f)-(h). The XPS data (FIG. 13 (j)-(k)) suggest the surface layer to be $Fe_2O_3$ and hydroxide, with Fe $2p_{3/2}$ for Fe (706.9 eV) and O 1s for $Fe_2O_3$ (529.8 eV) and hydroxide (531.2 eV).[65, 66] The TEM diffraction patterns and lattice fringes (FIG. 13 (i)) indicate $Fe_3O_4$ which is a common corrosion product after building up of hydroxide in the presence of excessive oxygen.[17] The presence of Fe oxides can help passivate the propagation of pits and simultaneously reduce the dissolution rate. The long incubation for pitting initiation in different locations and the passivation effects might cause for the observed plateaus in time dependence of the resistance (FIG. 7 (g)). Although Zn also shows non-uniform patterns of dissolution, the facile initiation of pits and high reaction rates eliminate plateaus in dissolution (FIG. 7 (d)). The degradation behavior of Fe in Hanks' solution is similar to that in DI water except at pH 5, in which a uniform dissolution in the absence of obvious surface oxide is observed, resulting from the acidic environment.

Similar to other transient metals, Zn thin films cease to be electrical continuous far sooner (~50 times faster) the thickness decreases to zero (Table 1, FIG. 7 (d) and FIG. 12 (c)). The hydrolysis products dissolve completely after about 5-7 days (FIGS. 12 (d), (h) and (j)). The dissolution rates of Zn oxides are estimated to be roughly ~120-170 nm/day. On the contrary, the Fe oxides do not seem to be dissolving after monitoring up to one month and the resulting total thickness is more than 10 times compared to the original thickness of the Fe films (FIG. 7 (i)), which makes it not desirable for transient electronic systems. Such retention of Fe oxides was also observed by in vivo tests.[6]

2.3 Degradation of Thin Film Transistors with Transient Metal Contacts

Figure 14:
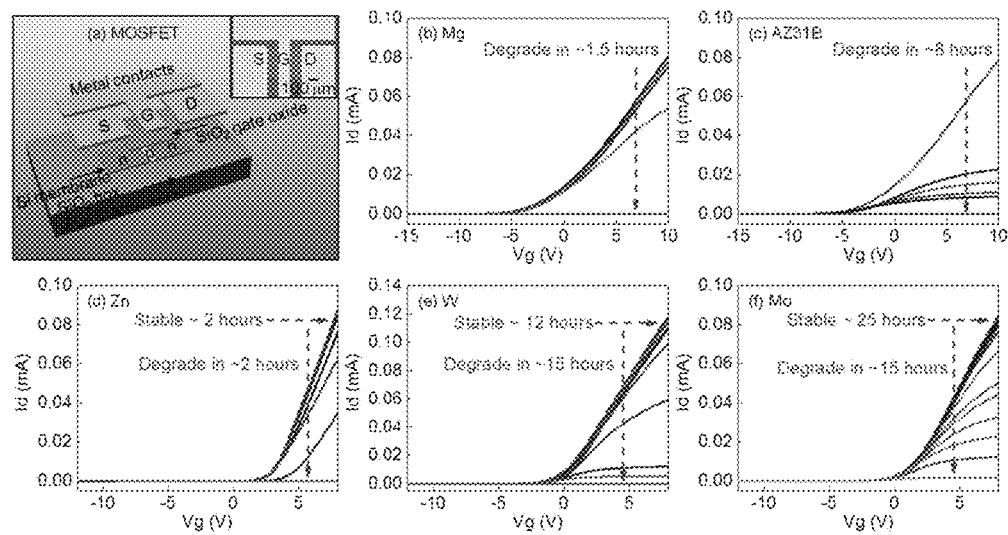
FIG. 14. (a) Geometry of n-channel MOSFET; (b)-(f) functionality degradation of n-channel MOSFET with transient metal contacts: Mg, AZ31B Mg alloy, Zn, W and Mo respectively.

Mg (300 nm), AZ31B Mg alloy (300 nm), Zn (300 nm), W (150 nm) and Mo (80 nm) without Cr adhesion layer are used as metal contacts for n-channel MOSFETs to demonstrate the feasibility of building transient systems based on these transient metals. The geometry of the thin film transistors (TFTs) build on an ultra thin silicon-on-insulation (SOI) wafer is illustrated in FIG. 14 (*a*), with length (L) 50 µm and width (W) 400 µm. The typical on/off ratio and mobility of these TFTs are >$10^4$ and 250 $cm^2$ $V^{-1}$ $s^{-1}$ respectively, regardless of the type of metal.

Figure 15:
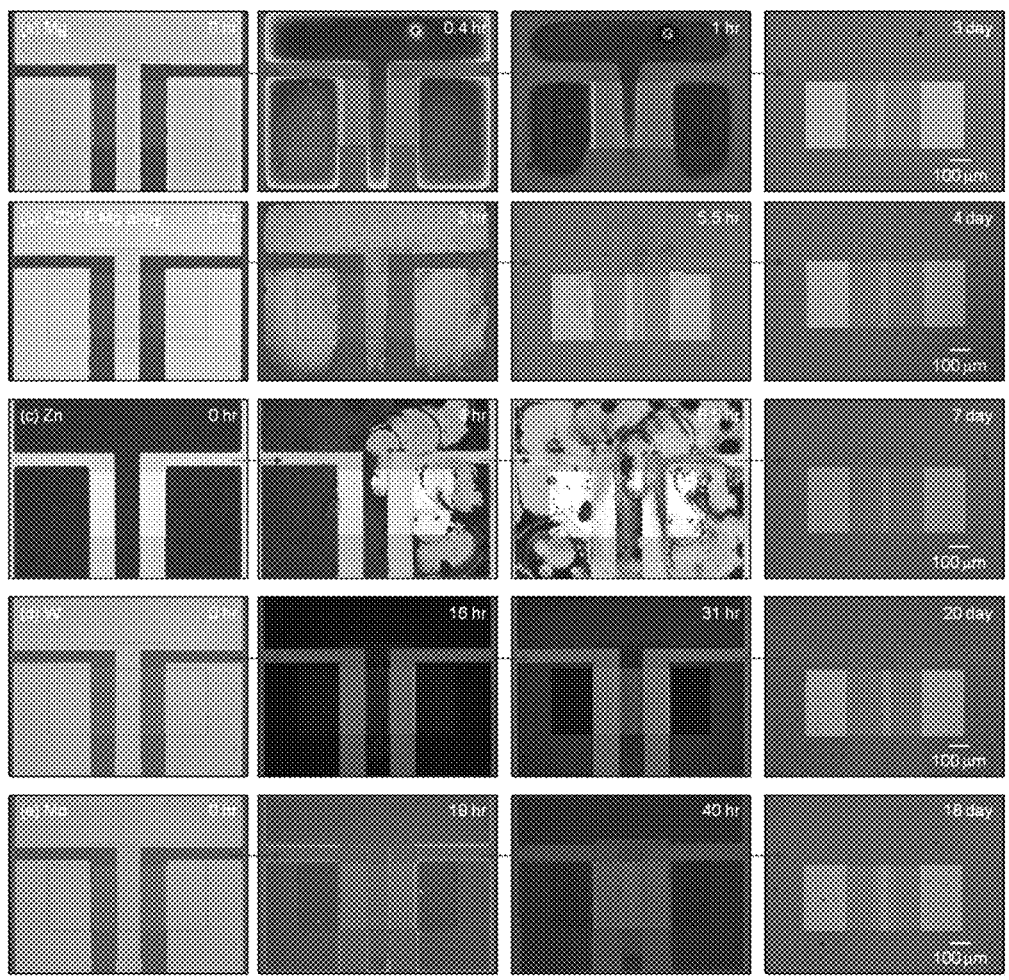
FIG. 15. Dissolution of metal contacts for n-channel MOSFETs: (a) Mg; (b) AZ31B Mg alloy; (c) Zn; (d) W and (e) Mo.

The functionality degradations of these TFT in DI water with various transient metals are shown in FIG. 14 (*b*)-(*f*), and the images for metal contact degradation are given in FIG. 15. Due to a much faster dissolution rate of metal contacts (~$5\times10^{-3}$-0.3 µm/hour) compared to silicon and silicon oxides (~$10^{-3}$-$10^{-4}$ µm/day)),[1] the degradation of TFT functionality mainly results from the conductivity lost of metal contacts as dissolution proceeds. As can be seen in FIG. 14, TFTs with Mg, AZ31B alloy and Zn contacts lost their function in ~2-8 hours (corresponding to an EDRs ~0.04-0.15 µm/hour); while TFTs with W and Mo contacts can have a stable operation period around 12 hours and 25 hours respectively even without any encapsulation, and then gradually lost their functions in about 15 hours (~(EDRs ~(2-5)×$10^{-3}$ µm/hour). These results are consistent with the aforementioned dissolution rates of metal traces.

Figure 16:
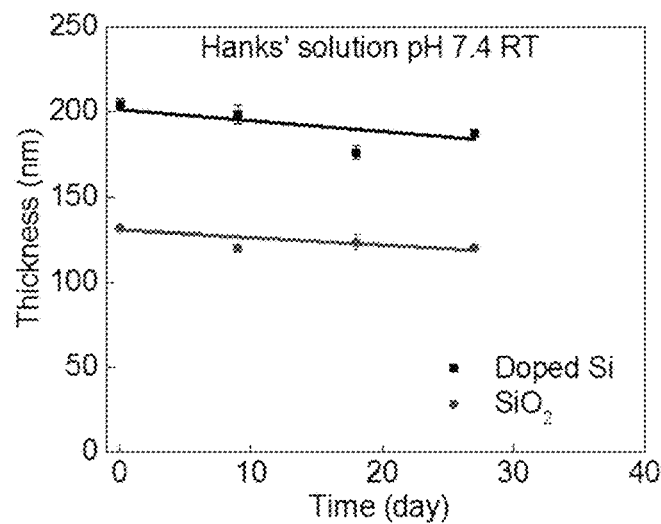
FIG. 16. Thickness changes of doped Si and $SiO_2$ gate oxides in n-channel MOSFETs upon dissolution in Hanks' solution pH 7.4 at RT.

After the disappearance of metals and their residual oxides, thin film silicon and silicon oxide can slowly dissolve away.[1,40] The degradation of doped Si and $SiO_2$ gate oxides in Hanks' solution pH 7.4 at RT in terms of thickness changes was also measured in the current study and is given in FIG. 16, indicating a fairly slow dissolution, ~0.8 and 0.3 nm/day for doped Si and $SiO_2$ respectively.

In all, combining various transient metals and encapsulation techniques, it is possible to adjust the function time from hours to weeks at the device level. By transfer printing such TFTs to degradable substrates, a fully dissolvable device with a tunable life time can be achieved as reported by Hwang et al.[1, 40]

3. Conclusions

Electrical dissolution behavior Mg, AZ31B Mg alloy, Zn, Fe, W and Mo thin films in de-ionized (DI) water and simulated body fluids (Hanks' solution pH 5-8) was systematically studied. Transient behavior at the device level of N-type silicon thin film transistors with transient metal contacts was also investigated. The following conclusions were found:

(1) Dissolution rates in terms of electrical conductivity of Mg, AZ31B Mg alloy and Zn (~0.5-3 µm/hour) are much faster compared to W, Mo and Fe (~$10^{-4}$-0.02 µm/hour). Such rates are different from the general corrosion rates in terms of mass lost of bulk materials due to the nature of thin films (purity, grain size and sensitivity to non-uniformity), although the dependency of pH and temperature is consistent. Both decrease in metal thickness and porosity formation contribute to the conductivity lost of metal thin films upon dissolution;

(2) Oxides as dissolution products are always found on the thin film surface, and the chemistry and oxide structure are similar to that of bulk materials.

(3) The degradation of metal thin films consist two stages with first a relatively fast degradation of the base metal followed by a much slower dissolution of residual oxides. Residual oxides of Mg, AZ31B Mg alloy and Zn of 300 nm can fully disappear within one week in DI water, while W (150 nm) and Mo (40 nm) have residual oxides ~20-40 nm that is expected to completely dissolve after several months. On the contrary, iron oxides seem insoluble and it is therefore not suitable for transient electronics.

(4) Mg, AZ31B Mg alloy, Zn, W and Mo were demonstrated to be feasible as transient contacts for TFTs.

4. Experimental Section

Metal thin films (40 nm-300 nm) deposited by electron beam evaporation (Fe) or by magnetron sputtering (all others) were patterned by photolithography (AZ® nLOF™ 2070 photoresist) and lift-off on glass substrates. The deposition conditions are 1 A/s for Fe; 50 W, 3 mT for Mg and AZ31B Mg alloy; 100 W, 100 mT for Zn; 150 W 5 mT for W; 150 W 3 mT for Mo. These conditions were chosen to minimize delamination while maintain the thin film quality and deposition yield. The vacuum level for metal deposition is all below 5×$10^{-5}$ Torr. In all cases, a layer of Cr (10 nm) deposited by either sputtering or electron beam evaporation served as an adhesion promoter, to eliminate delamination during the dissolution tests.

Dissolution behavior was studied in DI water and Hanks' solution (H 8264, Sigma-Aldrich®, St. Louis, Mo.). Small amounts of NaOH and HCl were added to the Hanks' solutions to control the pH. A Hanna HI 9126 portable pH/ORP meter (HANNA instruments, Smithfield, R.I.) was used to monitor the pH at various times during dissolution, to ensure that the value remained constant during the experiment (±0.2 pH units). Electrical probing occurred through contacts to two pads located outside of the solution. N-channel MOSFETs were prepared on silicon-on-insulator (SOI) wafers (320 nm top silicon layer, p-type, SOITEC, France). The source and drain areas were doped through diffusion of phosphorous at high temperature for 5 minutes (~1000° C.). The top device silicon was patterned by reactive ion etching (RIE) with sulfur hexafluoride ($SF_6$) gas. The gate dielectrics ($SiO_2$) ~130 nm were formed by plasma-enhanced chemical vapor deposition (PECVD) at 250° C., and patterned by photolithography and etching in buffered oxide etchant (BOE). Metal contacts were deposited using the same methods as mentioned previously, but without the Cr adhesion layer. The transient electrical properties of the MOSFETs were evaluated using a probe station and semiconductor parameter analyzer.

An Hitachi S-4800 high resolution scanning electron microscope (SEM, Hitachi high-technologies corporation, Japan) was used to example the surface and cross-sectional morpholoies of metal films at various stages of dissolution in DI water, using 10 kV applied voltage and 4 mm working distance. The surface chemistry was tracked by using X-ray Photoelectron Spectroscopy (XPS). The dissolution products and film morphologies were also studied by JEOL 2010$LaB_6$ transmission electron microscope (TEM, JEOL USA, Inc., Peabody, Mass.). TEM samples were prepared by depositing 100 nm of Mg and AZ31B Mg alloy and 50 nm of Zn, W, Mo and Fe on 15 nm silicon nitride grids (Ted Pella, Inc., Redding, Calif.). These samples were immersed in DI water for 0.5 hours (Mg), 1 hour (AZ31B Mg alloy), 10 hours (W), 40 hours (Mo), 2 hours (Zn) and 2 days (Fe) before TEM analysis. A Sloan Dektak profilometer was used to determine the changes in thicknesses of the metal thin films metal at various stages of dissolution in DI water. Thickness changes of doped Si and $SiO_2$ gate oxides in MOSFETs upon dissolution in Hanks' solution pH 7.4 at RT was measured by atomic force microscope (AFM, Cypher, Asylum Research, Santa Barbara, Calif.). The reported data correspond to averages of thicknesses evaluated at ten different locations. The standard deviations of these data were used as the error bars.

References

1. Hwang, S.-W., H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, and J. A. Rogers. Science, 2012. 337 (6102): p. 1640-1644.
2. Dagdeviren, C., S.-W. Hwang, Y. Su, S. Kim, H. Cheng, O. Gur, R. Haney, F. G. Omenetto, Y. Huang, and J. A. Rogers. Small, 2013: p. n/a-n/a.
3. Bevers, L. E., P.-L. Hagedoorn, and W. R. Hagen. Coordination Chemistry Reviews, 2009. 253(3-4): p. 269-290.
4. Barceloux, D. G., *Molybdenum*, in *Journal of Toxicology: Clinical Toxicology*. 1999. p. 231.
5. Trumbo, P., A. A. Yates; S. Schlicker, and M. Poos. Journal of the American Dietetic Association, 2001. 101 (3): p. 294-301.
6. Mueller, P. P., S. Arnold, M. Badar, D. Bormann, F.-W. Bach, A. Drynda, A. Meyer-Lindenberg, H. Hauser, and M. Peuster. Journal of Biomedical Materials Research Part A, 2012. 100A(11): p. 2881-2889.
7. Hermawan, H., A. Purnama, D. Dube, J. Couet, and D. Mantovani. Acta Biomaterialia, 2010. 6(5): p. 1852-1860.
8. Zeng, R., W. Dietzel, F. Witte, N. Hort, and C. Blawert. Advanced Engineering Materials, 2008. 10(8): p. B3-B14.
9. Witte, F. Acta Biomaterialia, 2010. 6(5): p. 1680-1692.
10. Kirkland, N. T., N. Birbilis, and M. P. Staiger. Acta Biomaterialia, 2012. 8(3): p. 925-936.
11. Wang, H. and Z. Shi. Journal of Biomedical Materials. Research Part B: Applied Biomaterials, 2011. 98B(2): p. 203-209.
12. Walker, J., S. Shadanbaz, N. T. Kirkland, E. Stace, T. Woodfield, M. P. Staiger, and G. J. Dias. Journal of Biomedical Materials Research Part B: Applied Biomaterials, 2012. 100B(4): p. 1134-1141.
13. Ng, W. F., K. Y. Chiu, and F. T. Cheng. Materials Science and Engineering: C, 2010. 30(6): p. 898-903.
14. Song, G. L. Corrosion Science, 2007. 49(4): p. 1696-1701.
15. Nie, F. L., Y. F. Zheng, S. C. Wei, C. Hu, and G. Yang. Biomedical Materials, 2010. 5(6).
16. Zhu, S. F., N. Huang, L. Xu, Y. Zhang, H. Q. Liu, H. Sun, and Y. X. Leng. Materials Science & Engineering C-Biomimetic and Supramolecular Systems, 2009. 29(5): p. 1589-1592.
17. Sherif, E.-S. M., R. M. Erasmus, and J. D. Comins. Electrochimica Acta, 2010. 55(11): p. 3657-3663.
18. Peuster, M., C. Hesse, T. Schloo, C. Fink, P. Beerbaum, and C. von Schnakenburg. Biomaterials, 2006. 27(28): p. 4955-4962.
19. Schwertmann, U. Plant and Soil, 1991. 130(1-2): p. 1-25.
20. Bowen, P. K., J. Drelich, and J. Goldman. Advanced Materials, 2013: p. n/a-n/a.
21. Zhou, J., N. S. Xu, and Z. L. Wang. Advanced Materials, 2006. 18(18): p. 2432-2435.
22. Patrick, E., M. E. Orazem, J. C. Sanchez, and T. Nishida. Journal of Neuroscience Methods, 2011. 198(2): p. 158-171.
23. Badawy, W. A. and F. M. Al-Kharafi. Electrochimica Acta, 1998. 44(4): p. 693-702.
24. Anik, M. and K. Osseo-Asare. Journal of The Electrochemical Society, 2002. 149(6): p. B224-B233.
25. Peuster, M., C. Fink, and C. von Schnakenburg. Biomaterials, 2003. 24(22): p. 4057-4061.
26. Strigul, N. Ecotoxicology and Environmental Safety, 2010. 73(6): p. 1099-1113.
27. *Uhlig's corrosion handbook*. Third ed, ed. R. W. Revie. 2011: John Wiley & Sons, Inc.
28. Song, G. and A. Atrens. Advanced Engineering Materials, 2003. 5(12): p. 837-858.
29. Ambat, R., N. N. Aung, and W. Zhou. J Appl Electrochem, 2000. 30(7): p. 865-874.
30. Zhang, X. G., *Corrosion and electrochemistry of zinc.* 1996, New York: Plenum Press.
31. Hixson, H. and P. M. A. Sherwood. Journal of the Chemical Society, Faraday Transactions, 1995. 91(20): p. 3593-3601.
32. Oikawa, H. Japanese Journal of Applied Physics, 1975. 14(5): p. 629-635:
33. Lang, W. and R. Zander. Industrial & Engineering Chemistry Fundamentals, 1986. 25(4): p. 775-782.
34. De Rosa, L., C. R. Tomachuk, J. Springer, D. B. Mitton, S. Saiello, and F. Bellucci. Materials and Corrosion, 2004. 55(8): p. 602-609.
35. Miyake, K., K. Ohashi, H. Takahashi, and T. Minemura. Surface and Coatings Technology, 1994. 65(1-3): p. 208-213.
36. Youssef, K. M. S., C. C. Koch, and P. S. Fedkiw. Corrosion Science, 2004. 46(1): p. 51-64.
37. Kneer, E. A., C. Raghunath, V. Mathew, S. Raghavan, and J. S. Jeon. Journal of The Electrochemical Society, 1997. 144(9): p. 3041-3049.
38. Blawert, C., V. Heitmann, N. Scharnagl, M. Stormer, J. Lutz, A. Prager-Duschke, D. Manova, and S. Mandl. Plasma Processes and Polymers, 2009. 6: p. S690-S694.
39. Schluter, K., C. Zamponi, A. Piorra, and E. Quandt. Corrosion Science, 2010. 52(12): p. 3973-3977.
40. Li, R., H. Cheng, Y. Su, S.-W. Hwang, L. Yin, H. Tao, M. A. Brenckle, D.-H. Kim, F. G. Omenetto, J. A. Rogers, and Y. Huang. Advanced Functional Materials, 2013: p. n/a-n/a.
41. Zhao, M.-C., P. Schmutz, S. Brunner, M. Liu, G.-I. Song, and A. Atrens. Corrosion Science, 2009. 51(6): p. 1277-1292.
42. Samaniego, A., I. Llorente, and S. Feliu Jr. Corrosion Science, 2013. 68(0): p. 66-71.
43. Jang, Y, B. Collins, J. Sankar, and Y. Yun. Acta Biomaterialia, (0).
44. Wu, G., W. Dai, L. Song, and A. Wang. Materials Letters, 2010. 64(3): p. 475-478.
45. Liu, M., S. Zanna, H. Ardelean, I. Frateur, P. Schmutz, G. Song, A. Atrens, and P. Marcus. Corrosion Science, 2009. 51(5): p. 1115-1127.
46. Santamaria, M., F. Di Quarto, S. Zanna, and P. Marcus. Electrochimica Acta, 2007. 53(3): p. 1314-1324.
47. Tie, D., F. Feyerabend, N. Hort, R. Willumeit, and D. Hoeche. Advanced Engineering Materials, 2010. 12(12): p. B699-B704.
48. Yao, H. B., Y. Li, and A. T. S. Wee. Applied Surface Science, 2000. 158(1-2): p. 112-119.
49. Zainal Abidin, N. I., D. Martin, and A. Atrens. Corrosion Science, 2011. 53(3): p. 862-872.
50. Taheri, M., R. C. Phillips, J. R. Kish, and G. A. Botton. Corrosion Science, 2012. 59(0): p. 222-228.
51. *Crc handbook of chemistry and physics.* 93 ed, ed. W. M. Haynes and D. R. Lide. 2012-2013, Boca Raton, Fla.: CRC Press.

52. Shpak, A. P., A. M. Korduban, M. M. Medvedskij, and V. O. Kandyba. Journal of Electron Spectroscopy and Related Phenomena, 2007. 156: p. 172-175.
53. Xie, F. Y., L. Gong, X. Liu, Y. T. Tao, W. H. Zhang, S. H. Chen, H. Meng, and J. Chen. Journal of Electron Spectroscopy and Related Phenomena, 2012. 185(3-4): p. 112-118.
54. Barreca, D., G. Carta, A. Gasparotto, G. Rossetto, E. Tondello, and P. Zanella. Surface Science Spectra, 2001. 8(4): p. 258-267.
55. Lillard, R. S., G. S. Kanner, and D. P. Butt. Journal of The Electrochemical Society, 1998. 145(8): p. 2718-2725.
56. Okonkwo, I. A., J. Doff, A. Baron-Wieched, G. Jones, E. V. Koroleva, P. Skeldon, and G. E. Thompson. Thin Solid Films, 2012. 520(19): p. 6318-6327.
57. Petrova, M., M. Bojinov, S. Zanna, and P. Marcus. Electrochimica Acta, 2011. 56(23): p. 7899-7906.
58. Tamboli, D., S. Seal, V. Desai, and A. Maury. J. Vac. Sci. Technol. A-Vac. Surf. Films, 1999. 17(4): p. 1168-1173.
59. Anik, M. and T. Cansizoglu. J Appl Electrochem, 2006. 36(5): p. 603-608.
60. Stefaniak, A. B. Particle and Fibre Toxicology, 2010. 7.
61. Wang, H., J. Xie, K. P. Yan, M. Duan, and Y. Zuo. Corrosion Science, 2009. 51(1): p. 181-185.
62. Dong, Z. H., W. Shi, and X. P. Guo. Corrosion Science, 2011. 53(4): p. 1322-1330.
63. Nicholas, N. J., G. V. Franks, and W. A. Ducker. CrystEngComm, 2012. 14(4): p. 1232-1240.
64. Lin, B. C., P. Shen, and S. Y. Chen. The Journal of Physical Chemistry C, 2010. 115(12): p. 5003-5010.
65. Barreca, D., G. A. Battiston, D. Berto, R. Gerbasi, and E. Tondello. Surface Science Spectra, 2001. 8(3): p. 240-245.
66. Suzuki, S., K. Yanagihara, and K. Hirokawa. Surface and Interface Analysis, 2000. 30(1): p. 372-376.

EXAMPLE 3

Transient Primary Batteries

Figure 18:
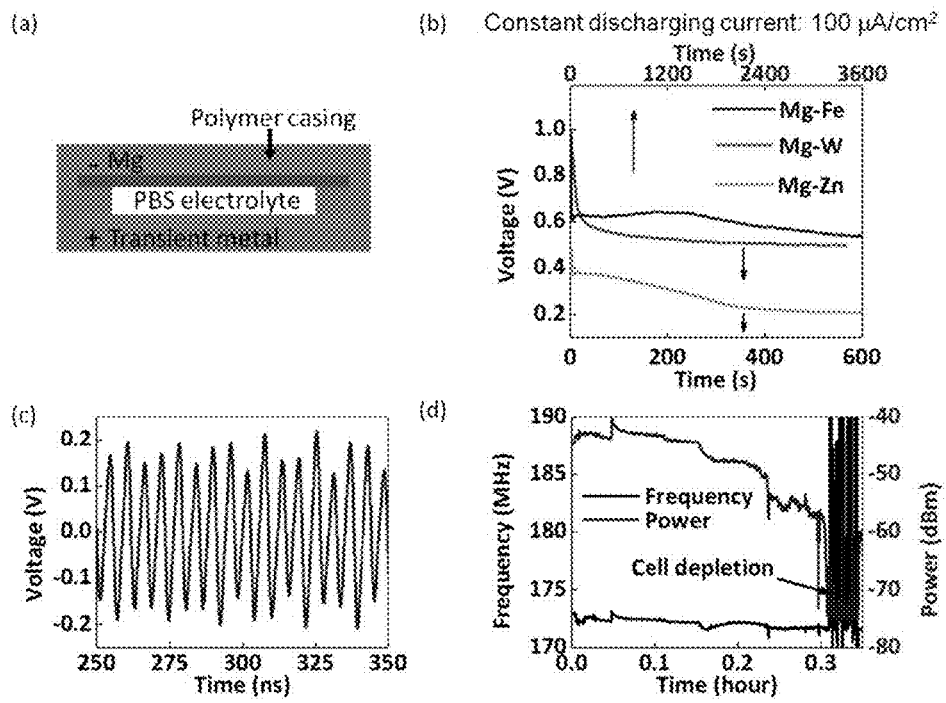
FIG. 18. (a) Schematic illustration of a transient primary battery system; (b) preliminary performance from devices with three different transient metal cathodes; (c) output of radio circuit powered by four transient Mg—Fe batteries connected in series; (d) frequency and power of radio circuit powered by Mg—Fe batteries as a function of time.

Batteries provide an important alternative to the RF approaches to power. This Example focuses on the development of a transient primary battery. Magnesium is an appealing anode material due to its high energy density, long shelf life and cost efficiency, and it is already widely used in high energy density water activated primary batteries for sonobuoys, electric torpedoes, air-sea rescue equipment, and others. The combined bio and CMOS compatibility of magnesium further enhances the appeal of this material choice. One construction of a transient primary battery appears in FIG. 18(a). Here, a Mg foil serves as anode and another transient metal foil, selected among Fe, W or Zn serves as the cathode. Encasing these electrodes in a transient package with an aqueous electrolyte completes the system. The driving reactions are: negative electrode Mg→Mg2++2e−; positive electrode H++e−→H2; overall reaction Mg+H2O→Mg(OH)2+H2. The total capacity depends directly on the amount of Mg. Results on battery performance in three different devices, i.e. Mg—Fe, Mg—W and Mg—Zn, are presented in FIG. 18(b). The output involves a constant discharge current density of ~100 µA/cm2, with a voltage between ~0.6 V, for Mg—Fe and ~0.2 V, for Mg—Zn. Measurements show that the Mg—Fe system supplies current for at least 3 hours, suggesting that surface products (e.g., Mg(OH)2) do not limit performance. Designs may be optimized via structuring of the Mg foil to increase the area and geometries to facilitate reactive flows. Data suggest that power of ~60 mW/cm2 can be generated by such batteries. Improved output voltages might be possible by connecting batteries in series. In these designs, the batteries provide sufficient power and voltages to operate RF transmitting systems, the output of which is shown in FIG. 18(c). The output is stable until the electrolyte eventually depletes (FIG. 1.8(d)).

EXAMPLE 4

Transient Electronics

This Example describes an exemplary mode of transforming a transient electronic device by providing, either as part of the transient electronic device or as a separate device operationally connected to the transient electronic device (e.g., in fluid communication with the transient electronic device), a reservoir of chemical reagents that react to produce a volume of gas. As the volume of gas increases, pressure increases within at least a portion of the reservoir until mechanical failure of the portion of the reservoir is achieved. For example, mechanical failure may be in the form of cracking, shattering, ripping, popping or any other action that opens a hole in the reservoir or otherwise compromises the structural integrity of the reservoir (e.g., transforms the reservoir from a contiguous material into a non-contiguous material). Mechanical failure of the portion of the reservoir exposes one or more inorganic semiconductor components or one or more metallic conductor components to a chemical agent. For example, the chemical agent may be water, a nonaqueous solvent, an aqueous solution, an acid, a base, an etchant, oxygen, or a combination. thereof. Any chemical agent capable of dissolving, degrading, etching or otherwise transforming a semiconductor component and/or a metallic conductor component is suitable for performing the transformation described in this Example.

Typically, at least two chemical reagents react in an electrochemical reaction or an electrolysis reaction to produce the gas that increases pressure within the reservoir. The gas may, for example, be $H_2$, $O_2$, $N_2$, CO, $CO_2$, $XeF_2$, $SF_6$, $CHF_3$, $CF_4$, or combinations thereof. In an embodiment, each of the chemical reagents may be held in a separate portion of the reservoir until a pre-selected time to prevent mixing of the reagents that produces the gas. For example, each of the chemical reagents may be held behind an internal wall of the reservoir comprising a selectively transformable material that the chemical reagent is able to transform over a period of time to reach a reaction chamber of the reservoir.

In another embodiment, the device includes an actuator responsive to a user initiated external trigger signal and operably connected to one or more inorganic semiconductor components or one or more metallic conductor components. When the device receives the external trigger signal the actuator directly or indirectly initiates at least partial transformation of the one or more active or passive electronic device components, such as the one or more inorganic semiconductor components or the one or more metallic conductor components, in response to the internal or external stimulus, thereby providing a programmable transformation of the transient electronic device in response to the external trigger signal. For example, the user initiated external trigger signal is a user initiated application of an electric field provided to the device, a user initiated application of electromagnetic radiation provided to the device, a user initiated mechanical impact provided to the device, a user initiated flow of heat provided to the device, a user initiated flow of heat from the device or a user initiated application of an RF electric field provided to the device. The device may, for example, be in one-way or two-way communication with a transmitter, where the transmitter provides the user initiated external trigger signal to a receiver of the device operationally connected to the actuator so as to initiate the at least partial transformation of the one or more active or passive electronic device components, such as the one or more inorganic semiconductor components or the one or more metallic conductor components, upon receiving the user initiated external trigger signal. For example, in an embodiment, when the device receives the user initiated external trigger signal, the actuator disperses chemical reagents into a reservoir, where the chemical reagents react to produce a volume of gas that increases pressure within at least a portion of the reservoir until mechanical failure of the portion of the reservoir is achieved. In another embodiment, the user initiated external trigger signal is the application of an RF electric field to the device, which receives the energy and utilizes it for an electrolysis reaction.

Figure 19:
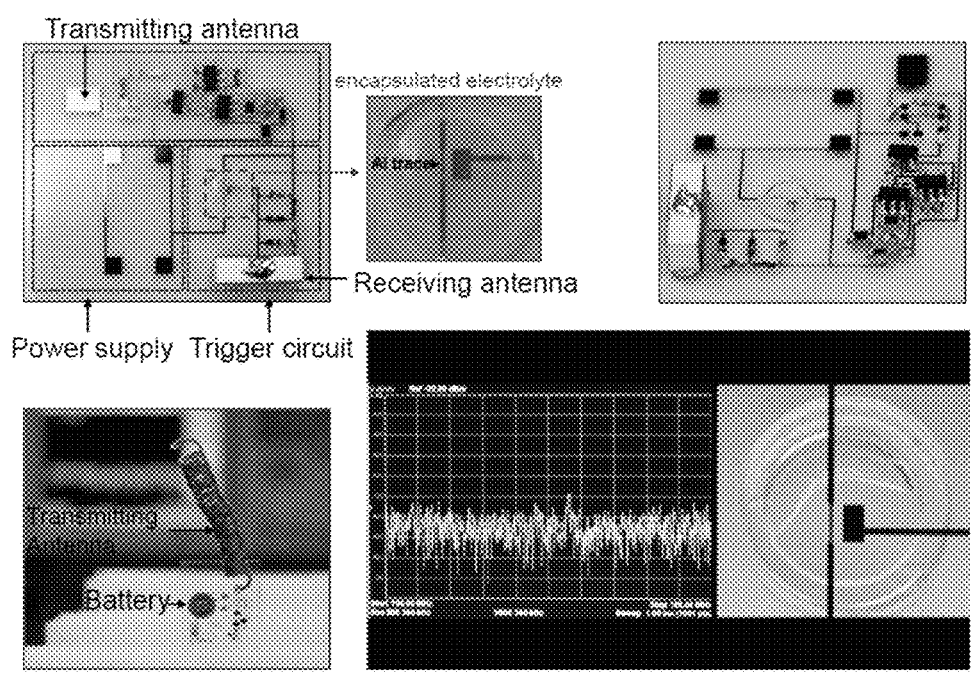
FIG. 19 shows RF triggered transience of function in a beacon circuit.

FIG. 19 shows RF triggered transience of function in a beacon circuit. An electrochemical cell incorporates a conductive trace that is part of the overall circuit. RF radiation induces electrochemical etching of that trace until it disappears. The system ceases to function as a result.

Figure 20:
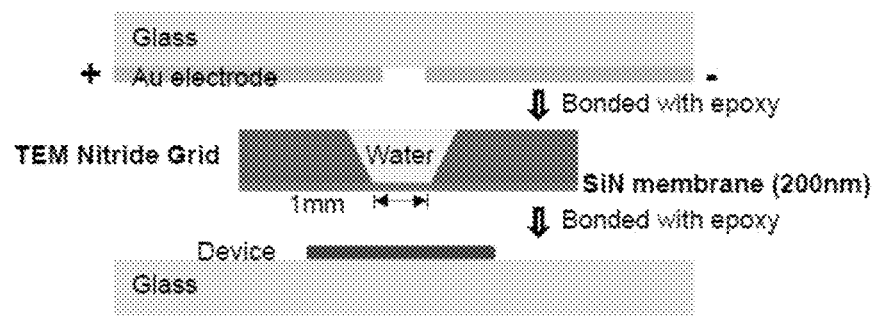
FIG. 20 shows RF triggered transience of an entire circuit.

FIG. 20 shows RF triggered transience of an entire circuit using a water or etchant reservoir with a breakable/removable/etchable barrier. Elimination of this barrier causes the etchant to spill out and cover the transient circuit, entirely or in part. In this embodiment, RF is used to initiate electrolysis in the water reservoir. Pressure build up from release of hydrogen and oxygen leads to the fracture of a thin barrier membrane, for example a SiN membrane. This rupture causes the water to flow onto a water-soluble circuit below.

EXAMPLE 5

Materials, Designs and Operational Characteristics for Fully Biodegradable Primary Batteries Transient electronics is an emerging technology whose key attribute is an ability to physically disappear, entirely or in part, in a controlled manner after a period of stable operation.[1] Applications include zero-waste environmental sensors, hardware-secure memory modules and temporary biomedical implants. For this third example, biodegradable electronics built using water soluble, biocompatible active and passive materials provide multifunctional operation to assist a transient biological event, such as wound healing.[1-5] Biodegradable power supply is an essential component for many such systems. Demonstrated strategies range from degradable radio frequency power transfer modules,[6] to silicon based photovoltaics[1] and mechanical energy harvesters.[7] Primary batteries represent versatile options that can complement these and other possibilities. One design involves adapted versions of water-activated battery technologies, in which the constituent materials are transient.[8,9] Kim et al. recently reported an edible sodium ion battery[8] with biologically derived melanin as an electrode.[10] Although few technical details are available, recent announcements suggest the use of isolated galvanic pairs of Mg and a copper salt as small-capacity power sources for ingestible pharmaceuticals that become activated upon exposure to the digestive tract[11]; the structures do not, however, exist a proper batteries, in the conventional sense, nor do they offer output powers useful for general classes of bioresorbable electronics: Magnesium (Mg) is, however, an appealing anode material due to its high energy density, long shelf-life and excellent biocompatibility.[12-14] Conventional Mg primary batteries use cathode materials (e.g., non-conductive AgCl, CuCl and MnO₂ for high performance, or copper, carbon and stainless steel for long lifetime)[13, 15] that are either non-degradable, toxic, and/or environmentally hazardous. Such devices also involve long-lasting current collectors and packages.[13,16] Replacing the cathode materials with biodegradable metals[17-20] (e.g., iron (Fe), tungsten (W) or molybdenum (Mo)) together with biodegradable polymers (e.g., polyanhydrides)[21] for packing creates an opportunity for the construction of fully transient batteries that can degrade, without harm, in biofluids or groundwater. In this design, the metallic cathode substitution reduces the operating voltages and current densities, but the overall performance can be compensated by monolithically integrating stacks of cells in series to increase the voltage and/or by enlarging the electrode area to increase the output current. Moreover, metal cathodes have the additional benefit that they simplify the assembly process. Here, the metal itself can serve as the current collector, thereby eliminating conductive binders that are required for standard materials such as AgCl or CuCl.

Figure 24:
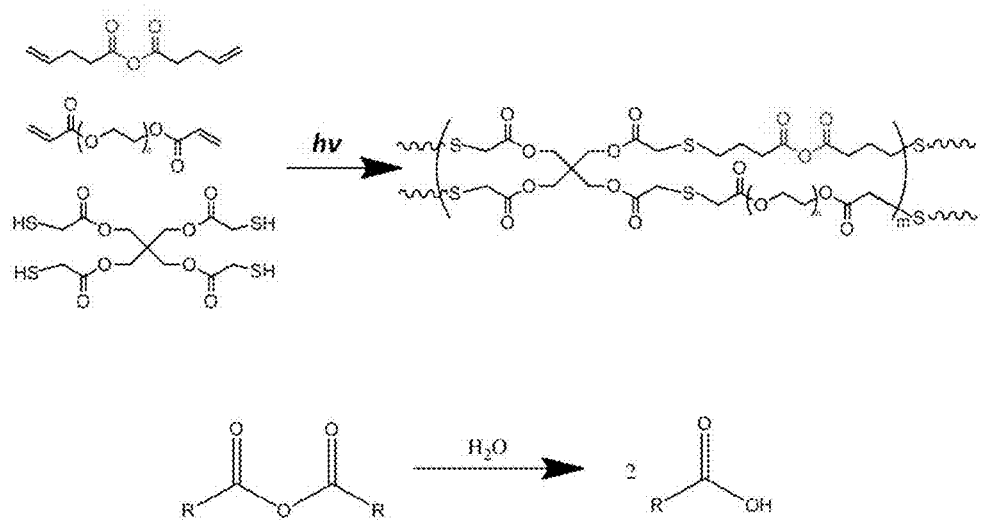
FIG. 24. Synthetic and degradation schemes of polyanhydrides.

The water-activated primary batteries that we report here involve constituent materials are all degradable, environmentally benign and biocompatible. Magnesium foils serve as the anodes, while metal foils based on Fe, W or Mo serve as the cathodes; the packages are formed with polyanhydrides[22-24] (See supporting information FIG. 24 for the synthetic scheme). Systematic studies reveal the achievable performance and the mechanisms for anode dissolution in single cells. Multi-cell packs that use Mg and Mo foils illustrate scalability in power, and include demonstrations in the powering of light-emitting diodes (LEDs) and radio transmitters.

The performance of single cell batteries that consist of Mg—X (X=Fe, W, or Mo) metal foils can be evaluated most conveniently by use of a PDMS liquid chamber filled with phosphate buffered saline (PBS) as the electrolyte. The testing structure appears in FIG. 21(a). The discharging behavior with an anode-cathode spacing of ~2 mm is summarized in FIG. 21(b), for the case of a constant discharge current density (0.1 mA/cm²). The operating voltages are ~0.75 V, ~0.65 V and ~0.45 V for Fe, W and Mo, respectively. In each case, the voltage is stable for at least 24 hours. The lifetime is limited by the depletion of the active material (Mg). For similar levels of discharging current, the observed output voltages are comparable to those in Mg deep seawater batteries with stainless steel cathodes,[15] but lower than conventional devices that use Mg/AgCl or Mg/CuCl (~1.5-1.6V).[13]

The principle electrochemical reactions of the battery are as follows[15, 16]:

(i) Anode

$$Mg \rightarrow Mg^{2+} + 2e^- \tag{1}$$

The following side reaction takes place simultaneously:

$$Mg + 2H_2O \rightarrow Mg(OH)_2 + H_2 \tag{2}$$

(ii) Cathode

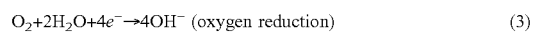

$$O_2 + 2H_2O + 4e^- \rightarrow 4OH^- \text{ (oxygen reduction)} \tag{3}$$

Or

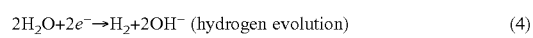

$$2H_2O + 2e^- \rightarrow H_2 + 2OH^- \text{ (hydrogen evolution)} \tag{4}$$

Figure 21:
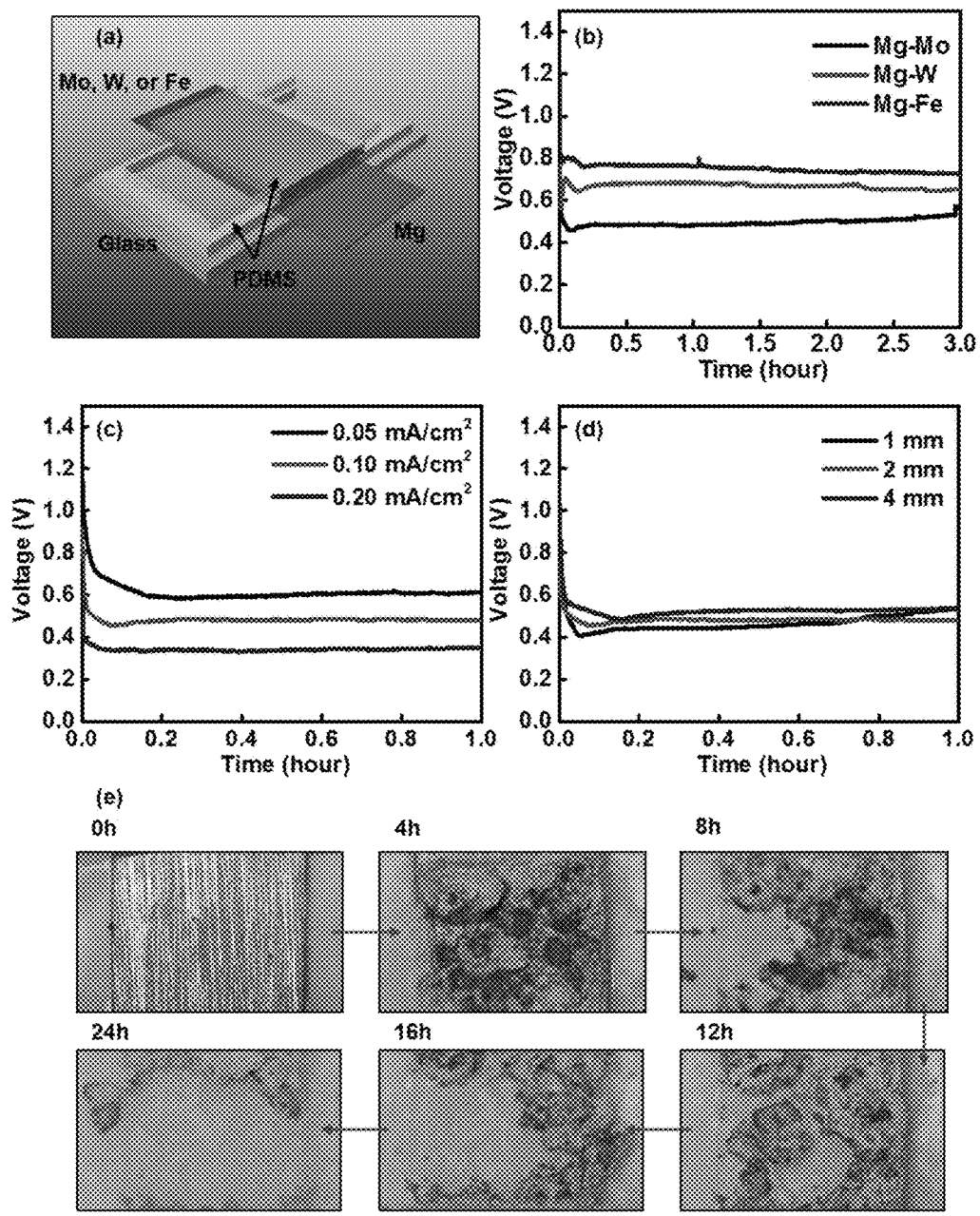
FIG. 21. (a) Configuration of a single Mg—X cell battery for performance evaluation; (b) discharging behavior of a Mg—X battery under constant current (0.1 mA/cm$^2$); (c) effects of discharging current density on Mg—Mo battery performance; (d) effects of anode-cathode spacing on Mg—Mo battery performance; (e) optical images of a Mg foil at various stages of degradation during the course of discharging a Mg—Mo battery (discharge current density: 0.1 mA/cm$^2$).

Oxygen reduction at the cathode site produces a higher potential compared to that for hydrogen reduction. The electrolyte typically contains a small amount of oxygen, such that the associated current densities are limited by diffusion of oxygen to the cathode surface. Hydrogen evolution enables improved current density, but with reduced output voltage. Electrochemical measurements of the cathodic reaction for Mg—X (X=Fe, W, or Mo) gives a potential ~−0.7 V vs. Ag/AgCl at a discharge current density of 0.1 mA/cm$^2$. This potential is less than the oxygen reduction potential (0.179V vs. Ag/AgCl) and higher than the hydrogen evolution potential (−1.05 V vs. Ag/AgCl), suggesting that both types of reactions could take place. The cathodic reaction shifts completely to hydrogen evolution (~1.2V vs. Ag/AgCl) at a current density of 1 mA/cm$^2$, with a significant increase of the amount of visible hydrogen bubbles at the cathode. As expected, increasing the discharge current density lowers the output voltage due to a shift of the cathodic reaction and an increase in the over potential at the electrode/electrolyte interface, as shown in FIG. 1(c) for Mg—Mo. Increasing the spacing between the anode and cathode from 1 mm to 4 mm does not obviously change the observed behaviors (FIG. 21(d)). As illustrated in FIG. 21(e), during discharging (Mg—Mo battery, 0.1 mA/cm$^2$), Mg gradually degrades due to reactions associated with operation, as well as those due to corrosion (self-discharging). As can be seen from the FIG. 1(e), degradation of Mg is non-uniform (pitting type corrosion). White deposits, consistent with Mg(OH)$_2$, often appear on the surface of the foil.[25]

With 1 cm$^2$ active area and with 50 μm thick Mg foil and 8 μm thick Mo foil, this type of battery contains 8.7 mg Mg and 8.2 mg Mo and offers a measured capacity of ~2.4 mAh (0.1 mA/cm$^2$ for 24 hours), corresponding to a specific capacity ~276 mAh g$^{-1}$ (normalized with anode mass). The amount of Mg is comparable to that in a single biodegradable Mg coronary arterial stent (~3-6 mg).[19] Due to the corrosion of Mg foils during operation, together with impurities that might accelerate self-discharging, the measured capacity is lower than the theoretical capacity of Mg (2.2 Ah g$^{-1}$). Nevertheless, compared to the recently reported biodegradable melanin sodium-ion battery,[10] the Mg battery exhibits slightly higher stable voltage (~0.4-0.7 V), higher discharge current density (0.1 mA/cm$^2$), longer lifetime (at least 24 hours) and higher specific capacity (~276 mAh g$^{-1}$). The shelf time of a non-activated Mg battery can be long, due to a reasonable resistance to Mg oxidation in air.[14] If activated by PBS, the battery will lose roughly half of its capacity in 1-3 days, due to corrosion of the Mg foil.[26,27]

Figure 22:
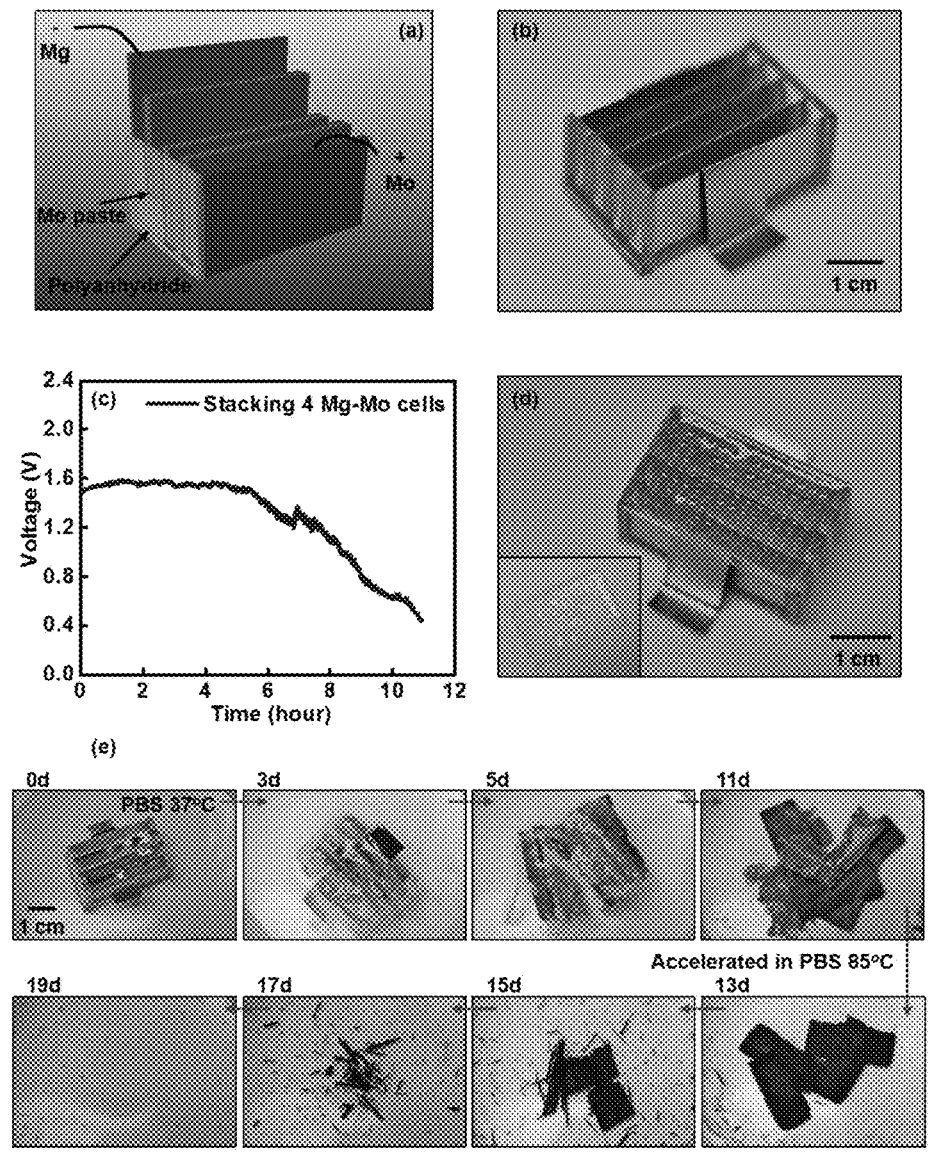
FIG. 22(1). (a) Configuration of battery pack that consists of four Mg—Mo cells in series; (b) optical images of the battery; (c) discharging behavior (0.1 mA/cm$^2$); (d) top porous polyanhydride cover to confine the electrolytes; (e) dissolution of the battery.
Figure 22:
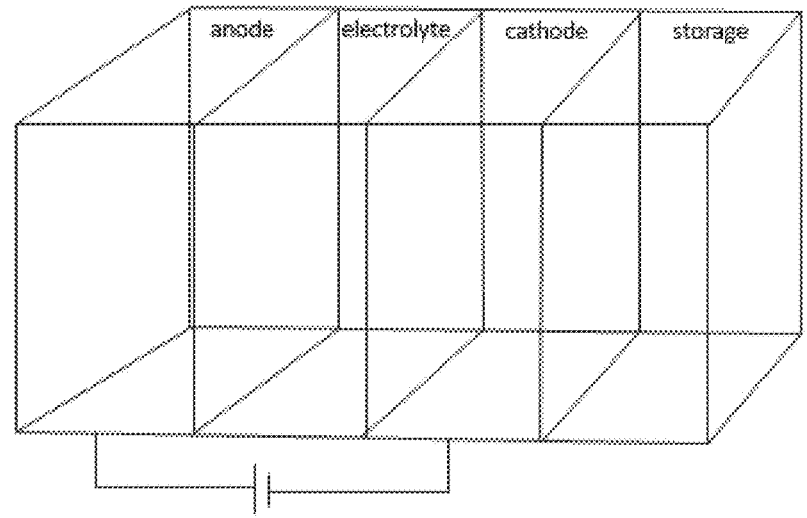
Figure 25:
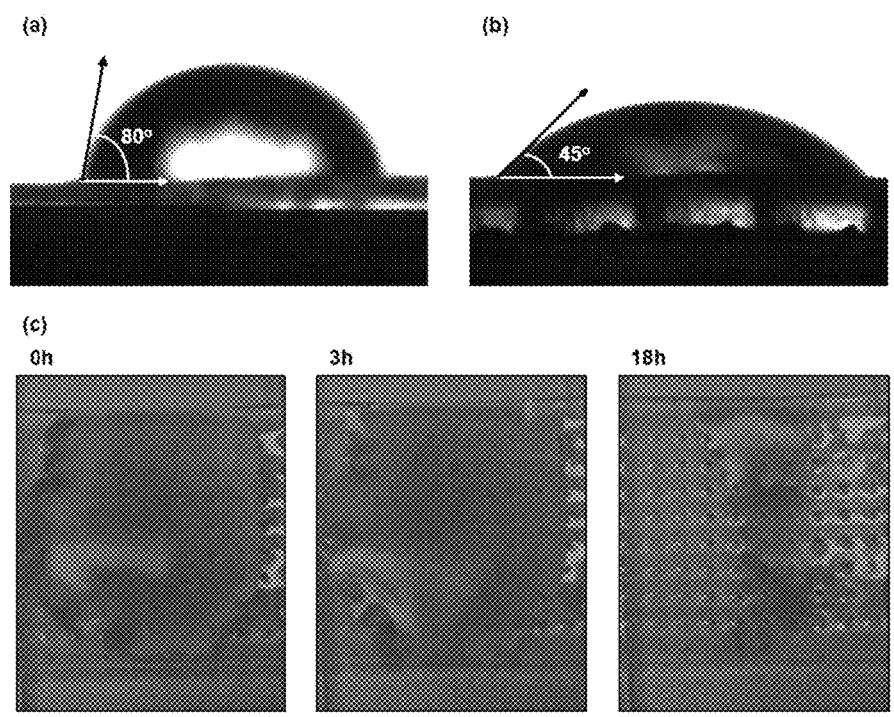
FIG. 25. Contact angle measurements of (a) polyanhydride film (~80°); (b) porous polyanhydride film (45°); (c) Effectiveness of porous polyanhydride film as a water barrier: the film hanging in air holds colored phosphate buffered saline without leaking through for up to 18 hours (saline evaporates into air at the same time during the observation process).

Stacking individual Mg cells in series allows increasing output voltage. The configuration of a four cell stack of Mg—Mo battery cells appears in FIG. 22(1)(a); the actual battery is in FIG. 22(1)(b). Here, the dimension of each metal foil is 3×1.3 cm, corresponding to an area of 3.9 cm$^2$. The anode-cathode spacing for each Mg—Mo cell is ~4 mm. The total weight of the stacked battery is ~3.5 g, including 0.14 g Mg and 0.13 g Mo and the encasing materials. A thin layer of polyanhydride serves as a spacer (~0.5 mm) to prevent electrical shorts between single cells, physically separating the electrolytes for each chamber. A Mo paste made of Mo powder and a water-soluble sodium carboxymethyl cellulose glue provides electrical connections between the individual cells, buried in the polyanhydride encasement to prevent shorts. Discharging the battery at a constant current density (0.1 mA/cm$^2$) gives a stable voltage output ~1.5-1.6V for up to 6 hours as shown in FIG. 22(1)(c). The slow degradation in voltage that follows this period occurs at a time earlier than that of a single battery cell, possibly due to slight leakage between cells that can arise from pitting corrosion of the foils and/or water permeation through or degradation of the polyanhydride spacers. As shown in FIG. 22(1)(c), a porous thin polyanhydride film (~0.5 mm) can be used as a top cover to confine the electrolyte. Small pores (~0.5 mm) in this film enable the release of hydrogen gas, but maintain as a barrier to retain the electrolyte due to a positive contact angle (~45°) of the polyanhydride (FIG. 25). FIG. 22(1)(e) demonstrates transience of the battery. The polyanhydride encasement degrades first to leave partially dissolved Mg and Mo foils after 11 days in PBS at 37° C. Accelerating the dissolution by increasing the temperature to 85° C. leads to elimination of the Mo foils after another 8 days.

FIG. 22(2) shows a schematic of a transient electrochemical device comprising a packaging component at least partially enclosing an anode, a cathode, and an electrolyte which is capable of conducting charge carriers between the anode and the cathode. At least one of the anode, the cathode, the electrolyte and the packaging component independently comprises a selectively transformable material. In an embodiment, to prevent transformation of the electrochemical device prior to discharge due to dissolution reactions, the electrolyte is stored away from the selectively transformable material(s) in a storage compartment. In preparation for use of the electrochemical device, the electrolyte is transferred to the electrolyte compartment between the anode and the cathode. For example, the electrolyte may be a fluid delivered through a shutter and optionally a tube. The storage compartment may feed directly to the electrolyte compartment or may be transferred through the cathode or anode (e.g., a porous cathode or anode). The electrical circuit between the anode and cathode is completed by external wiring.

Figure 23:
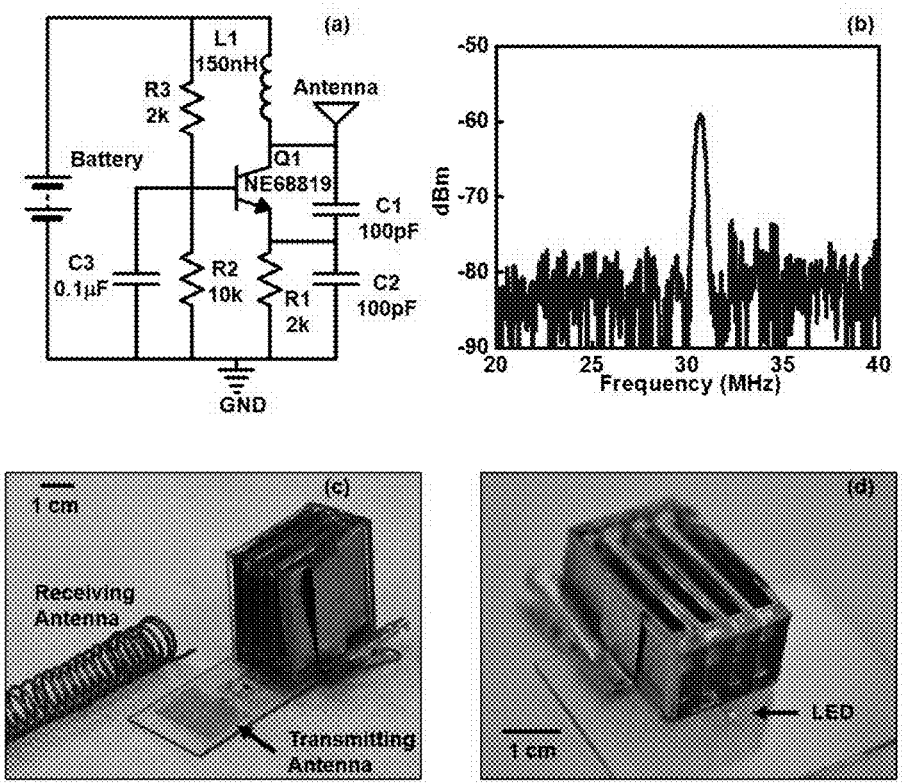
FIG. 23. (a) Radio circuit design; (b) Radio signal wirelessly received by a signal analyzer; (c) battery powered operation of a radio circuit; (d) battery powered operation of a red LED.

As shown in FIG. 23(d), the stacked Mg—Mo battery is able to power a conventional LED (threshold voltage ~1.6 V). A simple colpitts oscillator circuit is designed to generate a radio frequency of 58 MHz and transmits the signal through an electrical small dipole antenna as shown in FIG. 23(a). To power such a circuit, a voltage of 1.5 V and a total current of ~0.7 mA are required. The electrode area of the Mg—Mo stacked battery is therefore increased to 3×3.5 cm (10.5 cm$^2$), as shown in FIG. 23(c). The radio circuit powered by such battery successfully generates a signal approximately 30 MHz in frequency, which is lower than the designed frequency due to the frequency-dependent values of the passive components in the circuit. A signal analyzer connected by a hand-wound whip antenna can capture this signal ~2 cm away at a level of −60 dBm as shown in FIG. 23(b). Longer transmission distance can be achieved by proper impedance matching both at the radio circuit and the signal analyzer.

The results presented here indicate a range of options in transient batteries, with water soluble metals as the electrodes and biodegradable polymers as barrier layers and encasements. Voltage and current levels that can be achieved enable operation of realistic devices of potential practical importance for biodegradable electronics. Opportunities for future developments include foils with thickness or/and surface texture designed for controlling the transience times, schemes for programmable activation/deactivation of the battery to preserve the overall lifetime, and miniature cells for use in implantable sensors. In all such cases, the basic materials and architectures described here provide simple and scalable solutions batteries that provide biocompatible and environmentally benign sources of power.

Experimental Section

Single cell batteries involved metal foils, selected from the following: Mg (50 μm thick), Fe (25 μm thick), W (25

µm thick), and Mo (25 µm thick). Mg foils were purchased from GalliumSource, LLC, Scotts Valley, Calif., and Fe, W and Mo foils were purchased from Goodfellow Corporation, Coraopolis, Pa. The foils were cut into 1 cm×2 cm strips. PDMS serves as the chamber materials and fix metal foils on glass. The backsides of the metal foils were also covered by PDMS to define the exposed area. The anode-cathode spacing was controlled by a PDMS spacer. Stacks of such single cell batteries were fabricated by connecting four Mg—Mo cells. Foils were cut into 3×1.3 cm and a layer of polyanhydride spacer was laminated in between the cells. Polyanhydride was also used to encase metal foils and form the electrolyte chamber, by processes of casting with PDMS molds. UV-curable polyanhydride pre-cured polymer was prepared by mixing pentaerythritol tetrakis (3-mercaptopropionate), 4-pentenoic anhydride, and poly(ethylene glycol) diacrylate (molar ratio of 5:7:3) with the addition of 2,2-dimethoxy-2-phenylacetophenone (0.4 wt %) as the photoinitiator (all chemicals are purchased from Sigma-Aldrich Corporation, St. Louis, Mo.). The pre-cured polymer was molded using a PDMS mold and cured under UV-light (6 mW/cm$^2$) for 10 minutes. Mo paste was used to connect individual cells. These connections were buried in the polyanhydride encasement to prevent electrical shorts. The Mo paste was made by mixing Mo powder (10 µm) and sodium carboxymethyl cellulose with Mw 250000 (Sigma-Aldrich Corporation, St. Louis, Mo.). The top polyanhydride cover with multiple pores (0.5 mm) was made by casting against a PDMS mold. In both single battery cells and multiple stacked cells, phosphate buffered saline served as the electrolyte and was injected into the chamber with a syringe. Dissolution of the stacked battery system was carried out in PBS (refreshed everyday) on a hot plate at 37° C. and later at 85° C. to accelerate the dissolution. Mo foil with a thickness 8 µm (Goodfellow Corporation, Coraopolis, Pa.) was used for the stacking battery to reduce the dissolution time.

Battery performance was measured by a Gamry potentialstat Reference 600™ (Gamry Instruments, Warminster, Pa.) under a constant current discharging module using two-electrode configuration. Cathodic reaction was evaluated by a three-electrode configuration, with Ag/AgCl as the reference electrode (Bioanalytical Systems, Inc., West Lafayette, Ind.), battery cathode as the working electrode and Mg as the counter electrode.

The radio and LED circuits were fabricated by patterning a bilayer of Cr/Au (5 nm/200 nm) on a glass substrate. Electronic components (Digi-Key Corporation, Thief River Falls, Minn.) were mounted on the Au pads by silver paste to build the functional circuits. The wireless signals were received by a CXA N9000A signal analyzer (Agilent Technologies, Santa Clara, Calif.).

References

[1] S.-W. Hwang, H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, Science 2012, 337, 1640.

[2] C. J. Bettinger, Z. Bao, Adv. Mater. 2010, 22, 651.

[3] M. Irimia-Vladu, P. A. Troshin, M. Reisinger, L. Shmygleva, Y. Kanbur, G. Schwabegger, M. Bodea, R. Schwödiauer, A. Mumyatov, J. W. Fergus, V. F. Razumov, H. Sitter, N. S. Sariciftci, S. Bauer, Adv. Funct. Mater. 2010, 20, 4069.

[4] D. H. Kim, J. Viventi, J. J. Amsden, J. L. Xiao, L. Vigeland, Y. S. Kim, J. A. Blanco, B. Panilaitis, E. S. Frechette, D. Contreras, D. L. Kaplan, F. G. Omenetto, Y. G. Huang, K. C. Hwang, M. R. Zakin, B. Litt, J. A. Rogers, Nature Materials 2010, 9, 511.

[5] D. H. Kim, Y. S. Kim, J. Amsden, B. Panilaitis, D. L. Kaplan, F. G. Omenetto, M. R. Zakin, J. A. Rogers, Appl. Phys. Lett. 2009, 95.

[6] S.-W. Hwang, X. Huang, J.-H. Seo, J.-K. Song, S. Kim, S. Hage-Ali, H.-J. Chung, H. Tao, F. G. Omenetto, Z. Ma, J. A. Rogers, Adv. Mater. 2013, n/a.

[7] C. Dagdeviren, S.-W. Hwang, Y. Su, S. Kim, H. Cheng, 0. Gur, R. Haney, F. G. Omenetto, Y. Huang, J. A. Rogers, Small 2013, n/a.

[8] Y. J. Kim, S.-E. Chun, J. Whitacre, C. J. Bettinger, Journal of Materials Chemistry B 2013, 1, 3781.

[9] H. Jimbo, N. Miki, Sensors Actuators B: Chem. 2008, 134, 219.

[10] Y. J. Kim, W. Wu, S.-E. Chun, J. F. Whitacre, C. J. Bettinger, Proceedings of the National Academy of Sciences 2013.

[11] Proteus® Digital Health, http://www.proteus.com/.

[12] S. Keim, J. G. Brunner, B. Fabry, S. Virtanen, Journal of Biomedical Materials Research Part B: Applied Biomaterials 2011, 96B, 84.

[13] T. B. Reddy, D. Linden, Linden's Handbook of Batteries, McGraw-Hill, New York 2011.

[14] Uhlig's corrosion handbook, John Wiley & Sons, Inc., 2011.

[15] W. S. D. Wilcock, P. C. Kauffman, J. Power Sources 1997, 66, 71.

[16] K. Vuorilehto, J Appl Electrochem 2003, 33, 15.

[17] L. Yin, H. Cheng, S. Mao, R. Haasch, Y. Liu, X. Xie, S.-W. Hwang, H. Jain, S.-K. Kang, Y. Su, R. Li, Y. Huang, J. A. Rogers, Adv. Funct. Mater. 2013, n/a.

[18] M. Peuster, C. Fink, C. von Schnakenburg, Biomaterials 2003, 24, 4057.

[19] M. Peuster, C. Hesse, T. Schloo, C. Fink, P. Beerbaum, C. von Schnakenburg, Biomaterials 2006, 27, 4955.

[20] L. De Rosa, C. R. Tomachuk, J. Springer, D. B. Mitton, S. Saiello, F. Bellucci, Materials and Corrosion 2004, 55, 602.

[21] N. Ku mar, R. S. Langer, A. J. Domb, Adv. Drug Del. Rev. 2002, 54, 889.

[22] D. A. Shipp, C. W. McQuinn, B. G. Rutherglen, R. A. McBath, Chem. Commun. 2009, 6415.

[23] B. G. Rutherglen, R. A. McBath, Y. L. Huang, D. A. Shipp, Macromolecules 2010, 43, 10297.

[24] Q. Lou, D. A. Shipp, ACS Applied Materials & Interfaces 2012, 4, 4457.

[25] F. Sammoura, K. B. Lee, L. W. Lin, Sensors and Actuators a-Physical 2004, 111, 79.

[26] W. F. Ng, K. Y. Chiu, F. T. Cheng, Materials Science and Engineering: C 2010, 30, 898.

[27] G. L. Song, Corrosion Science 2007, 49, 1696.

EXAMPLE 6

Chemistry and Biocompatibility of Simile Crystalline Silicon Nanomembranes and Associated Materials for Transient Electronics Background and Motivation Single crystalline silicon nanomembranes (Si NMs) represent a critically important class of material for high performance forms of electronics that are capable of complete, controlled dissolution when immersed in water and/or bio-fluids, sometimes referred to as a type of 'transient' electronics. The results reported here include the kinetics of hydrolysis of Si NMs in bio-fluids and various aqueous solutions through a range of relevant pH values and temperatures, as well as the effects of dopant type and concentration. In vitro and in vivo investigations of Si NMs and other transient electronic materials demonstrate biocompatibility and bio-resorption, thereby suggesting potential for envisioned applications in active, biodegradable electronic implants.

Introduction

Developments in silicon integrated circuits over the last several decades have led to their use in nearly every aspect of daily life. Historically, engineering emphasis has been placed on materials and designs optimized for reliable, high performance operation. Time invariant behavior is now possible over periods of time that can be measured in decades. Recent work demonstrates that the opposite behavior could also be of interest, in which the devices not only cease to function but disappear completely over a well-defined but relatively short timeframe, in a controlled fashion. Potential applications range from temporary biomedical implants, to resorbable environmental monitors, disposable electronics, and non-recoverable covert components. One class of such technology involves functional materials, substrates and encapsulation layers that can dissolve or undergo hydrolysis in water or bio-fluids. Initial efforts on this particular form of 'transient' electronics used ultrasmall-scale components on water soluble substrates[1,2] and, separately, resorbable organic electronic materials.[3-5] Recent advances establish routes to completely transient inorganic semiconductor devices and systems, with diverse, advanced modes of operation.[6-10] Here, the active semiconductor materials include options such as ultrathin Si and ZnO; the gate/interlayer dielectrics include MgO and $SiO_2$; the metal interconnects and electrodes include Mg, Fe, W and Zn. Substrates and encapsulation materials range from silk fibroin, to poly lactic-co-glycolic acid (PLGA), a copolymer of poly lactic acid (PLA) and poly glycolic acid (PGA), PLA, polycaprolactone (PCL) and even rice paper. For high performance electronics, such as solar cells, photodetectors and many other devices, monocrystalline silicon in the form of nanomembranes (NMs) represents the material of choice. The mechanisms and kinetics of dissolution as well as the biocompatibility of the Si NMs and their reaction products are all important due to the essential role of this class of material in semiconductor devices for potential applications in bio-resorbable medical devices, eco-friendly electronics and environmental sensors. Previous studies of hydrolysis in silicon have focused on material forms, e.g. quantum dots[11,12], porous nanoparticles/membranes[13-18], bulk silicon[18], that have little relevance to electronics but provide some context and findings on biocompatibility. The results presented here focus on detailed studies of mechanisms of hydrolysis of single crystalline Si NMs under different conditions, measured using various modalities, and assessed for both in vitro and in vivo toxicity.

Results and Discussion

Figure 26:
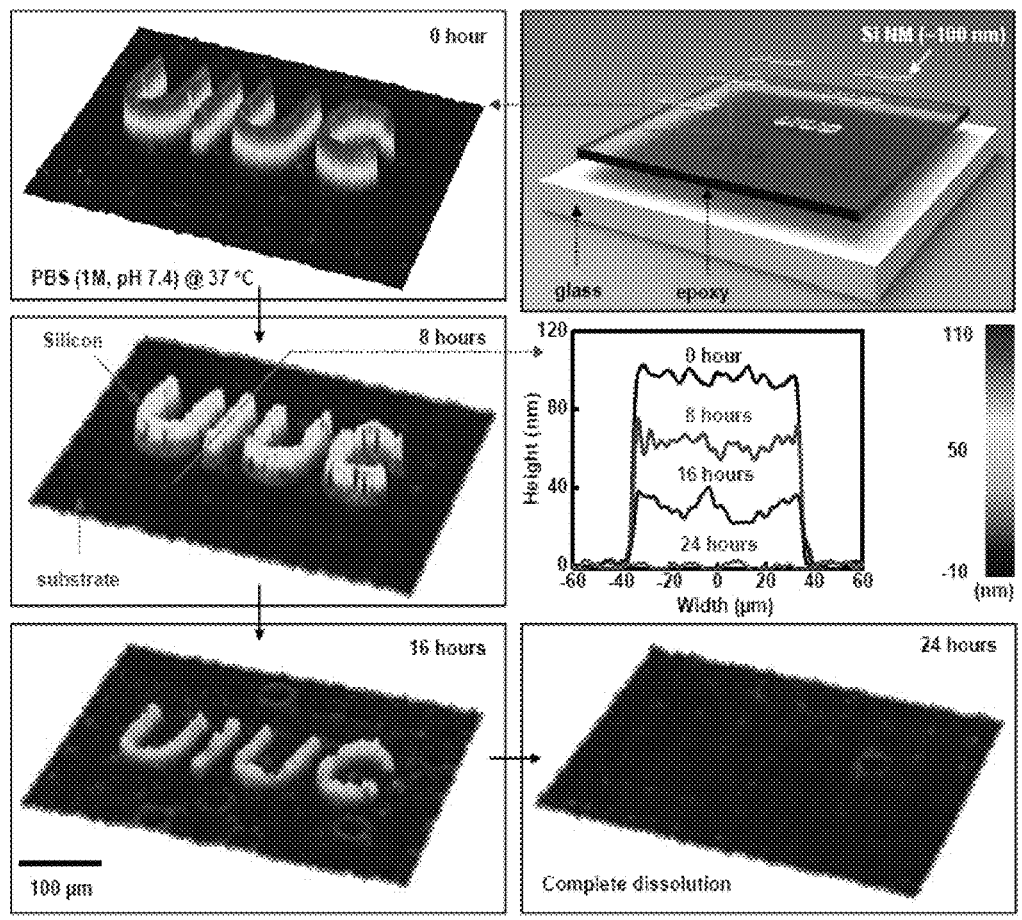
FIG. 26. Dissolution behaviors of monocrystalline silicon nanomembranes (Si NMs, UIUC logo, ~100 nm thick) studied over large areas using a phase sensitive microscopy technique for different times of immersion in phosphate buffer solution (PBS, 1 M, pH 7.4, Sigma-Aldrich, USA) at physiological temperature (37° C.): 0 (top left), 8 (middle left), 16 (bottom left) and 24 hours (bottom right). Line scan profiles for each stage of measurements appear in the middle right. An exploded view schematic illustration of the test structure shows Si NMs on a film of epoxy on a glass substrate (top right).
Figure 27:
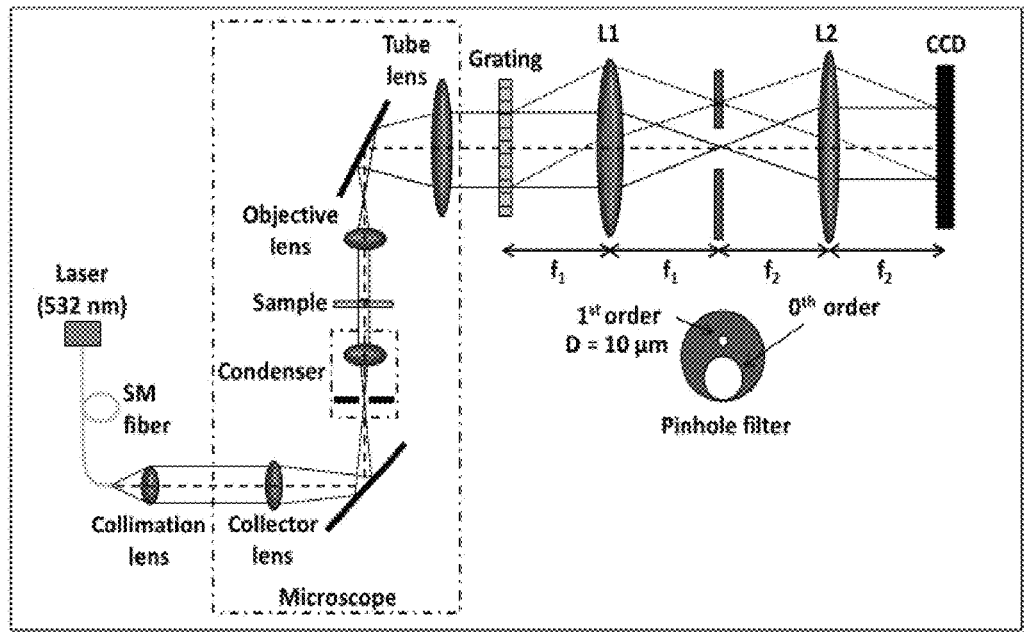
FIG. 27. (a) Experimental, setup for diffraction phase microscopy (DPM) operating in transmission mode.
Figure 28:
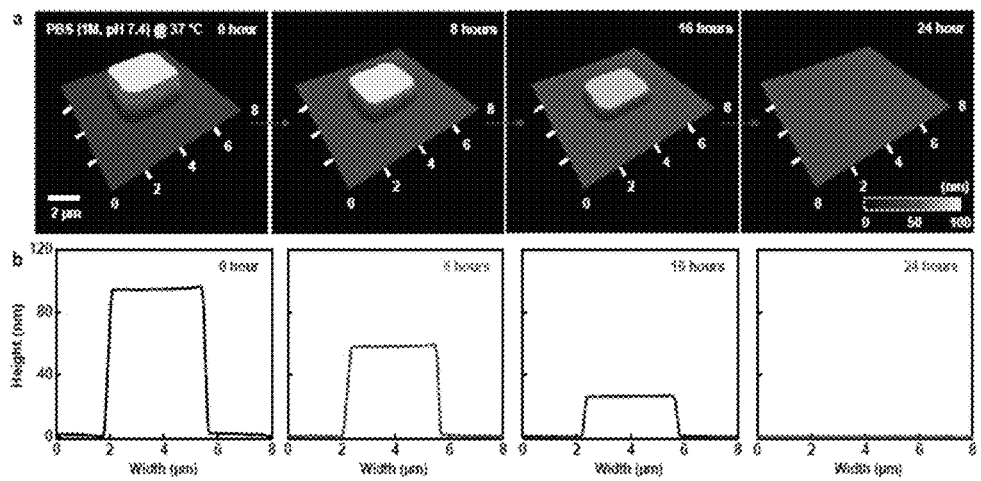
FIG. 28. (a) A set of AFM images showing the kinetics of dissolution of Si NMs (an array of square dots, 3 μm×3 μm×100 nm) in PBS (1 M, pH 7.4) at body temperature (37° C.) at various times of immersion: 0 hour (top left), 8 hours (top right), 16 hours (bottom right) and 24 hours (bottom left), respectively. (b) Thickness profiles of Si NMs extracted from the results in (a), 0 hour (black), 8 hours (red), 16 hours (blue) and dark cyan (24 hours), respectively.

Previous work[6] revealed the kinetics of hydrolysis of Si NMs by use of a time sequence of thickness measurements performed using atomic force microscope (AFM) imaging, on relatively small pieces of material (e.g. several $\mu m^2$) in simple, square geometries. FIG. 26 illustrates a set of images obtained by transmission-mode laser diffraction phase microscopy (DPM)[11-13] of Si NMs (~100 nm thick) in large, complex patterns (UIUC text) evaluated at various times (0 hour, top left; 8 hours, middle left; 16 hours, bottom left; 24 hours, bottom right) of immersion in phosphate buffer solution (PBS, 1 M, pH 7.4, Sigma-Aldrich, USA) at physiological temperature (37° C.). Details of the DPM system appear in FIG. 27 and the experimental section. The Si NM test structure used the top silicon layer of a silicon-on-insulator wafer (SOI, SOITEC, France) thinned 300 nm to 100 nm by repetitive thermal oxidation at 1100° C., followed by wet chemical etching in hydrofluoric acid (HF, 49% Electronic grade, ScienceLab, USA). Removal of the buried oxide by etching with HF released Si NMs from the SOI, and enabled their transfer printing onto a spin-cast film of epoxy (SU-8 2, MicroChem, USA) on a glass substrate. Photolithography and reactive ion etching (RIE; Plasma-therm, USA) with sulfur hexafluoride ($SF_6$) gas defined the 'UIUC' pattern, as illustrated in the top right frame of FIG. 26. Cross-sectional profiles (middle right) extracted from the DPM data indicate thicknesses of 97±2.6 nm (0 hour), 62±3.4 nm (8 hours), 29±6.1 nm (16 hours) and 0±1.5 nm (24 hours). The results illustrate spatially uniform removal of silicon by hydrolysis, with well-defined linear kinetics, all of which is consistent with AFM results in FIG. 28.

Figure 29:
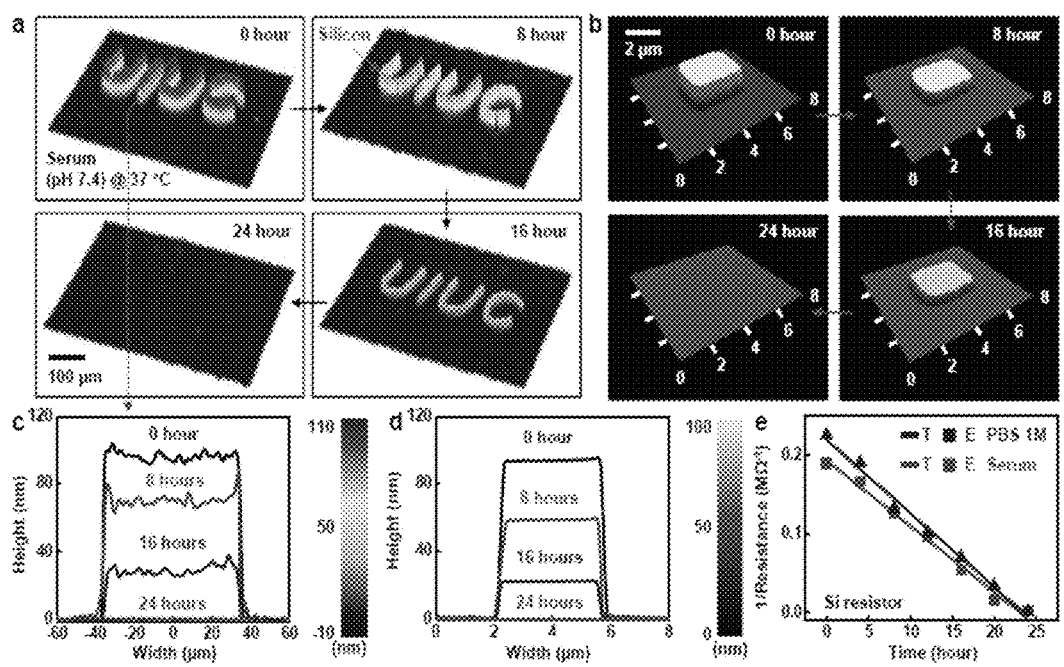
FIG. 29. Images of Si NMs at various stages of dissolution in bovine serum (pH~7.4) at physiological temperature (37° C.): 0 (top left), 8 (top right), 16 (bottom right) and 24 hours (bottom left), respectively, measured by, (a) DPM and (b) AFM. Thickness profiles extracted from the (c) DPM (d) AFM images in (a) and (b). (0 hour, black; 8 hours, red; 16 hours, blue; 24 hours, dark cyan) (e) Theoretical (lines) and measured (symbols) changes in resistance of a serpentine shaped Si NM resistor after various times of immersion in PBS (blue, 1 M, pH~7.4) and bovine serum (red, pH~7.4) at body temperature (37° C.).

The dissolution behaviors of Si NMs are particularly important in biofluids relevant to envisioned applications in implantable biomedical devices. FIGS. 29a and 29b provide a set of images obtained by the DPM and AFM, during dissolution via hydrolysis in bovine serum (pH~7.4, Sigma-Aldrich, USA) at body temperature (37° C.), and corresponding thickness profiles extracted from each data are shown in FIG. 29c-d. The results confirm that dissolution rates in a range expected based on studies in PBS, with good levels of temporal and spatial uniformity. Additionally, measurements of the electrical resistance of a Si NM (lightly boron doped, ~$10^{16}/cm^3$; resistivity, 10~20 Ω·cm) patterned into a meander shape and immersed in the same type of solution under the same conditions reveal results that match those based on expectation from the time dependent changes in thickness (FIG. 29e). Data from PBS solutions show the correspondence in rate. In all cases, the experiments involved removal of samples from solutions for measurements, and then return to fresh solutions for continued dissolution.

Figure 30:
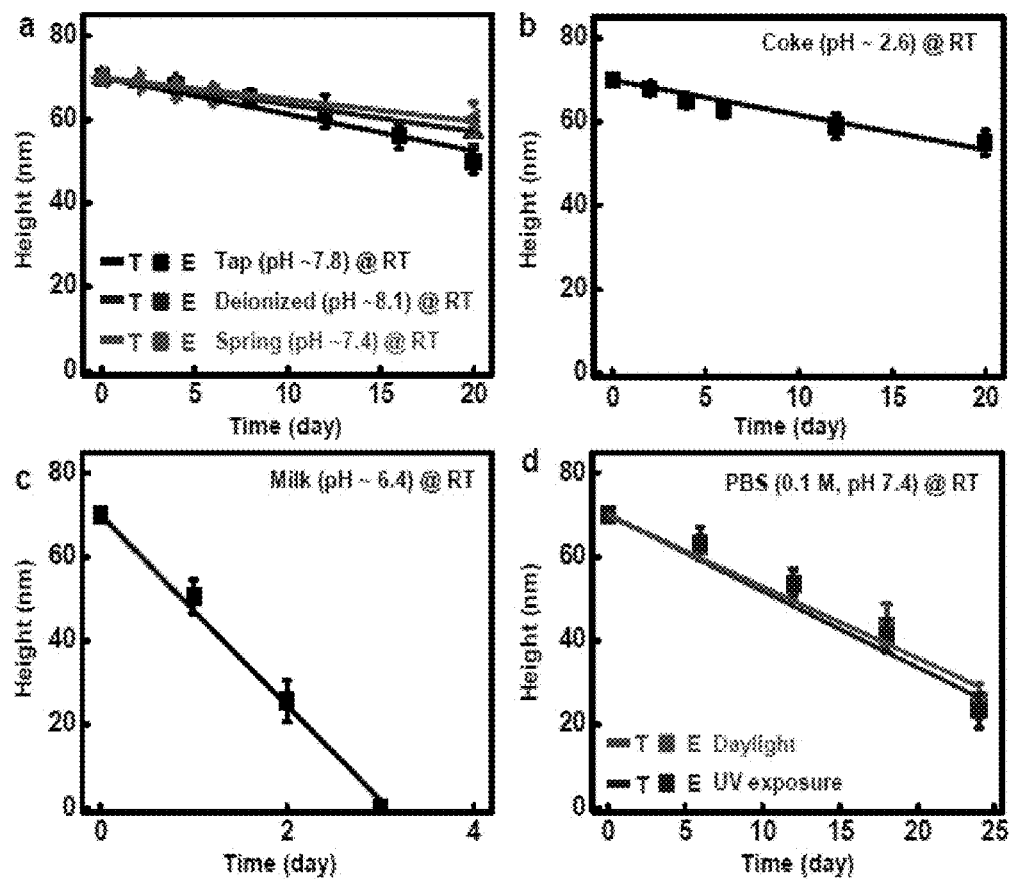
FIG. 30. Theoretical (T, lines) and experimental (E, symbols) changes in thickness as a function of time for dissolution of Si NMs in various solutions. (a) Tap (pH~7.8), deionized (DI, pH~8.1) and spring (pH~7.4) water, (b) Coke (pH~2.6) and (c) Milk (pH~6.4) at room temperature. (d) Study of dissolution behavior during exposure to daylight (red) and UV light (blue).

The processes of hydrolysis depend critically on the chemical composition of the solution, the temperature and the doping type and concentration for the Si NMs. FIG. 30a summarizes dissolution rates measured by AFM in various types of water at room temperature, including tap water (pH~7.8), deionized water (DI, pH~8.1) and spring water (pH~7.4). The results indicate rates in each case that are somewhat slower than those observed at similar pH levels using buffer solutions, likely due to the differences in ionic content. Dissolution in Coca-Cola (pH~2.6, FIG. 43b) and milk (pH~6.4, FIG. 30c) occurs at much faster solution rates than those of buffer solutions at similar pH. In addition, established methods that use light exposure to etch off semiconducting materials (i.e. photoelectrochemical etching)[14-17] suggest the potential influence of light on the dissolution rate. To examine the possible effects, samples were immersed in PBS (0.1 M, pH~7.4) at room temperature, and exposed to natural daylight and ultraviolet light (UV, λ=365 nm, 1=590 μW/$cm^2$ at a distance of 7 cm). No significant changes in dissolution rate were observed (FIG. 30d). Such effects might be relevant at high levels of illumination, e.g. from ~1 mW/$cm^2$ to ~500 mW/$cm^2$,[14-17] compared to those (590 μW/$cm^2$) examined here.

Figure 31:
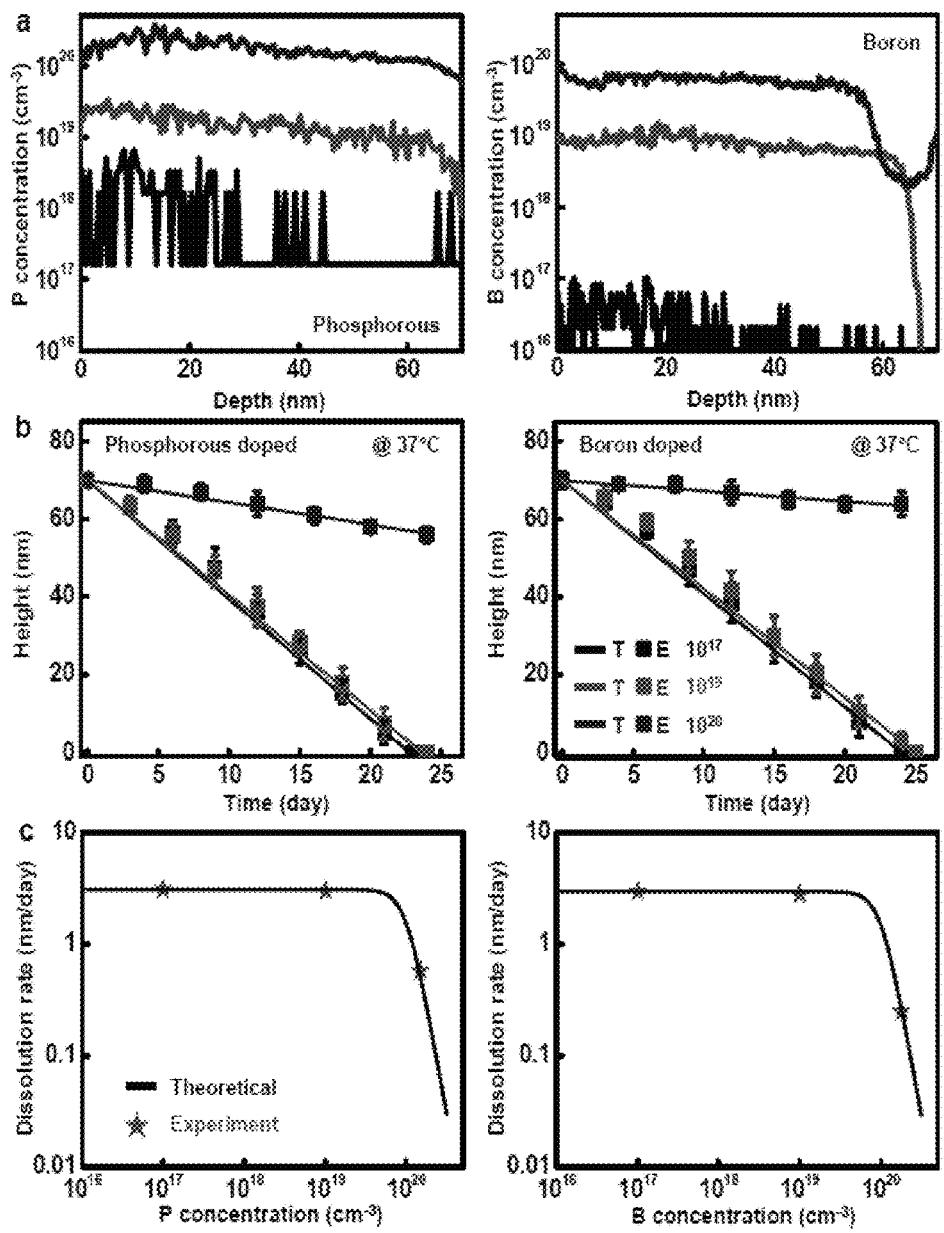
FIG. 31. The kinetics of dissolution on phosphorous and boron doped Si NMs (3 μm×3 μm×70 nm) in aqueous buffer solution (0.1M, pH 7.4) at physiological temperature (37° C.), as defined by the change in thickness as a function of time. (a) Dopant concentrations measured by secondary ion mass spectrometry (SIMS) for phosphorous (left) and boron (right). (b) Theoretical (T, lines) and experimental (E, symbols) results for the dissolution rates of Si NMs with different dopant concentrations ($10^{17}$ cm$^{-3}$, black; $10^{19}$ cm$^{-3}$, red; $10^{20}$ cm$^{-3}$, blue) with phosphorous (left) and boron (right) during immersion in phosphate buffer solution (0.1 M, pH 7.4, Sigma-Aldrich, USA) at physiological temperature (37° C.). (c) Calculated (lines, black) and measured (stars, red) dissolution rates as a function of dopant concentration, for phosphorous (left) and boron (right).

Types and concentrations of dopants in the Si NMs can be important. To examine the effects, Si NMs were doped with phosphorous and boron at three different concentrations ($10^{17}$ $cm^{-3}$, black; $10^{19}$ $cm^{-3}$, red; $10^{20}$ $cm^{-3}$, blue) using spin-on-dopant (SOD, Filmtronics, USA) techniques. Depth profiles of the dopants in these cases, evaluated by secondary ion mass spectrometry (SIMS), appear in FIG. 27a. FIG. 31b shows theoretical (T, lines; based on simple models of reactive diffusion described elsewhere)[6,19] and experimental (E, symbols) results of the dissolution kinetics for phosphorous (left) and boron (right) doped Si NMs in phosphate buffer solution (0.1 M, pH 7.4, Sigma-Aldrich, USA) at physiological temperature (37° C.), as measured by AFM. The results indicate a strong reduction of rate for dopant concentrations that exceed a certain level, such as $10^{20}$ cm$^{-3}$, as expected based on previous studies of silicon etching in different regimes of pH and temperature, e.g. KOH (10~57%), NaOH (24%), ethylenediamine-based solution (EDP) at between 20° C. and 115° C.[19] Variations in rate (extracted from the theoretical results shown in FIG. 31b) with dopant concentration appear in FIG. 31c. The rate remains constant ($R_i$) up to a critical dopant concentration ($C_0$). Above $C_0$, a sharp decrease occurs, which is inversely proportional to the fourth power of the dopant concentration (C) according to a form established from studies of silicon under conditions of high pH[19]

The nanoscale configurations of the Si NMs determine the timeframes for complete dissolution as well as the total mass content of each element, i.e. silicon, phosphorous and boron for present purposes. For instance, the estimated dissolution time for a standard silicon wafer platform (~700 μm thickness) is several hundred years, based on the chemical kinetics observed in Si NMs studied here. The concentrations of the end products follow a similar scaling. A Si NM (1 mm×1 mm×100 nm) at high doping concentration (phosphorous/boron, doped with ~$10^{20}$/cm$^3$) dissolved in 1 ml of water yields concentrations of 0.2 parts per million (ppm) for Si, 0.0005 ppm for phosphorous and 0.0002 ppm for boron. These levels are well below natural physiological values. The corresponding concentrations for the case of a piece of a Si wafer with similar lateral dimensions would be thousands of times higher, with potential consequences in biological and/or environmental responses, depending on the application. Details appear in Table 3.

TABLE 3

Concentrations of silicic acid, phosphorous and boron

Dimension (assume various sizes of silicon after dissolution in 1 ml of water)

| Dopants | Doping level (cm$^{-3}$) | unit | 1 mm × 1 mm × 20 nm | 1 mm × 1 mm × 100 nm | 1 mm × 1 mm × 300 nm | 1 mm × 1 mm × 700 μm |
|---|---|---|---|---|---|---|
| Phosphorous | 1E+20 | ppm | 0.000103 | 0.000515 | 0.001545 | 3.60465 |
|  |  | ppb | 0.10299 | 0.51495 | 1.54485 | 3604.651 |
|  | 1E+16 | ppm | 1.03E−08 | 5.15E−08 | 1.54E−07 | 0.00036 |
|  |  | ppb | 1.03E−05 | 5.15E−05 | 0.000154 | 0.360465 |
| Boron | 1E+20 | ppm | 3.59E−05 | 0.000179 | 0.000538 | 1.255814 |
|  |  | ppb | 0.03588 | 0.179402 | 0.538206 | 1255.814 |
|  | 1E+16 | ppm | 3.59E−09 | 1.79E−08 | 5.38E−08 | 0.000126 |
|  |  | ppb | 3.59E−06 | 1.79E−05 | 5.38E−05 | 0.125581 |
| Silicic acid |  | ppm | 0.04658 | 0.2329 | 0.6987 | 1630.3 |
|  |  | ppb | 4.658 | 23.29 | 69.87 | 163030 |

Typical concentration of each component in body/waters

| Elements | Body | Sea water | Ground water | Drinking water | (unit:ppm) |
|---|---|---|---|---|---|
| Phosphorous | 20-40 | 0.07 | 0.005-0.05 | 5-10 | **value ranges may |
| Boron | 0.7 | 4.5 | >0.005 | 0.75 | vary among locations |
| Silicic acid | 1-10 | 2 | 6-11 | 2-5 | and laboratories. |

$$R = \frac{R_i}{1 + (C/C_0)^4}, \quad (1)$$

Figure 32:
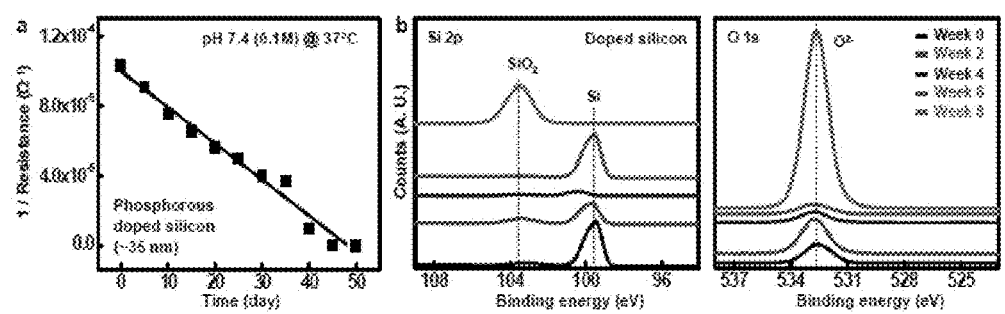
FIG. 32. (a) Changes in resistance of a meander trace formed from a phosphorous doped Si NM (~35 nm) in phosphate buffer solution (0.1 M, pH 7.4) at 37° C. (b) Surface analysis of phosphorous doped Si NMs (~35 nm) with X-ray photoelectron spectroscopy (XPS) during immersion in phosphate buffer solution (0.1 M, pH 7.4) at body temperature (37° C.) at various stages, Si 2p (left) and O 1s (right).

If $C_0=10^{20}$ cm$^{-3}$ for both dopants, and $R_i=3.08$ nm/day and $R_i=2.95$ nm/day for phosphorous and boron, respectively, then Equation 1 yields results that agree well with measurements, as shown in FIG. 31c. The larger reduction for boron compared to that for phosphorous can be attributed, as in studies of traditional etching of silicon, to an absence of electrons in the conduction band at high boron concentration.[19] Similar behaviors can be revealed through electrical, rather than AFM, measurements of a phosphorous-doped Si NM (~35 nm) in a resistor configuration. Results appear in FIG. 32a for similar solution conditions (0.1 M, pH 7.4, 37° C.). The surface chemistry of the phosphorous-doped Si NMs after immersion in buffer solution (0.1 M, pH 7.4, 37° C.) was examined by x-ray photoelectron spectroscopy (XPS). The results revealed no significant change in the chemistry (FIG. 32b).

Figure 33:
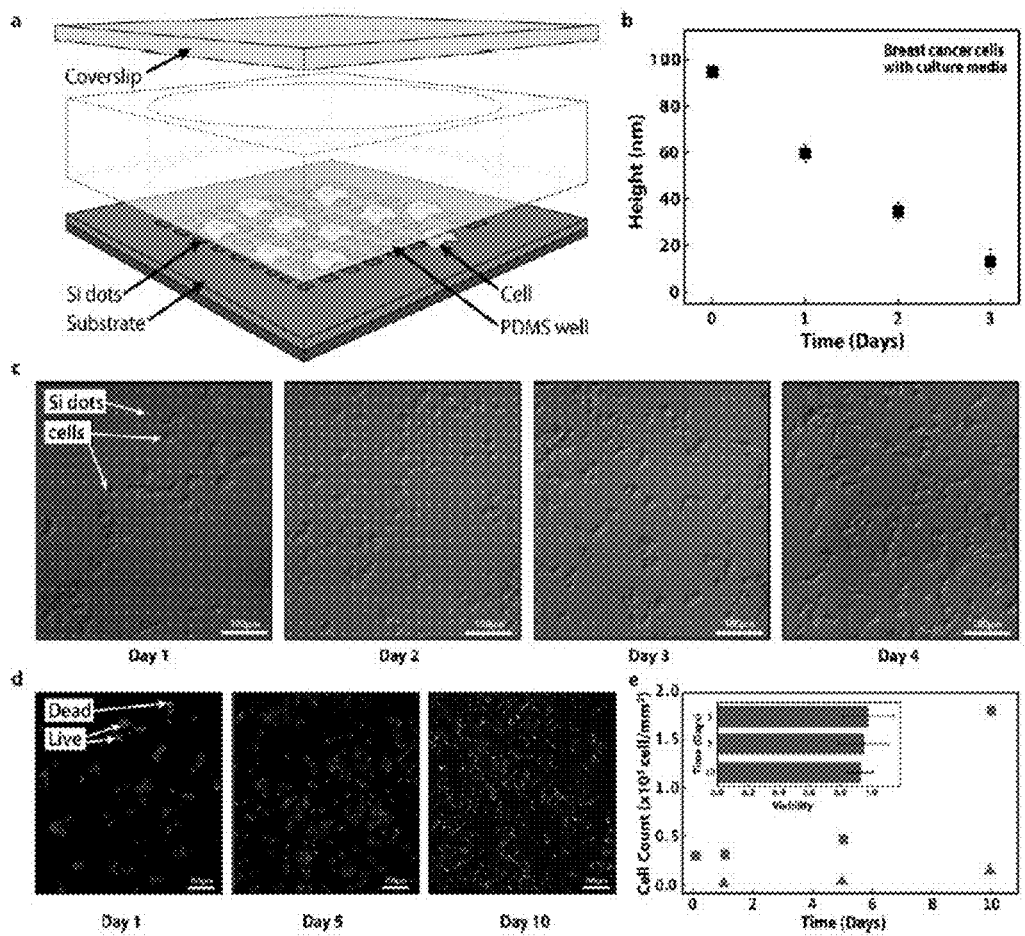
FIG. 33. In vitro, cell culture evaluations of degradation and cytotoxicity associated with Si NMs. (a) Schematic illustration of the test structure for culturing cells on Si NMs. (b) Measured changes in thickness of the Si NMs during culture of breast cancer cells. (c) Differential interference contrast (DIC) images showing the dissolution behaviors of Si NMs with adhered cells over 4 days, corresponding to the result in (b). (d) A set of fluorescent images describing cell viability using live/dead assay on Si NMs at days 1, 5, and 10, respectively. (e) Numbers of both live (green) and dead (red) cells over time as quantified from the live/dead assay in (d). As the cells divide they increase in number and become more confluent, which also leads to an increase in the number of dead cells. The viability of cells over 1, 5, and 10 days, calculated as the fraction of total alive cells, appears in the inset.

Many envisioned applications of silicon based transient electronics require studies of biocompatibility. For in vitro assessment of the cytotoxicity and dissolution behaviors, cells from a metastatic breast cancer cell line (MDA-MB-231) were cultured on a patterned array of Si NMs using a PDMS-based micro-incubation chamber, as shown in FIG. 33a. This breast cancer cell was selected due to rapid propagation and culture. Sterilizing and sealing the PDMS chamber against the solid substrate maintained appropriate conditions for the culture over multiple days. After culturing on the Si NMs for consecutive days, cells were removed from the surface using trypsin to allow measurement of changes in the thicknesses of the Si NMs by AFM (FIG. 33b). The series of differential contrast images (DIC) in FIG. 46c illustrates the growth and proliferation behaviors of cells over the course of four days. The arrays of square Si NMs were no longer visible on the fourth day, consistent with the data of FIG. 33b. Live/dead assays revealed viability, at 1, 5 and 10 days, as determined by a set of fluorescent images of stained cells. Here, viable, living cells appear green; dead cells appear red. FIG. 33e presents the change in numbers of live and dead cells; the inset shows the fraction of living cells as a measure of viability. Cell viability on day 1, 5 and 10 are 0.98±0.11, 0.95±0.08, and 0.93±0.04, respectively. The slight increase in dead cells on days 5 and 10 is likely due to cell death that naturally occurs as a culture reaches confluency. Additional details on the cell culture and associated procedures appear in the experimental section.

Figure 34:
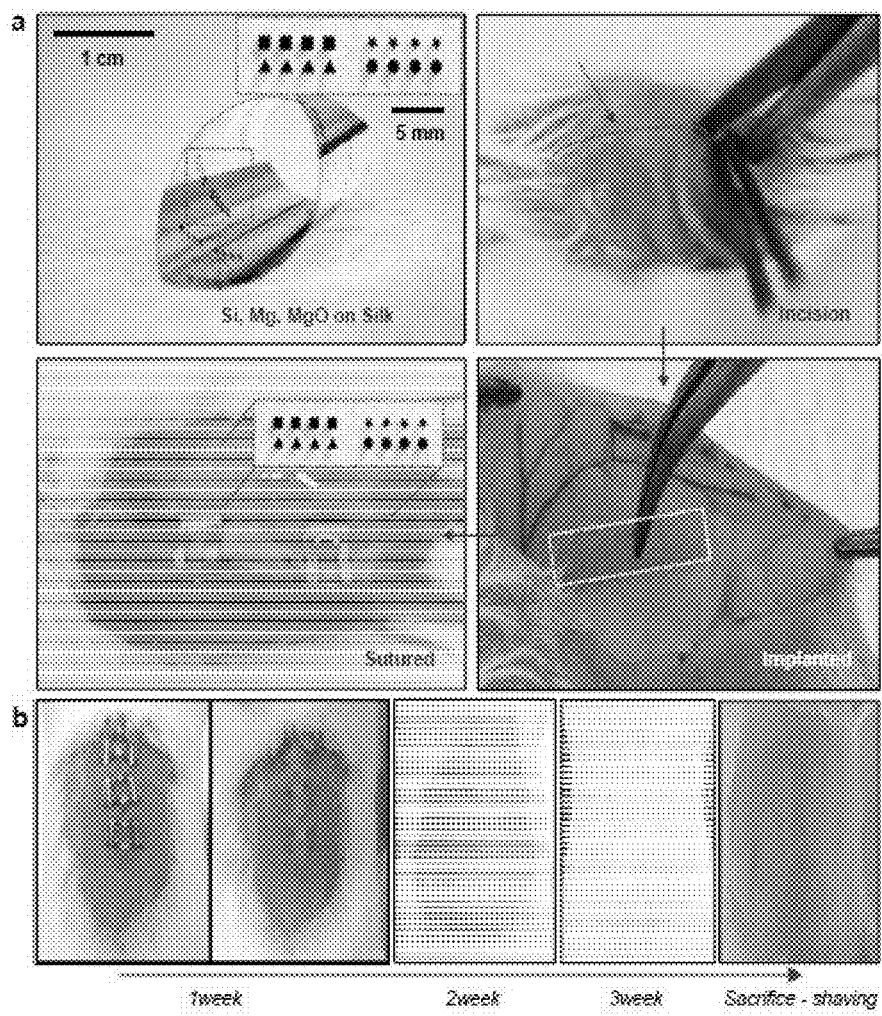
FIG. 34. (a) Stepwise procedure for implanting transient electronic materials in a dorsal pocket of an anaesthetized BALB/c mice, incision (top right), implanted (bottom right) and sutured (bottom left). (b) A set of images showing the wound-healing process.
Figure 35:
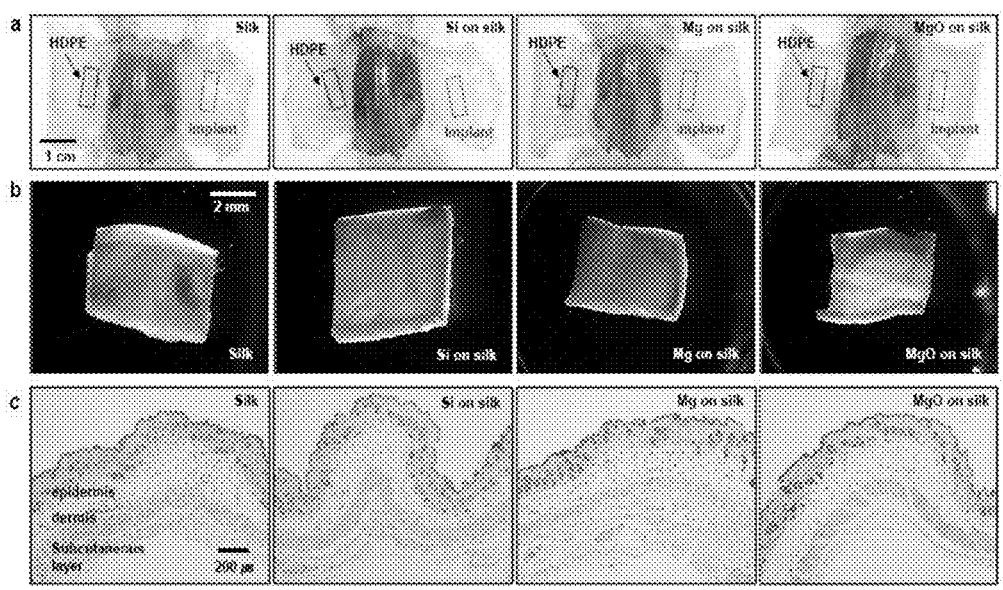
FIG. 35. (a) Images of a transient electronic test structure implanted in the sub-dermal dorsal region of a BALB/c mouse. (b) Microscopic images of representative skin tissues collected using a stereomicroscope. (c) H&E-staining of skin sections from mice 5 weeks post implantation.
Figure 36:
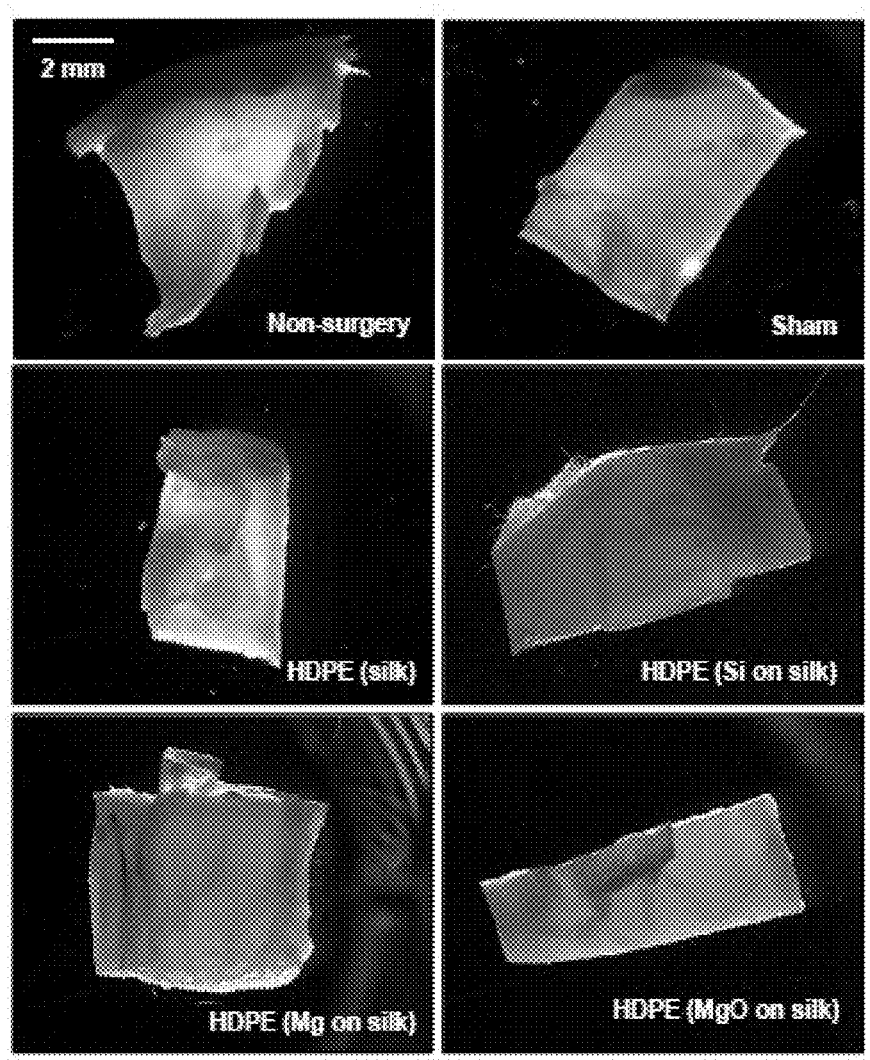
FIG. 36. Stereomicroscope images of tissues at the implant site, after 5 weeks, non-surgery (top left), sham operated (top right), HDPE (middle left, silk), HDPE (middle right, Si on silk), HDPE (bottom left, Mg on silk) and HDPE (bottom right, MgO on silk).
Figure 37:
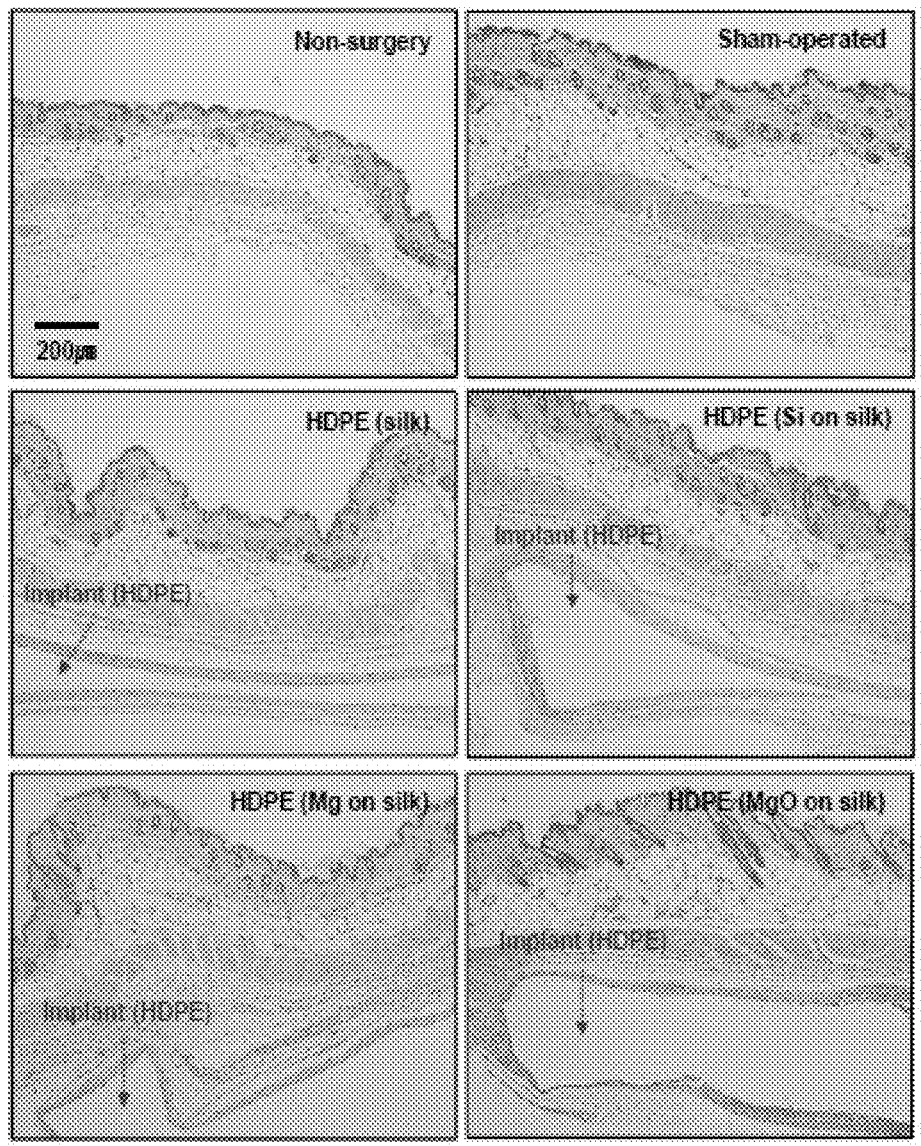
FIG. 37. Histological sections of tissues at the implant site, with HDPE from mice bearing both HDPE and samples, excised after 5 weeks, non-surgery (top left), sham operated (top right), HDPE (middle left, silk), HDPE (middle right, Si on silk), HDPE (bottom left, Mg on silk) and HDPE (bottom right, MgO on silk).
Figure 38:
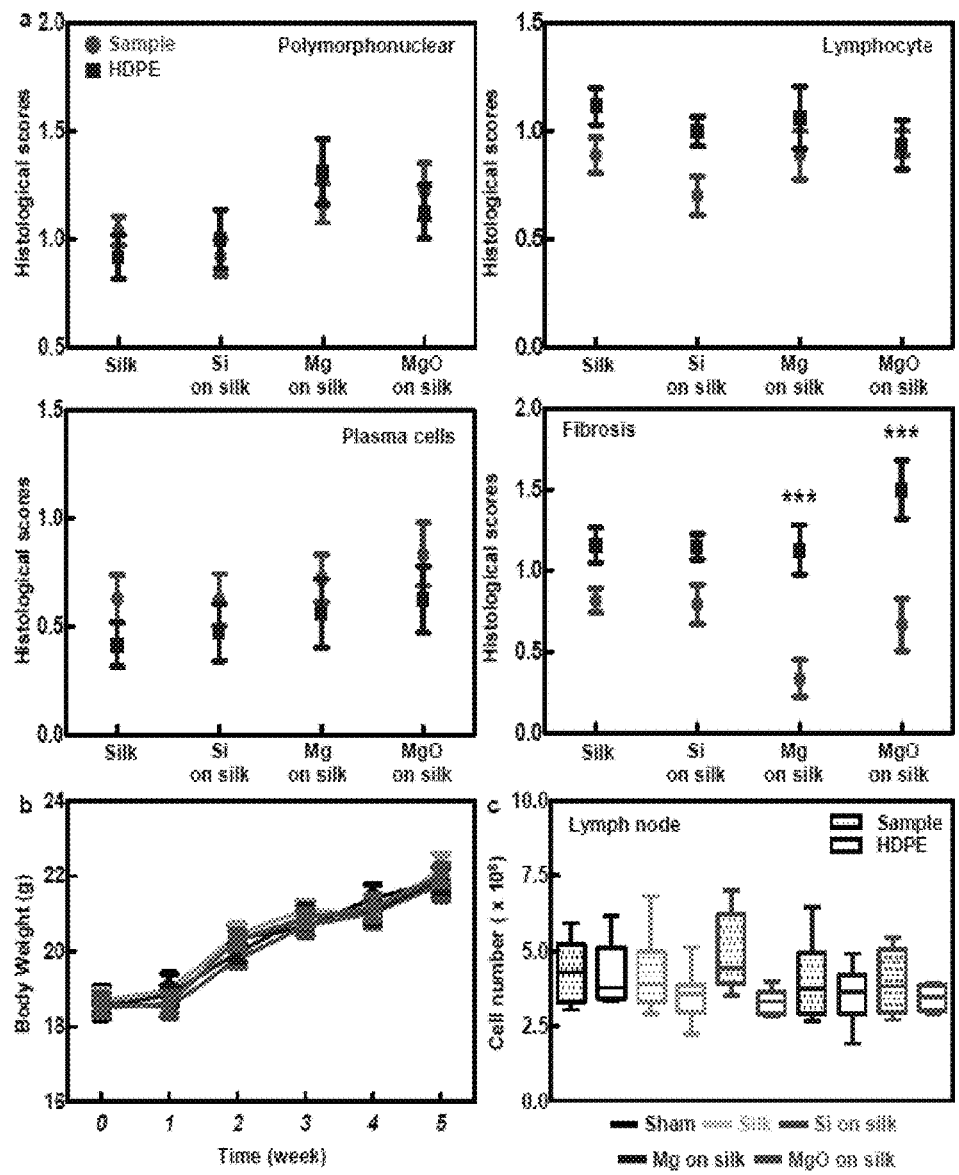
FIG. 38. (a) Histological scores of tissues at the 5-week period based on H&E staining of skin sections from five groups of animals. (b) Body weight changes of mice implanted with sham-operated (black), silk (green), Si on silk (red), Mg on silk (blue), and MgO on silk (purple) after a 5-week implantation period (n=8 per group). (c) Cell numbers in the axillary and branchial draining lymph nodes (DLNs).

In vivo toxicity and biodegradation studies of Si NMs as well as other transient electronic materials (silk, Mg and MgO) are important for applications in temporary implants. Experiments were performed by implanting various test samples (silk, Si NMs on silk, Mg on silk and MgO on silk) sterilized by exposure to ethylene oxide in the sub-dermal region of Balb/c mice in accordance with Institutional Animal Care and Use Committee (IACUC) protocols. The dorsal skin was incised (~1 cm lengthwise) to create a subcutaneous pocket. Test samples along with control materials (high-density polyethylene (HDPE), FDA approved) were implanted into the pocket (FIG. 34a). The skin incisions were closed with sterilized clips and the mice were returned to the animal facility until analysis (FIG. 34b). FIG. 35a shows the dorsal view of mice subcutaneously implanted with transient samples, at 5 weeks post-implantation. No residues were visible to the naked eye at the implant sites. To provide additional information, skin sections were stained with hematoxylin and eosin (H&E), and examined using stereomicroscopy. Broad scans of the implant sites revealed no remaining materials (FIG. 35b and FIG. 36): The numbers of polymorphonuclear cells (PMNs), lymphocytes and plasma cells presented in the implanted area were compared to those of a corresponding control sample of HDPE (FIG. 35c and FIG. 37). No significant histological responses of polymorphonuclear cells (PMNs), lymphocytes and plasma cells were observed, compared to the control group. The degree of fibrosis, measured by the thickness of collagen fibers, slightly increased in the HDPE-implanted tissue sections due to infiltration of collagen producing fibroblasts at the implantation area (FIG. 38a).[20] The degree of fibrosis in silk and Si NMs on silk is comparable to that observed in the control HDPE, and both are somewhat higher than with samples of Mg on silk and MgO on silk. As compared to the sham-operated (i.e. no implant) control group, no significant body weight loss was observed for mice in all cases during implantation period of 5 weeks (FIG. 38b). In addition, there was no cytotoxicity of the four different types of samples observed by immunoprofiling using primary immune cells from the axillary and branchial draining lymph nodes (DLNs) (FIG. 38c). Taken together, these results suggest the transient electronic materials examined here are biocompatible and have the potential to be used for long term implantation, from months to years.

Conclusion

In summary, the nanoscale dimensions of Si NMs are critically important for their use in transient, biocompatible electronics, simply due to their importance in defining the timescales for dissolution and the total mass content of the reaction products. Large area studies of hydrolysis of Si NMs demonstrate spatially uniform, controlled dissolution in a wide range of aqueous solutions. Electrical measurements reveal the results consistent with those determined by microscopy techniques. The dopant type and particularly the dopant concentration has a strong influence on the rate, while exposure to light over ranges of intensity expected in envisioned applications does not. In vitro and in vivo studies provide evidence for the biocompatibility of key materials for high performance, inorganic transient electronics as subdermal implants. Further studies involving fully functional systems in or on various other organs of the body will provide additional insights.

Comprehensive in vitro and in vivo studies of the kinetics of hydrolysis in silicon nanomembranes in various aqueous solutions at different pH levels and temperatures were presented for a class of water-soluble, biodegradable electronics. Changes in electrical characteristics accompanied by hydrolysis provide data directly relevant to applications in electronics and yield insights that complement those from microscope studies. Results indicate that the dopant type and concentration strongly influence the silicon hydrolysis. In vitro and in vivo assessments suggest potential for use of silicon nanomembranes and other transient electronic materials for realistic use in temporary biomedical implants and other areas.

Experimental Section

Laser diffraction phase microscopy (DPM) System: The output of a 532 nm frequency-doubled Nd:YAG laser was coupled into a single mode fiber (SMF) and collimated to insure full spatial coherence. This beam was aligned to the input port of a microscope. The collimated beam passed through the collector lens and focused at the condenser diaphragm, which was left open. The condenser lens created a collimated beam in the sample plane. Both the scattered and unscattered fields were captured by the objective lens and focused on its back focal plane. A beam splitter then redirected the light through a tube lens to create a collimated beam containing the image at the output image plane of the microscope. A diffraction grating placed at the output image plane of the microscope generated multiple copies of the image at different angles. Some of the orders were collected by a lens ($L_1$) located a distance $f_1$ from the grating, to produce a Fourier transform of the image at a distance $f_1$ behind the lens. Here, the $1^{st}$ order beam was spatially filtered using a 10 µm diameter pinhole, such that after passing through the second lens ($L_2$) this field approached a plane wave. This beam served as a reference for the interferometer. A large semi-circle allowed the full $0^{th}$ order to pass through the filter without windowing effects. Using the $0^{th}$ order as the image prevented aberrations since it passed through the center of the lenses along the optical axis. A blazed grating was employed where the +1 order is brightest. In this way, after the filter, the intensities of the two orders were closely matched, insuring optimal fringe visibility. A second 2f system with a different focal length was used to perform another spatial Fourier transform to reproduce the image at the CCD plane. The two beams from the Fourier plane formed an interferogram at the camera plane. The phase information was extracted via a Hilbert transform[11] to reconstruct the surface profile.[12,13]

Dissolution experiments: To fabricate test structures (array of squares, 3 µm×3 µm×70~100 nm) of single crystalline silicon nanomembranes (Si NMs), repetitive dry oxidation processes at 1100° C. followed by wet etching in hydrofluoric acid (HF, 49% Electronic grade, ScienceLab, USA) reduced the thickness of the top silicon of a silicon-on-insulator (SOI, SOITEC, France) wafer. Doping with phosphorous and boron used a spin-on dopant (SOD, Filmtronics, USA) at different temperatures to control the concentrations ($10^{16}$/cm$^3$~$10^{20}$/cm$^3$). Patterned reactive ion etching (RIE, Plasmatherm, USA) with sulfur hexafluoride ($SF_6$) gas defined Si NMs in square arrays. Samples were immersed in various solutions, including aqueous buffer solutions (Sigma-Aldrich, USA), tap/deionized (DO/spring water, Coca-Cola and milk at either room temperature or physiological temperature (37° C.). The samples were removed to measure the thickness of Si NMs by laser diffraction phase microscopy (DPM) and atomic force microscopy (AFM, Asylum Research MFP-3D, USA), and then reinserted into solutions, changed every two days.

Cell culture experiments: For seeding and culturing adherent cells on Si NMs, a 200 μL micro-incubation well was attached directly to each sample. To define the well, or culture chamber, a 6 mm dermal biopsy punch was pushed through a piece of polydimethylsiloxane (PDMS). The PDMS allowed for the culture well to be reversibly sealed with a coverslip for extended cultures at 37° C. Prior to cell seeding, the sample was sterilized by filling the well with 70% ethanol. Highly metastatic human breast adenocarcinoma cells (MDA-MB-231 ATCC #HTB-26) were cultured in Leibovitz's L-15 Medium (Sigma-Aldrich) with 10% fetal bovine serum and 1% penicillin streptomycin. For seeding, cells were released from a T-25 flask with 0.25% trypsin-EDTA (Gibco). Cells were separated from the trypsin by centrifuging the suspension with 3 to 5 mL media for 6 min at 1000 rpm. The cells were then re-suspended, diluted, and plated on the samples through the PDMS micro-incubation well, at a density of 300 cells/mm$^2$. Cells were left to settle for 15 min, and then the well was sealed with a coverslip. The live/dead assay (Invitrogen, Carlsbad, Calif.) was employed to test cell viability after extended on-chip culture. Tested samples with adhered cells were incubated with 1 μM of acetomethoxy derivative of calcein (calcein AM, green; live) and 2 μM of ethidium homodimer (red; dead) for 35 minutes in phosphate buffered saline (PBS). The cells were then rinsed twice with PBS and the samples were immediately imaged. Green fluorescence indicates that the cells are viable while red marks dead cells. Images were used for counting and calculating the densities of cells in the fluorescein isothiocyanate (FITC, green; live) and the tetramethylrhodamine (TRITC, red; dead) channels. The ratio of integrated density in the FITC to TRITC channel defined the cell viability.

In vivo tissue biocompatibility tests: Animal experiments were performed in accordance with the national and institutional guidelines and the Guide for the Care and Use Committees (KUIACUC-2013-93) of Laboratory Animals based on approved protocols by Korea University. Mice were anaesthetized by intraperitoneal injection of 30 mg/kg zolazepam hydrochloride (Zoletil 50; Virbac, Sao Paulo, Brazil) and 10 mg/kg zylazine hydrochloride (Rumpun; Bayer, Shawnee Mission, Kans.). The two sterile samples (one test and one control) were implanted subcutaneously into the dorsal pocket of mouse for periods of 5 weeks. Mice were euthanized via $CO_2$ asphyxiation and the implanted samples and surrounding tissue were excised. The tissue samples were fixed in 10% neutral buffered formalin, which were then embedded into paraffin, sliced at thickness of 4 μm, and stained with hematoxylin and eosin (H&E). The H&E-stained slices were imaged by optical microscopy. Images of tissue were taken on a Leica M165 FC stereomicroscope equipped with a LEICA DFC310FX camera using the Leica application suite version 3.4.1 software program.

Statistics: All data are represented as mean±SEM of three identical experiments made in three replicates. Statistical significance was determined by one-way analysis of variance (ANOVA) followed by Dunnett's multiple comparison test. Significance was ascribed at $p<0.05$. All analyses were conducted using the Prism software (Graph Pad Prism 5.0).

References

[1] D.-H. Kim, Y.-S. Kim, J. Amsden, B. Panilaitis, D. L. Kaplan, F. G. Omenetto, M. R. Zakin, J. A. Rogers, *Appl. Phys. Lett.* 2009, 95, 133701.

[2] D.-H. Kim, J. Viventi, J. Amsden, J. Xiao, L. Vigeland, Y.-S. Kim, J. A. Blanco, B. Panilaitis, E. S. Frechette, D. Contreras, D. L. Kaplan, F. G. Omenetto, Y. Huang, K.-C. Hwang, M. R. Zakin, B. Litt, J. A. Rogers, *Nat. Mater.* 2010, 9, 511.

[3] C. J. Bettinger, Z. Bao, *Adv. Mater.* 2010, 22, 651.

[4] M. Irimia-Vladu, P. A. Troshin, M. Reisinger, L. Shmygleva, Y. Kanbur, G. Schwabegger, M. Bodea, R. Schwödiauer, A. Mumyatov, J. W. Fergus, V. F. Razumov, Helmut Sitter, N. S. Sariciftci, S. Bauer, *Adv. Funct. Mater.* 2010, 20, 4069.

[5] C. Legnani, C. Vilani, V. L. Calil, H. S. Barud, W. G. Quirino, C. A. Achete, S. J. L. Ribeiro, M. Cremona, *Thin Solid Films*, 2008, 517, 1016.

[6] S.-W. Hwang, H. Tao, D.-H. Kim, H. Cheng, J.-K. Song, E. Rill, M. A. Brenckle, B. Panilaitis, S. M. Won, Y. S.-Kim. Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, *Science*, 2012, 337, 1640.

[7] S.-W. Hwang, X. Huang, J.-H. Seo, J.-K. Song, S. Kim, S. Hage-Ali, H.-J. Chung, H. Tao, F. G. Omenetto, Z. Ma, J. A. Rogers, *Adv. Mater.* 2013, 25, 3526.

[8] S.-W. Hwang, D.-H. Kim, H. Tao, T.-I. Kim, S. Kim, K. J. Yu, B. Panilaitis, J.-W. Jeong, J.-K. Song, F. G. Omenetto, J. A. Rogers, *Adv. Funct. Mater.* 2013, 23, 4087.

[9] C. Dagdeviren, S.-W. Hwang, Y. Su, S. Kim, H. Cheng, 0. Gur, R. Haney, F. G. Omenetto, Y: Huang, J. A. Rogers, *Small*, 2013, 9, 3398.

[10] L. Yin, H. Cheng, S. Mao, R. Haasch, Y. Liu, X. Xie, S.-W. Hwang, H. Jain, S.-K. Kang, Y. Su, R. Li, Y. Huang, J. A. Rogers, *Adv. Funct. Mater.* 2014, 24, 645.

[11] Erogbogbo F, Yong K-T, Roy I, Xu G, Prasad P N, Swihart M T. Biocompatible Luminescent Silicon Quantum Dots for Imaging of Cancer Cells. ACS Nano. 2008 2014/01/20; 2(5):873-8.

[12] Erogbogbo F, Yong K-T, Hu R, Law W-C, Ding H, Chang C-W, et al. Biocompatible Magnetofluorescent Probes: Luminescent Silicon Quantum Dots Coupled with Superparamagnetic Iron(III) Oxide. ACS Nano. 2010 2014/01/20; 4(9):5131-8.

[13] Larson D R, Ow H, Vishwasrao H D, Heikal A A, Wiesner U, Webb W W. Silica Nanoparticle Architecture Determines Radiative Properties of Encapsulated Fluorophores. Chemistry of Materials. 2008 2014/01/20; 20(8):2677-84.

[14] Park J-H, Gu L, von Maltzahn G, Ruoslahti E, Bhatia S N, Sailor M J. Biodegradable luminescent porous silicon nanoparticles for in vivo applications. Nat Mater. 2009; 8(4):331-6.

[15] Low S P, Voelcker N H, Canham L T, Williams K A. The biocompatibility of porous silicon in tissues of the eye. Biomaterials. 2009; 30(15):2873-80.

[16] Sun W, Puzas J E, Sheu T J, Liu X, Fauchet P M. Nano-to Microscale Porous Silicon as a Cell Interface for Bone-Tissue Engineering. Advanced Materials. 2007; 19(7):921-4.

[17] Gatti A M, Montanari S, Monari E, Gambarelli A, Capitani F, Parisini B. Detection of micro- and nano-sized biocompatible particles in the blood. Journal of Materials Science: Materials in Medicine. 2004; 15(4):469-72.

[18] Bayliss S C, Buckberry L D, Fletcher I, Tobin M J. The culture of neurons on silicon. Sensors and Actuators A: Physical. 1999; 74(1â€"3):139-42.

[11] G. Popescu, T. Ikeda, R. Dasari, M. S. Feld, *Optics Letters*, 2006, 31, 775.

[12] C. Edwards, A. Arbabi, G. Popescu, and L. L. Goddard, *Light Sci. Appl.* 2012, 1, 30.

[13] H. V. Pham, C. Edwards, L. L. Goddard, and G. Popescu, *Appl. Opt.* 2012, 52, A97.
[14] H. Maher, D. W. DiSanto, G. Soerensen, C. R. Bolognesia, H. Tang, J. B. Webb, *Appl. Phys. Lett.* 2000, 77, 3833.
[15] M. S. Minsky, M. White, E. L. Hu, *Appl. Phys. Lett.* 1996, 68, 1531.
[16] H. Cho, K. H. Auh, J. HAN, R. J. Shul, S. M. Donovan, C. R. Abernathy, E. S. Lambers, F. Ren, S. J. pearton, *J. of Electron. Mater,* 1999, 28, 290.
[17] J. van de Ven, H. J. P. Nabben, *J. Electrochem. Soc.* 1991, 138, 3401.
[18] H. Seidel, L. Csepregi, A. Heuberger, H. Baumgartel, *J. Electrochem. Soc.* 1990, 137, 3612.
[19] H. Seidel, L. Csepregi, A. Heuberger, H. Baumgartel, *J. Electrochem. Soc.,* 1990, 137, 3626.
[20] A. D. Bhrany, C. A. Irvin, K. Fujitani, Z. Liu, B. D. Ratner, *JAMA Facial Plast. Surg.* 2013, 15, 29.

EXAMPLE 7

Stretchable Transient Electronics

Figure 39:
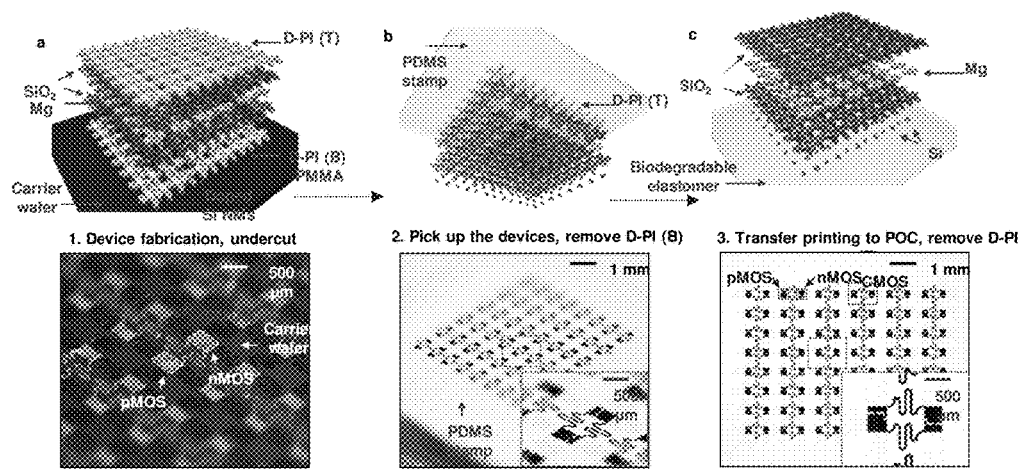
FIG. 39. Stretchable transient electronic circuits were fully fabricated on carrier wafers and transfer printed onto biodegradable elastomers using a PDMS stamp. The circuits were (a) fabricated on a carrier wafer, then undercut and (b) picked up with a transfer device, such as a PDMS stamp. D-PI was removed from the bottom of the stack and (c) the stack was transfer printed to POC. D-PI was then removed from the top of the stack. As shown in the accompanying photographs, pMOS, nMOS and CMOS devices were fabricated using this technique.

As shown in FIG. 39, stretchable transient electronic circuits were fully fabricated on carrier wafers and transfer printed onto biodegradable elastomers using a PDMS stamp. The circuits were (a) fabricated on a carrier wafer, then undercut and (b) picked up with a transfer device, such as a PDMS stamp. D-PI was removed from the bottom of the stack and (c) the stack was transfer printed to POC. D-PI was then removed from the top of the stack. As shown in the accompanying photographs, pMOS, nMOS and CMOS devices were fabricated using this technique.

Figure 40:
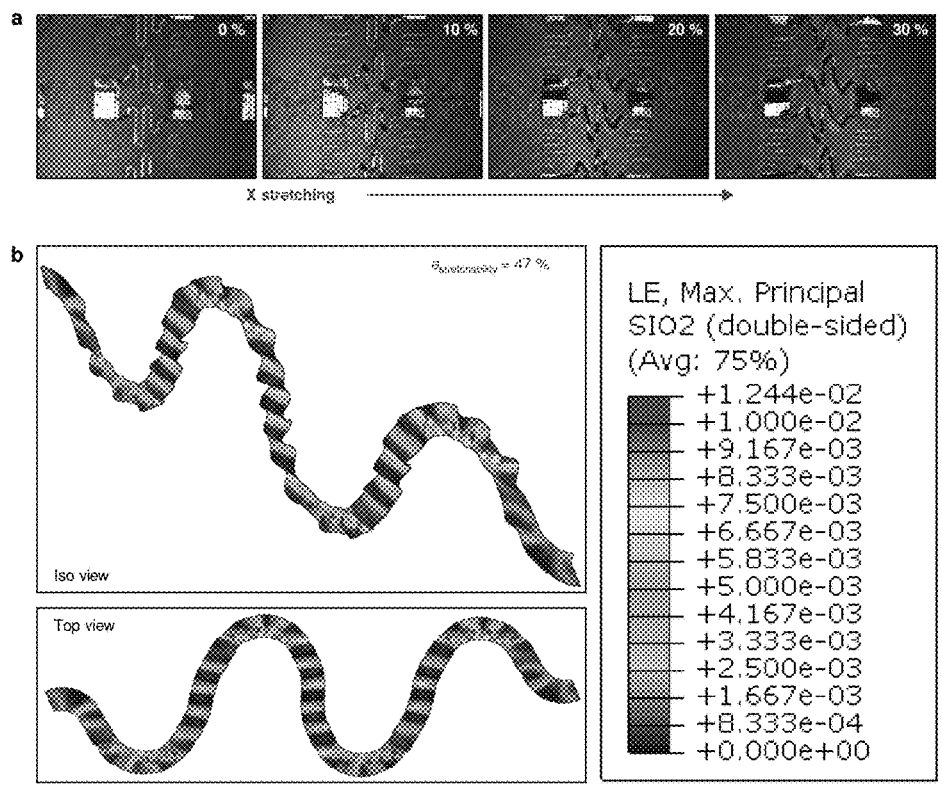
FIG. 40. Stretchable mechanics of exemplary transient electronics. Experimental results (a) provided stretchability of 30% for the design, while modelling (b) showed good stretchability to about 47%.

FIG. 40 shows the stretchable mechanics of exemplary transient electronics. Experimental results (a) provided stretchability of 30% for the design, while modelling (b) showed good stretchability to about 47%.

Figure 41:
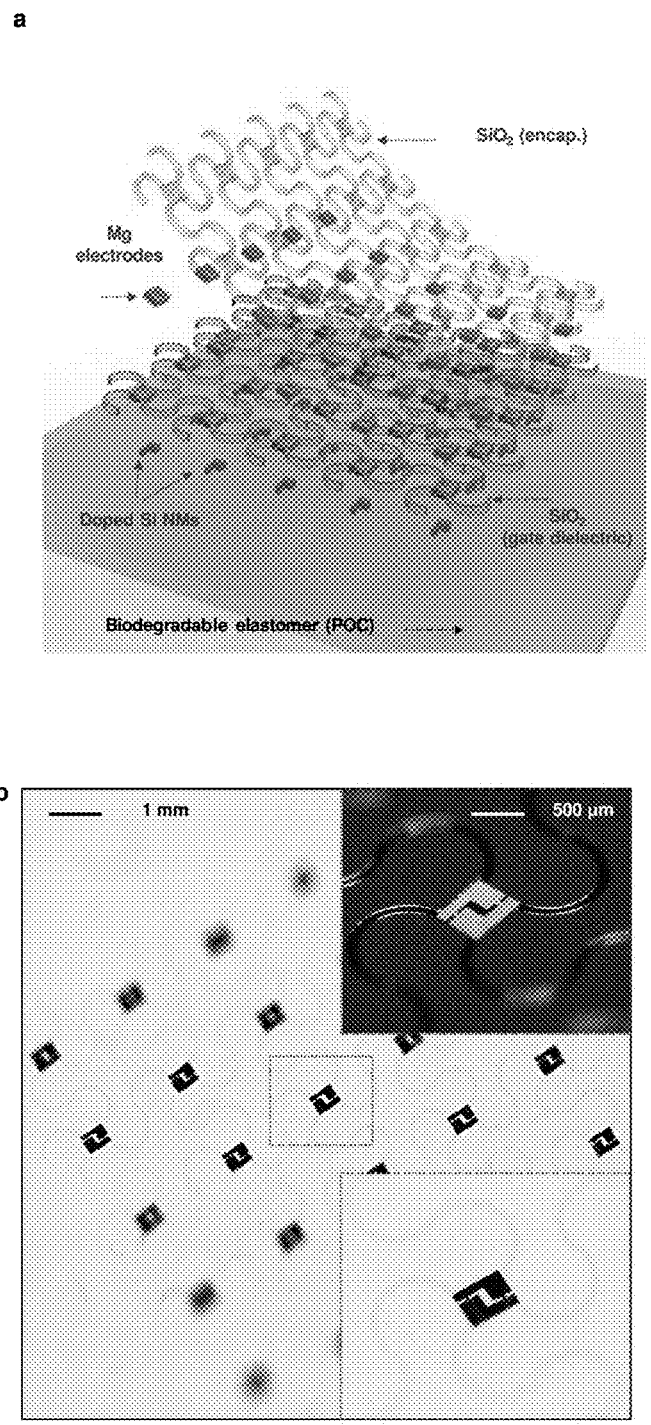
FIG. 41. Schematic (a) and photograph (b) of one design geometry used in the study of stretchable mechanics. (c) A series of photographs of an individual island stretched to 0%, 10%, 20% and 30%, where modeling of an array stretched to ~38% showed no high strain locations. (d) Plots showing performance of pMOS and nMOS transient devices preserved under stretching.

FIG. 41 provides a schematic (a) and photograph (b) of one design geometry used in the study of stretchable mechanics. An array of doped silicon nanomembrane (Si NM) devices was formed on a biodegradable elastomer (POC) according to the method shown in FIG. 39. The Si NMs were covered with $SiO_2$ gate dielectric material insulating the Si NMs from Mg electrodes, which were covered with a second layer of $SiO_2$ encapsulant. Each of the $SiO_2$ layers was formed in an island-interconnect geometry with islands having serpentine interconnects at each corner. FIG. 41c shows a series of photographs of an individual island stretched to 0%, 10%, 20% and 30%, where modeling of an array stretched to ~38% showed no high strain locations. FIG. 41d shows that the performance of pMOS and nMOS transient devices is preserved under stretching.

Stretchable Transient pH Sensor

Figure 42:
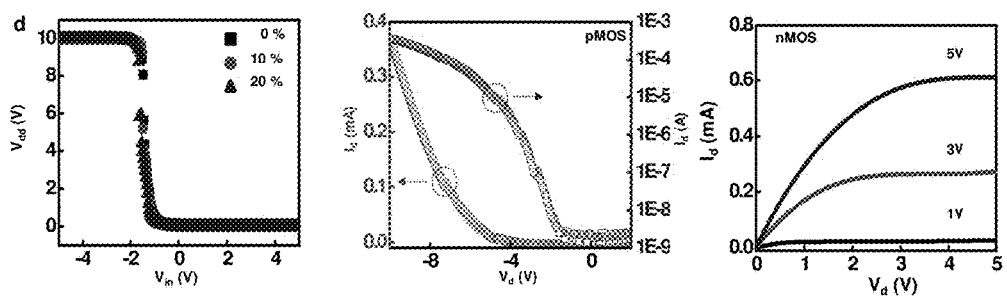
FIG. 42. A stretchable transient pH sensor. (a) shows pairs of Mg contacts connected by serpentine Mg, interconnects to ACF connections. As shown in the exploded view of (b), the Mg contacts are applied to a plurality of Si nanoribbons (Si NRs) disposed on a biodegradable elastomer (POC). The gap between the Mg contacts forms a sensing opening. The Mg components are then covered by a SiO2 encapsulant (c). (d) shows a plot of experimental data collected by the stretchable transient pH sensor. (e) provides photographs showing dissolution of the pH sensor in PBS (pH 7.4) over the course of 1 hour.
Figure 42:
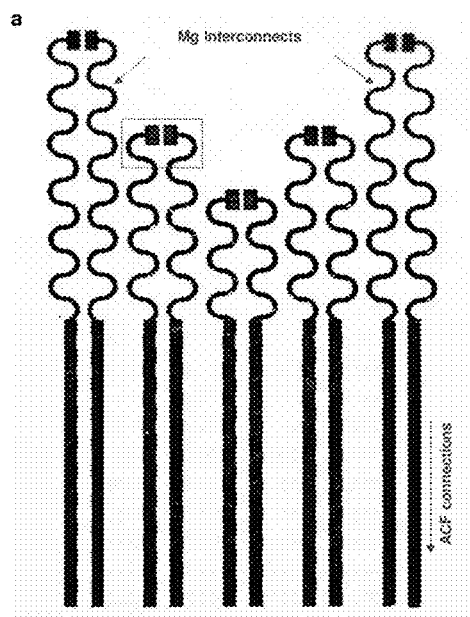

A stretchable transient pH sensor was also fabricated and tested. FIG. 42(a) shows pairs of Mg contacts connected by serpentine Mg interconnects to ACF connections. As shown in the exploded view of FIG. 42(b), the Mg contacts are applied to a plurality of Si nanoribbons (Si NRs) disposed on a biodegradable elastomer (POC). The gap between the Mg contacts forms a sensing opening. The Mg components are then covered by a $SiO_2$ encapsulant (FIG. 42(c)). FIG. 42(d) shows a plot of experimental data collected by the stretchable transient pH sensor. FIG. 42(e) provides photographs showing dissolution of the pH sensor in PBS (pH 7.4) over the course of 1 hour.

Transient Drug Delivery System

Figure 43:
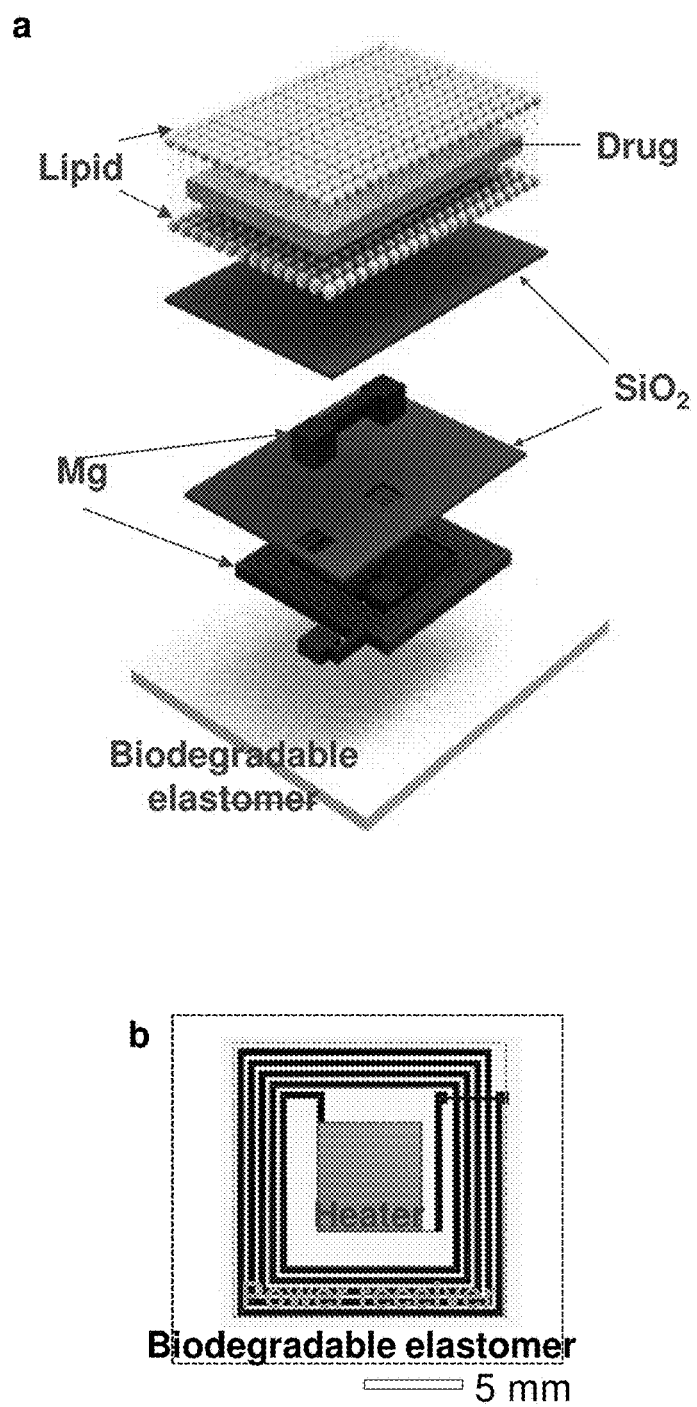
FIG. 43. A fully biodegradable drug delivery device. (a) shows a schematic of a transient drug delivery system comprising a lipid stabilized drug on a transient heating device. The heating device (b) comprises a Mg resistive heater and a power receiver coil coupled to a Mg microwave antennae. (c) provides an infrared image of the heater device reaching a maximum temperature of about 90° C. (d) shows an increase in fluorescent intensity as the drug is activated by heating over time.

A fully biodegradable drug delivery device was fabricated and tested ex vivo. FIG. 43(a) shows a schematic of a transient drug delivery system comprising a lipid stabilized drug on a transient heating device. The heating device (FIG. 43(b)) comprises a Mg resistive heater and a power receiver coil coupled to a Mg microwave antennae. The heating device is disposed on a biodegradable elastomer and covered with a $SiO_2$ encapsulant, except at contact areas between the antennae and the heating device. A second encapsulating layer of $SiO_2$ covers the Mg antennae and supports a lipid bilayer containing and stabilizing a drug. FIG. 43(c) provides an infrared image of the heater device reaching a maximum temperature of about 90° C. FIG. 43(d) shows an increase in fluorescent intensity as the drug is activated by heating over time.

While the present Example illustrates drug stabilization with a lipid bilayer, other stabilizing compositions are contemplated. For example, micelles, vesicles and liposomes may be used to stabilize drugs until disrupted by an internal or external stimulus.

EXAMPLE 8

Transient PCB Circuit and Printable Transient Paste

This Example discloses suitable materials and methods for making transient printed circuit board (PCB) circuits. In an embodiment, a transient conductive paste was developed and used in the fabrication of transient PCB circuits. Some exemplary transient conductive pastes comprised sodium carboxymethyl cellulose (Na-CMC), poly(ethylene) oxide (polyox), polylactic acid (PLA), polyglycolic acid (PGA), or polylactic-co-glycolic acid (PLGA). All of these polymers are water soluble and FDA approved. Cured Na-CMC polymer films have good mechanical strength and flexibility, which is useful for substrate materials. Cured polyox films have good elasticity and good adhesion to various surfaces, which is useful for binders.

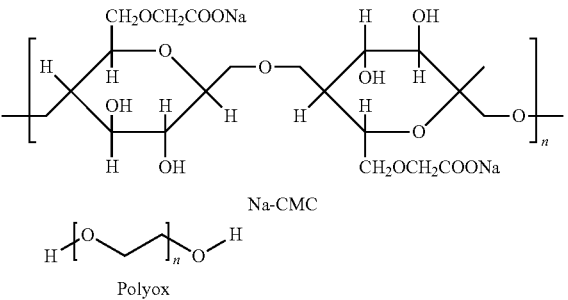

Na-CMC

Polyox

Figure 44:
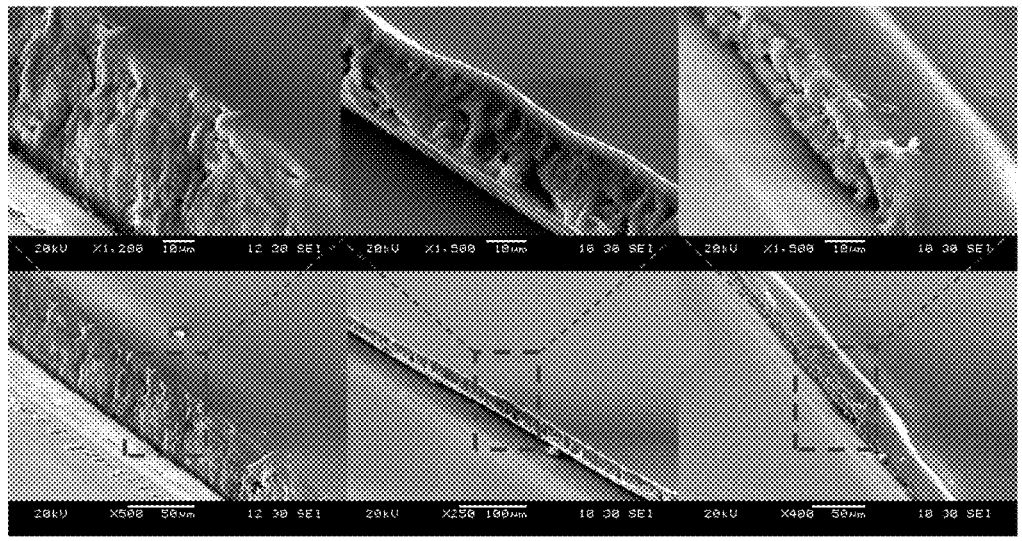
FIG. 44. Scanning electron micrograph images showing good uniformity of Na-CMC films with molecular weights selected from the range of 90 KD to 700 KD. Each of the films was cast as a 1 wt. % polymer solution to a thickness of 10 µm.

FIG. 44 shows good uniformity of Na-CMC films with molecular weights selected from the range of 90 KD to 700 KD. Each of the films was cast as a 1 wt. % polymer solution to a thickness of 10 μm.

As shown in FIGS. 45(a)-(d), a transient PCB circuit for wireless temperature determination was fabricated. The transient PCB circuit included an RF power harvester providing energy to a power management module, which powered a temperature sensor and voltage-controlled oscillator for converting analog signals to digital signals (FIG. 45(b)). To form the transient PCB circuit, a layer of polyox was sandwiched between layers of Na-CMC (FIG. 45(d)). Both faces of the polymer stack were patterned with Mg electrodes, $SiO_2$ insulating layers and electronic components (FIG. 45(a)), where for example pins of the electronic components were joined to the Mg electrode with transient conductive paste (FIG. 45(c)). FIG. 46 shows photographs demonstrating the size and flexibility of the transient PCB circuit.

Figure 47:
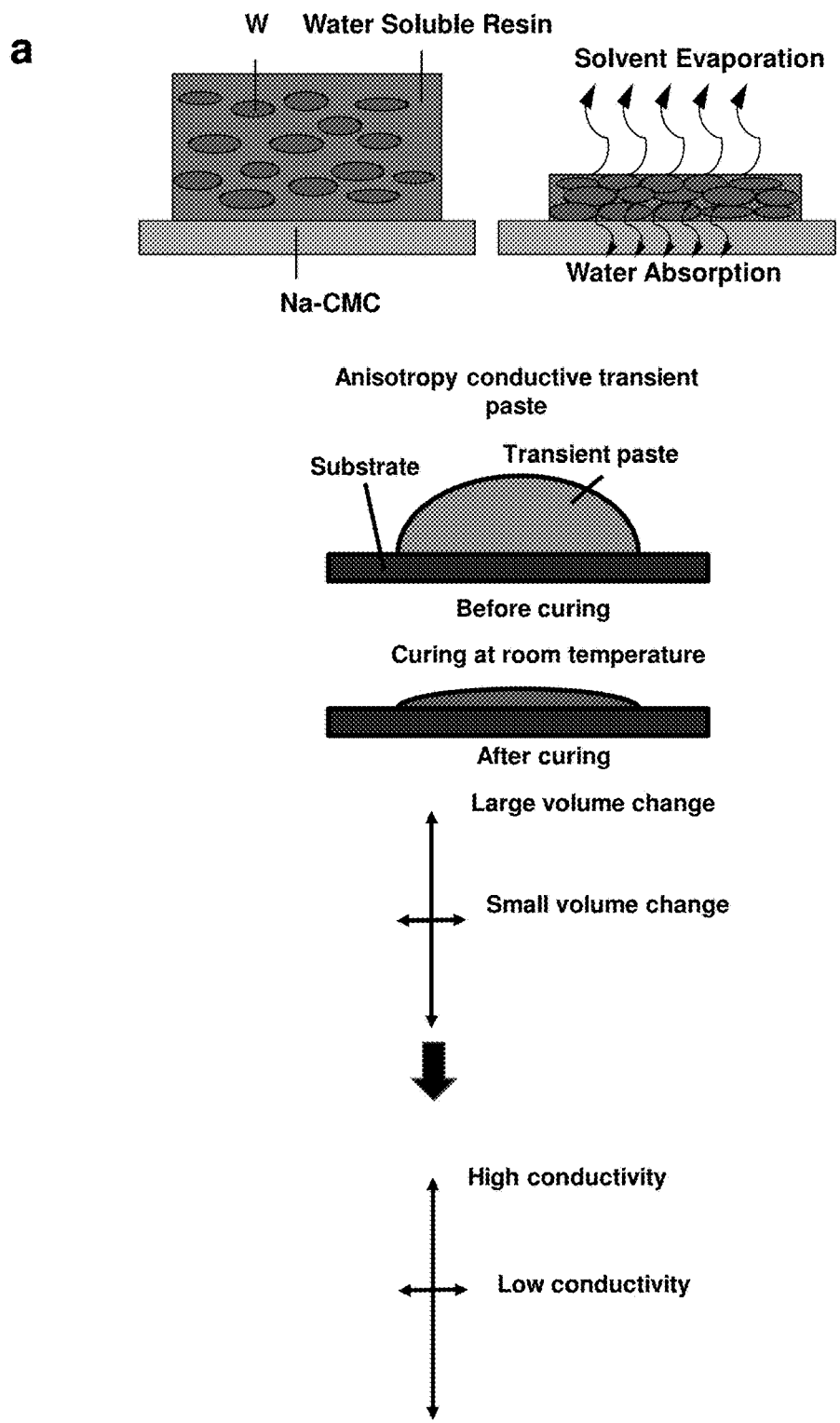
FIG. 47. Schematic of transient conductive pastes comprising microsized transient metal particles, a water soluble transient polymer/resin, and a volatile solvent. (a) The transient conductive paste was applied to a substrate and cured. The curing process changes the volume and conductivity of the paste anisotropically. (b) cross-sectional and top views of transient conductive pastes comprising tungsten or zinc microparticles.
Figure 51:
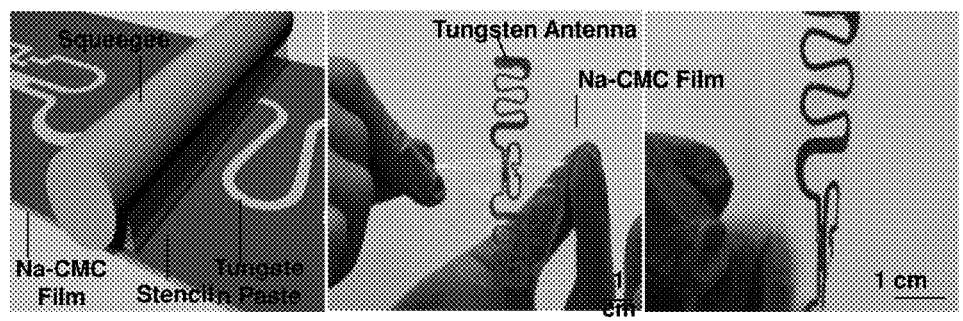
FIG. 51. Schematic of screen printing technique for forming stretchable, conductive and transient interconnects, electrical contacts, antennae and other electrical device components.

Transient conductive pastes used in the fabrication of the transient PCB circuit comprised microsized transient metal particles, a water soluble transient polymer/resin such as polyox, and a volatile solvent such as methanol, ethanol, acetone, etc. As shown in FIG. 47(a), the transient conductive paste was applied to a substrate, such as Na-CMC, and cured. In an embodiment, curing involves solvent evaporation and/or water absorption from the paste to the substrate. Curing may occur at room temperature. The curing process changes the volume and conductivity of the paste anisotropically. For example, the volume of the paste decreases to a greater extent in the vertical dimension than in the lateral or circumferential dimension. Likewise, conductivity is higher in the vertical dimension than in the lateral or circumferential dimension after curing. FIG. 47(b) shows cross-sectional and top views of transient conductive pastes comprising tungsten or zinc microparticles. The transient conductive pastes could be screen printed onto substrates by moving a squeegee over a stencil to produce stretchable, conductive and transient interconnects, electrical contacts, antennae and other electrical device components, (FIG. 51). In some embodiments, transient conductive pastes were advantageously used to conformally fill trenches and/or vias of printed circuit boards. Planar metal contacts and/or interconnects were generally formed by screen printing with transient conductive paste or by traditional deposition methods, such as evaporation or sputtering.

Figure 45:
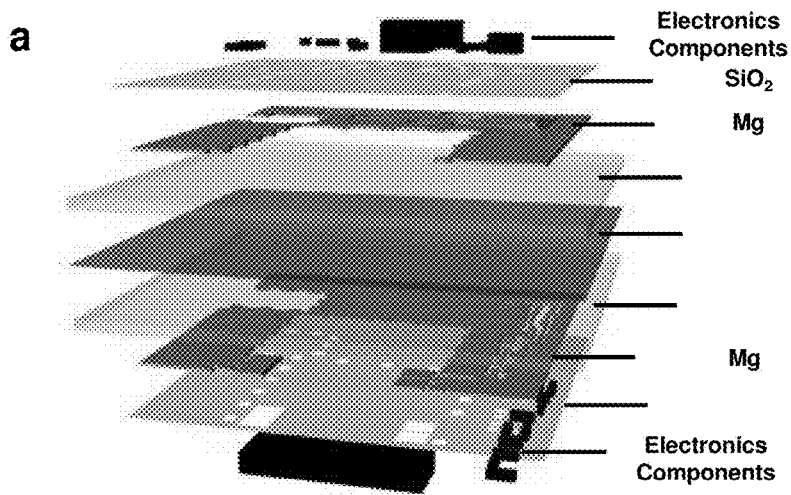
FIG. 45. A transient PCB circuit for wireless temperature determination. The transient PCB circuit included an RF power harvester providing energy to a power management module, which powered a temperature sensor and voltage-controlled oscillator for converting analog signals to digital signals (b). To form the transient PCB circuit, a layer of polyox was sandwiched between layers of Na-CMC (d). Both faces of the polymer stack were patterned with Mg electrodes, SiO2 insulating layers and electronic components (a), where for example pins of the electronic components were joined to the Mg electrode with transient conductive paste (c).
Figure 46:
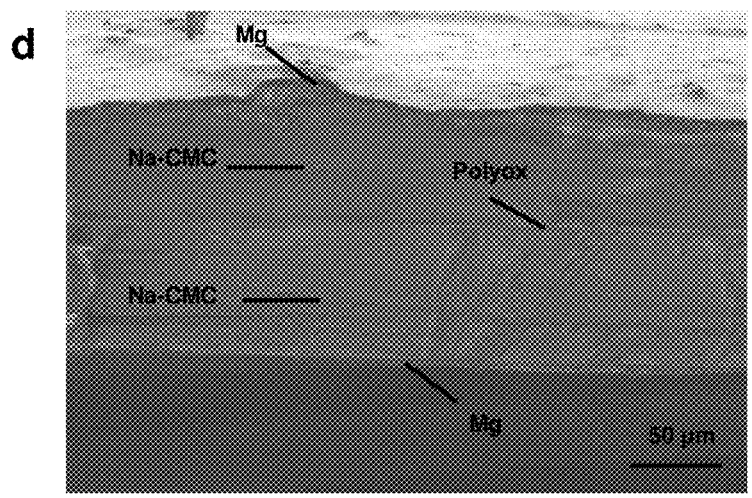
FIG. 46. Photographs demonstrating the size and flexibility of the transient PCB circuit of FIG. 45.
Figure 46:
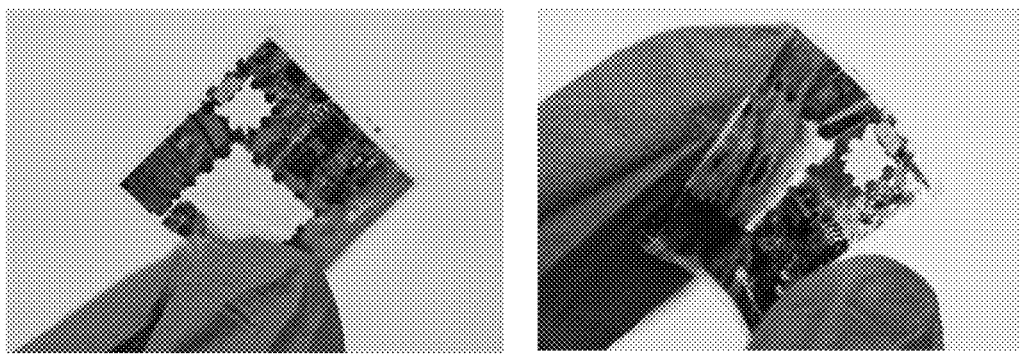
Figure 48:
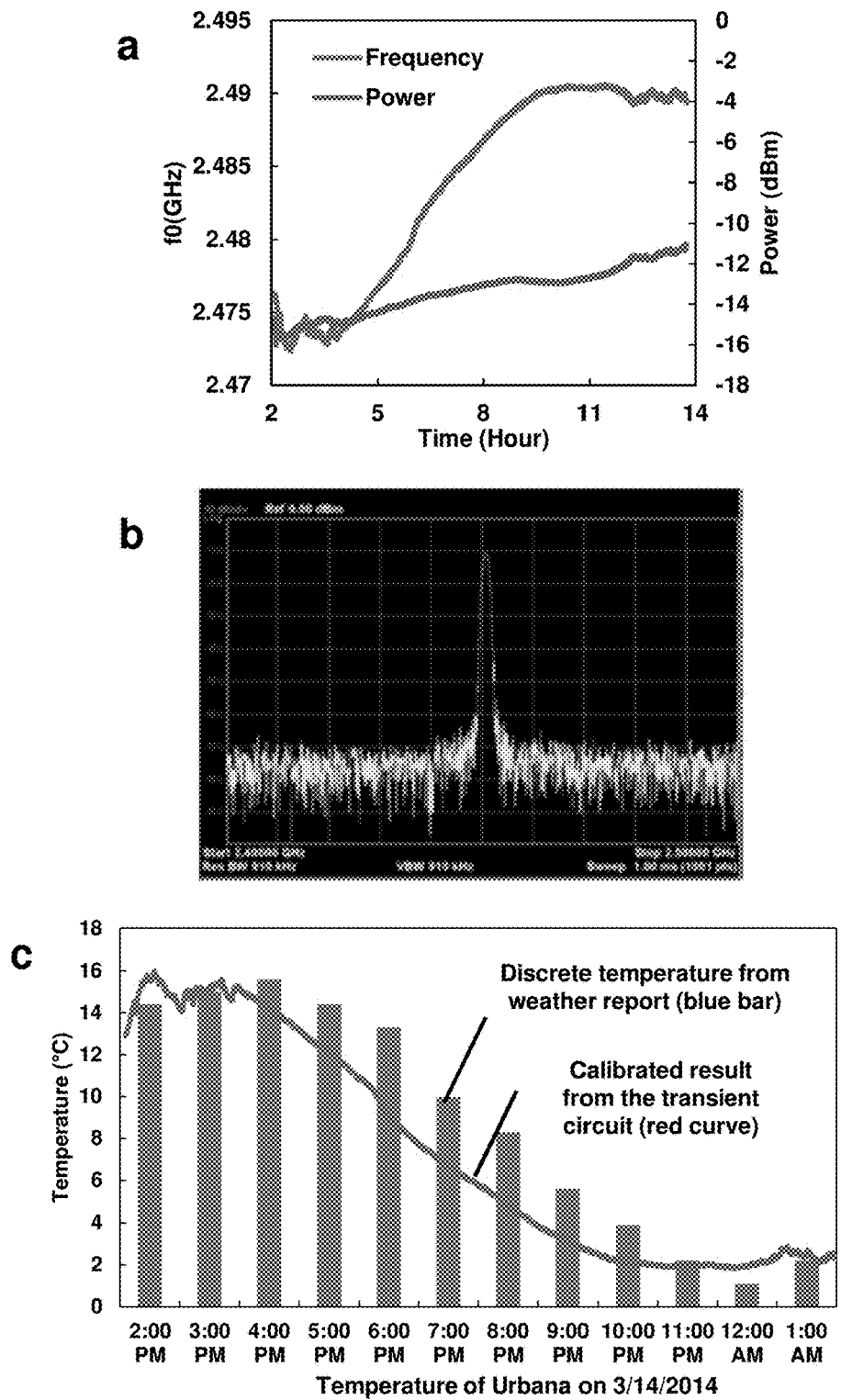
FIG. 48. The transient wireless temperature sensor of FIG. 45 was used to monitor ambient outdoor temperature in Urbana, Ill. over the course of twelve hours, (c). Power and frequency data from the wireless sensor (a)-(b) was captured through the antenna of a portable spectrum analyzer (e) located three meters away from the transient circuit on the inside of a window (d).
Figure 49:
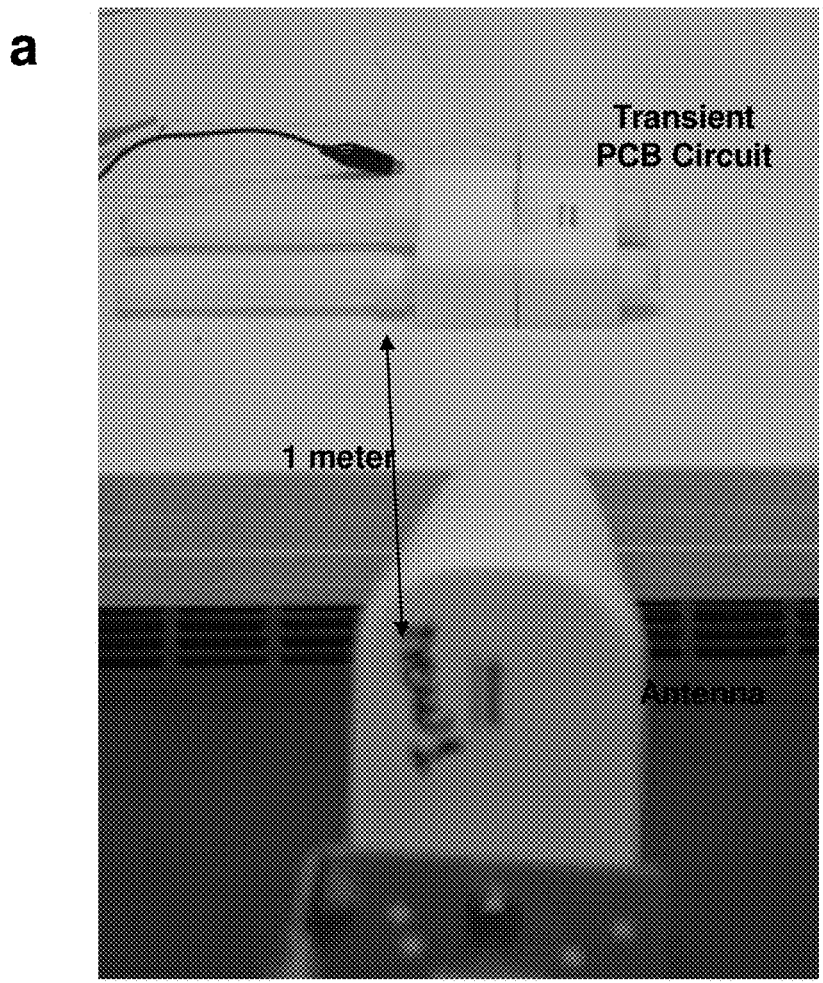
FIG. 49. The voltage output from the transient harvester as a function of frequency (b) and the power and frequency output as a function of time from the VCO supported by the harvester (c) were monitored by an antenna located one meter from the transient PCB circuit (a).
Figure 50:
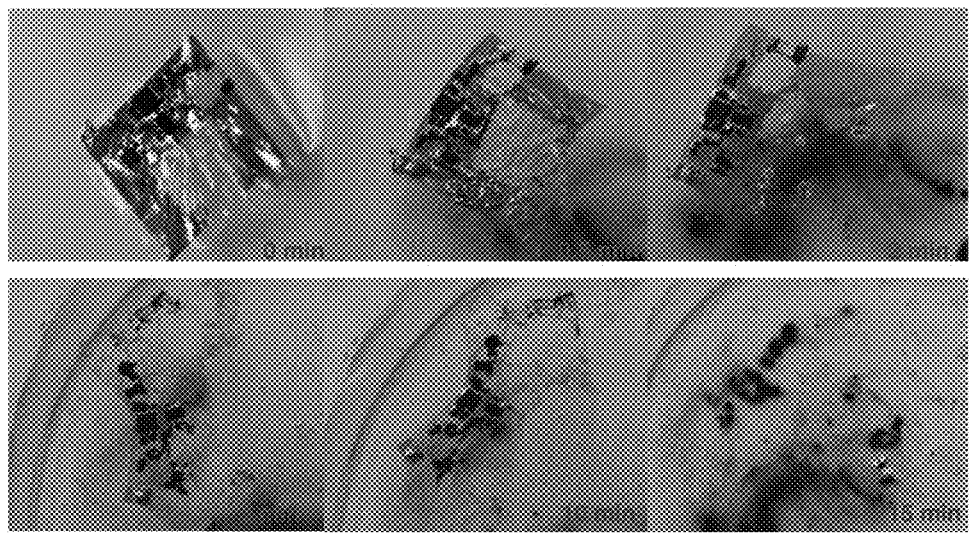
FIG. 50. Demonstration of dissolution of the transient PCB circuit over the course of 15 minutes in solution (e.g., water).

The transient wireless temperature sensor of FIG. 45 was used to monitor ambient outdoor temperature in Urbana, Ill. over the course of twelve hours, (FIG. 48(c)). Power and frequency data from the wireless sensor (FIGS. 48(a)-(b)) was captured through the antenna of a portable spectrum analyzer (FIG. 48e)) located three meters away from the transient circuit on the inside of a window (FIG. 48(d)). The voltage output from the transient harvester as a function of frequency (FIG. 49(b)) and the power and frequency output as a function of time from the VCO supported by the harvester (FIG. 49(c)) were monitored by an antenna located one meter from the transient PCB circuit (FIG. 49(a)). FIG. 50 shows dissolution of the transient PCB circuit over the course of 15 minutes in solution (e.g., water).

EXAMPLE 9

Actively Triggered Transience in a Liquid-Gas Embodiment

Figure 52:
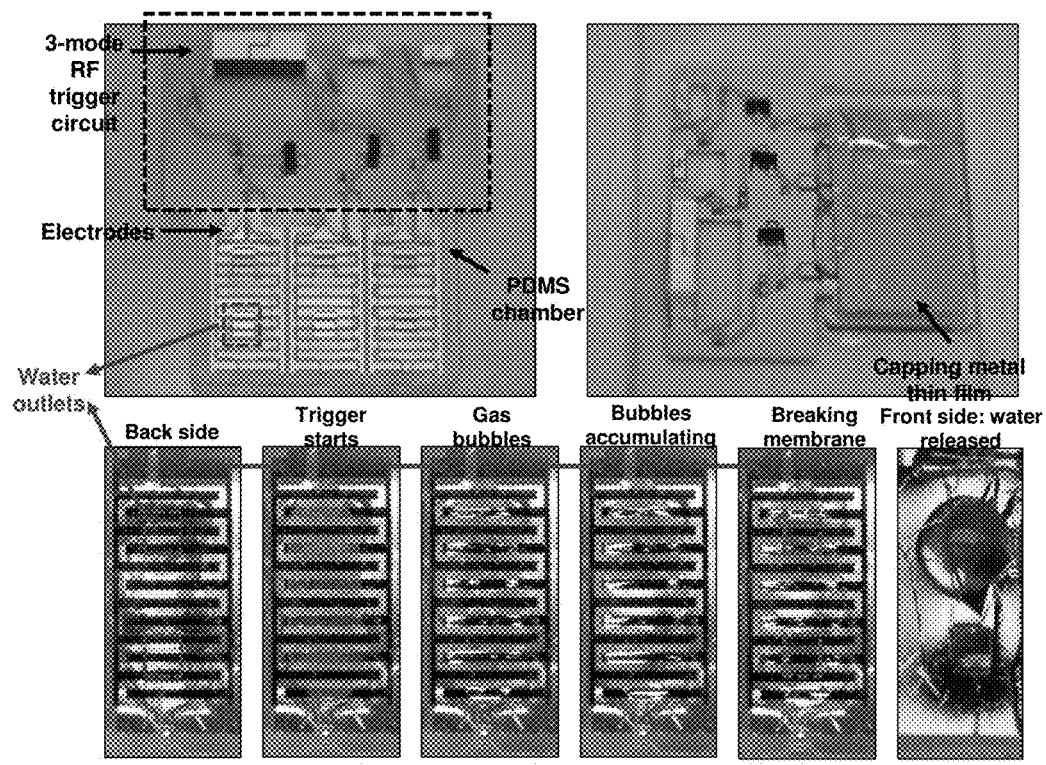
FIG. 52. A 3-mode RF trigger circuit connected to a plurality of transient electrodes in a PDMS chamber demonstrating actively triggered transience in a liquid-gas embodiment.

FIG. 52 shows a 3-mode RF trigger circuit connected to three transient electrodes in a PDMS chamber demonstrating actively triggered transience in a liquid-gas embodiment. The PDMS chamber comprises a plurality of reservoirs containing reactants, such as solids (e.g., powdered reactants), liquids (e.g., water, acid, base, etc.) or gases. In the example shown, the reservoirs are located on back sides of the electrodes and each reservoir contains water. A thin metal film is applied to the front sides of the electrodes to seal the reservoirs. Upon application of an active trigger in the form of an electric current, the water in the reservoirs is hydrolyzed to hydrogen and oxygen. Gas bubbles begin to form and accumulate in the reservoirs. Once sufficient gas pressure is produced, the thin metal film ruptures and water is released from the front sides of the electrodes. Rupturing of the metal film exposes the transient electrode components to the environment and accelerates decomposition/dissolution.

EXAMPLE 10

Actively Triggered Transience in a Multi Chamber or Single Chamber Embodiment

Figure 53A:
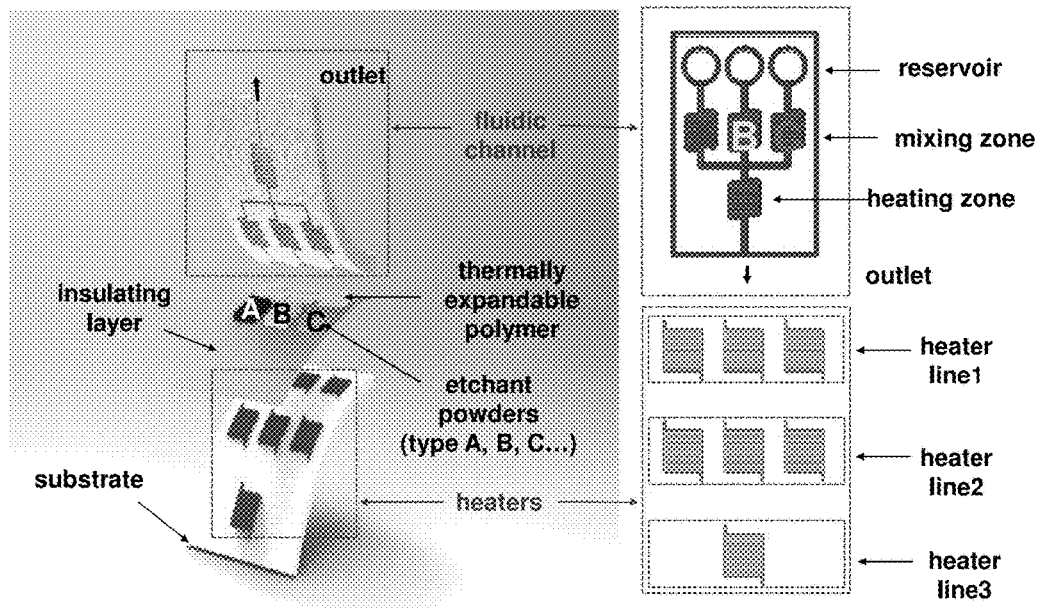
FIGS. 53A-53C. Schematics showing actively triggered transience in a (FIG. 53A) multi compartment embodiment and (FIG. 53B) in a single compartment embodiment.

FIG. 53A shows a schematic of actively triggered transience in a solid-liquid embodiment. In the embodiment shown, a first set of reservoirs (circles) contains at least one liquid and is in physical contact with a thermally expandable polymer, which may be in the reservoir or outside of the reservoir. Upon application of heat to heater line 1, the thermally expandable polymer expands and pushes liquid from the reservoirs through fluidic channels into a second set of reservoirs containing solids, such as etchant powders (A, B, C . . . ). The etchant powders are heated to an elevated temperature by heater line 2, and mixed with the liquid in this mixing zone. Next, all of the etchant solutions are transferred to a common reservoir in, a heating zone, where the temperature is controlled by heater line 3. From the common reservoir, the etchant solution may be released through an outlet and directed to a target device or component where it induces transience.

Figure 53B:
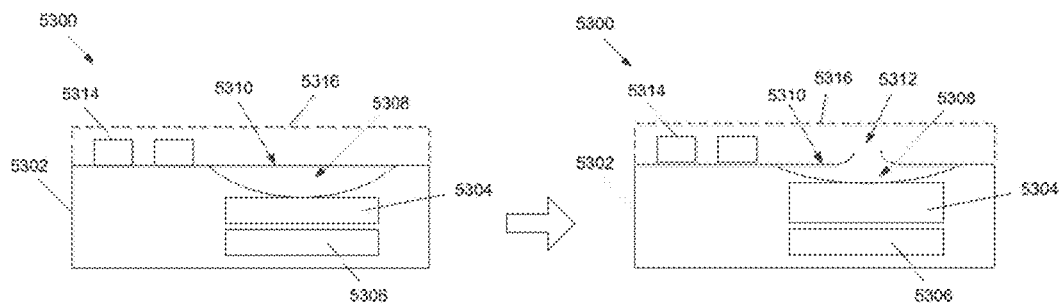

In the embodiment shown in FIG. 53B, an actively triggered device 5300 comprises a substrate 5302 of one or more layers encapsulating a thermally expandable polymer 5304 positioned between a heater 5306 and a reservoir 5308. A thin layer of material 5310 covers reservoir 5308. The thin layer may, for example, be a thin metal foil or polymer layer capable of being punctured upon application of pressure. Thermally expandable polymer 5304 expands and presses into reservoir 5308, thereby forcing the contents of reservoir 5308 (gas, liquid and/or solid) to be expelled through an opening 5312 that forms in layer 5310. The expelled contents of reservoir 5308 are free to interact with electronic devices or components 5314 on the surface of substrate 5302. In an embodiment, an optional cover 5316 over the surface of substrate 5302 maintains the expelled contents of reservoir 5308 near the surface of device 5300 and electronic devices or components 5314.

In an alternate embodiment, similar to that shown in FIG. 53A, a liquid is forced from a first reservoir or plurality of reservoirs through one or more microfluidic channels by a thermally expandable polymer(s). In the mixing zone, the liquid from the first reservoir or plurality of reservoirs encounters a solid composition in a second reservoir or plurality of reservoirs to form a solution. The solution may be expelled from the second reservoir or plurality of reservoirs by the mechanism shown in FIG. 53B, wherein a thermally expandable polymer applies pressure to puncture a thin layer covering the reservoir. Alternatively, the solution from the second reservoir may be transferred to a third reservoir prior to expulsion of the solution through a thin layer covering the reservoir according to the mechanism shown in FIG. 53B.

In any of the aforementioned embodiments, the gas, liquid or solid contained within a reservoir may be a pharmaceutical composition, a biological composition, an electrolyte, a pesticide, an herbicide, a chemical warfare agent, a sterilization agent or any other compound capable of being contained by the reservoir for a predetermined period.

Figure 53C:
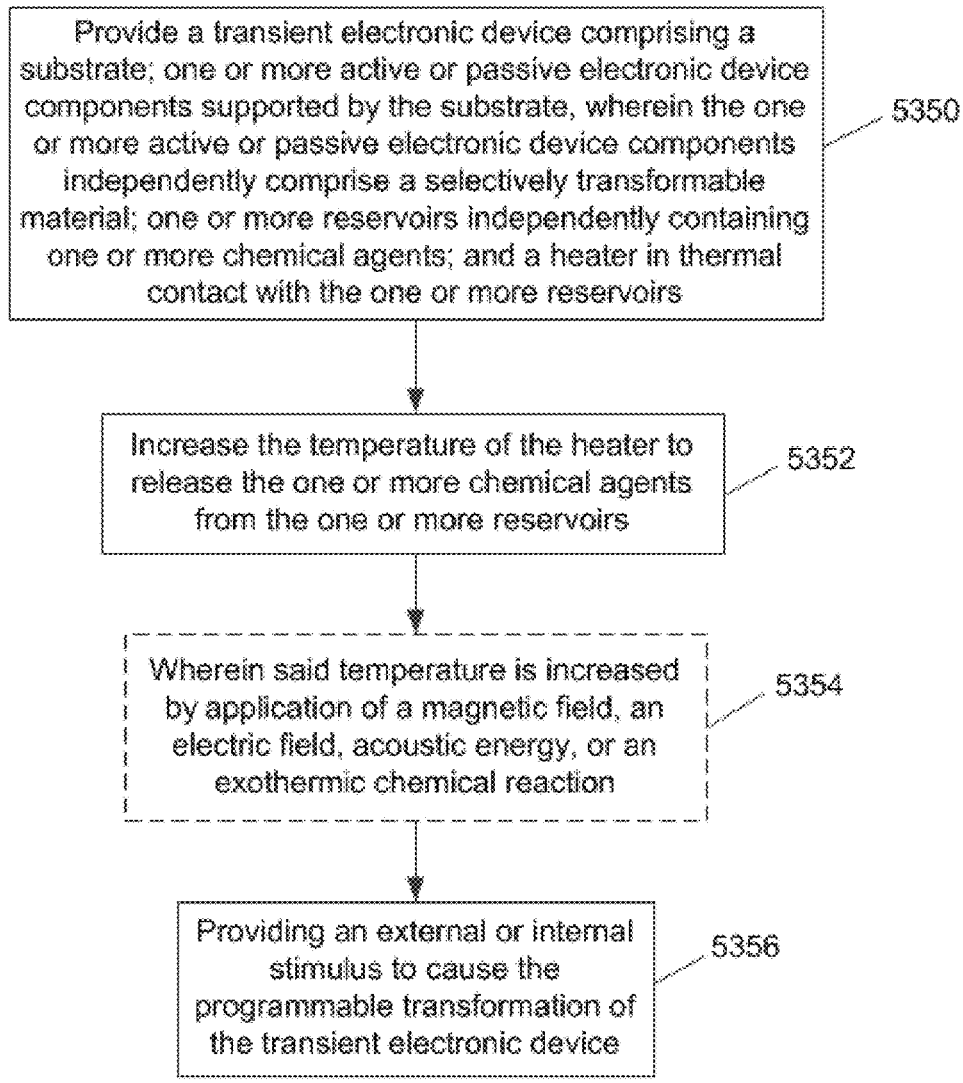

FIG. 53C provides a flowchart of a method of using a transient electronic device comprising actively triggered reservoirs. First, in step 5350, a transient electronic device is provided. The transient electronic device comprises a substrate; one or more active or passive electronic device components supported by the substrate, wherein the one or more active or passive electronic device components independently comprise a selectively transformable material; one or more reservoirs independently containing one or more chemical agents; and a heater in thermal contact with the one or more reservoirs. In step 5352, temperature of the heater is increased to release the one or more chemical agents from the one or more reservoirs. In an embodiment, shown as optional step 5354, the temperature is increased by application of a magnetic field, an electrical field, an acoustic field, or an exothermic chemical reaction. In step 5356, the release of the chemical agent provides the external or internal stimulus to cause at least partial transformation of the one or more active or passive electronic device components, which provides a programmable transformation of the transient electronic device.

EXAMPLE 11

Actively Triggered Transience in a Hydrogel Embodiment

Figure 54:
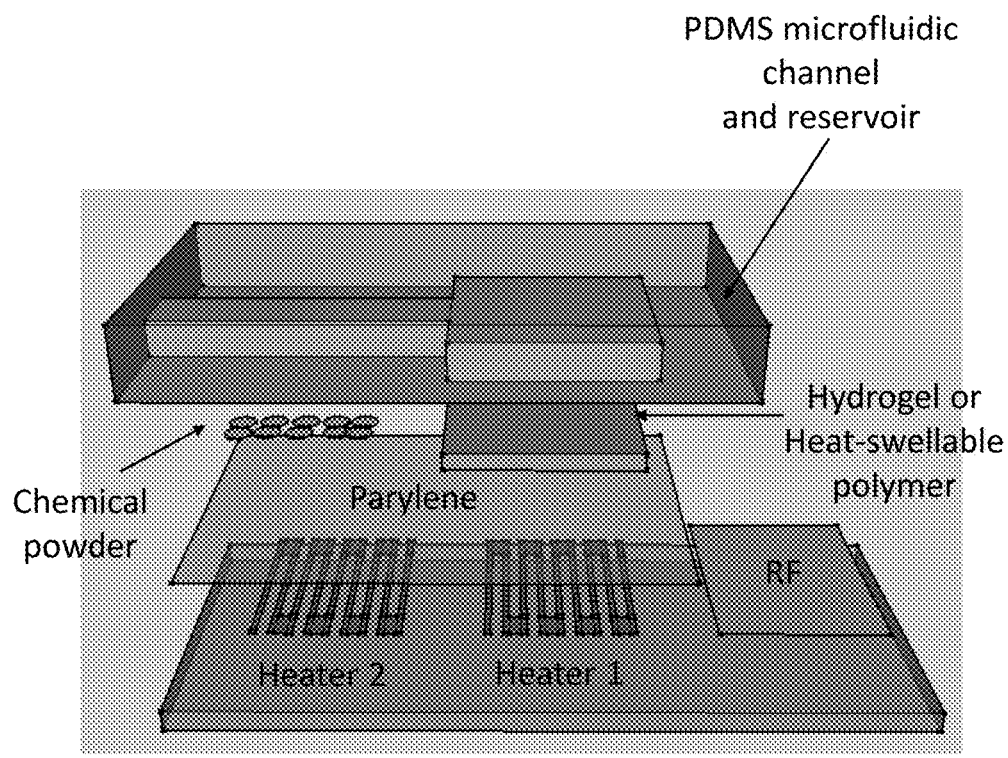
FIG. 54. Schematic of actively triggered transience in a hydrogel embodiment.

One challenge for actively triggered transient systems is that storage of corrosive and/or toxic solutions (e.g., KOH, HF) in reservoirs for an extended time is limited by the intrinsic properties of the reservoir material. To address this issue, FIG. 54 shows a schematic of actively triggered transience in a hydrogel embodiment, where water and/or another solvent is stored in a reservoir, hydrogel or heat swellable polymer. When heater 1, which is proximate to the reservoir, hydrogel or heat swellable polymer, is heated, water migrates to a microfluidic channel. The water is mixed with solid reactants (e.g., KOH pellets or powder) at elevated temperature. Heating is provided by heater 2, which is proximate the solid reactant(s). The mixed solution can be released through an outlet and directed to a target device or component (e.g., a memory device) where it induces transience. In an embodiment, parylene may be used to prevent evaporation of water and corrosion of device components (e.g., heaters) by the solid reactant.

In an alternate embodiment of actively triggered transience in a hydrogel embodiment, the hydrogel delivery device may store a dissolved pharmaceutical agent or drug. When a heater proximate to the hydrogel is heated, the hydrogel undergoes a phase change from a solid to a liquid, and liquid containing the pharmaceutical agent migrates through a microfluidic channel to a target tissue.

In some embodiments, drugs may be mixed with additional pharmaceutical agents, excipients, diluents, buffers, stabilizers, fillers and the like, which may be independently stored within an array of reservoirs. In an embodiment, the contents of the reservoirs may be sequentially released through a series of reservoirs and microfluidic channels.

EXAMPLE 12

Radio Frequency Identification (RFID) Tag

Figure 55A:
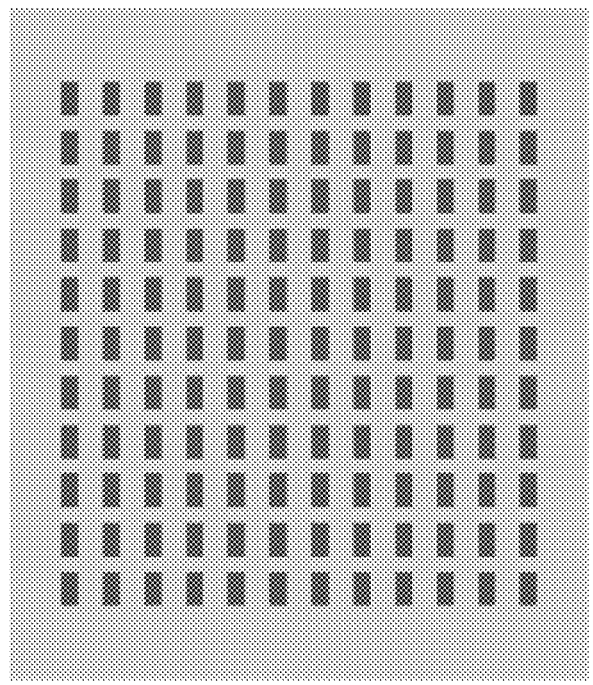
FIGS. 55A-55B.

FIGS. 55(A) and (B) show top plan and top perspective views, respectively, of passive RFID integrated circuit chiplets batch fabricated at a foundry using silicon-on-insulator wafers in a fabrication sequence which uses only transient materials. Tungsten, or another transient conductor material, is used for routing and interconnects on each chip. Bare die RFID ICs are undercut from the handle wafer in preparation for transfer printing.

Figure 55B:
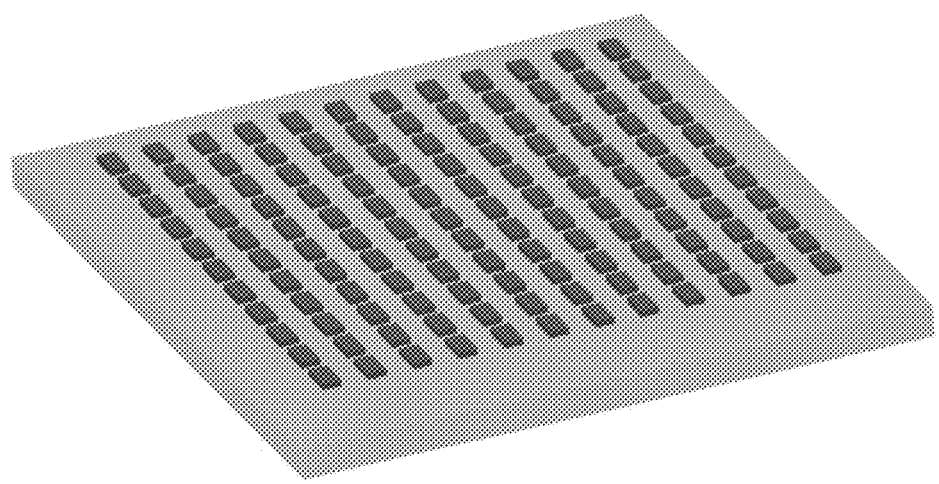
Figure 56A:
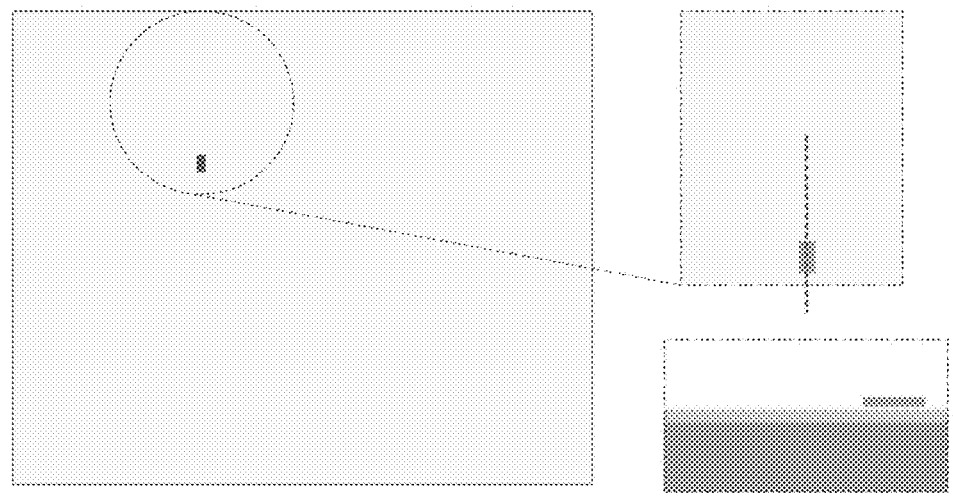
FIGS. 56A-56B. RFID chiplets are transfer printed from their original wafer onto a temporary handle wafer coated with PMMA and dilute polyimide (d-PI).
Figure 56B:
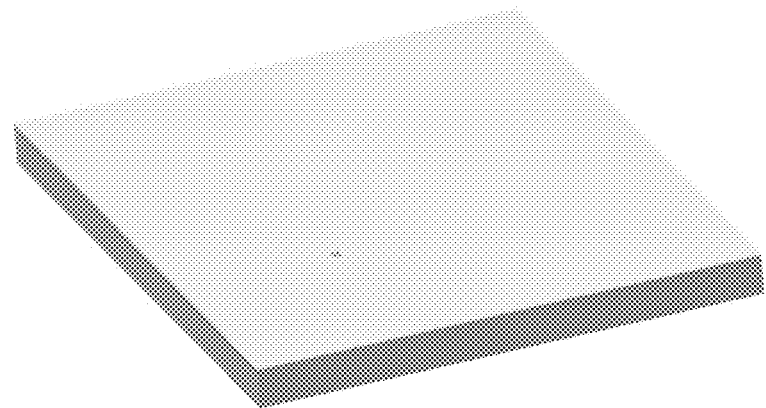

FIG. 56 shows the RFID chiplets of FIG. 55 transfer printed from their original wafer onto a temporary handle wafer coated with PMMA and dilute polyimide (d-PI). (A) Top plan view, exploded top plan view, and cross-sectional view along the dashed line shown in the exploded view, (B) top perspective view.

Figure 57A:
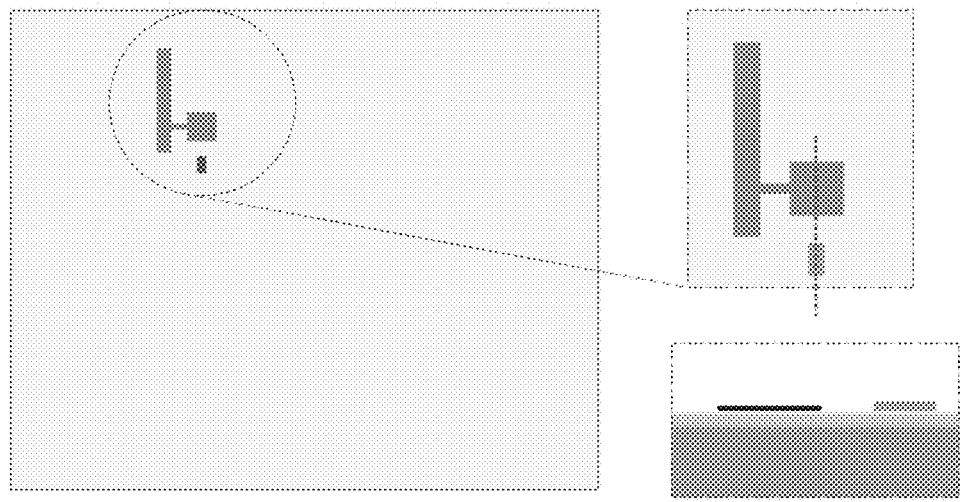
FIGS. 57A-57B. A bottom layer of transient metal is deposited and patterned on top of the d-PI layer of FIGS. 56A-56B.
Figure 57B:
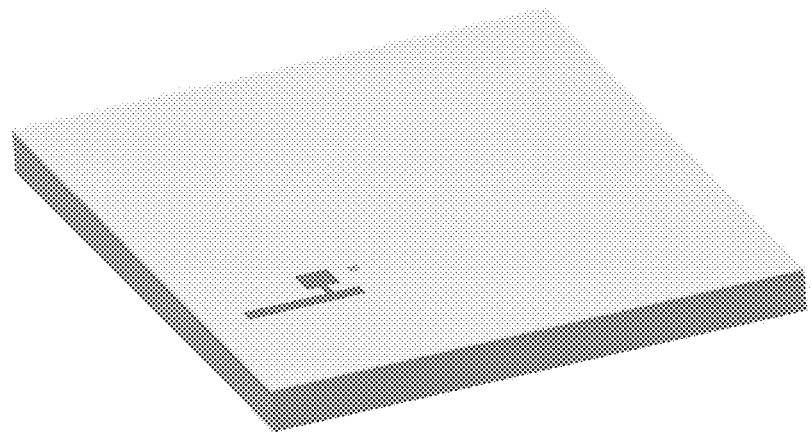

FIG. 57 shows a bottom layer of transient metal deposited and patterned on top of the d-PI layer of FIG. 56. This metal layer is used to form a bridge connecting the terminations of an antenna and also forms the bottom metal electrode for a resonant capacitor. (A) Top plan view, exploded top plan view, and cross-sectional view along the dashed line shown in the exploded view, (B) top perspective view.

Figure 58A:
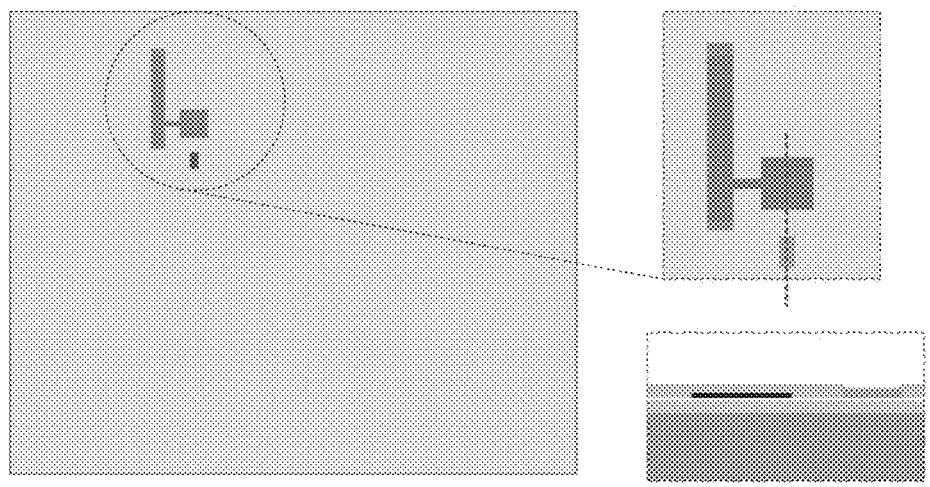
FIGS. 58A-58B. A transient planarizing dielectric layer is spun-coated (i.e. polymer or spin-on glass) or deposited (i.e. PECVD SiO2) onto the sample of FIGS. 57A-57B. The planarizing layer is selectively etched to open up interconnection points.
Figure 58B:
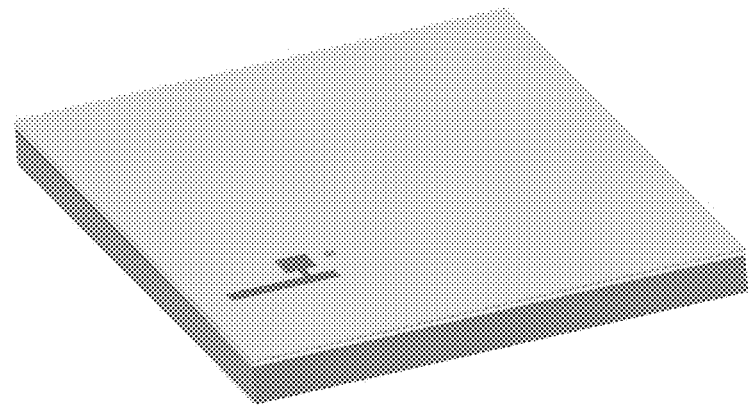

FIG. 58 shows a transient planarizing dielectric layer spun-coated (i.e. polymer or spin-on glass) or deposited (i.e. PECVD $SiO_2$) onto the sample of FIG. 57. The planarizing layer is selectively etched to open up interconnection points. (A) Top plan view, exploded top plan view, and cross-sectional view along the dashed line shown in the exploded view, (B) top perspective view.

Figure 59A:
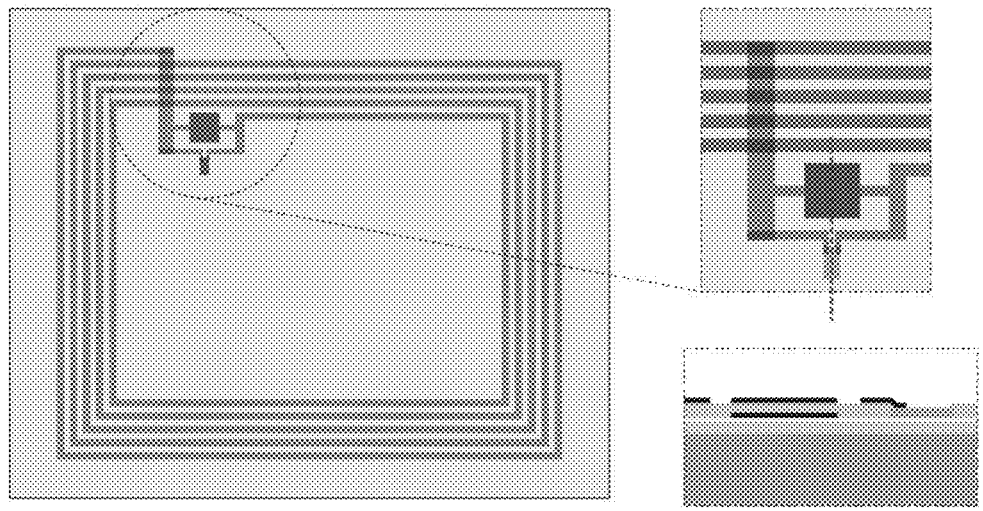
FIGS. 59A-59B. A top metal layer, which includes an antenna, is deposited and patterned on top of the planarizing dielectric layer of FIGS. 58A-58B. Openings allow for electrical contact between top and bottom metals. Capacitors are formed utilizing the planarizing layer as a dielectric.
Figure 59B:
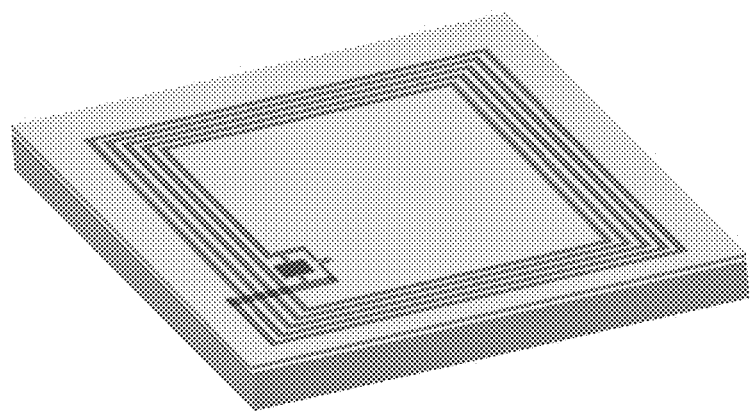

FIG. 59 shows a top metal layer, which includes an antenna, deposited and patterned on top of the planarizing dielectric layer of FIG. 58. In an embodiment, for example, the antenna may be formed by screen printing using a transient conductive paste. Openings allow for electrical contact between top and bottom metals. Capacitors are formed utilizing the planarizing layer as a dielectric. (A) Top plan view, exploded top plan view, and cross-sectional view along the dashed line shown in the exploded view, (B) top perspective view.

Figure 60A:
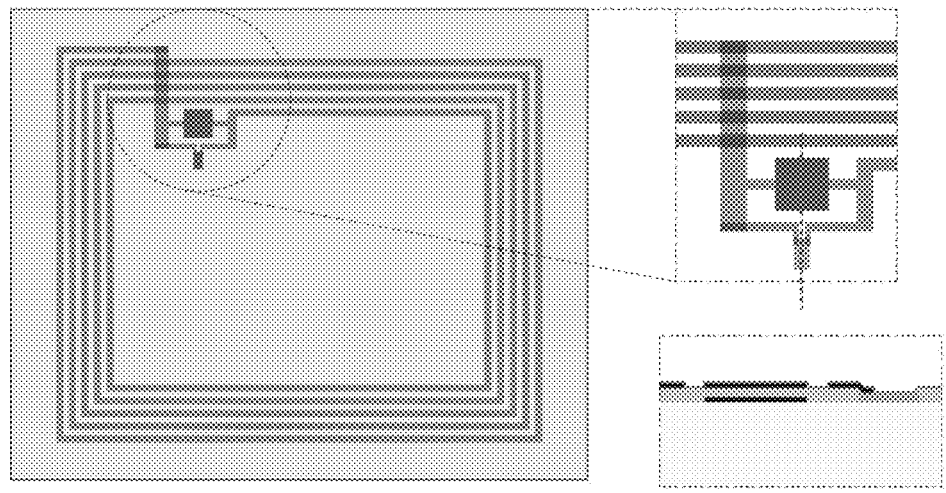
FIGS. 60A-60B. An encapsulating layer is deposited over the entire device. A temporary protective layer of d-PI is then patterned on top of the device and the PMMA is undercut in acetone to transfer print the device onto a transient substrate. The d-PI layers are etched away to reveal the completed transient RFID tag.
Figure 60B:
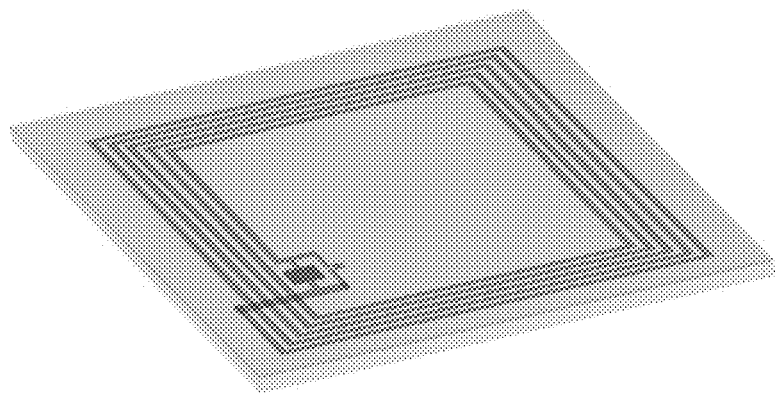

FIG. 60 shows an encapsulating layer deposited over the entire device. A temporary protective layer of d-PI is then patterned on top of the device and the PMMA is undercut in acetone to transfer print the device onto a transient substrate. The d-PI layers are etched away to reveal the completed transient RFID tag. (A) Top plan view, exploded top plan view, and cross-sectional view along the dashed line shown in the exploded view, (B) top perspective view.

EXAMPLE 13

Biodegradable Materials for Multilayer Transient Printed Circuit Boards

Figure 61:
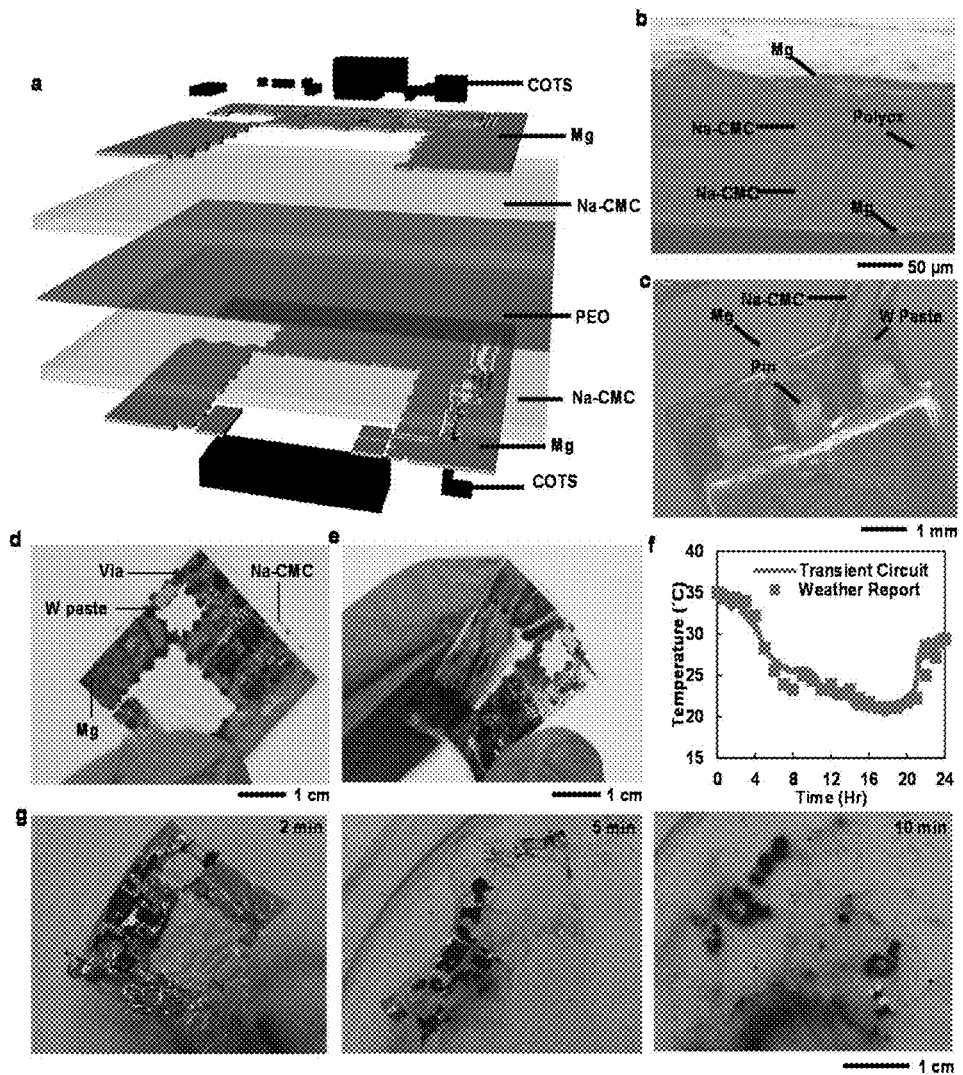
FIG. 61. Representative transient PCB device. (a) Schematic exploded view illustration of stacked layers of water dissoluble polymer films, transient metal patterns, and commercial off-the-shelf (COTS) components. (b) Colorized SEM cross sectional image. (c) Colorized SEM image of a COTS component mounted using W paste. Pictures of a representative completed system in (d) flat and (e) bent geometries. (f) Environmental temperature measured and wirelessly transmitted using this device, with comparisons to data from a local weather report. (g) Dissolution of the device at three time points after immersion in water.

FIG. 61(*a*) shows the structure of a transient PCB (23 mm×23 mm) that consists of stacked layers of transient metal traces and dielectric interlayers on a flexible support. This device example harvests radio frequency (RF) energy, senses the ambient temperature and transmits the corresponding data via a wireless signal. The construction involves two separately fabricated sodium carboxymethylcellulose (Na-CMC) substrates (~50 µm in thickness) with electrical interconnects made of transient metals (2 µm in thickness), e.g. magnesium (Mg), tungsten (W), and/or zinc (Zn)[20]. A layer of polyethylene oxide) (PEO) (1 µm in thickness) between the Na-CMC films bonds them together (FIGS. 61*a* and 61*b*). Transient metal pastes (FIG. 65*a*) enable mounting of commercial-of-the-shelf (COTS) components onto contact pads located on these platforms. The pastes consist of either W or Zn microparticles (4 to 12 µm in average diameter) dispersed in a binder of PEO in an organic solvent. Evaporation of the solvent at room temperature yields a solidified metal/polymer composite that offers good conductivity (up to 40 kS/m) and also serves as an adhesive between the pins of the COTS components and the PCB (FIG. 61c). Filling via holes with a W paste electrically connects the bottom and top circuit patterns (FIG. 61d), thereby allowing signal communication and power transmission. This set of materials forms a flexible laminate (FIG. 61e) capable of serving as a foundation for complex circuit assembly.

Figure 66:
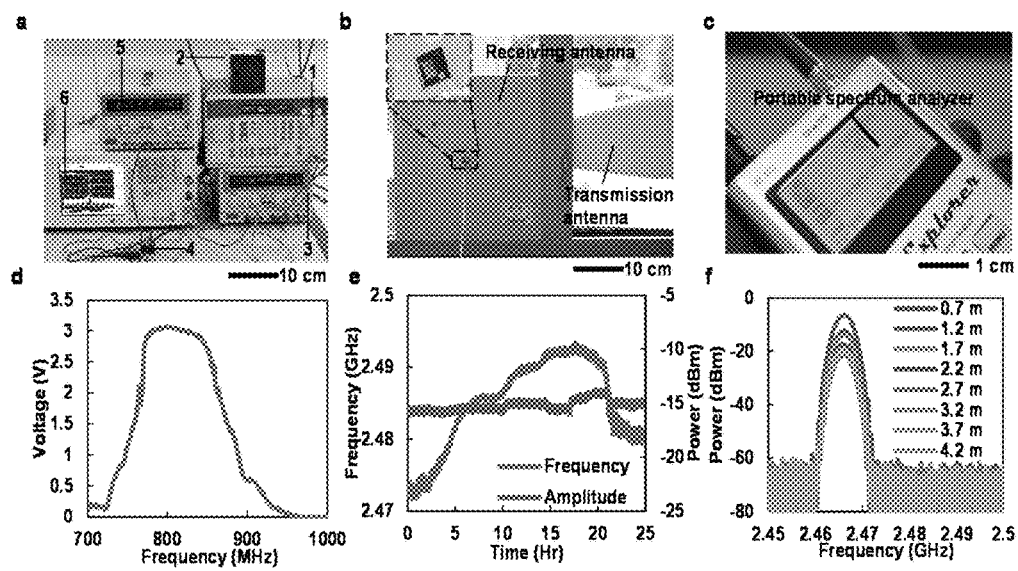
FIG. 66. (a) An experimental system that consist of 1. a RF signal generator, 2. a RF power amplifier for power transmission, 3. a power supply to support the RF power amplifier, 4. a miniaturized RF power amplifier for RF signal amplification, 5. a power supply to support the miniaturized RF amplifier, 6. a spectrum analyzer for recording RF signal. (b) Image of an extended experimental setup with a transmission antenna for power transmission, and a receiving antenna for receiving the signal from a transient PCB device attached on the other side of the window. (c) A portable spectrum analyzer for convenient mobile sensing using this transient PCB device. (d) Voltage output from the RF energy harvesting unit in the transient PCB device after voltage regulation at different matching capacitance values. (e) Signal received by a spectrum analyzer from the transient PCB device over a measurement period of 24 hours. (f) Signal loss as a function of distance between the PCB device and the receiving antenna.

The system of FIG. 61 measures variations in ambient temperature and communicates the results to an external recording system through a frequency-modulated wireless signal. Testing involves placing the system on the outer side of a window, with a receiving antenna located indoors (FIG. 66a). A transmission antenna, also indoors and located 30 cm away from the circuit provides power that allows the generation of a voltage (3V) by the wireless power harvester for operating the entire circuit (FIGS. 66b and 66d). The frequency of the wireless signal transmitted by the circuit increases from 2.47 to 2.49 GHz as the temperature varies from 35 to 18° C. The amplitude of the signal remains unchanged at ~15 dBm throughout this range (FIG. 66e). As the distance between the receiving antenna and the circuit increases from 0.7 to 4.2 m (FIG. 66f), the measurement system (FIG. 66a) records a power loss from −6.4 to −20.5 dBm. Benchtop systems can provide ultrasensitive signal detection (~160 dBm) (FIGS. 66a and 66b). Portable spectrum analyzers offer a compact alternative (FIG. 66c). The results in FIG. 61f show favorable comparison between the temperature measured by such a device and that from a local weather report, over a period of 24 hours (FIG. 61f). The entire system disintegrates completely upon immersion in water for 10 mins (FIG. 61g), leaving only the COTS chips and the transient metals, the latter of which react to yield soluble hydroxides on timescales of hours to days[20].

Figure 62:
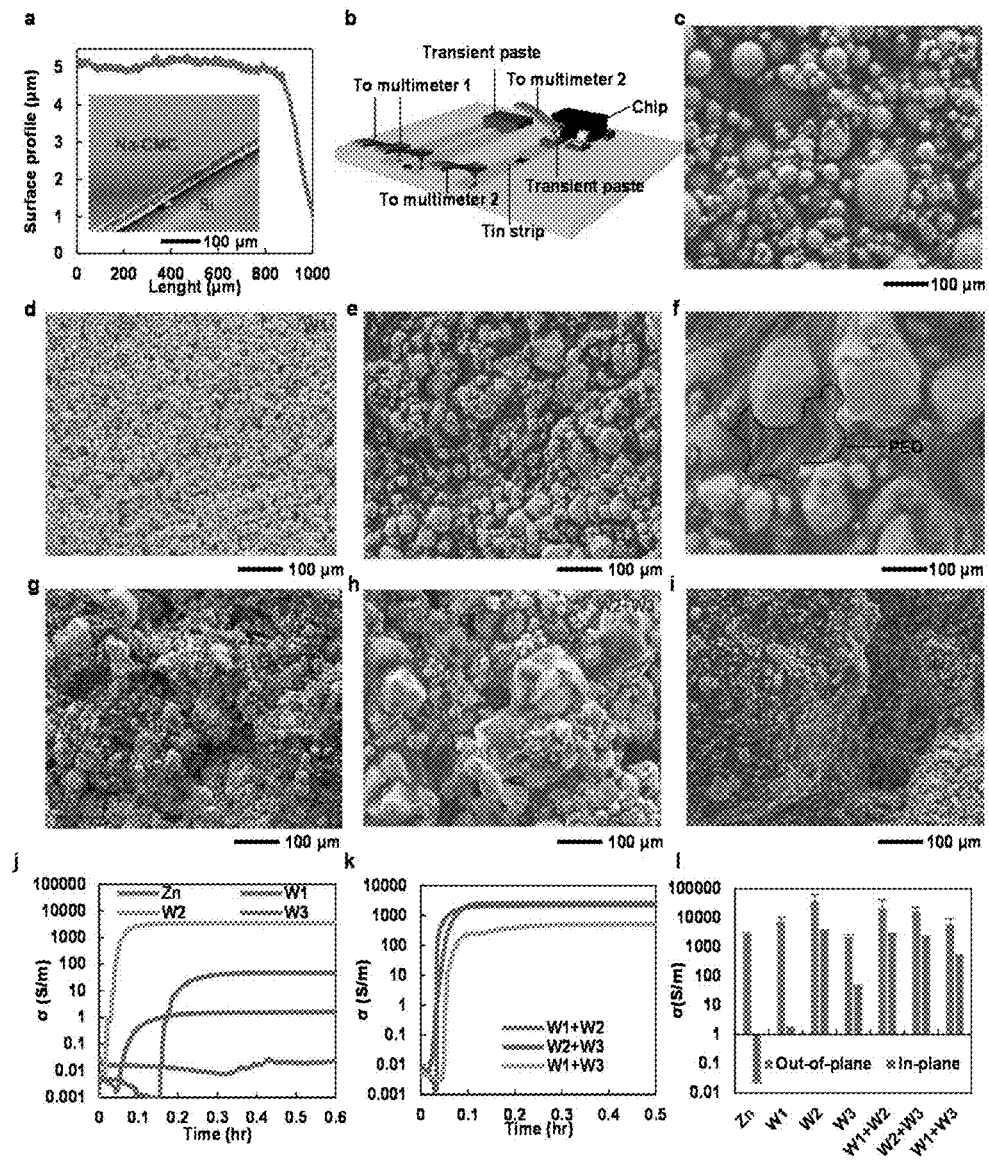
FIG. 62. Materials for constructing transient PCB devices. (a) SEM image of a Na-CMC film on a silicon wafer. The smooth surface is important for defining continuous metal traces by physical vapor deposition. (b) Schematic exploded view illustration of the test structure used to measure the in- and out-of-plane conductivity of transient metal pastes. SEM images of materials for (c) Zn pastes and for W pastes based on six kinds of W particles: (d) W1 (0.6~1 µm), (e) W2 (4~6 µm), (f) W3 (12 µm), (g) W1+W2, (h) W2+W3, and (i) W1+W3. Time dependent variation in conductivity for pastes containing (j) uniform sizes of metal particles and (k) mixtures of different particle sizes. (l) Comparison of the out-of-plane and in-plane conductivity for all seven transient pastes.
Figure 67:
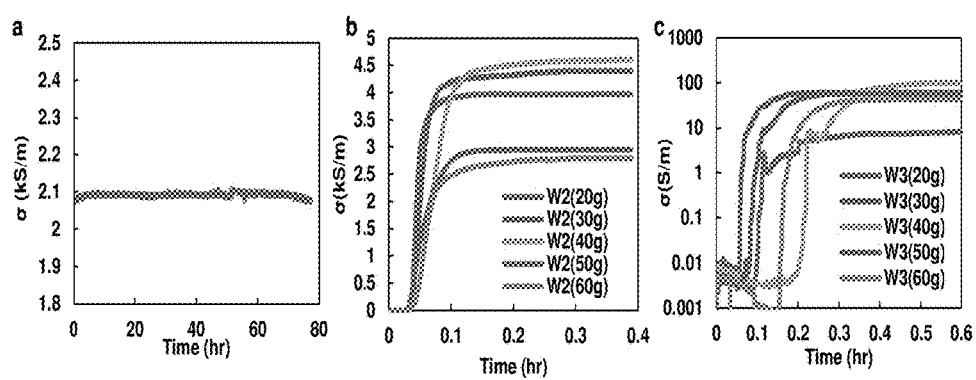
FIG. 67. (a) Time dependence of the conductivity of W paste over 3 days. Time dependence of the conductivity of transient pastes with (b) W2 and (c) W3 fillers at different weight ratios.

Both Na-CMC and PEO are water soluble[21, 22] and biocompatible[23, 24]; each has been used in food, pharmaceuticals, and cosmetics as stabilizers for emulsions[25, 26] and thickeners[27, 28]. As cast, the Na-CMC films have a surface roughness of ~8-9 nm, evaluated by profilometry (FIG. 62a). Transient pastes use fillers containing microparticles of Zn (average diameters <10 mm; FIG. 62c) or W (average diameters of 0.6-1 µm (W1), 4-6 µm (W2), 12 µm (W3), or mixtures of any two kinds of W particles at 1:2 weight ratio; FIG. 2d-2i) in PEO binders, to yield formulations that are compatible with screen printing. Three electroplated strips of tin (5 mm×20 mm each) spaced by 0.8 mm on a glass slide provide contacts for evaluating the electrical properties of these pastes (FIG. 62b). Two of the strips enable measurement of the in-plane conductivity of a fixed volume of paste (0.408 mm$^3$) applied by screen printing. Measurements of the out-of-plane conductivity use contacts between the third strips, on one side, and, on the other, the pins of COTS chips bonded on top via an applied layer of paste. All examined pastes show out-of-plane conductivities between 2000 and 40,000 S/m (FIG. 62j) when cured for 10-20 min at room temperature. The in-plane conductivities vary significantly depending on formulation and curing time. The cured Zn paste has a value of 0.024 S/m (FIG. 62I), likely limited by surface oxidation on the Zn particles and spherical shapes that result in point contacts (FIG. 62c). The W2 paste has a conductivity (3500 S/m) higher than that of W1 (1.6 S/m) and W3 (47 S/m). All W pastes exhibit conductivities that increase during the curing process (FIG. 62j), with terminal values that are stable over longer times (FIG. 67a). The conductivities, likely due to tunneling between adjacent particles[29,30], are comparable to those of commercial silver epoxies (5000 S/m)[31, 32].

The high conductivity of the W2 paste may arise, at least partly, from the polyhedral shapes of the W2 particles and the associated increased probabilities for physical contact over large areas (FIG. 62e) between particles. The low conductivities of W1 and W3 paste can be attributed to other factors. The submicron sizes of the W1 particles can increase the physical contact between particles (FIG. 62d), but with a high contact resistance[33]. The comparatively large particles in the W3 paste result in a large porosity (FIG. 62f), increased separation between particles and, thus, reduced chances for physical contacts. By mixing W particles at weight ratios (w.t.) of 1 (small particle sizes) to 2 (large particle size), all cases (W1+W2, W2+W3, W1+W3) show improved conductivities (2600, 2200, and 500 S/m, respectively), as might be expected based on considerations for pastes with W1 and W3 fillers (FIGS. 62g to 62i). Nevertheless, all mixed pastes still show lower conductivities than that of W2 only (FIG. 62k). The W2 case also exhibits good mechanical bendability, as determined by coating the paste (~40 µm) on a strip of Na-CMC (~50 µm) and conducting repeated bending tests with an automatic stage (FIGS. 3a and 10). In these tests, Na-CMC strips with conductive traces printed on their top surfaces are mechanically clamped at their ends, which present terminals for connection to a multimeter. For the radii of curvature examined here (3.5 mm), bending induces surface strains of ~1.3%. The observed changes in conductivity reversibly follow the bending, with no persistent change for over 1000 cycles.

Figure 63:
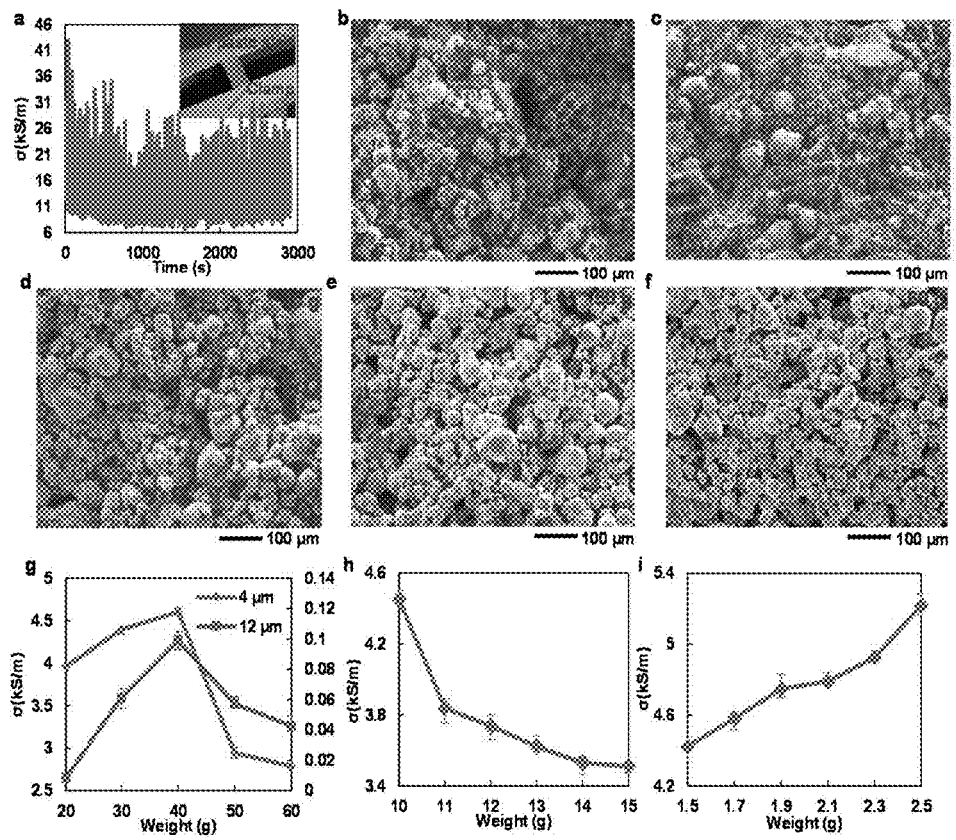
FIG. 63. Parametric studies of the conductivities of W pastes. (a) Conductivity measured at two terminals of a conductive trace of W paste screen-printed on a Na-CMC strip as a function of cycles of bending (1000 times). SEM images of W paste with (b) 20 g, (c) 30 g, (d) 40 g, (e) 50 g, and (f) 60 g filler weight. (g) Comparison of conductivities of pastes with W2 and W3 fillers at different weight with a binder solution of 1.5 g PEO and 10 g methanol. (h) Conductivity of W paste with 40 g W2, 1.5 g PEO, as a function of the weight of methanol. (i) Conductivity of W paste with 40 g W2, 10 g methanol, as a function of the weight of PEO.

Additional experiments reveal the dependence of the conductivity of the W2 paste on the weight of each component. A base solution of 1.5 g PEO and 10 g methanol mixed with W2 at weights between 20 g and 60 g (FIGS. 63b to 63f) shows that the in-plane conductivity achieves a maximum value of 4600 S/m at a filler weight of 40 g (FIG. 63g and FIG. 67b). A similar trend occurs with W3 fillers, although the conductivity is much lower (a maximum value at 100 S/m) compared to that of W2 (FIG. 63g and FIG. 67c). Investigations based on varying the weight of methanol (FIG. 63h) and PEO (FIG. 63i) with a fixed filler weight (40 g) indicate decreases in conductivity (from 4400 to 3500 S/m) with increases in methanol content (from 10 to 15 g) and opposite trends (from 4400 to 5200 S/m) for increases in PEO (from 1.5 to 2.5 g). The results suggest that all three constituent parts affect the conductivity of the W paste, due to their combined roles in determining the paths for charge transport, shrinkage in physical dimensions due to curing, and ionic conduction associated with the binders.

Figure 68:
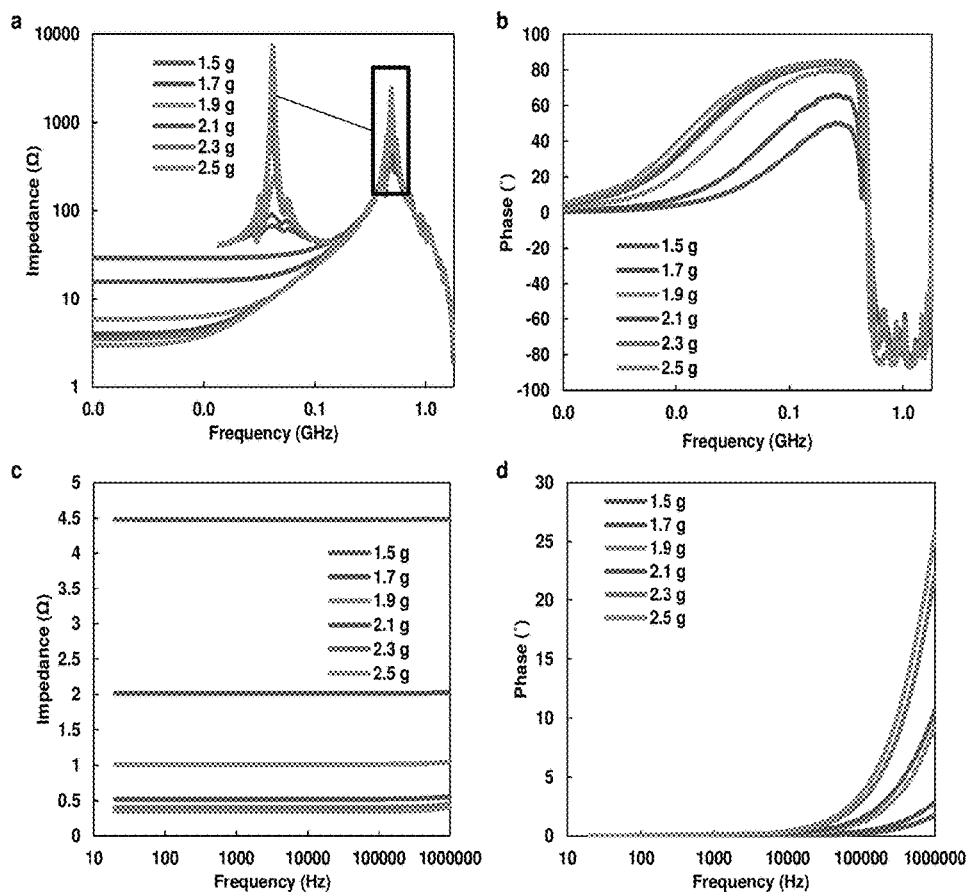
FIG. 68. (a) Magnitudes of the impedance of the W paste with different PEO content, between 1.5 g to 2.5 g, for frequencies between 1 MHz to 1.8 GHz. (b) Phases of the impedance of the same pastes. (c) Magnitudes of the impedance of the same pastes for frequencies between 20 Hz to 1 MHz. (d) Phases of the impedance of the same pastes.

Increases in efficiency of tunneling transport and physical contact area explain the increases in conductivity for pastes with W2 and W3 fillers at weights of 20 to 40 g[34] (FIGS. 63b to 63d). However, further increases of filler weight lead to reduced volume fractions of the PEO and methanol, which result in diminished dimensional shrinkage and reduced binder coverage (FIGS. 63e and 63f), likely causing a decrease in the conductivity with addition of W particles. For experiments with increasing methanol levels (from 10 to 15 g), the reduced volume ratio of W in the paste (from 9.8% to 7.6%) likely overcomes the conductivity enhancement caused by out-of-plane shrinkage of the paste after curing. The increases in conductivity with weight of PEO (FIG. 63i) may be explained by increases in the coverage of W particles with PEO and its ionic conductivity. The methanol can react with the W and surface oxide[35, 36] to form solid electrolytes with PEO[37-39], in a way that may facilitate ionic conduction between W particles. Impedance measurements of cured pastes with various PEO content (from 1.5 to 2.5 g) using an impedance analyzer (from 1 MHz to 1.8 GHz) (FIGS. 8a and 8b) and a RLC meter (from 20 Hz to 1 MHz) (FIGS. 68c and 68d) confirm that increasing the PEO contents reduces the impedance at low frequency (20 Hz to 300 MHz). Resonance peaks occur at frequencies near 500 MHz in all cases, with largest magnitude in W pastes with 2.5 g of PEO. These observations suggest significant ionic polarization effects, increasing with PEO contents. The difference in the impedance of the W paste gradually diminishes at higher frequency (680 MHz to 1.8 GHz) due to the reduced effect of ionic conduction.

Figure 64:
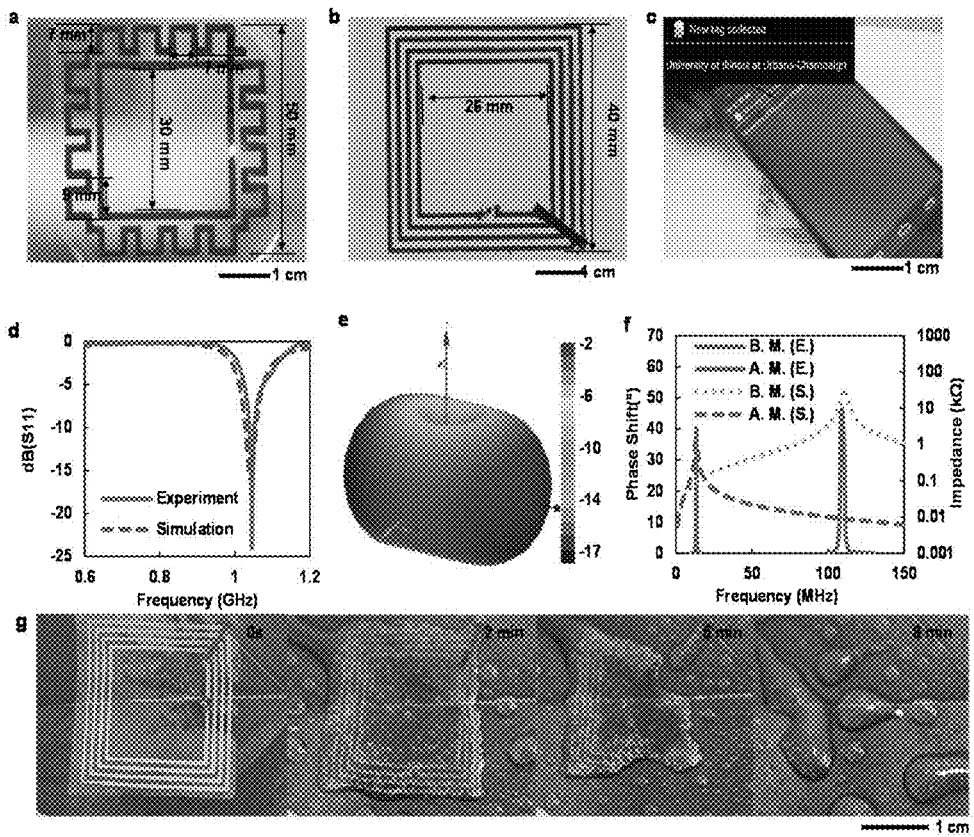
FIG. 64. Printed transient RF antenna structures and PCB devices that incorporate them. (a) A transient RF power harvesting circuit with a meander loop antenna formed using a screen-printed W paste. The blue LED attached to the antenna demonstrates wireless power harvesting with an half-wave rectification circuit. (b) A transient NFC circuit with an inductive coupling coil. (c) Image showing readout of the NCF circuit using a cellphone. (d) Comparison of S11 as a function of frequency for a meander antenna obtained through measurement with a network analyzer and simulation using a commercial software package (Ansys HFSS). (e) Far-field radiation pattern of the meander loop antenna obtained using HFSS. (f) Frequency dependence of the phase shift and impedance of an NFC coil before (B.M.) and after (A.M.) capacitance matching obtained through inductive coupling method (E.) and simulation using HFSS (S.). (g) Dissolution of an NFC coil on a leaf under a gentle spray of water.
Figure 69:
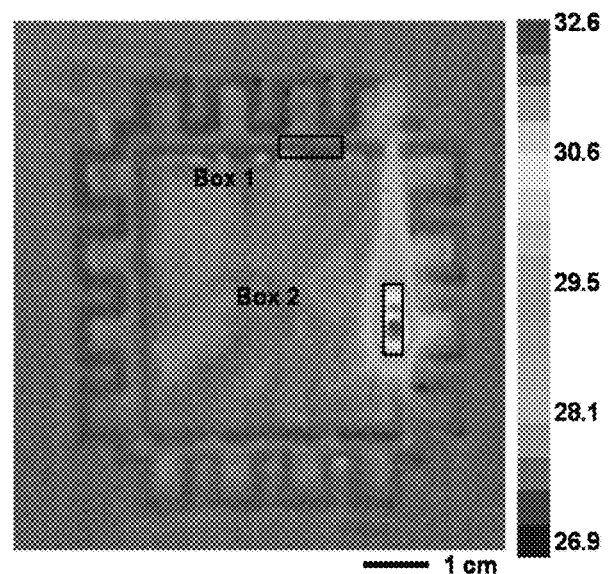
FIG. 69. Thermal IR image of a screen-printed antenna connected to an LED with a rectification circuit for RF power harvesting.
Figure 70:
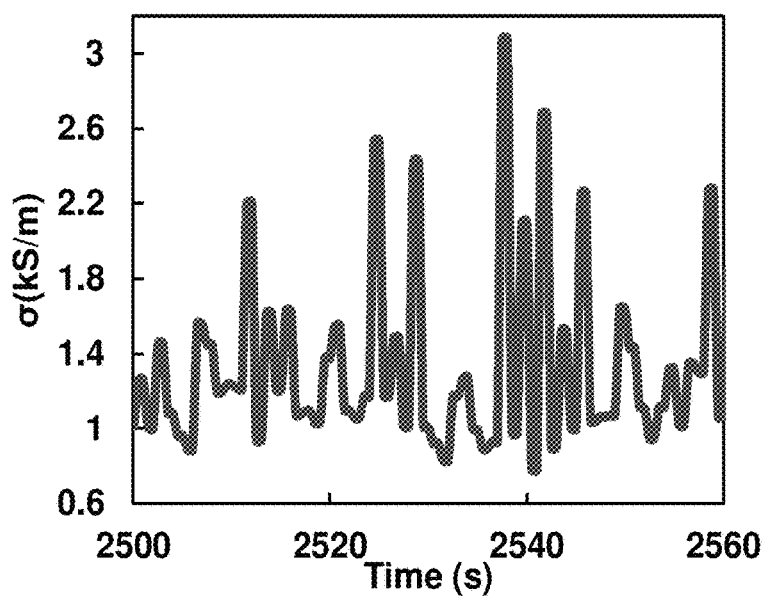
FIG. 70. Conductivity as a function of time from 2500 s to 2560 s. The data is extracted from the experimental results of a Na-CMC strip printed with transient paste as shown in FIG. 63(a).

Screen printing methods similar to those used in manufacturing of conventional PCBs are useful for fabricating transient analogs. As examples, screen-printed transient conductive pastes on Na-CMC substrates can yield circuits for wireless power harvesting and near field communication (NFC) devices. The harvester consists of a two-turn meander loop antenna with a line width of 1.5 mm and an overall size of 50×50 mm$^2$. The inner loop consists of a straight line coil with a length of 33 mm on each edge; the other loop involves meander structures formed by four evenly distributed teeth on individual edges (Detailed geometry in FIG. 64a). A load circuit formed by a half-wave rectifier and an LED connects to the antenna for demonstrations of power harvesting from an external RF source. The LED can operate at a distance of 1 m from a transmission antenna that provides a power output of 20 W at 1.03 GHz (FIG. 64a). An infrared image (FIG. 69) indicates negligible changes in temperature in the vicinity of the antenna (highlighted by box 1) and increases of 7° C. near the load circuit (box 2). Such results are consistent with power dissipation primarily in the load, as expected based on the design. The S11 parameters of the meander loop antenna obtained using a network analyzer reveal a working frequency of ~1.04 GHz, consistent with simulated results (Ansys HFSS, Canonsburg, Pa., USA). The far field radiation pattern obtained by HFSS has an expected donut shape with a maximum gain of ~−2 dB in the plane of the antenna.

FIG. 64b shows a four-turn NFC coil with a line-width of 1 mm and an overall dimension of 40 mm×40 mm. The edge of the inner turn of the coil is 26 mm, and the spacing between individual turns is 1 mm. The coil exhibits a resonance frequency at 109 MHz as determined using an impedance analyzer, consistent with HFSS (FIG. 64f). By adding a 130 pF capacitor and a NFC chip (Mifare Classic, NXP Semiconductors, Eindhoven, Netherlands) with an input capacitance of 17 pF, the resonance frequency of the coil can be tuned to 13.5 MHz, thereby matching the frequency of the NFC. Information can be retrieved with any NFC enabled Android smartphone (FIG. 64c). The entire system, except for the COTS chips, dissolves under a spray of water within a few minutes (FIG. 64g).

The results reported here establish a set of materials and methods for transient PCBs with performance comparable to that of conventional devices, but with the capability for dissolving into benign end products upon immersion in water. The transient printable conductive pastes are useful not only in this context but also separately for antennas, resonant coils and other components. Further improvements in the conductivities might be possible by increasing the shape anisotropy of the metal particles to reduce the percolation thresholds[40] or by exploiting low temperature pulsed ultraviolet sintering techniques to facilitate physical contacts between particles[41–43].

Experimental Section

The Na-CMC polymer solution is formed by dissolving Na-CMC particles (Sigma-Aldrich Co., St. Louis, Mo., USA) with a molecular weight of 250000 in water at a 2% weight ratio (w.t.) with constant agitation at 600 rpm for over 2 hours. Passing the resulting solution through a Nylon filter (PELCO® Precision Woven Mesh, 300 mesh) and then a syringe filter (Millex-HV 0.45 μm, EMD Millipore, Billerica, Mass., USA) removes undissolved particulates. PEO (polyox N-80, Dow Chemical Co., Charleston, Ill., USA) is mixed with methanol to 20% w.t. at 80° C. with constant agitation at 120 rpm for 1 hour. The resulting solution is then allowed to stand at 80° C. for 2 hours to yield a PEO anhydrous solution.

Zn (Sigma-Aldrich Co., St. Louis, Mo., USA) and W (Inframat Advanced Materials, LLC, Manchester, Conn., USA) pastes are prepared using metal microparticles with average diameters between 4 and 10 μm. Preparation begins with addition of microparticles to methanol at 80% w.t. in a glove box filled with Argon. The resulting mixture is then combined with PEO particles at 15% w.t. with respect to the methanol, followed by 120 rpm agitation for 1 hour at 80° C. and standing at the same temperature for an additional hour.

The fabrication of the transient PCB circuit starts with casting 9 mL of 2% Na-CMC solution onto a 3 inch silicon wafer, followed by curing at 50° C. for 2 hours. A polyimide film (thickness 75 μm) with laser cut openings in the desired circuit geometry attaches to the Na-CMC film to serve as a shadow mask for electron beam deposition of 2 μm of Mg. The resulting film can be manually delaminated from the wafer. Two films fabricated in this manner, each with a different circuit pattern, are then aligned and bonded together using a solution of PEO in methanol.

Figure 71:
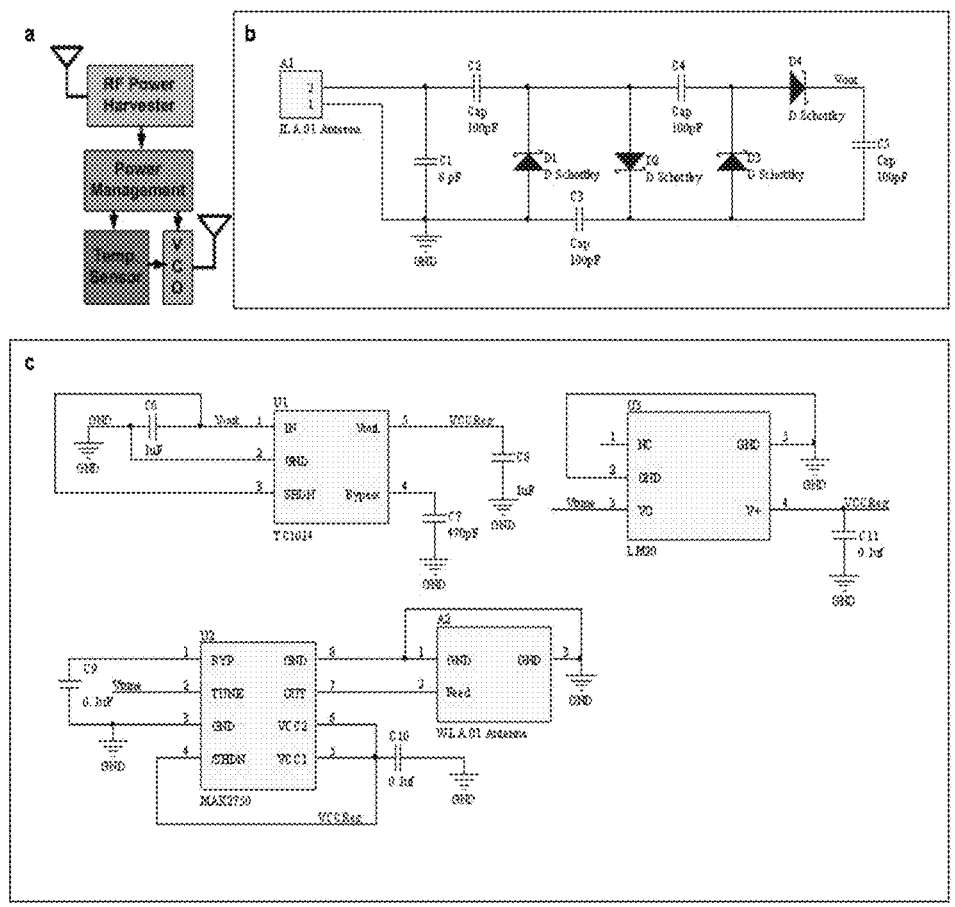
FIG. 71. (a) Schematic illustration of a transient PCB device for remote, wireless temperature sensing. (b) Circuit diagram of the bottom layer of the transient PCB device for wireless power harvesting. (c) Circuit diagram of the top layer of the transient PCB device for wireless temperature sensing.

The circuit for wireless temperature sensing (FIG. 71a) incorporates two stacked layers bound together with PEO (FIG. 61a). The bottom circuit provides signal conditioning and includes a receiving antenna (868 MHz; ILA. 02, Taoglas Limited, San Diego, Calif., USA) and a voltage quadrupler (FIG. 71b). This circuit converts RF energy received by the antenna into DC power with an amplitude four times larger than the voltage amplitude available at the antenna. The top circuit, which connects to the bottom circuit through vias filled with W paste, contains a voltage regulator (TC1014, Microchip Technology Inc., Chandler, Ariz., USA), a temperature sensor (LM20, Texas Instruments Inc., Dallas, Tex., USA), and a voltage controlled oscillator (MAX2750, Maxim Integrated, San Jose, Calif., USA) (FIG. 71c). The voltage control oscillator sends a continuous frequency-modulated RF signal determined by $V_{tune}$, the voltage output from the temperature sensor, to an external signal analyzer through a 2.3~2.5 GHz antenna (WLA. 01, Taoglas Limited, San Diego, Calif., USA).

Figure 72:
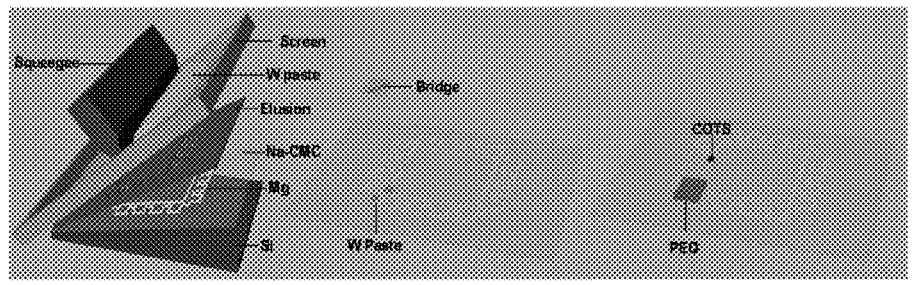
FIG. 72. Schematic illustration of the process for screen-printing a meander loop antenna using a transient paste.

Similar procedures enable fabrication of the meander loop antenna and the NFC coil (FIG. 72). Taking the loop antenna as example, a pattern of Mg (1 μm in thickness) is formed on a Na-CMC film on a silicon wafer by electron beam evaporation. Next, a W paste (100 μm in thickness) is printed on top of this pattern using a 230 mesh nylon screen. A similarly patterned interconnecting bridge of W paste connects the inner terminal with the outer terminal of the antenna. The gap between the bridge and the antenna is filled with PEO solution, to form a dielectric layer (20 μm in thickness) after curing. Peeling the resulting film from the Si wafer allows mounting of electrical components with W paste to complete the fabrication.

Figure 65:
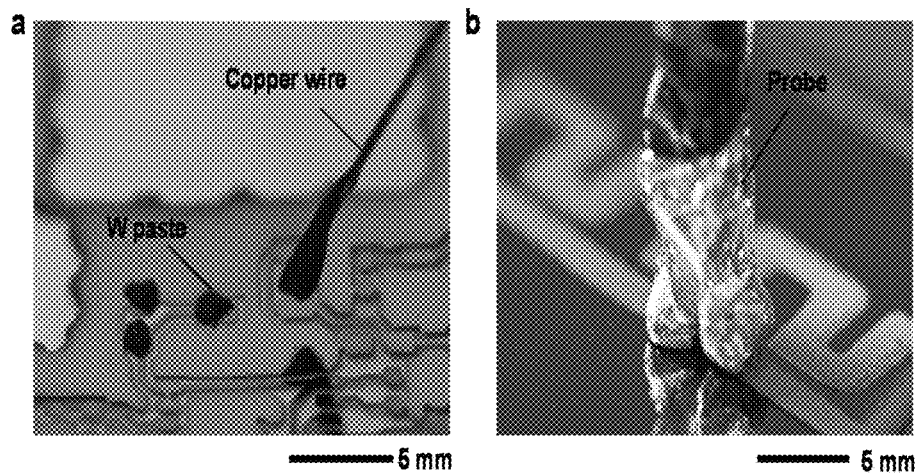
FIG. 65. (a) Image showing application of W paste to bonding pads on a transient PCB. The W paste is applied to the designated region using the tip of a copper wire. (b) Measurement of the S parameters of meander coils formed using W paste, with a home-made two-point probe connected to a network analyzer.

The experimental setup for the wireless temperature sensing circuit appears in FIG. 6. The system includes a HP 8648A RF signal generator (Agilent Technologies, Santa Clara, Calif., USA) that provides a −10 dBm RF signal at 868 MHz to an RF power amplifier (Module 1119, Empower RF Systems, Inglewood, Calif., USA) with a 20 W output. This power is transmitted through a wideband antenna (Modal 204411, Wilson Electronics, St. George, Utah, USA) with a working frequency from 700 MHz to 2.7 GHz and a gain of 10.5 dBi: To receive the RF signal from the wireless temperature sensing circuit, an antenna (PA2419, ARC Wireless, Deland, Fla., USA) with a working frequency from 2.3 to 2.5 GHz is used. The received signal is amplified by a RF amplifier (MGA-3-27, RF Bay, Inc., Rockville, Md., USA) and then displayed and recorded using a N9000A spectrum analyzer (Agilent Technologies, Santa Clara, Calif., USA). Wireless powering of the LED with a meander loop antenna is demonstrated using the same experimental setup. The scattering parameters of the meander loop antenna are measured using an E5062A network analyzer (Agilent Technologies, Santa Clara, Calif., USA) with home-made two point probe in contact with the antenna output ports (FIG. 65b). The resonance frequency of the NFC RFID coil is measured using a setup introduced previously[44, 45]. Briefly, the transient coil is evaluated using a HP 4291A impedance analyzer (Agilent Technologies, Santa Clara, Calif., USA) that connects to a one-turn hand-wound copper primary coil placed 2 mm away from the transient coil. The impedance phase of the primary coil measured by the analyzer exhibits a phase peak/dip at a frequency close to the resonance frequency of the transient coil.

References

[1] F. T. Wallenberger, P. A. Bingham, A. Longobardo, in *Fiberglass and Glass Technology*, Springer U.S. Pat. No. 2,010,175.
[2] B. H. Robinson, Science of The Total Environment 2009, 408, 183.
[3] L. Luther, Managing Electronic Waste: Issues with Exporting E-Waste, DIANE Publishing Company, 2010.
[4] A. Leung, Z. W. Cai, M. H. Wong, Journal of Material Cycles and Waste Management 2006, 8, 21.
[5] R. Widmer, H. Oswald-Krapf, D. Sinha-Khetriwal, M. Schnellmann, H. Boni, Environmental Impact Assessment Review 2005, 25, 436.
[6] K. Grant, F. C. Goldizen, P. D. Sly, M.-N. Brune, M. Neira, M. van den Berg, R. E. Norman, The Lancet Global Health 2013, 1, e350.
[7] A. Terazono, S. Murakami, N. Abe, B. Inanc, Y. Moriguchi, S.-i. Sakai, M. Kojima, A. Yoshida, J. Li, J. Yang, M. H. Wong, A. Jain, I.-S. Kim, G. L. Peralta, C.-C. Lin, T. Mungcharoen, E. Williams, Journal of Material Cycles and Waste Management 2006, 8, 1.
[8] D. H. P. Kang, M. Chen, 0. A. Ogunseitan, Environmental Science & Technology 2013, 47, 5495.
[9] D. Xiang, P. Mou, J. Wang, G. Duan, H. Zhang, Int J Adv Manuf Technol 2007, 34, 1030.
[10] J. Li, H. Lu, J. Guo, Z. Xu, Y. Zhou, Environmental Science & Technology 2007, 41, 1995.
[11] H.-Y. Kang, J. M. Schoenung, Resources, Conservation and Recycling 2005, 45, 368.
[12] W. J. Deng, J. S. Zheng, X. H. Bi, J. M. Fu, M. H. Wong, Environment International 2007, 33, 1063.
[13] X. Xu, H. Yang, A. Chen, Y. Zhou, K. Wu, J. Liu, Y. Zhang, X. Huo, Reproductive Toxicology 2012, 33, 94.
[14] K. Huang, J. Guo, Z. Xu, Journal of Hazardous Materials 2009, 164, 399.
[15] S.-W. Hwang, H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, Science 2012, 337, 1640.
[16] S.-W. Hwang, D.-H. Kim, H. Tao, T.-i. Kim, S. Kim, K. J. Yu, B. Panilaitis, J.-W. Jeong, J.-K. Song, F. G. Omenetto, J. A. Rogers, Advanced Functional Materials 2013, 23, 4087.
[17] C. Dagdeviren, S.-W. Hwang, Y. Su, S. Kim, H. Cheng, 0. Gur, R. Haney, F. G. Omenetto, Y. Huang, J. A. Rogers, Small 2013, 9, 3398.
[18] L. Yin, X. Huang, H. Xu, Y. Zhang, J. Lam, J. Cheng, J. A. Rogers, Advanced Materials, n/a.
[19] S.-W. Hwang, X. Huang, J.-H. Seo, J.-K. Song, S. Kim, S. Hage-Ali, H.-J. Chung, H. Tao, F. G. Omenetto, Z. Ma, J. A. Rogers, Advanced Materials 2013, 25, 3526.
[20] L. Yin, H. Cheng, S. Mao, R. Haasch, Y. Liu, X. Xie, S.-W. Hwang, H. Jain, S.-K. Kang, Y. Su, R. Li, Y. Huang, J. A. Rogers, Advanced Functional Materials 2014, 24, 644.
[21] H. A. Shelanski, A. M. Clark, Journal of Food Science 1948, 13, 29.
[22] J. Israelachvili, Proceedings of the National Academy of Sciences 1997, 94, 8378.
[23] A. Hebeish, M. Hashem, M. M. A. El-Hady, S. Sharaf, Carbohydrate Polymers 2013, 92, 407.
[24] C. Weber, R. Hoogenboom, U. S. Schubert, Progress in Polymer Science 2012, 37, 686.
[25] M. Adeyeye, A. Jain, M. M. Ghorab, W. Reilly, AAPS PharmSciTech 2002, 3, 16.
[26] N. Diftis, V. Kiosseoglou, Food Chemistry 2003, 81, 1.
[27] K. Pal, A. K. Banthia, D. K. Majumdar, Biomedical Materials 2006, 1, 85.
[28] S. Bayarri, L. Gonzalez-Tomas, E. Costell, Food Hydrocolloids 2009, 23, 441.
[29] S. Kirkpatrick, Reviews of Modern Physics 1973, 45, 574.
[30] S. M. Aharoni, Journal of Applied Physics 1972, 43, 2463.
[31] MG Chemicals, 8331 Silver Conductive Epoxy Adhesive, www.mgchemicals.com/products/adhesives/electrically-conductive/silver-conductive-epoxy-8331/.
[32] Structure Probe Inc., SPI COnductive Silver Epoxy, www.2spi.com/catalog/spec_prep/inform.html.
[33] H. H. Lee, K. S. Chou, Z. W. Shih, International Journal of Adhesion and Adhesives 2005, 25, 437.
[34] E. Sancaktar, L. Bai, Polymers 2011, 3, 427.
[35] R. S. Mann, S. K. Jain, M. K. Dosi, Journal of Applied Chemistry and Biotechnology 1977, 27, 198.
[36] K.-W. Park, K.-S. Ahn, Y.-C. Nah, J.-H. Choi, Y.-E. Sung, The Journal of Physical Chemistry B 2003, 107, 4352.
[37] W. Preechatiwong, J. M. Schultz, Polymer 1996, 37, 5109.
[38] W. Wieczorek, D. Raducha, A. Zalewska, J. R. Stevens, The Journal of Physical Chemistry B 1998, 102, 8725.
[39] X. Li, Y. Zhao, L. Cheng, M. Yan, X. Zheng, Z. Gao, Z. Jiang, J Solid State Electrochem 2005, 9, 609.
[40] A. Aharony, D. Stauffer, *Introduction To Percolation Theory*, Taylor & Francis, 2003.
[41] R. Dharmadasa, I. M. Dharmadasa, T. Druffel, Advanced Engineering Materials 2014, n/a.
[42] D. J. Lee, S. H. Park, S. Jang, H. S. Kim, J. H. Oh, Y. W. Song, Journal of Micromechanics and Microengineering 2011, 21, 125023.
[43] H.-S. Kim, S. Dhage, D.-E. Shim, H. T. Hahn, Appl. Phys. A 2009, 97, 791.

[44] X. Huang, Y. Liu, K. Chen, W.-J. Shin, C.-J. Lu, G.-W. Kong, D. Patnaik, S.-H. Lee, J. F. Cortes, J. A. Rogers, Small 2014, n/a.
[45] X. Huang, Y. Liu, H. Cheng, W.-J. Shin, J. A. Fan, Z. Liu, C.-J. Lu, G.-W. Kong, K. Chen, D. Patnaik, S.-H. Lee, S. Hage-Ali, Y. Huang, J. A. Rogers, Advanced Functional Materials 2014, 24, 3846.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

U.S. Provisional Application No. 61/811,603, filed Apr. 12, 2013, is hereby incorporated by reference in its entirety.

The following references relate generally to flexible and/or stretchable semiconductor materials and devices and are each hereby incorporated by reference in their entireties: U.S. patent application Ser. No. 12/778,588, filed on May 12, 2010, PCT International Application No. PCT/US05/19354, filed Jun. 2, 2005 and published under No. WO2005/122285 on Dec. 22, 2005, U.S. Provisional Patent Application No. 61/313,397, filed Mar. 12, 2010, U.S. patent application Ser. No. 11/851,182, filed Sep. 6, 2007 and published under No. 2008/0157235 on Jul. 3, 2008, and PCT International Application No. PCT/US07/77759, filed Sep. 6, 2007 and published under No. WO2008/030960 on Mar. 13, 2008.

The following references relate generally to bioresorbable substrates and methods of making bioresorbable substrates and are each hereby incorporated by reference in its entirety: PCT Patent Application PCT/US03/19968 filed Jun. 24, 2003, PCT Patent Application PCT/US04/000255 filed Jan. 7, 2004, PCT Patent Application PCT/US04/11199 filed Apr. 12, 2004, PCT Patent Application PCT/US05/20844 filed Jun. 13, 2005, and PCT Patent Application PCT/US06/029826 filed Jul. 28, 2006.

The following references relate generally to transient electronic devices and methods and are each hereby incorporated by reference in its entirety: U.S. provisional application No. 61/565,907, filed Dec. 1, 2011, U.S. provisional application No. 61/636,510, filed Apr. 20, 2012, U.S. nonprovisional application Ser. No. 13/624,096, filed Sep. 21, 2012 and PCT International application no. PCT/US2012/056538, filed Sep. 21, 2012.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods and method steps set forth in the present description. As will be obvious to one of skill in the art, methods and devices useful for the present embodiments can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

The following references relate generally to fabrication methods, structures and systems for making electronic devices, and are hereby incorporated by reference to the extent not inconsistent with the disclosure in this application.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

| Application No. | Filing Date | Publication No. | Publication Date | Patent No. | Issue Date |
|---|---|---|---|---|---|
| 11/001,689 | Dec. 1, 2004 | 2006/0286488 | Dec. 21, 2006 | 7,704,684 | Apr. 27, 2010 |
| 11/115,954 | Apr. 27, 2005 | 2005/0238967 | Oct. 27, 2005 | 7,195,733 | Mar. 27, 2007 |

| Application No. | Filing Date | Publication No. | Publication Date | Patent No. | Issue Date |
|---|---|---|---|---|---|
| 11/145,574 | Jun. 2, 2005 | 2009/0294803 | Dec. 3, 2009 | 7,622,367 | Nov. 24, 2009 |
| 11/145,542 | Jun. 2, 2005 | 2006/0038182 | Feb. 23, 2006 | 7,557,367 | Jul. 7, 2009 |
| 11/421,654 | Jun. 1, 2006 | 2007/0032089 | Feb. 8, 2007 | 7,799,699 | Sep. 21, 2010 |
| 11/423,287 | Jun. 9, 2006 | 2006/0286785 | Dec. 21, 2006 | 7,521,292 | Apr. 21, 2009 |
| 11/423,192 | Jun. 9, 2006 | 2009/0199960 | Aug. 13, 2009 | 7,943,491 | May 17, 2011 |
| 11/465,317 | Aug. 17, 2006 | — | — | — | — |
| 11/675,659 | Feb. 16, 2007 | 2008/0055581 | Mar. 6, 2008 | — | — |
| 11/782,799 | Jul. 25, 2007 | 2008/0212102 | Sep. 4, 2008 | 7,705,280 | Apr. 27, 2010 |
| 11/851,182 | Sep. 6, 2007 | 2008/0157235 | Jul. 3, 2008 | 8,217,381 | Jul. 10, 2012 |
| 11/585,788 | Sep. 20, 2007 | 2008/0108171 | May 8, 2008 | 7,932,123 | Apr. 26, 2011 |
| 11/981,380 | Oct. 31, 2007 | 2010/0283069 | Nov. 11, 2010 | 7,972,875 | Jul. 5, 2011 |
| 12/372,605 | Feb. 17, 2009 | — | — | — | — |
| 12/398,811 | Mar. 5, 2009 | 2010/0002402 | Jan. 7, 2010 | 8,552,299 | Oct. 8, 2013 |
| 12/405,475 | Mar. 17, 2009 | 2010/0059863 | Mar. 11, 2010 | 8,198,621 | Jun. 12, 2012 |
| 12/418,071 | Apr. 3, 2009 | 2010/0052112 | Mar. 4, 2010 | 8,470,701 | Jun. 25, 2013 |
| 12/522,582 | Jul. 9, 2009 | — | — | — | — |
| 12/564,566 | Sep. 22, 2009 | 2010/0072577 | Mar. 25, 2010 | 7,982,296 | Jul. 19, 2011 |
| 12/669,287 | Jan. 15, 2010 | 2011/0187798 | Aug. 4, 2011 | 9,061,494 | Jun. 23, 2015 |
| 12/778,588 | May 12, 2010 | 2010/0317132 | Dec. 16, 2010 | 8,865,489 | Oct. 21, 2014 |
| 12/844,492 | Jul. 27, 2010 | 2010/0289124 | Nov. 18, 2010 | 8,039,847 | Oct. 18, 2011 |
| 12/892,001 | Sep. 28, 2010 | 2011/0230747 | Sep. 22, 2011 | 8,666,471 | Mar. 4, 2014 |
| 12/916,934 | Nov. 1, 2010 | 2012/0105528 | May 3, 2012 | 8,562,095 | Oct. 22, 2013 |
| 12/947,120 | Nov. 16, 2010 | 2011/0170225 | Jul. 14, 2011 | 9,057,994 | Jun. 16, 2015 |
| 12/996,924 | Dec. 8, 2010 | 2011/0147715 | Jun. 23, 2011 | 8,946,683 | Feb. 3, 2015 |
| 12/968,637 | Dec. 15, 2010 | 2012/0157804 | Jun. 21, 2012 | — | — |
| 13/046,191 | Mar. 11, 2011 | 2012/0165759 | Jun. 28, 2012 | — | — |
| 13/071,027 | Mar. 24, 2011 | 2011/0171813 | Jul. 14, 2011 | — | — |
| 13/095,502 | Apr. 27, 2011 | — | — | — | — |
| 13/100,774 | May 4, 2011 | 2011/0266561 | Nov. 3, 2011 | 8,722,458 | May 13, 2014 |
| 13/113,504 | May 23, 2011 | 2011/0220890 | Sep. 15, 2011 | 8,440,546 | May 14, 2013 |
| 13/120,486 | Aug. 4, 2011 | 2011/0277813 | Nov. 17, 2011 | 8,679,888 | Mar. 25, 2014 |
| 13/228,041 | Sep. 8, 2011 | 2011/0316120 | Dec. 29, 2011 | — | — |
| 13/270,954 | Oct. 11, 2011 | 2012/0083099 | Apr. 5, 2012 | 8,394,706 | Mar. 12, 2013 |
| 13/349,336 | Jan. 12, 2012 | 2012/0261551 | Oct. 18, 2012 | — | — |
| 13/441,618 | Apr. 6, 2012 | 2013/0100618 | Apr. 25, 2013 | 8,754,396 | Jun. 17, 2014 |
| 13/441,598 | Apr. 6, 2012 | 2012/0327608 | Dec. 27, 2012 | 8,729,524 | May 20, 2014 |
| 13/472,165 | May 15, 2012 | 2012/0320581 | Dec. 20, 2012 | — | — |
| 13/486,726 | Jun. 1, 2012 | 2013/0072775 | Mar. 21, 2013 | 8,934,965 | Jan. 13, 2015 |
| 13/492,636 | Jun. 8, 2012 | 2013/0041235 | Feb. 14, 2013 | — | — |
| 13/549,291 | Jul. 13, 2012 | 2013/0036928 | Feb. 14, 2013 | — | — |
| 13/596,343 | Aug. 28, 2012 | 2012/0321785 | Dec. 20, 2012 | 8,367,035 | Feb. 5, 2013 |
| 13/624,096 | Sep. 21, 2012 | 2013/0140649 | Jun. 6, 2013 | — | — |
| 13/801,868 | Mar. 13, 2013 | 2013/0320503 | Dec. 5, 2013 | 8,664,699 | Mar. 4, 2014 |
| 13/835,284 | Mar. 15, 2013 | 2014/0220422 | Aug. 7, 2014 | — | — |
| 13/853,770 | Mar. 29, 2013 | 2013/0333094 | Dec. 19, 2013 | — | — |
| 13/974,963 | Aug. 23, 2013 | 2014/0140020 | May 22, 2014 | 8,905,772 | Dec. 9, 2014 |
| 14/033,765 | Sep. 23, 2013 | 2014/0092158 | Apr. 3, 2014 | — | — |
| 14/140,299 | Dec. 24, 2013 | 2014/0163390 | Jun. 12, 2014 | — | — |
| 14/155,010 | Jan. 14, 2014 | 2014/0191236 | Jul. 10, 2014 | — | — |
| 14/173,525 | Feb. 5, 2014 | 2014/0216524 | Aug. 7, 2014 | — | — |
| 14/209,481 | Mar. 13, 2014 | 2014/0373898 | Dec. 25, 2014 | — | — |
| 14/220,910 | Mar. 20, 2014 | 2014/0374872 | Dec. 25, 2014 | — | — |
| 14/220,923 | Mar. 20, 2014 | 2015/0001462 | Jan. 1, 2015 | — | — |
| 14/246,962 | Apr. 7, 2014 | 2014/0361409 | Dec. 11, 2014 | — | — |
| 14/250,671 | Apr. 11, 2014 | 2014/0305900 | Oct. 16, 2014 | — | — |
| 14/251,259 | Apr. 11, 2014 | 2014/0323968 | Oct. 30, 2014 | — | — |
| 12/778,588 | Sep. 5, 2014 | 2015/0132873 | May 14, 2015 | — | — |
| 14/504,736 | Oct. 2, 2014 | 2015/0141767 | May 21, 2015 | — | — |
| 14/521,319 | Oct. 22, 2014 | — | — | — | — |
| 14/532,687 | Nov. 4, 2014 | 2015/0080695 | Mar. 19, 2015 | — | — |
| 14/599,290 | Jan. 16, 2015 | — | — | — | — |
| 12/669,287 | Apr. 14, 2015 | — | — | — | — |
| 12/398,811 | May 7, 2015 | — | — | — | — |
| PCT/US2014/015825 | Feb. 19, 2014 | WO2014/126927 | Aug. 21, 2014 | — | — |

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood, that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

We claim:

1. A transient printed circuit board (PCB) comprising:
a substrate;
a plurality of electrical interconnects supported by said substrate; wherein at least a portion of said plurality of electrical interconnects comprises at least one pad for receiving a lead from an electronic component;
wherein at least one of said substrate and said plurality of electrical interconnects comprises a selectively transformable material; and
an actuator responsive to a user initiated external trigger signal, wherein upon a receiver of said transient PCB receiving said external trigger signal said actuator, which is operationally connected to said receiver, directly or indirectly initiates at least partial transformation of said selectively transformable material, thereby providing a programmable transformation of the transient PCB in response to said external trigger signal, wherein said programmable transformation provides a change in function of the transient PCB from a first condition to a second condition; and
wherein said user initiated external trigger signal is a user initiated application of an electric field provided to said transient PCB, a user initiated application of electromagnetic radiation provided to said transient PCB, a user initiated mechanical impact provided to said transient PCB, a user initiated flow of heat provided to said transient PCB, a user initiated flow of heat from said transient PCB or a user initiated application of an RF electric field provided to said transient PCB.

2. The transient PCB of claim 1, wherein said selectively transformable material undergoes a transformation upon application of an internal or external stimulus.

3. The transient PCB of claim 2, wherein said transformation is dissolution or biodegradation to benign end products.

4. The transient PCB of claim 2, wherein said transformation is a change from a first functionally operable state to a second functionally inoperable state.

5. The transient PCB of claim 2, wherein said selectively transformable material undergoes said transformation at a preselected rate.

6. The transient PCB of claim 1, wherein said selectively transformable material is stable in the absence of an internal or external stimulus for a period of at least 5 days.

7. The transient PCB of claim 1, wherein upon exposure to said internal or external stimulus said selectively transformable material is completely transformed within a period of 5 days or less.

8. The transient PCB of claim 1 further comprising an adhesive layer joining said substrate of said transient PCB with a substrate of a second transient PCB to form a double-sided transient PCB.

9. The transient PCB of claim 8 further comprising at least one via structure for electrically connecting the electrical interconnects of said transient PCB with electrical interconnects of said second transient PCB.

10. The transient PCB of claim 9, wherein said via structure is filled with a conductive paste.

11. The transient PCB of claim 1 further comprising a second transient PCB laminated to said transient PCB to form a double-sided transient PCB.

12. The transient PCB of claim 11 further comprising at least one via structure for electrically connecting the electrical interconnects of said transient PCB with electrical interconnects of said second transient PCB.

13. The transient PCB of claim 1 further comprising a plurality of transient PCBs laminated together in a multilayer stacked geometry.

14. The transient PCB of claim 1, wherein the transient PCB has an average thickness selected from the range of 1 cm to 5 µm.

15. The transient PCB of claim 1, wherein the transient PCB has an average modulus selected from the range of 3 KPa to 10 GPa.

16. The transient PCB of claim 1, wherein the transient PCB has a net bending stiffness selected from the range of 0.1 nN m to 1 nN m.

17. The transient PCB of claim 1, wherein the electronic component is selected from the group consisting of a resistor, a capacitor, a diode, an inductor, a sensor, an actuator, an antenna, a coil or an electromagnetic shielding layer.

18. The transient PCB of claim 1, wherein the electronic component is an energy harvesting structure, a near-field communication (NFC) device, a radio-frequency identification (RFID) device, an energy storage device, a chemical/biological sensor, a photosensitive element or a combination thereof.

19. The transient PCB of claim 1, wherein the electronic component is a commercial off the shelf (COTS) component.

20. The transient PCB of claim 1, wherein the electronic component is formed by screen printing a conductive paste.

21. The transient PCB of claim 1, wherein the electronic component comprises a selectively transformable material.

22. The device of claim 1 in one-way or two-way communication with a transmitter, wherein said transmitter provides said user initiated external trigger signal to said receiver of said transient PCB operationally connected to said actuator.

23. The transient PCB of claim 1, wherein at least a portion of said plurality of electrical interconnects is formed by a conductive paste.

24. The transient PCB of claim 23, wherein said conductive paste is a composite material.

25. The transient PCB of claim 24, wherein said composite material comprises a water-soluble transient polymer and transient metal particles.

26. The transient PCB of claim 25, wherein said transient metal particles have an average diameter selected from 10 nm to 100 μm.

27. The transient PCB of claim 25, wherein said transient metal particles have a bimodal distribution of particle sizes.

28. The transient PCB of claim 25, wherein said transient metal particles are tungsten particles or zinc particles.

29. The transient BCP of claim 25, wherein said transient metal particles are substantially spherical, substantially polyhedral or a combination thereof.

30. The transient PCB of claim 24, wherein said composite material comprises a water-soluble transient polymer and transient metal particles in a ratio between 1:1000 and 1000:1.

31. The transient PCB of claim 23, wherein said conductive paste comprises a conductivity between $5 \times 10^7$ S/m and 0.1 S/m.

32. The transient PCB of claim 23, wherein said conductive paste has a net bending stiffness of 0.1 nN m to 1 N m.

33. The transient PCB of claim 1, wherein at least a portion of said plurality of electrical interconnects is formed by screen printing a conductive paste.

34. The transient PCB of claim 1, wherein said substrate is a flexible substrate or a stretchable substrate.

35. The transient PCB of claim 1, wherein said substrate has a net bending stiffness of 0.1 nN m to 1 N m.

36. The transient PCB of claim 1, wherein said substrate is an insulator.

37. The transient PCB of claim 1, wherein said substrate comprises sodium carboxymethyl cellulose (Na-CMC), poly (ethylene) oxide (PEO), polylactic acid (PLA), polyglycolic acid (PGA), polylactic-co-glycolic acid (PLGA) or combinations thereof.

38. The transient PCB of claim 1, wherein said substrate has an average thickness selected from a range of 1 cm to 5 μm.

39. The transient PCB of claim 1, wherein said substrate is biodegradable, water soluble, ecocompatible or a combination thereof.

40. The transient PCB of claim 1, wherein said electrical interconnects comprise magnesium, tungsten, zinc, iron, molybdenum or an alloy thereof.

41. The transient PCB of claim 1, wherein said plurality of electrical interconnects comprises one or more solidified metal thin film structures.

42. The transient PCB of claim 1, wherein said plurality of electrical interconnects is formed by screen printing.

43. The transient PCB of claim 1, wherein said plurality of electrical interconnects is formed by metallization and screen printing.

44. The transient PCB of claim 1 further comprising one or more encapsulating layers at least partially encapsulating one or more of said electrical interconnects.

45. The transient PCB of claim 44, wherein said encapsulating material comprises a material selected from the group consisting of MgO, silk, collagen, gelatin, PLGA, polyvinylalcohol (PVA), PLA, Si, $SiO_2$, polyanhydrides (polyesters), polyhydroxyalkanates (PHAs) and polyphosphates.

46. The transient PCB of claim 1, wherein each of said pads of said electrical interconnects has an average area of 10 μm² to 5 mm².

47. A transient electronic device comprising:
a transient printed circuit board (PCB) comprising:
  a substrate;
  a plurality of electrical interconnects supported by said substrate; wherein at least a portion of said plurality of electrical interconnects comprises at least one pad;
  one or more electronic device components electrically connected to said at least one pad;
  wherein at least one of said substrate, said plurality of electrical interconnects and said one or more electronic device components comprises a selectively transformable material; and
  an actuator responsive to a user initiated external trigger signal, wherein upon a receiver of said transient PCB receiving said external trigger signal said actuator, which is operationally connected to said receiver, directly or indirectly initiates at least partial transformation of said selectively transformable material, thereby providing a programmable transformation of the transient PCB in response to said external trigger signal, wherein said programmable transformation provides a change in function of the transient PCB from a first condition to a second condition; and
  wherein said user initiated external trigger signal is a user initiated application of an electric field provided to said transient PCB, a user initiated application of electromagnetic radiation provided to said transient PCB, a user initiated mechanical impact provided to said transient PCB, a user initiated flow of heat provided to said transient PCB, a user initiated flow of heat from said transient PCB or a user initiated application of an RF electric field provided to said transient PCB.

48. The transient electronic device of claim 47, wherein said one or more electronic device components is selected from the group consisting of a resistor, a capacitor, a diode, an inductor, a sensor, an actuator, an antenna, a coil or an electromagnetic shielding layer.

49. A method of using a transient PCB, said method comprising the steps of:
providing the transient PCB comprising:
a substrate; and
a plurality of electrical interconnects supported by said substrate; wherein at least a portion of said plurality of electrical interconnects comprises at least one pad for receiving a lead from an electronic component;
wherein at least one of said substrate and said plurality of electrical interconnects comprises a selectively transformable material; and
an actuator responsive to a user initiated external trigger signal, wherein upon a receiver of said transient PCB receiving said external trigger signal said actuator, which is operationally connected to said receiver, directly or indirectly initiates at least partial transformation of said selectively transformable material, thereby providing a programmable transformation of the transient PCB in response to said external trigger signal, wherein said programmable transformation provides a change in function of the transient PCB from a first condition to a second condition; and wherein said user initiated external trigger signal is a user initiated application of an electric field provided to said transient PCB, a user initiated application of electromagnetic radiation provided to said transient PCB, a user initiated mechanical impact provided to said transient PCB, a user initiated flow of heat provided to said transient PCB, a user initiated flow of heat from said transient PCB or a user initiated application of an RF electric field provided to said transient PCB; and exposing said transient PCB to an internal or external stimulus, thereby programmably transforming said transient PCB.

50. The method of claim 49, wherein upon exposure to said internal or external stimulus said selectively transformable material is completely transformed within a period of 5 days or less.

\* \* \* \* \*